(12) United States Patent
Page et al.

(10) Patent No.: US 11,524,003 B2
(45) Date of Patent: Dec. 13, 2022

(54) ALPHA-AMINO ESTERS OF HYDROXYPROPYLTHIAZOLIDINE CARBOXAMIDE DERIVATIVE AND SALT FORM, CRYSTAL POLYMORPH THEREOF

(71) Applicant: ObsEva S.A., Plan-les-Ouates (CH)

(72) Inventors: Patrick Naxos Page, Saint-Julien-en Genevois (FR); Matthias Schwarz, Gland (CH); Catherine Jorand-Lebrun, Arlington, MA (US); Anna Quattropani, Rolle (CH); Vincent Pomel, Groisy (FR); Ernest Loumaye, Cologny (CH); Oliver Pohl, Plan-les-Ouates (CH); Jean-Pierre Gotteland, Geneva (CH)

(73) Assignee: ObsEva S.A., Plan-les-Ouates (CH)

( * ) Notice: Subject to any disclaimer, the term of this patent is extended or adjusted under 35 U.S.C. 154(b) by 101 days.

(21) Appl. No.: 16/752,961

(22) Filed: Jan. 27, 2020

(65) Prior Publication Data

US 2020/0155515 A1     May 21, 2020

Related U.S. Application Data

(62) Division of application No. 16/066,921, filed as application No. PCT/EP2017/050099 on Jan. 4, 2017, now Pat. No. 10,555,934.

(60) Provisional application No. 62/407,918, filed on Oct. 13, 2016, provisional application No. 62/395,664, filed on Sep. 16, 2016, provisional application No. 62/274,674, filed on Jan. 4, 2016.

(51) Int. Cl.

| | | |
|---|---|---|
| *A61K 31/426* | (2006.01) | |
| *A61K 9/00* | (2006.01) | |
| *A61P 15/06* | (2006.01) | |
| *A61K 45/06* | (2006.01) | |
| *A61K 31/40* | (2006.01) | |
| *A61K 31/4422* | (2006.01) | |
| *A61K 38/095* | (2019.01) | |
| *A61K 9/20* | (2006.01) | |
| *A61K 9/48* | (2006.01) | |
| *A61K 9/16* | (2006.01) | |

(52) U.S. Cl.
CPC .......... *A61K 31/426* (2013.01); *A61K 9/0019* (2013.01); *A61K 9/0053* (2013.01); *A61K 31/40* (2013.01); *A61K 31/4422* (2013.01); *A61K 38/095* (2019.01); *A61K 45/06* (2013.01); *A61P 15/06* (2018.01); *A61K 9/0095* (2013.01); *A61K 9/16* (2013.01); *A61K 9/20* (2013.01); *A61K 9/48* (2013.01)

(58) Field of Classification Search
CPC .. A61K 31/426; A61K 31/40; A61K 31/4422; A61K 38/095; A61K 9/0053; A61K 45/06; A61K 9/0019; A61K 9/20; A61P 15/06
See application file for complete search history.

(56) References Cited

U.S. PATENT DOCUMENTS

| | | | |
|---|---|---|---|
| 5,508,045 | A | 4/1996 | Harrison et al. |
| 5,872,126 | A | 2/1999 | Cukierski et al. |
| 8,415,480 | B2 | 4/2013 | Page et al. |
| 9,447,055 | B1 | 9/2016 | Page et al. |
| 9,834,528 | B2 | 12/2017 | Page et al. |
| 10,259,795 | B2 | 4/2019 | Page et al. |
| 10,555,934 | B2 | 2/2020 | Page et al. |
| 2006/0211626 | A1 | 9/2006 | Peri et al. |
| 2018/0201591 | A1 | 7/2018 | Page et al. |
| 2019/0000812 | A1 | 1/2019 | Page et al. |
| 2019/0194151 | A1 | 6/2019 | Page et al. |

FOREIGN PATENT DOCUMENTS

| | | |
|---|---|---|
| EP | 1487442 B1 | 12/2010 |
| JP | H09-504108 A | 4/1997 |
| JP | 2005-531524 A | 10/2005 |
| JP | 2005-537225 A | 12/2005 |
| WO | WO-03/082278 A1 | 10/2003 |
| WO | WO-2015/192878 A1 | 12/2015 |

OTHER PUBLICATIONS

Page et al., "Alpha-Amino Esters of Hydroxypropylthiazolidine Carboxamide Derivative and Salt Form, Crystal Polymorph Thereof," U.S. Appl. No. 16/289,235, filed Feb. 28, 2019 (122 pages).
Written Opinion for International Application No. PCT/EP2017/050101, dated Apr. 5, 2017 (8 pages).
NICE guideline, "Preterm labour and birth," <https://www.nice.org.uk/guidance/ng25>, published Nov. 20, 2015 (24 pages).
Arrowsmith et al., "Oxytocin: Its Mechanism of Action and Receptor Signalling in the Myometrium," J Neuroendocrinol. 26(6):356-69 (2014).
Flenady et al., "Calcium channel blockers for inhibiting preterm labour and birth," Cochrane Database Syst Rev. (6):CD002255 (2014) (179 pages).
MacDougall et al., "Pharmacokinetics of valaciclovir," J Antimicrob Chemother. 53(6):899-901 (2004).
Gyetvai et al., "Tocolytics for preterm labor: a systematic review," Obstet Gynecol. 94(5 Pt 2):869-77 (1999).

(Continued)

*Primary Examiner* — Sahar Javanmard
(74) *Attorney, Agent, or Firm* — Clark & Elbing LLP

(57) ABSTRACT

The invention provides α-amino esters of a hydroxypropylthiazolidine carboxamide derivative, (2S)-3-([1,1'-biphenyl]-4-ylsulfonyl)-N-[(1S)-3-hydroxy-1-phenylpropyl]-1,3-thiazolidine-2-carboxamide, as well as salts and crystal polymorphs thereof, that can be used to inhibit prostaglandin F receptor. The invention further encompasses methods of treating disorders such as preterm labor at the early gestational stage by the administration of these substances to a patient in need of treatment.

20 Claims, 127 Drawing Sheets

(56) References Cited

OTHER PUBLICATIONS

International Search Report for International Application No. PCT/EP2017/050099, dated Mar. 29, 2017 (5 pages).
Written Opinion for International Application No. PCT/EP2017/050099, dated Mar. 29, 2017 (8 pages).
Jobe et al., "Choice and dose of corticosteroid for antenatal treatments," Am J Obstet Gynecol. 190(4):878-81 (2004).
Vig et al., "Amino acids as promoieties in prodrug design and development," Adv Drug Deliv Rev. 65(10):1370-85 (2013).
Huttunen et al., "Prodrugs—from serendipity to rational design," Pharmacol Rev. 63(3):750-71 (2011).
Ahmad et al., "Selective modulation of the prostaglandin F2alpha pathway markedly impacts on endometriosis progression in a xenograft mouse model," Mol Hum Reprod. 21(12):905-16 (2015).
Miracle et al., "Guideline for the use of antenatal corticosteroids for fetal maturation," J Perinat Med. 36(3):191-6 (2008).
Haas et al., "Short-term tocolytics for preterm delivery—current perspectives," Int J Womens Health. 6:343-9 (2014).
International Search Report for International Application No. PCT/EP2017/050101, dated Apr. 5, 2017 (5 pages).
First Office Action for Eurasian Patent Application No. 201891095/28, dated Feb. 22, 2019 (6 pages).
Search Report and Written Opinion for Singaporean Patent Application No. 11201804594Y, dated Sep. 6, 2019 (10 pages).
Read et al., "The use of a calcium antagonist (nifedipine) to suppress preterm labour," Br J Obstet Gynaecol 93(9):933-7 (1986).
Singhal et al., "Drug polymorphism and dosage form design: a practical perspective," Adv Drug Deliv Rev. 56(3):335-47 (2004).
Caira, M.R., Crystalline Polymorphism of Organic Compound, *Design of Organic Solids*. Springer Verlag Berlin Heidelberg 163-208 (2003).

FIG. 4

| Method | Observations | NMR Results |
|---|---|---|
| Addition of NaOH solution (H₂O) to salt solution (CH₂Cl₂) | Rotary evaporated to dryness, dried in vacuum oven | methanesulfonic acid peak present |
| Addition of NaOH solution (H₂O) to salt solution (CH₂Cl₂) | Yellow paste, dried in vacuum oven | methanesulfonic acid peak present |
| Water added to CH₂Cl₂ solution Agitated by hand. Removed the water CH₂Cl₂ layer, evaporated. | Solids precipitate in the water layer | - |
| Added NaOH (in water) to the water layer. Added CH₂Cl₂, agitated by hand. | Sticky solid, dried in vacuum oven | - |
| Removed CH₂Cl₂ layer, evaporated | Paste, dried in vacuum oven. | methanesulfonic acid peak present |
| Addition of NaOH solution (EtOH) to salt solution (EtOH) | Slight precipitation, white, placed in refrigerator. Rotary evaporated, dried in vacuum oven. | methanesulfonic acid peak present |
| Addition of NaOH solution (EtOH) to salt solution (EtOH) 2:1. Evaporated | Paste, dried in vacuum oven. | free base |
| Addition of NaOH solution (EtOH) to salt solution (EtOH) 2:1. Evaporated | Dried in vacuum oven. | free base |
| Addition of NaOH solution (EtOH) to salt solution (EtOH) 2:1. Evaporated. | Paste, dried in vacuum oven. | free base |
| Addition of aqueous NaOH solution to salt solution in CH₂Cl₂ (2:1). Evaporated. | Paste, dried in vacuum oven. | free base |

FIG. 5

| Salt | Method | Observations | NMR Result |
|---|---|---|---|
| Besylate | Acid solution added to filtered base solution, EtOH | Clear solution, evaporated. Clear glass like solid, slurried in ether. White, glass like solids. | Benzenesulfonate salt |
| | Free base solution added to acid slurry (CH$_2$Cl$_2$) | Clear solution-refrigerated. Placed in freezer. | - |
| | Acid solution added to base solution (Acetone) | Slightly hazy, yellow tinted solution. Very small amount of solid, refrigerated. | - |
| Citrate | Free base solution added to acid slurry (EtOAc) | White precipitate. Slurried, solid appears paste-like. Evaporated. | - |
| | Free base solution added to acid slurry (EtOAc) | White precipitate, paste-like. Placed on the orbit shaker, at 50 °C. Clear solution, refrigerated. | - |
| | Free base solution added to acid slurry (EtOAc) | Paste-like precipitate. The solution is slightly hazy, stirred. Clear solution, white paste. Placed in vacuum oven. White solid, unknown morphology/clear glassy film in areas. No birefringence | Citrate salt |
| Edisylate | Free base solution added to acid slurry (Dioxane) | Clear solution. Refrigerated. Solution solidifies, brought to RT, clear solution, evaporated. | - |
| | Acid solution (hazy-Dioxane) added to base solution (EtOAc) | No precipitate. Clear yellow tinted solution, refrigerated. Slowly evaporated – colorless oil. Vacuum dried at ambient | - |
| HCl | HCl in Et$_2$O was added to base solution in Et$_2$O | White precipitate, suspension stirred for ~ 30 mins, vacuum filtered. Solid of unknown morphology, no birefringence | HCl salt |
| | HCl in Et$_2$O was added to base solution in CH$_2$Cl$_2$/Et$_2$O | White precipitate, suspension stirred for ~ 15 mins, vacuum filtered. Viscous solid. Added acetone, slurried for 2 days | HCl salt |

FIG. 5 (Continued)

| Salt | Method | Observations | NMR Result |
|---|---|---|---|
| Esylate | Acid added to filtered base solution, $CH_2Cl_2$ | Clear solution, evaporated. Clear glass-like solid, slurried in ether. White film like solid, does not have a distinct habit, no birefringence. | Ethanesulfonate salt |
| Fumarate | Acid added to base solution, EtOAc | No immediate precipitate. Very small amount of solids w/stirring. Refrigerated. | - |
| | Free base solution added to acid slurry (acetone) | Very little precipitate w/stirring. Partially evaporated. Refrigerated. | - |
| Glutamate | Acid solution ($H_2O$) added to base solution ($H_2O$/EtOH) | Droplets of oily material, solvent decanted, oil dried in ambient vacuum oven. | - |
| | Acid solution ($H_2O$) added to base solution (acetone) | Yellowish oil precipitate, cloudy white solution. Sonicated, refrigerated. | - |
| Maleate | Free base solution added to acid slurry (acetone) | Clear solution. Refrigerated. | - |
| | Acid added to base solution, EtOAc | Immediate precipitate, goes into solution w/stirring. Very slight precipitate, refrigerated. | - |
| Mesylate | Acid added to base solution in $Et_2O$ | Immediate white precipitate, stirred for approx. 30 mins. Vacuum filtered – viscous solid, washed with ether, vacuum dried at ambient. Glassy, no birefringence | Mesylate salt |
| Phosphate | Acid ($H_2O$) added to base solution (hazy) EtOH | Slightly hazy solution. Evaporated. Fine white solids-freezer. Broken glass, aggregates of unknown morphology, white. Does not appear birefringent - storage. | - |
| | Acid added to base solution (acetone) | No precipitate. Refrigerated. Light yellow oil, vacuum dried at ambient. | - |
| Sulfate | Acid ($H_2O$) added to base solution in a mixture of $Et_2O$ and $CH_2Cl_2$ | Heterogeneous reaction. Light precipitate, vigorous stirring for approx. 30 mins. - white suspension, left for evaporation | Sulfate salt |

FIG. 5 (Continued)

| Salt | Method | Observations | NMR Result |
|---|---|---|---|
| Hydrosulfate (~25 molar excess of $H_2SO_4$ used) | Acid ($H_2O$) added to base solution (hazy) EtOH | White precipitate, slurried on the rotator. Clear solution. Refrigerated. White, milky solution - freezer. White solids, decanted, placed in the hood to evaporate - solids go into residual solution, clear. Vacuum dried. The solids remain paste-like, no birefringence - storage. | - |
| | Acid ($H_2O$) added to filtered base solution (acetone) | Hazy solution, refrigerated. Placed in freezer. Solids - most likely due to the water in the acid solution, partial evaporation. Poured off the remaining solvent, white solid. Tiny needles, spherulites, birefringence. Vacuum dried. Brown paste - storage. | - |
| | Acid ($H_2O$) added to filtered base solution (acetone) | White precipitate, sticky. Sonicated, approx 30 mins. White fluffy solid, paste on the bottom of the vial. Refrigerated. Fluffy solids, tiny needles. | Hydrosulfate salt |
| Tosylate | Acid solution added to base solution (hazy) EtOH | Small amount of solids. Refrigerated. Fine white solids - freezer. | - |
| | Acid solution added to base solution, EtOAc | No precipitate. Refrigerated. Slowly evaporated – colorless oil. Vacuum dried at ambient. | - |

FIG. 6

| Salt | Observations | XRPD Result |
|---|---|---|
| Besylate | light yellow solid, glassy, no birefringence | - |
| Citrate | glassy, no birefringence | amorphous |
| | glassy, no birefringence | - |
| | unknown morphology, clear glassy film, no birefringence | - |
| Edisylate | glassy, no birefringence | amorphous |
| | pink glassy solid, no birefringence | - |
| Esylate | white glassy solid, no birefringence | - |
| Fumarate | orange glassy solid, no birefringence | - |
| Glutamate | glassy, no birefringence | - |
| Maleate | white glassy solid, no birefringence | - |
| Phosphate | white solid, unknown morphology, no birefringence | - |
| Hydrosulfate | fluffy solid, needles | crystalline X |
| | light yellow oil | - |
| | light yellow oil | - |
| Sulfate | white solid, unknown morphology, no birefringence | - |
| Tosylate | glassy, no birefringence | - |
| | glassy, no birefringence | - |
| HCl | white solid of unknown morphology, no birefringence | - |

FIG. 7

| Salt/Sample ID | Solvent | Method[a] | Observations | XRPD Result |
|---|---|---|---|---|
| Citrate | methanol: toluene 1:2 | SE | glassy, partially birefringent | amorphous |
| | acetone: iso-propanol 1:2 | SE | glassy, no birefringence | - |
| | methanol: ethyl acetate 1:2 | SE | glassy, no birefringence | - |
| | acetone: ethyl acetate: heptane 2:3:1 | SE | glassy, no birefringence | - |
| | acetone: toluene | VD | glassy, no birefringence | - |
| Hydrosulfate | ethyl acetate: heptane 6:1 | SE | partially glassy, partially birefringent | amorphous |
| | ethyl acetate | SE | - | amorphous |
| | | SE | very viscous oil | - |
| | MEK: n-butyl acetate 1:1 | vacuum-dried | off white solid, glassy, no birefringence | - |
| Sulfate | acetone: toluene 2:1 | | glassy, no birefringence | - |
| | MEK: n-butyl acetate 1:1 | SE | glassy white solid, no birefringence | - |
| | methanol: toluene 2:1 | | glassy, no birefringence | - |
| Dihydrophosphate | methanol: ethyl acetate 1:2 | SE | glassy, no birefringence | - |
| | methanol: acetonitrile 1:2 | SE | mostly glassy, slightly birefringent | amorphous |
| | methanol: toluene 1:2 | SE | unknown morphology, no birefringence | - |
| | methyl ethyl ketone: n-butyl acetate 1:1 | SE | white solid of unknown morphology, birefringent | crystalline X |
| | | SE | white solid, agglomerated plates, birefringent | low crystalline X |
| | | SE | viscous solid | - |
| | | vacuum-dried | viscous light yellow solid | - |
| Glutamate | ethyl acetate: heptane 1:1 | SE | glassy, no birefringence | - |
| | methanol: toluene 1:1 | SE | glassy, no birefringence | - |
| Tosylate | methanol: toluene 1:2 | SE | glassy, no birefringence | - |
| | acetone: iso-propanol 1:2 | SE | glassy, no birefringence | - |
| | CH₃CN: toluene 1:2 | SE | glassy, no birefringence | - |
| | ethyl acetate: n-butyl acetate: heptane | VD | glassy, no birefringence | - |
| | methyl ethyl ketone: heptane 3:2 | SE | glassy, no birefringence | - |
| | acetone: toluene 1:1 | SE | glassy, no birefringence | - |
| HCl | ethyl acetate: heptane 5:1 | SE | partially glassy, no birefringence | - |
| | acetone: toluene 1:1 | SE | white solid of unknown morphology, birefringent | crystalline A |
| | | SE | white solid of unknown morphology, birefringent | crystalline A |
| | Et₂O: CH₂Cl₂ | FE | agglomerates of needles, birefringent | crystalline A |
| | acetone | slurry, 2d | white fluffy solid, thin needles, birefringent | crystalline A |
| | dried in vacuum at ambient | | - | crystalline A | a. SE = slow evaporation, FE = fast evaporation, SC = slow cooling, CC = crash cooling
b. original sample

FIG. 7 (continued)

| Salt/ Sample ID | Solvent | Method[a] | Observations | XRPD Result |
|---|---|---|---|---|
| Mesylate | methanol: toluene 1:2 | SE | glassy, no birefringence | - |
| | acetone: *iso*-propanol 1:2 | SE | glassy, no birefringence | - |
| | MEK: n-butyl acetate 1:1 | SE | viscous solid | - |
| | CH₃CN: n-butyl acetate 1:1 | SE | viscous solid | - |
| | CH₂Cl₂: EtOAc: Et₂O | SE | glassy, no birefringence | - |
| | *iso*-propyl acetate: methanol 30:1 | SC | clear solution | - |
| | | FE | glassy, no birefringence | - |
| | | CC | clear solution | - |
| | | SE | clear glassy solid | - |
| | heptane:MEK: ethanol 6:1:2 | SC | clear solution | - |
| | | FE | glassy, no birefringence | - |
| | | CC | clear solution | - |
| | | SE | clear, glassy solid | - |
| | acetone: MTBE 1:2 | SE | glassy, no birefringence | - |
| | acetone: toluene 1:2 | FE | glassy, no birefringence | - |
| | *iso*-propanol: toluene 3:1 | FE | glassy, no birefringence | - |
| | *iso*-propanol: *iso*-propyl ether 1:1 | FE | clear, glassy solid | - |
| | CH₃CN: water 1:1 | CC | clear solution | - |
| | | SE | morphology unknown, no birefringence | - |
| | *iso*-propyl ether: CH₃CN:MeOH 20:5:2 | CC | clear solution | - |
| | | SE | glassy, no birefringence | |
| Fumarate | acetone: n-butyl acetate 1:1 | SE | glassy, no birefringence | - |
| | CH₂Cl₂: *iso*-propanol 1:1 | SE | glassy, no birefringence | - |
| | methanol: toluene 1:1 | SE | partially glassy, some birefringence | crystalline B |
| | methanol: ethyl acetate 1:1 | SE | partially glassy, partially birefringent | amorphous |
| | methanol: toluene 1:1 | SE | partially oily, partially birefringent (fibers) | - |
| | | | light yellow oil | |
| | | vacuum-dried | light yellow solid, unknown morphology, birefringent | amorphous + peak |
| | methanol: toluene 4:1 | SE | glassy, no birefringence | - | a. SE = slow evaporation, FE = fast evaporation, SC = slow cooling, CC = crash cooling
b. original sample

FIG. 7 (continued)

| Salt/ Sample ID | Solvent | Method[a] | Observations | XRPD Result |
|---|---|---|---|---|
| Esylate | MeOH: n-butyl acetate 1:1 | SE | glassy, no birefringence | - |
| | acetone: toluene 1:1 | SE | glassy, no birefringence | - |
| Besylate | ethyl acetate: heptane 4:1 | SE | glassy, no birefringence | - |
| | acetone: toluene 1:1 | SE | glassy, no birefringence | - |
| | $CH_2Cl_2$: iso-propanol 1:1 | SE | glassy, no birefringence | - |
| | MEK: n-butyl acetate 1:1 | SE | glassy, no birefringence | - |
| Edisylate | acetone: n-butyl acetate 1:1 | SE | glassy, no birefringence | - |
| | MeOH: MEK: toluene 1:1:1 | SE | partially glassy, partially birefringent | amorphous |
| Maleate | MeOH: n-butyl acetate 1:1 | SE | glassy, no birefringence | - |
| | acetone: iso-propanol 1:2 | SE | glassy, no birefringence | - | a. SE =slow evaporation, FE =fast evaporation, SC =slow cooling, CC =crash cooling
b. original sample

FIG. 8

| Salt | Solubility (mg/mL)[a] |
|---|---|
| HCl | < 1 |
| hydrosulfate | < 1 |
| fumarate | < 0.5 (became viscous) |
| mesylate | < 46 | a. Solubilities are calculated based on the total solvent used to give a solution; actual solubilities may be greater because of the volume of the solvent portions utilized or a slow rate of dissolution. Solubilities are reported to the nearest mg/mL.

FIG. 9

| Salt | Notes | Relative humidity, % | Time | Observations | Weight change, % |
|---|---|---|---|---|---|
| HCl | - | 95% | ~2d | looks dry | 0[a] |
| HCl | Vacuum dried | 95% | ~2d | looks dry | ~6[a] |
| Hydrosulfate | - | 43% | ~20 h | looks dry | 0[c] |
| Hydrosulfate |  | 53% | ~3 h | looks dry |  |
| Hydrosulfate |  | 65% | ~1 d | looks dry | ~2[c] |
| Hydrosulfate |  | 43% | ~3 d | looks dry |  |
| Hydrosulfate |  | 53% | ~20 h | looks dry | ~2[b] |
| Hydrosulfate |  | 65% | ~3 h | looks dry |  |
| Fumarate | - | 65% | ~1 d | looks partially oily yellow oil with small amount of solid material | ~4[c] |
| Fumarate |  |  | ~3 d |  |  |

FIG. 10

| Sample Source | Technique | Analysis/Result |
|---|---|---|
| From acetone Blurry | XRPD | crystalline I |
| | DSC[a] | endo 147, 228 (decomp.) |
| | TG[b] | 0.55 @ 25-100<br>4.10 @ 25-160 |
| | MB[c] | 0.3 % wt loss at 5% RH<br>0.9 % wt gain from 5-95% RH<br>0.7 % wt loss from 95-5% RH |
| | $^1$H NMR[d] | consistent w/structure |
| Vacuum dried | XRPD | crystalline I |
| | DSC[a] | endo 146 |
| | TG[b] | 0.21 @ 25-100<br>2.53 @ 100-160 | a. endo= endotherm; temperatures (°C) reported are transition maxima. Temperatures are rounded to the nearest degree.
b. weight loss (%) at a certain temperature (°C); weight changes (%) are rounded to 2 decimal places; temperatures are rounded to the nearest degree.

FIG. 11

| Technique | Analysis/Result |
|---|---|
| XRPD | crystalline I |
| DSC[a] | shouldered endo 188, 206, 272 |
| TG[b] | 0.0 @ 25-165<br>6.7 @ 165-220 |
| ¹H NMR | 0.12 molar % of EtOH | a. endo= endotherm; temperatures (°C) reported are transition maxima. Temperatures are rounded to the nearest degree.
b. weight loss (%) at a certain temperature (°C); weight changes (%) are rounded to 2 decimal places; temperatures are rounded to the nearest degree.

FIG. 27

| Elap Time min | Weight mg | Weight % chg | Samp Temp deg C | Samp RH % |
|---|---|---|---|---|
| 0.1 | 4.894 | 0.000 | 25.06 | 4.67 |
| 185.6 | 4.880 | -0.279 | 25.07 | 4.95 |
| 369.1 | 4.881 | -0.255 | 25.06 | 14.98 |
| 552.6 | 4.885 | -0.192 | 25.06 | 25.17 |
| 738.2 | 4.888 | -0.123 | 25.06 | 34.94 |
| 923.7 | 4.892 | -0.029 | 25.05 | 44.85 |
| 1109.2 | 4.897 | 0.058 | 25.05 | 54.90 |
| 1294.8 | 4.902 | 0.170 | 25.06 | 64.87 |
| 1480.7 | 4.908 | 0.291 | 25.05 | 74.97 |
| 1666.2 | 4.915 | 0.435 | 25.04 | 84.82 |
| 1851.8 | 4.923 | 0.602 | 25.04 | 94.94 |
| 2037.8 | 4.920 | 0.528 | 25.03 | 84.97 |
| 2223.3 | 4.915 | 0.428 | 25.03 | 74.96 |
| 2410.8 | 4.910 | 0.321 | 25.03 | 65.01 |
| 2598.3 | 4.904 | 0.214 | 25.03 | 55.07 |
| 2783.9 | 4.899 | 0.101 | 25.04 | 45.13 |
| 2969.4 | 4.893 | -0.020 | 25.03 | 34.89 |
| 3154.9 | 4.887 | -0.131 | 25.06 | 25.04 |
| 3338.4 | 4.882 | -0.236 | 25.02 | 15.23 |
| 3521.5 | 4.888 | -0.114 | 25.04 | 33.97 |

FIG. 55

| Sampling time | Compound (I) | | | Compound (II) | | |
|---|---|---|---|---|---|---|
| | Concentration μM | | | Concentration μM | | |
| 0 min | 1.48 | 3.08 | 5.96 | 1.54 | 2.97 | 6.07 |
| 120 min | 1.43 | 2.86 | 5.65 | 1.48 | 3.04 | 5.74 |
| Recovery | 97% | 93% | 95% | 96% | 102% | 95% |

| | Apical to basolateral: Compound (II) detected | | | | | |
|---|---|---|---|---|---|---|
| | 1.5 µM | | 3 µM | | 6 µM | |
| | % passage | | % passage | | % passage | |
| Sampling time | Mean ± SD | | Mean ± SD | | Mean ± SD | |
| 60 min | 5.39 ± 0.46 | | 2.27 ± 0.38 | | 4.41 ± 0.38 | |
| 120 min | 20.22 ± 1.47 | | 4.11 ± 0.73 | | 7.54 ± 0.99 | |

| | Basolateral to apical: Compound (II) detected | | | | | |
|---|---|---|---|---|---|---|
| | 1.5 µM | | 3 µM | | 6 µM | |
| | % passage | | % passage | | % passage | |
| Sampling time | Mean ± SD | | Mean ± SD | | Mean ± SD | |
| 60 min | 5.81 ± 0.95 | | 1.04 ± 0.34 | | 0.42 ± 0.16 | |
| 120 min | 5.25 ± 0.92 | | 1.06 ± 0.25 | | 0.60 ± 0.01 | |

Recovery in the apical compartment at the end of treatment (120 min)

Recovery in the apical compartment at the end of treatment (120 min)

|  | 1.5 µM | 3 µM | 6 µM |
|---|---|---|---|
| Compound (I) | 2% | 0.6% | 3.1% |
| Compound (II) | 349% | 217% | 302% |

FIG. 57A

| Sampling time | Apical to Basolateral | | | | | | | | |
|---|---|---|---|---|---|---|---|---|---|
| | 1.5 µM | | | 3 µM | | | 6 µM | | |
| | % passage | | | % passage | | | % passage | | |
| | Mean | ± | SD | Mean | ± | SD | Mean | ± | SD |
| 60 min | n.d. | ± | n.d. | 17.83 | ± | 1.19 | 18.48 | ± | 4.76 |
| 120 min | n.d. | ± | n.d. | 33.08 | ± | 1.12 | 23.37 | ± | 4.60 |

FIG. 57B

| Sampling time | Basolateral to Apical | | | | | | | | |
|---|---|---|---|---|---|---|---|---|---|
| | 1.5 µM | | | 3 µM | | | 6 µM | | |
| | % passage | | | % passage | | | % passage | | |
| | Mean | ± | SD | Mean | ± | SD | Mean | ± | SD |
| 60 min | n.d | ± | n.d | 2.56 | ± | 1.11 | 1.28 | ± | 0.66 |
| 120 min | n.d | ± | n.d | 1.78 | ± | 0.07 | 3.00 | ± | 0.68 |

FIG. 57C

| | 60 min | 120 min |
|---|---|---|
| Overall mean (mean% ± SD) | 1.84% ± 1.18 | 4.36% ± 3.62 |
| Papp (x$10^{-6}$) nm/sec | 0.56 | 2.79 |

| | Apical to basolateral: Compound (II) detected ||||||
|---|---|---|---|---|---|---|
| | 1.5 µM ||  3 µM || 6 µM ||
| | % passage || % passage || % passage ||
| Sampling time | Mean ± SD || Mean ± SD || Mean ± SD ||
| 60 min | 25.11 ± | 2.82 | 11.72 ± | 5.34 | 3.25 ± | 0.50 |
| 120 min | 14.47 ± | 5.15 | 13.26 ± | 5.66 | 5.46 ± | 1.72 |

Recovery in the apical compartment at the end of treatment (120 min)

| | 1.5 µM | 3 µM | 6 µM |
|---|---|---|---|
| Compound (I) | 0.8% | 1.8% | 0.3% |
| Compound (II) | 37.1% | 39.1% | 156.3% |

FIG. 59

| Analytical equipment | |
|---|---|
| HPLC | Surveyor Binar Pump |
| Auto sampler | CTC, Pal |
| Detector | Mass spectrometer Thermo Finnigan, DECA XP Plus |
| Data System | Excalibur Software |
| MS interface | ESI |
| Scan type | MRM |
| Polarity | Positive |
| Ion monitored  Compound (I) | 501.2 m/z (parent ion 484.1 – 501.9 – 349.9 m/z) |
| Ion monitored  Compound (II) | 502.1 m/z (parent ion 349.5 m/z) |

| Chromatographic and Mass Spectrometric conditions | | | |
|---|---|---|---|
| Analytical column | Xterra 5uM $C_{18}$ (2), 2.0 x 30 mm, Waters | | |
| Column temperature | 22 °C | | |
| Mobile phase A | FOA 0.1% in water | | |
| Mobile phase B | $CH_3CN$ | | |
| Flow rate | 400 µL/min | | |
| Injection volumes | 10 µL | | |
| Gradient | Time (min) | Mobile phase % A | Mobile phase %B |
| | 0 | 85 | 15 |
| | 2.0 | 5 | 95 |
| | 3.0 | 5 | 95 |
| | 3.1 | 85 | 15 |
| | 5.6 | 85 | 15 |

Time post RU486 or LPS injection (hours)

ALPHA-AMINO ESTERS OF HYDROXYPROPYLTHIAZOLIDINE CARBOXAMIDE DERIVATIVE AND SALT FORM, CRYSTAL POLYMORPH THEREOF

FIELD OF THE INVENTION

The invention relates to chemical compositions, such as compounds, salts, and crystal polymorphs, that are capable of binding and inhibiting the activity of prostaglandin F2α (PGF2α) receptor, as well as methods of preventing preterm labor at the early gestational stage by administration of these compositions to a patient in need of treatment.

BACKGROUND OF THE INVENTION

Preterm delivery represents a prevalent cause of perinatal mortality in the developed world and occurs in approximately 7% to 10% of all deliveries (Berkowitz et al. Epidemiol. Rev. 15:414-443 (1993)). Severe morbidity, especially respiratory distress syndrome, intraventricular hemorrhage, bronchopulmonary dysplasia, and necrotizing enterocolitis, are far more common in preterm than in term infants. Long-term impairment, such as cerebral palsy, visual impairment, and hearing loss, are also more common in preterm infants. At present, preterm birth remains a leading cause of infant mortality and morbidity in the United States, where, despite the significant improvements in obstetrical medicine, the infant mortality rate is higher than in many other industrialized nations, causing costs exceeding $5 billion per year for neonatal intensive care of low birth-weight babies. The actual costs associated with this care are even higher when taking into consideration the healthcare provision of preterm childbirth-related ailments, such as respiratory distress syndrome, heart conditions, cerebral palsy, epilepsy, and severe learning disabilities.

During the past 40 years of clinical investigations, and despite the use of multiple therapeutic agents, the rate of preterm birth has not drastically declined. The prevention of preterm labor is difficult and although tocolytic therapy remains the cornerstone of management of preterm labor, there is not universal agreement as to its value in this condition. The available tocolytic agents on their own do not prolong labor for more than 48 hours, and the majority of these agents lack uterine selectivity and can thus cause potentially serious side effects both for the mother and the fetus.

Fundamentally, term and preterm labor are similar processes in that they share a common physiological endpoint characterized by uterine contractions, cervical dilatation, and activation of the fetal membranes. The differences lie in the gestational age at which these processes occur and the mechanisms by which they are activated. Term labor is thought to result from physiological activation of the terminal pathway, whereas preterm labor is a pathological condition characterized by multiple etiologies in which one or more components of this pathway are aberrantly activated.

Uterine contractility is stimulated or inhibited by various receptors in myometrial cells. It is hypothesized that activation of the myometrium results from the coordinated expression of contraction-associated proteins (CAPs), including actin, myosin, connexin-43, and the receptors for oxytocin and prostaglandins. In general, receptors that provoke calcium entry or calcium release from intracellular stores stimulate contractility. However, receptors coupled to the production of cyclic nucleotides, such as cyclic adenosine monophosphate (cAMP) relax the uterus. For instance, oxytocin and prostaglandin F (FP) receptors are stimulatory, while β2 adrenoceptors and prostaglandin E2 receptors coupled to cAMP formation are inhibitory.

In uterine tissues, prostaglandins E2 (PGE2) and F2α (PGF2α) have been shown to induce cervical changes and elicit uterine contractility, two key events in the physiology of labor and parturition. Activation of the FP receptor in the human myometrium by PGF2α results in the elevation of intracellular calcium concentration, which, in turn, leads to contraction of the uterine smooth cell muscle (Abramovitz et al. J. Biol. Chem. 269:2632-2636 (1994) and Senior et al. Br. J. Pharmacol. 108:501-506 (1993)). FP receptors are up-regulated in uterine tissues towards term (Al-Matubsi et al. Biol. Reprod. 65:1029-1037 (2001)). Inhibitors of prostaglandin synthesis (such as indomethacin and nimesulide) have shown some tocolytic effect but are not devoid of side effects and their un-licensed use in the clinic has raised concerns regarding fetal safety (Norton et al. New Engl. J. Med. 329:1602-1067 (1993) and Peruzzi et al. New Engl. J. Med. 354:1615 (1999)). There remains a need to develop therapeutics with myometrial selectivity that permit lasting inhibition of uterine contractions that lead to labor and that prolong pregnancy to a stage where increased fetal maturation raises the chances of survival.

SUMMARY OF THE INVENTION

The invention encompasses alpha-amino esters of a hydroxypropylthiazolidine carboxamide derivative, as well as salts thereof, that are capable of antagonizing the interaction between prostaglandin F2α (PGF2α) and the prostaglandin F receptor. These compounds can be administered to a subject, such as a pregnant human female subject, in order to treat or prevent preterm labor. The invention additionally provides methods of synthesizing these compounds, as well as methods for preparing crystal forms thereof.

In a first aspect, the invention provides a compound represented by formula (I),

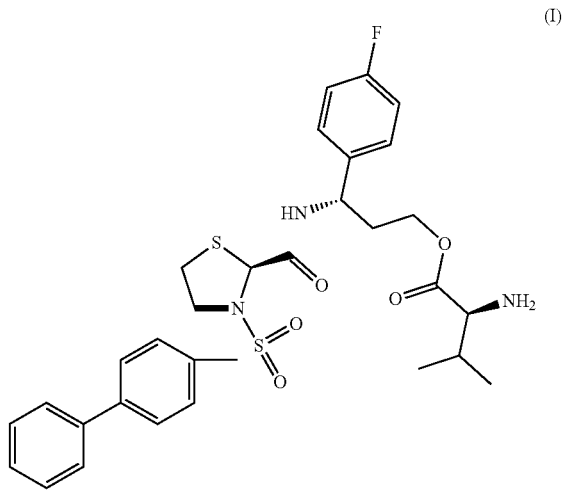

(3S)-3-({[(2S)-3-(biphenyl-4-ylsulfonyl)-1,3-thiazolidin-2-yl]carbonyl}-amino)-3-(4-fluorophenyl)propyl L-valinate, or a pharmaceutically acceptable salt thereof. In some embodiments, the compound is represented by formula (III), (3S)-3-({[(2S)-3-(biphenyl-4-ylsulfonyl)-1,3-thiazolidin-2-yl]carbonyl}-amino)-3-(4-fluorophenyl)propyl L-valinate hydrochloride.

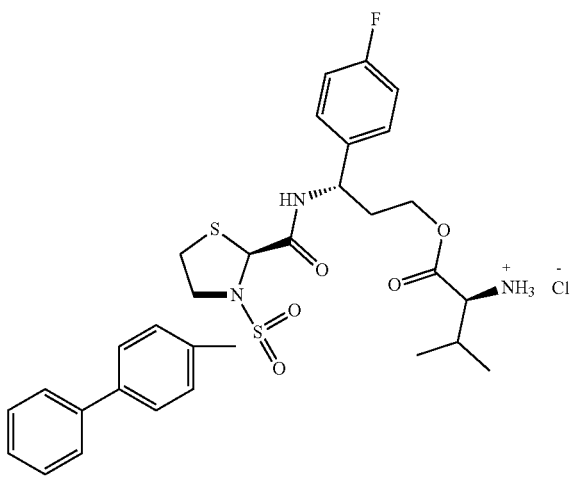

(III)

In some embodiments, the compound binds human prostaglandin F2α receptor with an affinity of about 1 nM. Compounds of the invention demonstrate the ability to selectively bind prostaglandin F receptors, such as prostaglandin F2a, over other prostaglandin receptor subtypes. For instance, compounds of the invention exhibit an affinity for prostaglandin F2α receptor that is about 10-fold greater than that observed for prostaglandin E2 receptor. Additionally, compounds of the invention exhibit an affinity for prostaglandin F2α receptor that is about 100-fold or above (e.g., from about 100-fold to about 1,000-fold, such as about 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 410-fold, 420-fold, 430-fold, 440-fold, 450-fold, 460-fold, 470-fold, 480-fold, 490-fold, 500-fold, 510-fold, 520-fold, 530-fold, 540-fold, 550-fold, 560-fold, 570-fold, 580-fold, 590-fold, 600-fold, 610-fold, 620-fold, 630-fold, 640-fold, 650-fold, 660-fold, 670-fold, 680-fold, 690-fold, 700-fold, 710-fold, 720-fold, 730-fold, 740-fold, 750-fold, 760-fold, 770-fold, 780-fold, 790-fold, 800-fold, 810-fold, 820-fold, 830-fold, 840-fold, 850-fold, 860-fold, 870-fold, 880-fold, 890-fold, 900-fold, 910-fold, 920-fold, 930-fold, 940-fold, 950-fold, 960-fold, 970-fold, 980-fold, 990-fold, 1,000-fold, or above) greater than for other prostaglandin receptor subtypes, such as prostaglandin E1, E3, E4, D1, D2, I1, and I2 receptor subtypes. In some embodiments, the compound is soluble in aqueous solution at a concentration of from about 300 μg/mL to about 500 μg/mL, such as at a concentration of about 380 μg/mL.

In some embodiments, the compound inhibits synthesis of inositol triphosphate in a cell, such as a mammalian cell. In some embodiments, the mammalian cell is a human cell, such as a myometrial cell. In some embodiments, the myometrial cell is a uterine myocyte. In some embodiments, the compound induces a reduction in the amplitude of uterine contractions in a subject following administration of the compound to the subject. For instance, the compound may induce a reduction of from about 40% to about 50% relative to a measurement of the amplitude of uterine contractions in the subject recorded prior to the administration. In some embodiments, the compound exhibits a half life in a subject of from about 1 to about 4 hours following administration of the compound to the subject. In some embodiments, the compound reaches a maximum plasma concentration in a subject within from about 0.25 to about 2 hours following administration of the compound to the subject.

In some embodiments, the subject is a mammal. In some embodiments, the mammal is a human. In some embodiments, the mammal is a non-human, such as canine or a rat. In some embodiments, the compound is administered to the subject orally. In some embodiments, the compound is administered to the subject intravenously.

In another aspect, the invention encompasses a compound represented by formula (III)

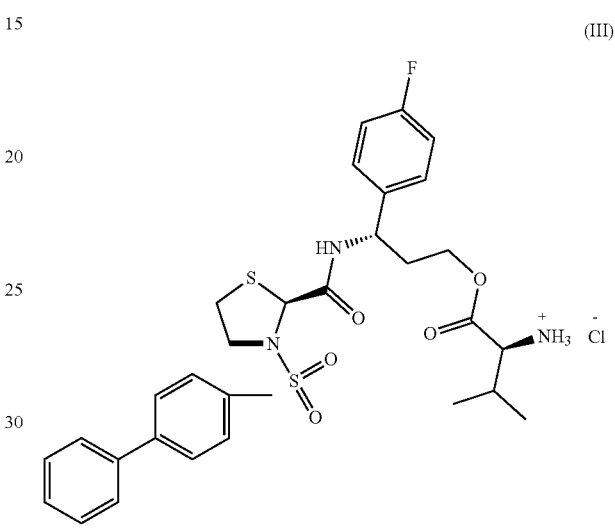

(III)

wherein the compound is in a crystalline state.

In some embodiments, the compound exhibits characteristic X-ray powder diffraction peaks at about 7.0° 2θ, about 8.1° 2θ, about 10.0° 2θ, about 20.1° 2θ, about 21.0° 2θ, and about 23.5° 2θ. In some embodiments, the compound additionally exhibits X-ray powder diffraction peaks at about 12.0° 2θ, about 13.1° 2θ, about 14.1° 2θ, about 16.4° 2θ, about 18.4° 2θ, and about 29.5° 2θ. In some embodiments, the compound is characterized by an X-ray powder diffraction spectrum substantially as depicted in any one of FIGS. 19, 22, 29, 45-49, and 54. For instance, in some embodiments, the compound is characterized by an X-ray powder diffraction spectrum substantially as depicted in FIG. 49.

In some embodiments, the compound exhibits $^1$H nuclear magnetic resonance (NMR) peaks centered at about 1.1 ppm, about 3.3 ppm, about 4.9 ppm, about 5.4 ppm, about 7.1 ppm, about 7.7 ppm, about 7.9 ppm, and about 8.0 ppm. In some embodiments, the compound is characterized by a $^1$H NMR spectrum substantially as depicted in FIG. 21.

In some embodiments, the compound exhibits an endotherm at from about 145° C. to about 147° C. as measured by differential scanning calorimetry. In some embodiments, the compound exhibits an additional endotherm at about 214° C. as measured by differential scanning calorimetry. In some embodiments, the compound is characterized by a differential scanning calorimetry curve substantially as depicted in FIG. 20. In some embodiments, the compound exhibits an additional endotherm at about 228° C. as measured by differential scanning calorimetry. In some embodiments, the compound is characterized by a differential scanning calorimetry curve substantially as depicted in FIG. 23.

In some embodiments, the compound exhibits a weight loss of from about 0.2% to about 0.6% when heated from 25° C. to 100° C. as measured by thermogravimetric analysis. In some embodiments, the compound exhibits a weight loss of from about 2.5% to about 3.5% when heated from 100° C. to 160° C. as measured by thermogravimetric analysis. In some embodiments, the compound exhibits a thermogravimetric analysis curve substantially as depicted in FIG. 24.

In an additional aspect, the invention provides a pharmaceutical composition containing the compound of any of the above-described aspects. The pharmaceutical composition may optionally contain one or more excipients. In some embodiments, the compound has a purity of at least 90%, 91%, 92%, 93%, 94%, 95%, 96%, 97%, 98%, 99%, or 99.9%, e.g., as ascertained by high pressure liquid chromatography (HPLC) or NMR spectroscopy. In some embodiments, the compound and/or pharmaceutical composition is formulated for oral administration to a subject. In some embodiments, the pharmaceutical composition is a tablet, capsule, gel cap, powder, liquid solution, or liquid suspension. In some embodiments, the compound and/or pharmaceutical composition is formulated for intravenous administration to a subject.

In some embodiments, the pharmaceutical composition contains two or more therapeutic agents, such as a compound of the invention (e.g., a compound represented by formula (I) or a pharmaceutically acceptable salt thereof, such as a compound represented by formula (III)) and an additional therapeutic agent. For instance, the pharmaceutical composition may contain two or more therapeutic agents admixed with one another for co-administration to a patient, such as for the treatment or prevention of preterm labor. A pharmaceutical composition of the invention may be administered to a subject to delay the onset of labor in the subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). In some embodiments, the subject is undergoing preterm labor. In some embodiments, the pharmaceutical composition is administered to the subject (e.g., a human subject) prior to the initiation of preterm labor. A pharmaceutical composition of the invention can be administered to a subject (e.g., a human subject) to prevent labor prior to cesarean delivery. A pharmaceutical composition of the invention can be administered to a subject (e.g., a human subject) for the treatment or prevention of dysmenorrhea. A pharmaceutical composition of the invention can be administered to a subject, such as a pregnant female human subject, in order to alleviate one or more symptoms associated with labor, such as vaginal bleeding and rupture of uterine membranes.

In some embodiments, the additional therapeutic agent is an additional tocolytic agent.

In some embodiments, the pharmaceutical composition comprises a compound represented by formula (I), or a pharmaceutically acceptable salt thereof, and an additional tocolytic agent. In some embodiments, the pharmaceutical composition comprises a compound represented by formula (III) and an additional tocolytic agent.

In some embodiments, the additional tocolytic agent is an oxytocin receptor antagonist, such as atosiban, retosiban, barusiban, epelsiban, and nolasiban, or one or more variants, formulations, crystalline forms, or derivatives thereof.

In some embodiments, the pharmaceutical composition comprises a compound represented by formula (I), or a pharmaceutically acceptable salt thereof, and atosiban. In some embodiments, the pharmaceutical composition comprises a compound represented by formula (III) and atosiban. In some embodiments, the pharmaceutical composition comprises a compound represented by formula (I), or a pharmaceutically acceptable salt thereof, and a variant of atosiban, such as a variant described in U.S. Pat. No. 4,504,469 or 4,402,942, the disclosures of each of which are incorporated herein by reference. In some embodiments, the pharmaceutical composition comprises a compound represented by formula (III) and a variant of atosiban, such as a variant described in U.S. Pat. No. 4,504,469 or 4,402,942.

In some embodiments, the pharmaceutical composition comprises a compound represented by formula (I), or a pharmaceutically acceptable salt thereof, and retosiban. In some embodiments, the pharmaceutical composition comprises a compound represented by formula (III) and retosiban. In some embodiments, the pharmaceutical composition comprises a compound represented by formula (I), or a pharmaceutically acceptable salt thereof, and a variant of retosiban, such as a variant described in U.S. Pat. Nos. 7,514,437; 8,367,673; 8,541,579; 8,071,594; 8,357,685; 8,937,179; or US 2016/0074413, the disclosures of each of which are incorporated herein by reference. In some embodiments, the pharmaceutical composition comprises a compound represented by formula (III) and a variant of retosiban, such as a variant described in U.S. Pat. Nos. 7,514,437; 8,367,673; 8,541,579; 8,071,594; 8,357,685; 8,937,179; or US 2016/0074413.

In some embodiments, the pharmaceutical composition comprises a compound represented by formula (I), or a pharmaceutically acceptable salt thereof, and barusiban. In some embodiments, the pharmaceutical composition comprises a compound represented by formula (III) and barusiban. In some embodiments, the pharmaceutical composition comprises a compound represented by formula (I), or a pharmaceutically acceptable salt thereof, and a variant of barusiban, such as a variant described in U.S. Pat. Nos. 6,143,722; 7,091,314; 7,816,489; or US 2016/0175283, the disclosures of each of which are incorporated herein by reference. In some embodiments, the pharmaceutical composition comprises a compound represented by formula (III) and a variant of barusiban, such as a variant described in U.S. Pat. Nos. 6,143,722; 7,091,314; 7,816,489; or US 2016/0175283.

In some embodiments, the pharmaceutical composition comprises a compound represented by formula (I), or a pharmaceutically acceptable salt thereof, and epelsiban. In some embodiments, the pharmaceutical composition comprises a compound represented by formula (III) and epelsiban. In some embodiments, the pharmaceutical composition comprises a compound represented by formula (I), or a pharmaceutically acceptable salt thereof, and a variant of epelsiban, such as a variant described in U.S. Pat. Nos. 7,514,437; 8,367,673; 8,541,579; 7,550,462; 7,919,492; 8,202,864; 8,742,099; 9,408,851; 8,716,286; or 8,815,856, the disclosures of each of which are incorporated herein by reference. In some embodiments, the pharmaceutical composition comprises a compound represented by formula (III) and a variant of epelsiban, such as a variant described in U.S. Pat. Nos. 7,514,437; 8,367,673; 8,541,579; 7,550,462; 7,919,492; 8,202,864; 8,742,099; 9,408,851; 8,716,286; or 8,815,856.

In some embodiments, the pharmaceutical composition comprises a compound represented by formula (I), or a pharmaceutically acceptable salt thereof, and nolasiban. In some embodiments, the pharmaceutical composition comprises a compound represented by formula (III) and nolasiban. In some embodiments, the pharmaceutical composition comprises a compound represented by formula (I), or a pharmaceutically acceptable salt thereof, and a variant, formulation, or crystalline form of nolasiban, such as a variant, formulation, or crystalline form described in U.S. Pat. No. 7,115,754 or US Patent Application Publication No. 2015/0073032; 2015/0164859; or 2016/0002160, the disclosures of each of which are incorporated herein by reference. In some embodiments, the pharmaceutical composition comprises a compound represented by formula (III) and a variant, formulation, or crystalline form of nolasiban, such as a variant, formulation, or crystalline form described in U.S. Pat. No. 7,115,754 or US Patent Application Publication No. 2015/0073032; 2015/0164859; or 2016/0002160.

In some embodiments, the additional tocolytic agent is a betamimetic, such as terbutaline, ritodrine, hexoprenaline, albuterol, fenoterol, nylidrin, or orciprenaline.

In some embodiments, the additional tocolytic agent is a calcium channel inhibitor, such as a dihydropyridine. In some embodiments, the calcium channel inhibitor is nifedipine. In some embodiments, the calcium channel inhibitor is nicardipine.

In some embodiments, the additional tocolytic agent is a magnesium salt, such as magnesium sulfate.

In some embodiments, the additional tocolytic agent is a nitric oxide donor, such as nitroglycerine.

In some embodiments, the additional tocolytic agent is an oxytocin receptor antagonist, such as atosiban, retosiban, barusiban, epelsiban, nolasiban, or a variant, formulation, crystalline form, or derivative thereof, for instance, as described herein.

In some embodiments, the compound represented by formula (I), or a pharmaceutically acceptable salt thereof, is formulated for oral administration, and the additional tocolytic agent is formulated for oral administration. In some embodiments, the compound represented by formula (I), or a pharmaceutically acceptable salt thereof, is formulated for intravenous administration, and the additional tocolytic agent is formulated for intravenous administration. In some embodiments, the compound represented by formula (I), or a pharmaceutically acceptable salt thereof, is formulated for oral administration, and the additional tocolytic agent is formulated for intravenous administration. In some embodiments, the compound represented by formula (I), or a pharmaceutically acceptable salt thereof, is formulated for intravenous administration, and the additional tocolytic agent is formulated for oral administration. In some embodiments, the compound represented by formula (I), or a pharmaceutically acceptable salt thereof, is formulated for oral administration, and the additional tocolytic agent is formulated for intramuscular administration. In some embodiments, the compound represented by formula (I), or a pharmaceutically acceptable salt thereof, is formulated for intravenous administration, and the additional tocolytic agent is formulated for intramuscular administration.

In some embodiments, the compound represented by formula (III) is formulated for oral administration, and the additional tocolytic agent is formulated for oral administration. In some embodiments, the compound represented by formula (III) is formulated for intravenous administration, and the additional tocolytic agent is formulated for intravenous administration. In some embodiments, the compound represented by formula (III) is formulated for oral administration, and the additional tocolytic agent is formulated for intravenous administration. In some embodiments, the compound represented by formula (III) is formulated for intravenous administration, and the additional tocolytic agent is formulated for oral administration. In some embodiments, the compound represented by formula (III) is formulated for oral administration, and the additional tocolytic agent is formulated for intramuscular administration. In some embodiments, the compound represented by formula (III) is formulated for intravenous administration, and the additional tocolytic agent is formulated for intramuscular administration.

In some embodiments, the additional therapeutic agent is progesterone or a variant or derivative thereof, such as 17-α-hydroxyprogesterone caproate.

In some embodiments, the pharmaceutical composition comprises a compound represented by formula (I), or a pharmaceutically acceptable salt thereof, and progesterone or 17-α-hydroxyprogesterone caproate. In some embodiments, the compound represented by formula (I), or a pharmaceutically acceptable salt thereof, is formulated for oral administration and the progesterone or 17-α-hydroxyprogesterone caproate is formulated for intravaginal administration. In some embodiments, the compound represented by formula (I), or a pharmaceutically acceptable salt thereof, is formulated for intravenous administration and the progesterone or 17-α-hydroxyprogesterone caproate is formulated for intravaginal administration. In some embodiments, both the compound represented by formula (I), or a pharmaceutically acceptable salt thereof, and the progesterone or 17-α-hydroxyprogesterone caproate are formulated for oral administration. In some embodiments, the compound represented by formula (I), or a pharmaceutically acceptable salt thereof, is formulated for intravenous administration and the progesterone or 17-α-hydroxyprogesterone caproate is formulated for oral administration.

In some embodiments, the pharmaceutical composition comprises a compound represented by formula (III) and progesterone or 17-α-hydroxyprogesterone caproate. In some embodiments, the compound represented by formula (III) is formulated for oral administration and the progesterone or 17-α-hydroxyprogesterone caproate is formulated for intravaginal administration. In some embodiments, the compound represented by formula (III) is formulated for intravenous administration and the progesterone or 17-α-hydroxyprogesterone caproate is formulated for intravaginal administration. In some embodiments, both the compound represented by formula (III) and the progesterone or 17-α-hydroxyprogesterone caproate are formulated for oral administration. In some embodiments, the compound represented by formula (III) is formulated for intravenous administration and the progesterone or 17-α-hydroxyprogesterone caproate is formulated for oral administration.

In some embodiments, the additional therapeutic agent is a corticosteroid. In some embodiments, the corticosteroid is betamethasone. In some embodiments, the corticosteroid is dexamethasone. In some embodiments, the corticosteroid is hydrocortisone. In some embodiments, the compound represented by formula (I), or a pharmaceutically acceptable salt thereof, is formulated for oral administration and the corticosteroid (e.g., betamethasone, dexamethasone, or hydrocortisone) is formulated for intramuscular administration. In some embodiments, the compound represented by formula (I), or a pharmaceutically acceptable salt thereof, is formulated for intravenous administration and the corticosteroid (e.g., betamethasone, dexamethasone, or hydrocortisone) is formulated for intramuscular administration. In some embodiments, the compound represented by formula (I), or a pharmaceutically acceptable salt thereof, is formulated for oral administration and the corticosteroid (e.g., betamethasone, dexamethasone, or hydrocortisone) is formulated for oral administration. In some embodiments, the compound represented by formula (I), or a pharmaceutically acceptable salt thereof, is formulated for intravenous administration and the corticosteroid (e.g., betamethasone, dexamethasone, or hydrocortisone) is formulated for oral administration. In some embodiments, the compound represented by formula (III) is formulated for oral administration and the corticosteroid (e.g., betamethasone, dexamethasone, or hydrocortisone) is formulated for intramuscular administration. In some embodiments, the compound represented by formula (III) is formulated for intravenous administration and the corticosteroid (e.g., betamethasone, dexamethasone, or hydrocortisone) is formulated for intramuscular administration. In some embodiments, the compound represented by formula (III) is formulated for oral administration and the corticosteroid (e.g., betamethasone, dexamethasone, or hydrocortisone) is formulated for oral administration. In some embodiments, the compound represented by formula (III) is formulated for intravenous administration and the corticosteroid (e.g., betamethasone, dexamethasone, or hydrocortisone) is formulated for oral administration.

In another aspect, the invention provides a method of synthesizing a compound represented by formula (I)

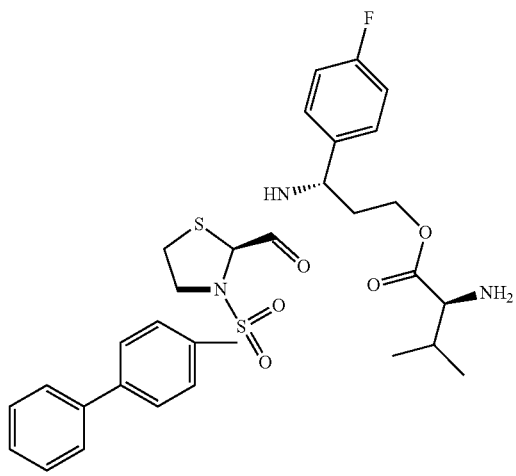

(I)

or a pharmaceutically acceptable salt thereof by reacting a precursor represented by formula (IV)

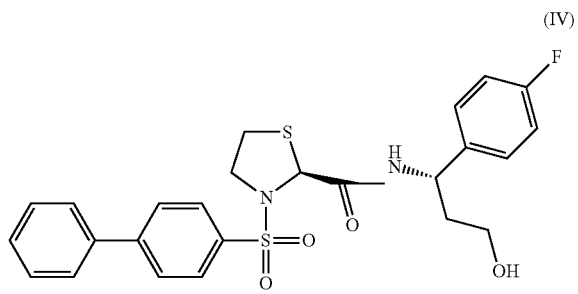

(IV)

with a precursor represented by formula (V)

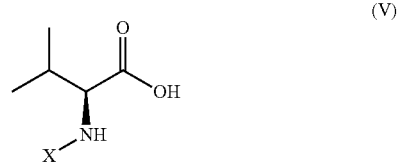

(V)

to form an amino ester, wherein X is a protecting group. In some embodiments, the method includes deprotecting the amino ester. In some embodiments, the compound is represented by formula (III).

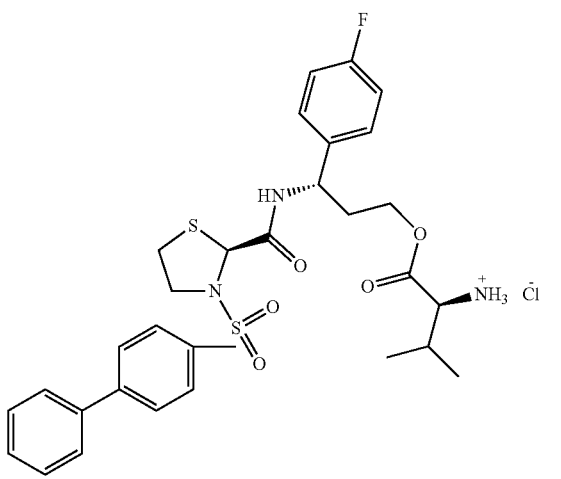

(III)

In some embodiments, the method includes reacting the amino ester with a reagent capable of deprotecting the amino ester. In some embodiments, the protecting group is selected from the group consisting of tert-butoxycarbonyl, trityl, 4-monomethoxytrityl, 4-methyltrityl, 3,5-dimethoxyphenylisopropoxycarbonyl, 2-(4-biphenyl)isopropoxycarbonyl, 2-nitrophenylsulfenyl, 9-fluorenylmethoxycarbonyl, 2-(4-nitrophoneylsulfonyl)ethoxycarbonyl, (1,1-dioxobenzo[b]thiophene-2-yl)methoxycarbonyl, 1-(4,4-dimethyl-2,6-dioxocyclohex-1-ylidene)-3-methylbutyl, 2,7-di-tert-butyl-9-fluorenylmethoxycarbonyl, 2-fluoro-9-fluorenylmethoxycarbonyl, 2-monoisooctyl-9-fluorenylmethoxycarbonyl, 2,7-diisooctyl-9-fluorenylmethoxycarbonyl, tetrachlorophthaloyl, 2-[phenyl(methyl)sulfonio]ethyloxycarbonyl tetrafluoroborate, ethanesulfonylethoxycarbonyl, 2-(4-sulfophenylsulfonyl)ethoxycarbonyl, benzyloxycarbonyl, allyloxycarbonyl, o-nitrobenzenesulfonyl, 2,4-dinitrobenzenesulfonyl, benzothiazole-2-sulfonyl, 2,2,2-trichloroethyloxycarbonyl, dithiasuccinoyl, p-nitrobenzyloxycarbonyl, an α-azidoacid, propargyloxycarbonyl, 9-(4-bromophenyl)-9-fluorenyl, azidomethoxycarbonyl, hexafluoroacetone, 2-chlorobenzyloxycarbonyl, trifluoroacetyl, 2-(methylsulfonyl)ethoxycarbonyl, phenyldisulfanylethyloxycarbonyl, and 2-pyridyldisulfanylethyloxycarbonyl.

In some embodiments, the reagent is selected from the group consisting of methanesulfonic acid, hydrochloric acid, trifluoroacetic acid, acetic acid, piperidine, 1,8-diazabicyclo[5.4.0]undec-7-ene, morpholine, hexamethyleneimine, ammonia, diethylamine, piperazine, tris(2-aminoethyl)amine, hydrazine, 1-methylpyrrolidine, sodium hydrogen carbonate, sodium hydroxide, barium hydroxide, sodium carbonate, molecular hydrogen, hydrobromic acid, boron tribromide, tetrakis(triphenylphosphine)palladium, thiophenol, β-mercaptoethanol, 2-mercaptoacetic acid, aluminum amalgam, zinc, hypophosphorous acid, sodium borohydride, N-mercaptoacetamide, tin(II) chloride, trimethylphosphine, tributylphosphine, triphenylphosphine, benzyltriethylammonium tetrathiomolybdate, palladium(II) acetate, hydrofluoric acid, trimethylsilyl chloride, trimethylsilyl trifluoromethanesulfonate, and trifluoromethanesulfonic acid.

In some embodiments, the protecting group is tert-butoxycarbonyl and the reagent is selected from the group consisting of methanesulfonic acid, hydrochloric acid, and trifluoroacetic acid, such as methanesulfonic acid.

In some embodiments, the method includes exposing the amino ester to electromagnetic radiation. In some embodiments, the protecting group is selected from the group consisting of o-nitrobenzyloxycarbonyl, 4-nitroveratryloxycarbonyl, 2-(2-nitrophenyl)propyloxycarbonyl, and 2-(3,4-methylenedioxy-6-nitrophenyl)propyloxycarbonyl. In some embodiments, the electromagnetic radiation is characterized by a wavelength of from about 300 to about 400 nm.

In some embodiments, the method includes reacting the precursor represented by formula (IV) with the precursor represented by formula (V) and a diimide. In some embodiments, the diimide is selected from the group consisting of 1-ethyl-3-(3-dimethylaminopropyl)carbodiimide, N,N'-diisopropylcarbodiimide, and N,N'-dicyclohexylcarbodiimide. In some embodiments, the diimide is 1-ethyl-3-(3-dimethylaminopropyl)carbodiimide. In some embodiments, the method includes reacting the precursor represented by formula (IV) with the precursor represented by formula (V) and a benzotriazole derivative, such as a benzotriazole derivative selected from the group consisting of 1-hydroxybenzotriazole, 6-chloro-1-hydroxybenzotriazole, and 1-hydroxy-7-azabenzotriazole. In some embodiments, the benzotriazole derivative is 1-hydroxybenzotriazole.

In some embodiments, the method includes reacting the precursor represented by formula (IV) with the precursor represented by formula (V) and a base, such as N,N-dimethylaminopyridine.

In some embodiments, the method includes synthesizing the precursor represented by formula (IV) by reacting a precursor represented by formula (VI)

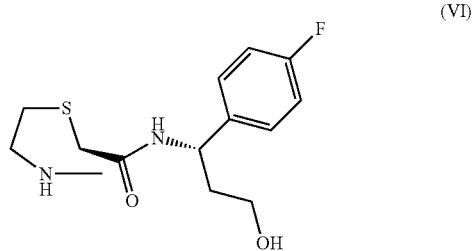

(VI)

with a precursor represented by formula (VII).

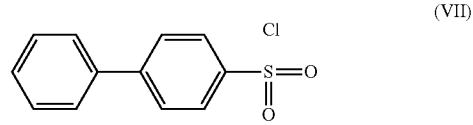

(VII)

In some embodiments, the method includes reacting the precursor represented by formula (VI) with the precursor represented by formula (VII) and one or more bases. In some embodiments, the one or more bases are selected from the group consisting of diisopropylethylamine, triethylamine, and N,N-dimethylaminopyridine.

In some embodiments, the method includes reacting the precursor represented by formula (VI) with the precursor represented by formula (VII), diisopropylethylamine, and N,N-dimethylaminopyridine.

In an additional aspect, the invention provides a method of making a compound represented by formula (III),

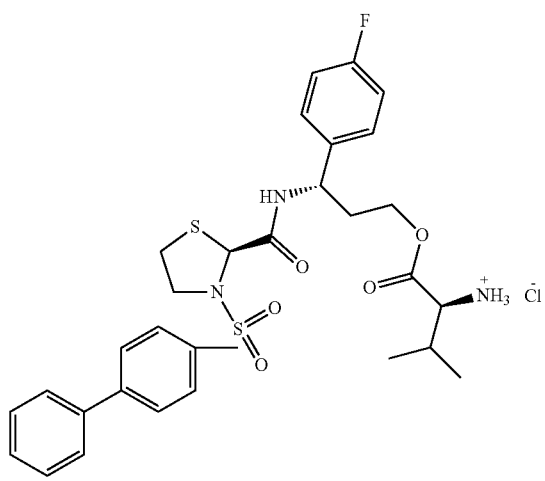

(III)

wherein the method includes mixing a compound represented by formula (I)

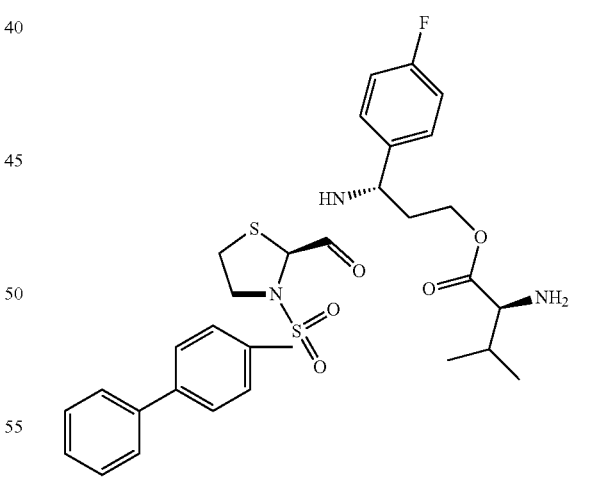

(I)

with hydrochloric acid.

In some embodiments, the hydrochloric acid is aqueous hydrochloric acid. The aqueous hydrochloric acid may be prepared, for instance, by diluting the hydrochloric acid in water, such as distilled or deionized water. In some embodiments, the method includes making the compound represented by formula (III) in a crystalline state.

In some embodiments, the method includes dissolving the compound represented by formula (I) in ethanol. In some embodiments, the method includes mixing the hydrochloric acid with ethanol. In some embodiments, the method includes mixing the hydrochloric acid with ethyl acetate. In some embodiments, the method includes adding the compound represented by formula (I) to the hydrochloric acid over a period of from about 20 to about 30 minutes to form a mixture. In some embodiments, the method includes maintaining the temperature of the mixture at from about 15° C. to about 25° C. during the adding. In some embodiments, the method includes reducing the temperature of the mixture to about 5° C. following the adding. In some embodiments, the method includes stirring the mixture for from about 50 minutes to about 70 minutes at from about 0° C. to about 5° C. following the reducing.

In some embodiments, the method includes mixing the compound represented by formula (I) and the hydrochloric acid in equimolar amounts.

In another aspect, the invention encompasses a compound produced by any of the above-described methods.

In an additional aspect, the invention provides a method of treating preterm labor in a subject by administering to the subject a therapeutically effective amount of the compound or pharmaceutical composition of any of the above-described aspects of the invention.

In an additional aspect, the invention provides a method of preventing preterm labor in a subject by administering to the subject a therapeutically effective amount of the compound or pharmaceutical composition of any of the above-described aspects of the invention.

In another aspect, the invention provides a method of preventing labor prior to cesarean delivery in a subject by administering to the subject a therapeutically effective amount of the compound or pharmaceutical composition of any of the above-described aspects of the invention.

In another aspect, the invention provides a method of treating or preventing dysmenorrhea in a subject by administering to the subject a therapeutically effective amount of the compound or pharmaceutical composition of any of the above-described aspects of the invention.

In another aspect, the invention provides a method of treating or preventing endometriosis in a subject by administering to the subject a therapeutically effective amount of the compound or pharmaceutical composition of any of the above-described aspects of the invention.

In some embodiments, the subject is characterized by a gestational age of from about 24 to about 34 weeks. In some embodiments, the subject exhibits a reduction in the amplitude of uterine contractions following the administering, such as a reduction of by from about 40% to about 50% (e.g., about 40%, 41%, 42%, 43%, 44%, 45%, 46%, 47%, 48%, 49%, or 50%) relative to a measurement of the amplitude of uterine contractions in the subject recorded prior to the administering. In some embodiments, the compound exhibits a half life of from about 1 to about 4 hours in the subject (e.g., about 1 hour, 1.1 hours, 1.2 hours, 1.3 hours, 1.4 hours, 1.5 hours, 1.6 hours, 1.7 hours, 1.8 hours, 1.9 hours, 2.0 hours, 2.1 hours, 2.2 hours, 2.3 hours, 2.4 hours, 2.5 hours, 2.6 hours, 2.7 hours, 2.8 hours, 2.9 hours, 3.0 hours, 3.1 hours, 3.2 hours, 3.3 hours, 3.4 hours, 3.5 hours, 3.6 hours, 3.7 hours, 3.8 hours, 3.9 hours, or 4.0 hours). In some embodiments, the compound reaches a maximum plasma concentration in the subject within from about 0.25 to about 2 hours of the administering (e.g., about 0.25 hours, 0.3 hours, 0.4 hours, 0.5 hours, 0.6 hours, 0.7 hours, 0.8 hours, 0.9 hours, 1.0 hours, 1.1 hours, 1.2 hours, 1.3 hours, 1.4 hours, 1.5 hours, 1.6 hours, 1.7 hours, 1.8 hours, 1.9 hours, or 2.0 hours). In some embodiments, the subject is a mammal, such as a human.

In some embodiments, the method includes orally administering the compound or pharmaceutical composition to the subject. In some embodiments, the method includes intravenously administering the compound or pharmaceutical composition to the subject.

In some embodiments, the compound is administered to the subject in combination with an additional therapeutic agent. In some embodiments, the compound is administered to the subject in combination with an additional tocolytic agent.

In some embodiments, the compound is administered to the subject in combination with an oxytocin receptor antagonist. In some embodiments, the method includes orally administering the oxytocin receptor antagonist to the subject. In some embodiments, the method includes intravenously administering the oxytocin receptor antagonist to the subject. The compound may be administered to the subject at the same time as the oxytocin receptor antagonist is administered. In some embodiments, the compound is administered to the subject before administration of the oxytocin receptor antagonist to the subject. In some embodiments, the compound is administered to the subject after administration of the oxytocin receptor antagonist to the subject. In some embodiments, the compound is admixed with the oxytocin receptor antagonist, and these agents are administered to the subject concurrently. In some embodiments, the oxytocin receptor antagonist is atosiban, retosiban, barusiban, epelsiban, or nolasiban, or a variant, formulation, crystalline form, or derivative thereof.

In some embodiments, the oxytocin receptor antagonist is atosiban, or a variant of atosiban, such as a variant described in U.S. Pat. No. 4,504,469 or 4,402,942, the disclosures of each of which are incorporated herein by reference.

In some embodiments, the oxytocin receptor antagonist is retosiban, or a variant of retosiban, such as a variant described in U.S. Pat. Nos. 7,514,437; 8,367,673; 8,541,579; 8,071,594; 8,357,685; 8,937,179; or US 2016/0074413, the disclosures of each of which are incorporated herein by reference.

In some embodiments, the oxytocin receptor antagonist is barusiban, or a variant of barusiban, such as a variant described in U.S. Pat. Nos. 6,143,722; 7,091,314; 7,816,489; or US 2016/0175283, the disclosures of each of which are incorporated herein by reference.

In some embodiments, the oxytocin receptor antagonist is epelsiban, or a variant of epelsiban, such as a variant described in U.S. Pat. Nos. 7,514,437; 8,367,673; 8,541,579; 7,550,462; 7,919,492; 8,202,864; 8,742,099; 9,408,851; 8,716,286; or 8,815,856, the disclosures of each of which are incorporated herein by reference.

In some embodiments, the oxytocin receptor antagonist is nolasiban, or a variant, formulation, or crystalline form of nolasiban, such as a variant, formulation, or crystalline form described in U.S. Pat. No. 7,115,754 or US Patent Application Publication No. 2015/0073032; 2015/0164859; or 2016/0002160, the disclosures of each of which are incorporated herein by reference.

In some embodiments, the compound is administered to the subject in combination with a betamimetic, such as terbutaline, ritodrine, hexoprenaline, albuterol, fenoterol, nylidrin, or orciprenaline. In some embodiments, the method includes orally administering the betamimetic to the subject. In some embodiments, the method includes intravenously administering the betamimetic to the subject. The compound may be administered to the subject at the same time as the betamimetic is administered. In some embodiments, the compound is administered to the subject before administration of the betamimetic to the subject. In some embodiments, the compound is administered to the subject after administration of the betamimetic to the subject. In some embodiments, the compound is admixed with the betamimetic, and these agents are administered to the subject concurrently.

In some embodiments, the compound is administered to the subject in combination with a calcium channel inhibitor, such as a dihydropyridine. In some embodiments, the calcium channel inhibitor is nifedipine. In some embodiments, the calcium channel inhibitor is nicardipine. In some embodiments, the method includes orally administering the calcium channel inhibitor to the subject. In some embodiments, the method includes intravenously administering the calcium channel inhibitor to the subject. The compound may be administered to the subject at the same time as the calcium channel inhibitor is administered. In some embodiments, the compound is administered to the subject before administration of the calcium channel inhibitor to the subject. In some embodiments, the compound is administered to the subject after administration of the calcium channel inhibitor to the subject. In some embodiments, the compound is admixed with the calcium channel inhibitor, and these agents are administered to the subject concurrently.

In some embodiments, the compound is administered to the subject in combination with a magnesium salt, such as magnesium sulfate. In some embodiments, the method includes intravenously administering the magnesium salt to the subject. In some embodiments, the method includes intramuscularly administering the magnesium salt to the subject. In some embodiments, the method includes orally administering the magnesium salt to the subject. The compound may be administered to the subject at the same time as the magnesium salt is administered. In some embodiments, the compound is administered to the subject before administration of the magnesium salt to the subject. In some embodiments, the compound is administered to the subject after administration of the magnesium salt to the subject. In some embodiments, the compound is admixed with the magnesium salt, and these agents are administered to the subject concurrently.

In some embodiments, the compound is administered to the subject in combination with a nitric oxide donor, such as nitroglycerin. In some embodiments, the method includes orally administering the nitric oxide donor to the subject. In some embodiments, the method includes intravenously administering the nitric oxide donor to the subject. The compound may be administered to the subject at the same time as the nitric oxide donor is administered. In some embodiments, the compound is administered to the subject before administration of the nitric oxide donor to the subject. In some embodiments, the compound is administered to the subject after administration of the nitric oxide donor to the subject. In some embodiments, the compound is admixed with the nitric oxide donor, and these agents are administered to the subject concurrently.

In some embodiments, the compound is administered to the subject in combination with progesterone or a variant or derivative thereof, such as 17-α-hydroxyprogesterone caproate. In some embodiments, the method includes orally administering the progesterone or a variant or derivative thereof, such as 17-α-hydroxyprogesterone caproate, to the subject. In some embodiments, the method includes intravaginally administering the progesterone or a variant or derivative thereof, such as 17-α-hydroxyprogesterone caproate, to the subject. The compound may be administered to the subject at the same time as the progesterone or a variant or derivative thereof, such as 17-α-hydroxyprogesterone caproate, is administered. In some embodiments, the compound is administered to the subject before administration of the progesterone or a variant or derivative thereof, such as 17-α-hydroxyprogesterone caproate, to the subject. In some embodiments, the compound is administered to the subject after administration of the progesterone or a variant or derivative thereof, such as 17-α-hydroxyprogesterone caproate, to the subject. In some embodiments, the compound is admixed with the progesterone or a variant or derivative thereof, such as 17-α-hydroxyprogesterone caproate (e.g., in an oral formulation, among others), and these agents are administered to the subject concurrently.

In some embodiments, the compound is administered to the subject in combination with a corticosteroid. In some embodiments, the corticosteroid is betamethasone. In some embodiments, the corticosteroid is dexamethasone. In some embodiments, the method includes orally administering the corticosteroid to the subject. In some embodiments, the method includes intramuscularly administering the corticosteroid to the subject. The compound may be administered to the subject at the same time as the corticosteroid is administered. In some embodiments, the compound is administered to the subject before administration of the corticosteroid to the subject. In some embodiments, the compound is administered to the subject after administration of the corticosteroid to the subject. In some embodiments, the compound is admixed with the corticosteroid (e.g., in an oral formulation, among others), and these agents are administered to the subject concurrently.

In some embodiments, the invention provides a kit containing the compound or pharmaceutical composition of any of the above-described aspects of the invention, as well as a package insert. In some embodiments, the package insert instructs a user of the kit to administer the compound or pharmaceutical composition to a subject presenting with preterm labor or at risk of undergoing preterm labor, such as a subject presenting with one or more symptoms of preterm labor described herein. In some embodiments, the subject is characterized by a gestational age of from about 24 to about 34 weeks. In some embodiments, the package insert instructs a user of the kit to mix the compound or pharmaceutical composition with an aqueous solution. In some embodiments, the package insert instructs a user of the kit to orally administer the compound to the subject. In some embodiments, the package insert instructs a user of the kit to intravenously administer the compound to the subject.

In an additional aspect, the invention provides a pharmaceutical composition containing a compound represented by formula (II),

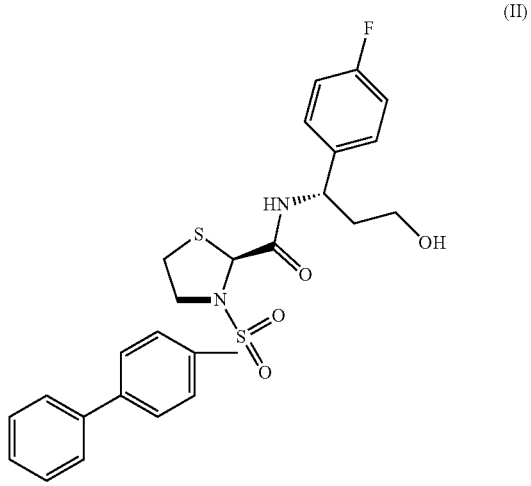

(II)

3-([1,1'-biphenyl]-4-ylsulfonyl)-N-[1-(4-fluorophenyl)-3-hydroxypropyl]-1,3-thiazolidine-2-carboxamide. In some embodiments, the pharmaceutical composition contains the compound represented by formula (II) and an additional therapeutic agent. In some embodiments, the pharmaceutical composition contains the compound represented by formula (II) and an additional tocolytic agent. The pharmaceutical composition may optionally contain one or more excipients. In some embodiments, the compound represented by formula (II) has a purity of at least 90%, 91%, 92%, 93%, 94%, 95%, 96%, 97%, 98%, 99%, or 99.9%, e.g., as ascertained by high pressure liquid chromatography (HPLC) or NMR spectroscopy. In some embodiments, the compound and/or pharmaceutical composition is formulated for oral administration to a subject. In some embodiments, the compound and/or pharmaceutical composition is a tablet, capsule, gel cap, powder, liquid solution, or liquid suspension. In some embodiments, the compound and/or pharmaceutical composition is formulated for intravenous administration to a subject.

In some embodiments, the pharmaceutical composition contains two or more therapeutic agents, such as the compound represented by formula (II) and an additional therapeutic agent. For instance, the pharmaceutical composition may contain two or more therapeutic agents admixed with one another for co-administration to a patient, such as for the treatment or prevention of preterm labor. The pharmaceutical composition may be administered to a subject to delay the onset of labor in the subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). In some embodiments, the subject is undergoing preterm labor. In some embodiments, the pharmaceutical composition is administered to the subject (e.g., a human subject) prior to the initiation of preterm labor. The pharmaceutical composition can be administered to a subject (e.g., a human subject) to prevent labor prior to cesarean delivery. The pharmaceutical composition can be administered to a subject (e.g., a human subject) for the treatment or prevention of dysmenorrhea. The pharmaceutical composition can be administered to a subject, such as a pregnant female human subject, in order to alleviate one or more symptoms associated with labor, such as vaginal bleeding and rupture of uterine membranes.

In some embodiments, the additional therapeutic agent is an additional tocolytic agent.

In some embodiments, the additional tocolytic agent is an oxytocin receptor antagonist, such as atosiban, retosiban, barusiban, epelsiban, and nolasiban, or one or more variants, formulations, crystalline forms, or derivatives thereof.

In some embodiments, the pharmaceutical composition comprises a compound represented by formula (II) and atosiban. In some embodiments, the pharmaceutical composition comprises a compound represented by formula (II) and a variant of atosiban, such as a variant described in U.S. Pat. No. 4,504,469 or 4,402,942, the disclosures of each of which are incorporated herein by reference.

In some embodiments, the pharmaceutical composition comprises a compound represented by formula (II) and retosiban. In some embodiments, the pharmaceutical composition comprises a compound represented by formula (II) and a variant of retosiban, such as a variant described in U.S. Pat. Nos. 7,514,437; 8,367,673; 8,541,579; 8,071,594; 8,357,685; 8,937,179; or US 2016/0074413, the disclosures of each of which are incorporated herein by reference.

In some embodiments, the pharmaceutical composition comprises a compound represented by formula (II) and barusiban. In some embodiments, the pharmaceutical composition comprises a compound represented by formula (II) and a variant of barusiban, such as a variant described in U.S. Pat. Nos. 6,143,722; 7,091,314; 7,816,489; or US 2016/0175283, the disclosures of each of which are incorporated herein by reference.

In some embodiments, the pharmaceutical composition comprises a compound represented by formula (II) and epelsiban. In some embodiments, the pharmaceutical composition comprises a compound represented by formula (II) and a variant of epelsiban, such as a variant described in U.S. Pat. Nos. 7,514,437; 8,367,673; 8,541,579; 7,550,462; 7,919,492; 8,202,864; 8,742,099; 9,408,851; 8,716,286; or 8,815,856, the disclosures of each of which are incorporated herein by reference.

In some embodiments, the pharmaceutical composition comprises a compound represented by formula (II) and nolasiban. In some embodiments, the pharmaceutical composition comprises a compound represented by formula (II) and a variant, formulation, or crystalline form of nolasiban, such as a variant, formulation, or crystalline form described in U.S. Pat. No. 7,115,754 or US Patent Application Publication No. 2015/0073032; 2015/0164859; or 2016/0002160, the disclosures of each of which are incorporated herein by reference.

In some embodiments, the additional tocolytic agent is a betamimetic, such as terbutaline, ritodrine, hexoprenaline, albuterol, fenoterol, nylidrin, or orciprenaline.

In some embodiments, the additional tocolytic agent is a calcium channel inhibitor, such as a dihydropyridine. In some embodiments, the calcium channel inhibitor is nifedipine. In some embodiments, the calcium channel inhibitor is nicardipine.

In some embodiments, the additional tocolytic agent is a magnesium salt, such as magnesium sulfate.

In some embodiments, the additional tocolytic agent is a nitric oxide donor, such as nitroglycerine.

In some embodiments, the additional tocolytic agent is an oxytocin receptor antagonist, such as atosiban, retosiban, barusiban, epelsiban, nolasiban, or a variant, formulation, crystalline form, or derivative thereof, for instance, as described herein.

In some embodiments, the compound represented by formula (II) is formulated for oral administration, and the additional tocolytic agent is formulated for oral administration. In some embodiments, the compound represented by formula (II) is formulated for intravenous administration, and the additional tocolytic agent is formulated for intravenous administration. In some embodiments, the compound represented by formula (II) is formulated for oral administration, and the additional tocolytic agent is formulated for intravenous administration. In some embodiments, the compound represented by formula (II) is formulated for intravenous administration, and the additional tocolytic agent is formulated for oral administration. In some embodiments, the compound represented by formula (II) is formulated for oral administration, and the additional tocolytic agent is formulated for intramuscular administration. In some embodiments, the compound represented by formula (II) is formulated for intravenous administration, and the additional tocolytic agent is formulated for intramuscular administration.

In some embodiments, the additional therapeutic agent is progesterone or a variant or derivative thereof, such as 17-α-hydroxyprogesterone caproate.

In some embodiments, the pharmaceutical composition comprises a compound represented by formula (II) and progesterone or 17-α-hydroxyprogesterone caproate. In some embodiments, the compound represented by formula (II) is formulated for oral administration and the progesterone or 17-α-hydroxyprogesterone caproate is formulated for intravaginal administration. In some embodiments, the compound represented by formula (II) is formulated for intravenous administration and the progesterone or 17-α-hydroxyprogesterone caproate is formulated for intravaginal administration. In some embodiments, both the compound represented by formula (II) and the progesterone or 17-α-hydroxyprogesterone caproate are formulated for oral administration. In some embodiments, the compound represented by formula (II) is formulated for intravenous administration and the progesterone or 17-α-hydroxyprogesterone caproate is formulated for oral administration.

In some embodiments, the additional therapeutic agent is a corticosteroid. In some embodiments, the corticosteroid is betamethasone. In some embodiments, the corticosteroid is dexamethasone. In some embodiments, the corticosteroid is hydrocortisone. In some embodiments, the compound represented by formula (II) is formulated for oral administration and the corticosteroid (e.g., betamethasone, dexamethasone, or hydrocortisone) is formulated for intramuscular administration. In some embodiments, the compound represented by formula (II) is formulated for intravenous administration and the corticosteroid (e.g., betamethasone, dexamethasone, or hydrocortisone) is formulated for intramuscular administration. In some embodiments, the compound represented by formula (II) is formulated for oral administration and the corticosteroid (e.g., betamethasone, dexamethasone, or hydrocortisone) is formulated for oral administration. In some embodiments, the compound represented by formula (II) is formulated for intravenous administration and the corticosteroid (e.g., betamethasone, dexamethasone, or hydrocortisone) is formulated for oral administration.

In an additional aspect, the invention provides a method of treating preterm labor in a subject by providing (e.g., administering) to the subject a therapeutically effective amount of a compound represented by formula (II),

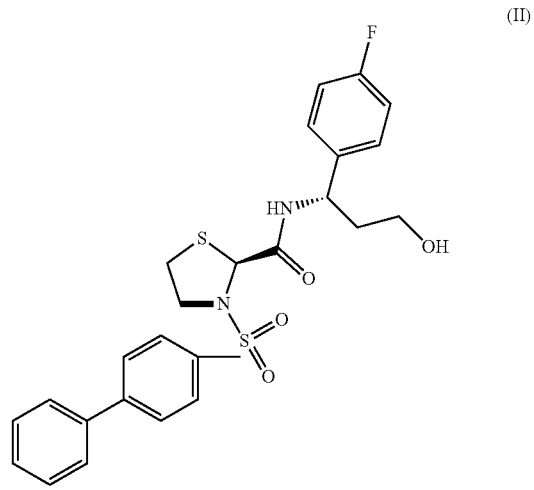

3-([1,1'-biphenyl]-4-ylsulfonyl)-N-[1-(4-fluorophenyl)-3-hydroxypropyl]-1,3-thiazolidine-2-carboxamide, or a pharmaceutical composition containing the compound represented by formula (II) according to any of the above-described aspects of the invention.

In an additional aspect, the invention provides a method of preventing preterm labor in a subject by providing (e.g., administering) to the subject a therapeutically effective amount of the compound represented by formula (II) or a pharmaceutical composition containing the compound represented by formula (II) according to any of the above-described aspects of the invention.

In another aspect, the invention provides a method of preventing labor prior to cesarean delivery in a subject by providing (e.g., administering) to the subject a therapeutically effective amount of the compound represented by formula (II) or a pharmaceutical composition containing the compound represented by formula (II) according to any of the above-described aspects of the invention.

In another aspect, the invention provides a method of treating or preventing dysmenorrhea in a subject by providing (e.g., administering) to the subject a therapeutically effective amount of the compound represented by formula (II) or a pharmaceutical composition containing the compound represented by formula (II) according to any of the above-described aspects of the invention.

In another aspect, the invention provides a method of treating or preventing endometriosis in a subject by providing (e.g., administering) to the subject a therapeutically effective amount of the compound represented by formula (II) or a pharmaceutical composition containing the compound represented by formula (II) according to any of the above-described aspects of the invention.

In some embodiments, the compound represented by formula (II) is provided to the subject in combination with an additional therapeutic agent. In some embodiments, the compound is provided to the subject in combination with an additional tocolytic agent. In some embodiments, the compound is provided to the subject by administering the compound to the subject. In some embodiments, the compound is provided to the subject by administering to the subject a prodrug that is metabolized in vivo so as to produce the compound represented by formula (II).

In some embodiments, the compound represented by formula (II) is provided to the subject in combination with an oxytocin receptor antagonist. In some embodiments, the method includes orally administering the oxytocin receptor antagonist to the subject. In some embodiments, the method includes intravenously administering the oxytocin receptor antagonist to the subject. The compound represented by formula (II) may be provided to the subject at the same time as the oxytocin receptor antagonist is administered. In some embodiments, the compound represented by formula (II) is provided to the subject before administration of the oxytocin receptor antagonist to the subject. In some embodiments, the compound represented by formula (II) is provided to the subject after administration of the oxytocin receptor antagonist to the subject. In some embodiments, the compound represented by formula (II) or a prodrug thereof is admixed with the oxytocin receptor antagonist, and these agents are administered to the subject concurrently. In some embodiments, the oxytocin receptor antagonist is atosiban, retosiban, barusiban, epelsiban, or nolasiban, or a variant, formulation, crystalline form, or derivative thereof.

In some embodiments, the oxytocin receptor antagonist is atosiban, or a variant of atosiban, such as a variant described in U.S. Pat. No. 4,504,469 or 4,402,942, the disclosures of each of which are incorporated herein by reference.

In some embodiments, the oxytocin receptor antagonist is retosiban, or a variant of retosiban, such as a variant described in U.S. Pat. Nos. 7,514,437; 8,367,673; 8,541,579; 8,071,594; 8,357,685; 8,937,179; or US 2016/0074413, the disclosures of each of which are incorporated herein by reference.

In some embodiments, the oxytocin receptor antagonist is barusiban, or a variant of barusiban, such as a variant described in U.S. Pat. Nos. 6,143,722; 7,091,314; 7,816,489; or US 2016/0175283, the disclosures of each of which are incorporated herein by reference.

In some embodiments, the oxytocin receptor antagonist is epelsiban, or a variant of epelsiban, such as a variant described in U.S. Pat. Nos. 7,514,437; 8,367,673; 8,541,579; 7,550,462; 7,919,492; 8,202,864; 8,742,099; 9,408,851; 8,716,286; or 8,815,856, the disclosures of each of which are incorporated herein by reference.

In some embodiments, the oxytocin receptor antagonist is nolasiban, or a variant, formulation, or crystalline form of nolasiban, such as a variant, formulation, or crystalline form described in U.S. Pat. No. 7,115,754 or US Patent Application Publication No. 2015/0073032; 2015/0164859; or 2016/0002160, the disclosures of each of which are incorporated herein by reference.

In some embodiments, the compound represented by formula (II) is provided to the subject in combination with a betamimetic, such as terbutaline, ritodrine, hexoprenaline, albuterol, fenoterol, nylidrin, or orciprenaline. In some embodiments, the method includes orally administering the betamimetic to the subject. In some embodiments, the method includes intravenously administering the betamimetic to the subject. The compound represented by formula (II) may be provided to the subject at the same time as the betamimetic is administered. In some embodiments, the compound represented by formula (II) is provided to the subject before administration of the betamimetic to the subject. In some embodiments, the compound represented by formula (II) is provided to the subject after administration of the betamimetic to the subject. In some embodiments, the compound represented by formula (II) or a prodrug thereof is admixed with the betamimetic, and these agents are administered to the subject concurrently.

In some embodiments, the compound represented by formula (II) is provided to the subject in combination with a calcium channel inhibitor, such as a dihydropyridine. In some embodiments, the calcium channel inhibitor is nifedipine. In some embodiments, the calcium channel inhibitor is nicardipine. In some embodiments, the method includes orally administering the calcium channel inhibitor to the subject. In some embodiments, the method includes intravenously administering the calcium channel inhibitor to the subject. The compound represented by formula (II) may be provided to the subject at the same time as the calcium channel inhibitor is administered. In some embodiments, the compound represented by formula (II) is provided to the subject before administration of the calcium channel inhibitor to the subject. In some embodiments, the compound represented by formula (II) is provided to the subject after administration of the calcium channel inhibitor to the subject. In some embodiments, the compound represented by formula (II) or a prodrug thereof is admixed with the calcium channel inhibitor, and these agents are administered to the subject concurrently.

In some embodiments, the compound represented by formula (II) is provided to the subject in combination with a magnesium salt, such as magnesium sulfate. In some embodiments, the method includes intravenously administering the magnesium salt to the subject. In some embodiments, the method includes intramuscularly administering the magnesium salt to the subject. In some embodiments, the method includes orally administering the magnesium salt to the subject. The compound represented by formula (II) may be provided to the subject at the same time as the magnesium salt is administered. In some embodiments, the compound represented by formula (II) is provided to the subject before administration of the magnesium salt to the subject. In some embodiments, the compound represented by formula (II) is provided to the subject after administration of the magnesium salt to the subject. In some embodiments, the compound represented by formula (II) or a prodrug thereof is admixed with the magnesium salt, and these agents are administered to the subject concurrently.

In some embodiments, the compound represented by formula (II) is provided to the subject in combination with a nitric oxide donor, such as nitroglycerin. In some embodiments, the method includes orally administering the nitric oxide donor to the subject. In some embodiments, the method includes intravenously administering the nitric oxide donor to the subject. The compound represented by formula (II) may be provided to the subject at the same time as the nitric oxide donor is administered. In some embodiments, the compound represented by formula (II) is provided to the subject before administration of the nitric oxide donor to the subject. In some embodiments, the compound represented by formula (II) is provided to the subject after administration of the nitric oxide donor to the subject. In some embodiments, the compound represented by formula (II) or a prodrug thereof is admixed with the nitric oxide donor, and these agents are administered to the subject concurrently.

In some embodiments, the compound represented by formula (II) is provided to the subject in combination with progesterone or a variant or derivative thereof, such as 17-α-hydroxyprogesterone caproate. In some embodiments, the method includes orally administering the progesterone or a variant or derivative thereof, such as 17-α-hydroxyprogesterone caproate, to the subject. In some embodiments, the method includes intravaginally administering the progesterone or a variant or derivative thereof, such as 17-α-hydroxyprogesterone caproate, to the subject. The compound represented by formula (II) may be provided to the subject at the same time as the progesterone or a variant or derivative thereof, such as 17-α-hydroxyprogesterone caproate, is administered. In some embodiments, the compound represented by formula (II) is provided to the subject before administration of the progesterone or a variant or derivative thereof, such as 17-α-hydroxyprogesterone caproate, to the subject. In some embodiments, the compound represented by formula (II) is provided to the subject after administration of the progesterone or a variant or derivative thereof, such as 17-α-hydroxyprogesterone caproate, to the subject. In some embodiments, the compound represented by formula (II) or a prodrug thereof is admixed with the progesterone or a variant or derivative thereof, such as 17-α-hydroxyprogesterone caproate (e.g., in an oral formulation, among others), and these agents are administered to the subject concurrently.

In some embodiments, the compound represented by formula (II) is provided to the subject in combination with a corticosteroid. In some embodiments, the corticosteroid is betamethasone. In some embodiments, the corticosteroid is dexamethasone. In some embodiments, the method includes orally administering the corticosteroid to the subject. In some embodiments, the method includes intramuscularly administering the corticosteroid to the subject. The compound represented by formula (II) may be provided to the subject at the same time as the corticosteroid is administered. In some embodiments, the compound represented by formula (II) is provided to the subject before administration of the corticosteroid to the subject. In some embodiments, the compound represented by formula (II) is provided to the subject after administration of the corticosteroid to the subject. In some embodiments, the compound represented by formula (II) or a prodrug thereof is admixed with the corticosteroid (e.g., in an oral formulation, among others), and these agents are administered to the subject concurrently.

In some embodiments, the subject is characterized by a gestational age of from about 24 to about 34 weeks. In some embodiments, the subject exhibits a reduction in the amplitude of uterine contractions following the administering, such as a reduction of by from about 40% to about 50% (e.g., about 40%, 41%, 42%, 43%, 44%, 45%, 46%, 47%, 48%, 49%, or 50%) relative to a measurement of the amplitude of uterine contractions in the subject recorded prior to the administering. In some embodiments, the subject is a mammal, such as a human.

In some embodiments, the method includes orally administering the compound or pharmaceutical composition to the subject. In some embodiments, the method includes intravenously administering the compound or pharmaceutical composition to the subject.

In some embodiments, the invention provides a kit containing the compound or pharmaceutical composition of any of the above-described aspects of the invention, as well as a package insert. In some embodiments, the package insert instructs a user of the kit to administer the compound or pharmaceutical composition to a subject presenting with preterm labor or at risk of undergoing preterm labor, such as a subject presenting with one or more symptoms of preterm labor described herein. In some embodiments, the subject is characterized by a gestational age of from about 24 to about 34 weeks. In some embodiments, the package insert instructs a user of the kit to mix the compound or pharmaceutical composition with an aqueous solution. In some embodiments, the package insert instructs a user of the kit to orally administer the compound to the subject. In some embodiments, the package insert instructs a user of the kit to intravenously administer the compound to the subject.

Definitions

As used herein, the term "about" refers to a value that is within 10% above or below the value being described.

As used herein, the term "affinity" refers to the strength of a binding interaction between two molecules, such as a ligand and a receptor. The term "$K_i$", as used herein, is intended to refer to the inhibition constant of an antagonist for a particular molecule of interest, and is expressed as a molar concentration (M). $K_i$ values for antagonist-target interactions can be determined, e.g., using methods established in the art. Methods that can be used to determine the $K_i$ of an antagonist for a molecular target include competitive binding experiments, such as competitive radioligand binding assays, e.g., as described in U.S. Pat. No. 8,415,480. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the term "corticosteroid" refers to any of the steroid hormones produced by the adrenal cortex or their synthetic equivalents. Exemplary corticosteroids include betamethasone, dexamethasone, and hydrocortisone, among others, as well as variants thereof. Corticosteroids for use in conjunction with the compositions and methods described herein include those capable of inducing fetal lung maturation, for instance, so as to prevent the development of respiratory distress syndrome in preterm infants. Exemplary corticosteroids for use in conjunction with the compositions and methods described herein include those described in Jobe et al. Am. J. Obstet. Gynecol. 190:878-881 (2004) and Miracle et al. J. Perinat. Med. 36:191-196 (2008), the disclosures of each of which are incorporated herein by reference.

As used herein, the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted therefrom.

As used herein, the term "gestational age" describes how far along a particular pregnancy is, and is measured from the first day of a pregnant female subject's last menstrual cycle to the current date. As used herein, the term "labor" (which may also be termed birth) relates to the expulsion of the fetus and placenta from the uterus of a pregnant female subject. For a normal pregnancy, labor may occur at a gestational age of about 40 weeks. "Preterm labor" as used herein refers to a condition in which labor commences more than three weeks before the full gestation period, which is typically about 40 weeks. That is, preterm labor occurs at any stage prior to, e.g., 38 weeks of gestation. Preterm labor typically leads to the occurrence of labor, or physiological changes associated with labor in a pregnant female subject, if not treated. Preterm labor may or may not be associated with vaginal bleeding or rupture of uterine membranes. Preterm labor may also be referred to as premature labor. The avoidance of preterm labor in a subject will prolong the term of pregnancy and may therefore avoid preterm delivery, thus reducing the risk of neonatal mortality and morbidity.

As used herein, the term "$IC_{50}$" refers to the concentration of a substance (antagonist) that reduces the efficacy of a reference agonist or the constitutive activity of a biological target by 50%, e.g., as measured in a competitive ligand binding assay. Exemplary competitive ligand binding assays include competitive radioligand binding assays, competitive enzyme-linked immunosorbent assays (ELISA), and fluorescence anisotropy-based assays, among others known in the art.

As used herein in the context of providing or administering two or more therapeutic agents to a subject, the phrase "in combination with" refers to the delivery of two or more therapeutic agents to a subject (e.g., a mammalian subject, such as a human subject), for instance, either concurrently or at different times. For example, one therapeutic agent may be administered to a subject in combination with another by administering both agents to the subject concurrently, such as in a single pharmaceutical composition or in separate compositions that are administered to the subject simultaneously (e.g., by different routes of administration). In another example, one therapeutic agent may be administered to a subject in combination with another by first administering to the subject one therapeutic agent and subsequently administering the other therapeutic agent, either by the same or different route of administration.

As used herein, the term "nolasiban" refers to (3Z,5S)-5-(hydroxymethyl)-1-[(2'-methyl-1,1'-biphenyl-4-yl)carbonyl]pyrrolidin-3-one O-methyloxime, represented by the following structural formula:

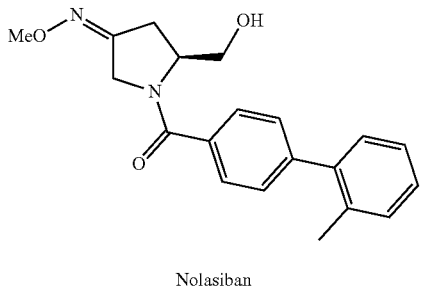 [SMILES: CO/N=C1/C[C@@H](CO)N(C(=O)c2ccc(-c3ccccc3C)cc2)C1]

Nolasiban

Variants, formulations, and crystalline form of nolasiban are described, e.g., in U.S. Pat. No. 7,115,754 and US Patent Application Publication No. 2015/0073032; 2015/0164859; and 2016/0002160, the disclosures of each of which are incorporated herein by reference.

As used herein, the term "oral bioavailability" refers to the fraction of a compound administered to a subject, such as a mammal (e.g., a human) that reaches systemic circulation in the subject, and that is not sequestered in a non-target organ or excreted without absorption via the gastrointestinal tract. The term refers to a blood plasma concentration that is integrated over time and is typically expressed as a percentage of the orally administered dose.

As used herein, the term "oxytocin receptor antagonist" or "oxytocin antagonist" refers to a compound capable of inhibiting the interaction between oxytocin and the oxytocin receptor, for example, such that activity of one or more downstream signaling molecules in the oxytocin signal transduction cascade is inhibited. Oxytocin antagonists for use with the compositions and methods described herein include compounds that bind and inhibit the oxytocin receptor, such as atosiban, retosiban, barusiban, epelsiban, and nolasiban, as well as variants, formulations, crystalline forms, and derivatives thereof, including those described herein, among others.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "pharmaceutical composition" means a mixture containing a therapeutic compound to be administered to a subject, such as a mammal, e.g., a human, in order to prevent, treat or control a particular disease or condition affecting the mammal, such as preterm labor or dysmenorrhea, among others, e.g., as described herein.

As used herein, the term "protecting group" refers to a chemical moiety which, when bound to a functional group, renders the functional group inert to one or more chemical reactions. Such reactions may modify one or more substituents of the compound and, in the absence of a protecting group, might result in undesired chemical modification (e.g., electrophilic addition, solvolysis, oxidation, reduction, or functional group interconversion) of a moiety of interest (e.g., an amino, hydroxyl, carboxyl, or carboxamide moiety). Protecting groups may, at the appropriate time, be chemically reacted so as to regenerate the original functionality. The identity of the protecting group can be selected so as to be compatible with the remainder of the molecule, e.g., such that the protecting group is not removed during other steps of the synthesis or modification of the molecule, and optionally, such that the reaction conditions used to effect the removal of the protecting group do not result in the removal of different protecting groups located at other substituents on the molecule. Exemplary protecting groups include those that can be covalently bound to, e.g., an amino substituent, such as the amino group of an α-amino ester. The subsequent removal of a protecting group, referred to herein as the "deprotection" of a chemical moiety, can be achieved using reagents and conditions known in the art. Examples of protecting groups include, without limitation, benzyl, acetyl, oxyacetyl, carboxybenzyl, 9-fluorenyloxycarbonyl, 2-chloro-1-indanylmethoxy-carbonyl, benz [f] indene-3-methoxycarbonyl, 2-(tert-butylsulfonyl)-2-propenyloxycarbonyl, benzothiophene sulfone-2-methylcarbonyl, tort-butoxycarbonyl, tert-amyloxycarbonyl, ß-trimethylsilylethyloxycarbonyl, adamantyloxycarbonyl, 1-methylcyclobutyloxycarbonyl, 2-(p-biphenylyl)propyl-2-oxycarbonyl, 2-(p-phenylazophenyl)propyl-2-oxycarbonyl, 2-2-dimethyl-3,5-dimethyloxybenzyloxycarbonyl, 2-phenylpropyl-2-oxycarbonyl, benzyloxycarbonyl, p-toluenesulfonylaminocarbonyl, o-nitrophenylsulfenyl, dithiasuccinoyl, phthaloyl, piperidinooxycarbonyl, formyl, trifluoroacetyl, 2,4,6-trimethoxybenzyl, 2,3,6-trimethyl-4 methoxybenzenesulfonyl, tert-butoxymethyl, pentamethylchromanesulfonyl, adamantly, ß-trimethylsilylethyl, ß-trimethylilylethyloxycarbonyl, tert-butyl, tert-butylbenzyl, cyclopentyl, triphenylmethyl, benzyloxycarbonyl, formyl, and trifluoroacetyl, among others. Protecting groups may be suitable for a particular chemical substituent. For instance, examples of hydroxyl protecting groups include, without limitation, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of protecting groups may be found, e.g., in Greene and Wuts, Protective Groups in Organic Synthesis, 2d Ed., 1991, John Wiley & Sons, as well as in McOmie, Protective Groups in Organic Chemistry, 1975, Plenum Press, the disclosures of each of which are incorporated herein by reference. Other examples of protecting groups are described, e.g., in U.S. Pat. Nos. 3,835,175; 4,508,657; 3,839,396; 4,581,167; 4,460,501; and 4,108,846, the disclosures of each of which are incorporated herein by reference.

As used herein in the context of therapeutic treatment, the terms "provide" and "providing" refer to the delivery of a therapeutic agent to a subject (e.g., a mammalian subject, such as a human) in need of treatment, such as a subject experiencing or at risk of undergoing preterm labor. A therapeutic agent may be provided to a subject in need thereof, for instance, by direct administration of the therapeutic agent to the subject, or by administration of a prodrug that is converted in vivo to the therapeutic agent upon administration of the prodrug to the subject. Exemplary prodrugs include, without limitation, esters, phosphates, and other chemical functionalities susceptible to hydrolysis upon administration to a subject. Prodrugs include those known in the art, such as those described, for instance, in Vig et al., Adv. Drug Deliv. Rev. 65:1370-1385 (2013), and Huttunen et al., Pharmacol. Rev. 63:750-771 (2011), the disclosures of each of which are incorporated herein by reference.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 ppm and 100 nM). A ligand that does not exhibit specific binding to a protein or a domain thereof will exhibit a $K_D$ of greater than 100 nM (e.g., greater than 200 nM, 300 nM, 400 nM, 500 nM, 600 nM, 700 nM, 800 nM, 900 nM, 1 μM, 100 μM, 500 μM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are interchangeable and refer to an organism that receives treatment for a particular disease or condition as described herein (such as preterm labor or dysmenorrhea) or that is diagnosed as having a disease or condition according to the methods described herein. Examples of subjects and patients include mammals, such as humans, receiving treatment for diseases or conditions, for example, preterm labor at an early gestational age (e.g., 24-34 weeks).

A compound, salt form, crystal polymorph, therapeutic agent, or other composition described herein may be referred to as being characterized by graphical data "substantially as depicted in" a figure. Such data may include, without limitation, powder X-ray diffractograms, NMR spectra, differential scanning calorimetry curves, and thermogravimetric analysis curves, among others. As is known in the art, such graphical data may provide additional technical information to further define the compound, salt form, crystal polymorph, therapeutic agent, or other composition. As is understood by one of skill in the art, such graphical representations of data may be subject to small variations, e.g., in peak relative intensities and peak positions due to factors such as variations in instrument response and variations in sample concentration and purity. Nonetheless, one of skill in the art will readily be capable of comparing the graphical data in the figures herein with graphical data generated for a compound, salt form, crystal polymorph, therapeutic agent, or other composition and confirm whether the two sets of graphical data are characterizing the same material or two different materials. For instance, a crystal form of (3S)-3-({[(2S)-3-(biphenyl-4-ylsulfonyl)-1,3-thiazolidin-2-yl]carbonyl}-amino)-3-(4-fluorophenyl)propyl L-valinate hydrochloride referred to herein as being characterized by graphical data "substantially as depicted in" a figure will thus be understood to include any crystal form of (3S)-3-({[(2S)-3-(biphenyl-4-ylsulfonyl)-1,3-thiazolidin-2-yl]carbonyl}-amino)-3-(4-fluorophenyl)propyl L-valinate hydrochloride characterized by the graphical data, optionally having one or more of small variations, e.g., one or more variations described above or known to one of skill in the art.

As used herein, the terms "treat" or "treatment" refer to therapeutic treatment, in which the object is to prevent or slow down (lessen) an undesired physiological change or disorder, such as the progression of preterm labor at an early gestational age (e.g., 24-34 weeks). Beneficial or desired clinical results include, but are not limited to, alleviation of symptoms, such as vaginal bleeding or membrane rupture, and the delay or slowing of labor. Those in need of treatment include, e.g., pregnant female subjects already experiencing preterm labor, as well as those prone to developing this condition.

As used herein, the term "tocolytic agent" refers to a substance capable of delaying the onset of labor in a subject (e.g., a mammalian subject, such as a human subject). Tocolytic agents may function to suppress uterine contractility, for instance, by increasing cytoplasmic cAMP levels and inhibiting the mobilization of intracellular $Ca^{2+}$. Exemplary tocolytic agents are described, for instance, in Haas et al. Int. J. Womens Health. 6:343-349 (2014), the disclosure of which is incorporated herein by reference. Tocolytic agents for use in conjunction with the compositions and methods described herein include, without limitation, the substances listed in Table 1, below.

TABLE 1

Exemplary tocolytic agents

| Pharmacological class | Exemplary tocolytic agents | Reference |
|---|---|---|
| Betamimetics | Terbutaline, ritodrine, hexoprenaline, albuterol, fenoterol, nylidrin, orciprenaline | Conde-Agudelo et al. Am. J. Obstet. Gynecol. 204:e1-e20 (2011); Creasy et al. Creast and Resnik's Maternal Fetal Medicine: Principles and Practice. Ed. 6. Philadelphia, PA (2009) |
| Calcium channel inhibitors | Dihydropyridines, such as nifedipine, nicardipine | Nassar et al. Am. J. Perinatol. 281:57-66 (2011) |
| Magnesium salts | Magnesium sulfate | Mercer et al. Obstet. Gynecol. 114:650-668 (2009) |
| Oxytocin receptor antagonists | atosiban, retosiban, barusiban, epelsiban, nolasiban | Papatsonis et al. Cochrane Database Syst. Rev. 3:CD004452 (2005) |
| Nitric oxide donors | Nitroglycerine | Duckitt et al. Cochrane Database Syst. Rev. 3:CD002860 (2002) |

BRIEF DESCRIPTION OF THE FIGURES

FIG. 4 is a table summarizing various methods used to generate the free base of compound I, as well as observations regarding the physical characteristics and NMR spectra of compound I as generated by each method.

FIG. 5 is a table summarizing various methods used to generate salts of compound I, as well as observations regarding the physical characteristics and NMR spectra of these salts as generated by each method.

FIG. 6 is a table summarizing physical characteristics as well as X-ray powder diffraction (XRPD) spectra of various salts of compound I.

FIG. 7 is a table summarizing methods used to generate crystal forms of various compound I salts, as well as observations regarding the physical properties and XRPD spectra of each crystal form.

FIG. 8 is a table summarizing the solubility of various compound I salts in aqueous solution.

FIG. 9 is a table summarizing the stability of crystal forms of various compound I salts at the indicated relative humidity (RH).

FIG. 10 is a table summarizing various characteristics of compound III as determined by X-ray powder diffraction (XRPD), differential scanning calorimetry (DSC), thermogravimetric (TG) analysis, moisture sorption/desorption (MB), and $^1$H nuclear magnetic resonance (NMR).

FIG. 11 is a table summarizing various characteristics of the hydrosulfate salt of compound I as determined by X-ray powder diffraction (XRPD), differential scanning calorimetry (DSC), thermogravimetric (TG) analysis, and $^1$H nuclear magnetic resonance (NMR).

FIG. 27 is a table reporting the data obtained from moisture sorption/desorption experiments performed with the chloride salt of compound I.

FIG. 55 is a table summarizing the stability of the mesylate salt of compound I and compound II in the buffer used in Caco-2 penetration experiments: Hank's Balanced Salt Solution (HBSS) buffer, 2% final concentration of DMSO.

FIG. 57a is a table reporting data obtained from analysis of the ability of compound II to pass from the apical to the basolateral compartment of a transwell coated with a Caco-2 cell monolayer. Cultured Caco-2 cells were incubated with the indicated concentration of compound II in the apical compartment of the transwell, and aliquots from the basolateral compartment were sampled at the indicated sampling times in order to determine the presence of compound II. The data reports the concentration of compound II in the basolateral compartment as a percentage of the indicated initial concentration of compound II. FIG. 57b is a table reporting data obtained from analysis of the ability of compound II to pass from the basolateral to the apical compartment of a transwell coated with a Caco-2 cell monolayer. Cultured Caco-2 cells were incubated with the indicated concentration of compound II in the basolateral compartment of the transwell, and aliquots from the apical compartment were sampled at the indicated sampling times in order to determine the presence of compound II. The data reports the concentration of compound II in the basolateral compartment as a percentage of the indicated initial concentration of compound II. FIG. 57c is a table showing the recovery of compound II in the apical compartment following 60 and 120 minutes of incubation in the basolateral compartment, as well as the permeability rate of compound II through the Caco-2 cell monolayer.

FIG. 59 is a table summarizing the chromatography and mass spectrometry parameters used for the analysis of concentrations of compound I and compound II in Caco-2 cell penetration experiments described herein.

MS (ADINSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spon." A DMSO control or atosiban was then added to each myometrial sample at the indicated concentrations and the effects of control or atosiban on work done per contraction were measured over the ensuing 10-minute period. This time point is represented on the x-axis as "Ato." The effects of atosiban on work done per contraction in the presence of PGE2 were subsequently measured by challenging the myometrial tissue samples with increasing concentrations of PGE2 (1 nM, 10 nM, and 100 nM) at sequential 10-minute intervals. These time points are represented on the x-axis as "PGE2 1 nM," "PGE2 10 nM," and "PGE2 100 nM," respectively. Values along the y-axis represent the work done per contraction as a percentage of the work done per contraction for spontaneous baseline contractions.

respectively. Values along the y-axis represent the frequency of contractions as a percentage of the frequency of spontaneous baseline contractions.

DETAILED DESCRIPTION

Figure 1:
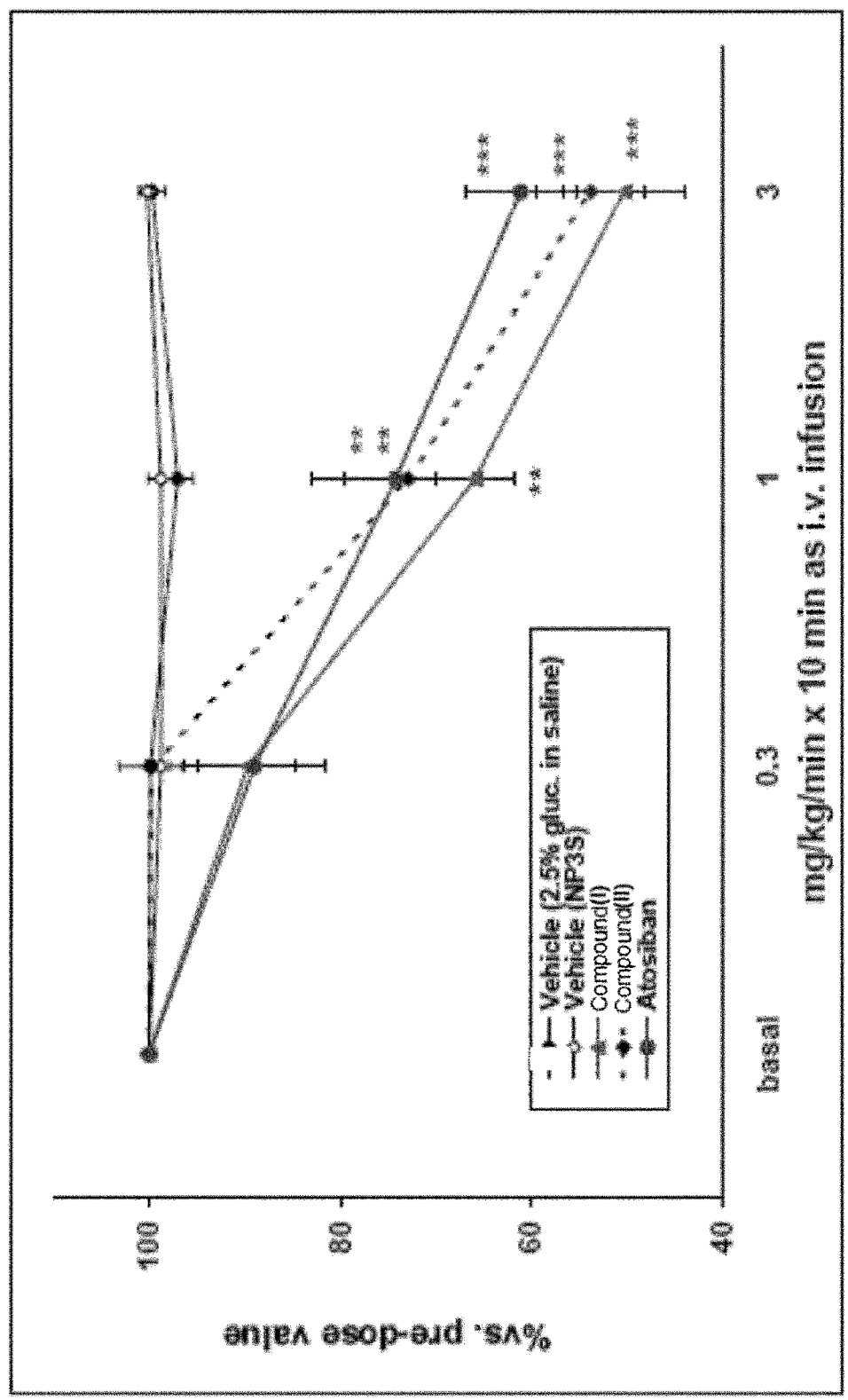
FIG. 1 is a graph demonstrating the effect of compound II and compound III on spontaneous uterine contractility in late-term pregnant rats following intravenous administration.
Figure 2:
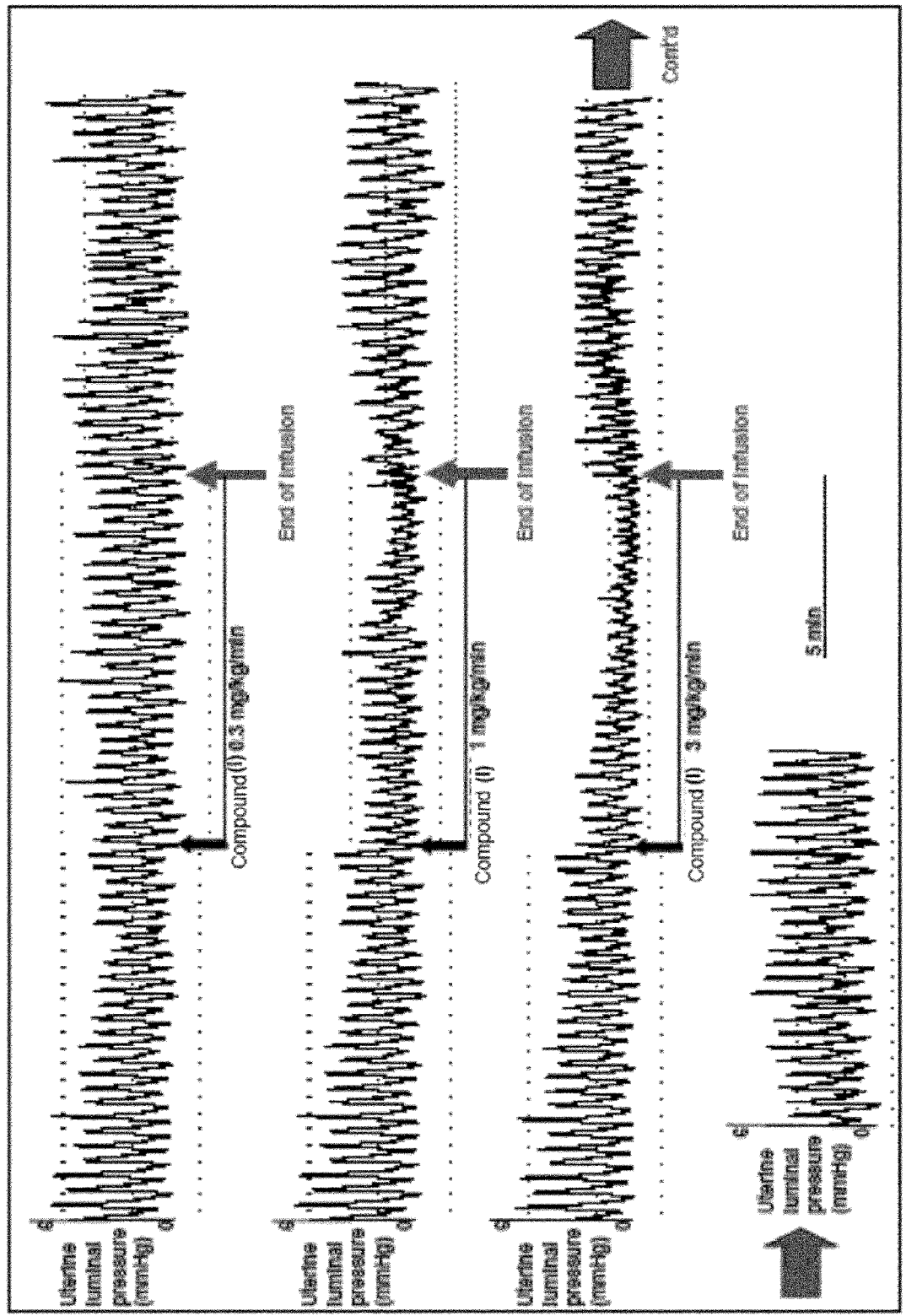
FIG. 2 is a graph showing the dose-dependent and reversible effect of compound I on spontaneous uterine contraction in late-term pregnant rats.

The invention provides α-amino esters of a thiazolidine carboxamide, such as (3S)-3-({[(2S)-3-(biphenyl-4-ylsulfonyl)-1,3-thiazolidin-2-yl]carbonyl}-amino)-3-(4-fluorophenyl)propyl L-valinate, as well as salt forms and crystal polymorphs thereof. These compounds are capable of inhibiting the activity of proteins of the prostaglandin F receptor (FP-R) family, such as prostaglandin F2α (PGF2α) receptor. The compounds, salts, and crystal polymorphs described herein can be used to inhibit the activity of the prostaglandin F receptor in vitro and in vivo, and represent effective therapeutic compositions for the treatment of preterm labor. The compounds, salts, and crystal polymorphs described herein can be administered to a subject (e.g., a mammalian subject, such as a human) that is undergoing or is at risk of undergoing labor at an early gestational age, e.g., prior to 38 weeks (e.g., from about 20 to about 37 weeks, such as a gestational age of about 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, or 37 weeks, preferably from about 24 to about 34 weeks, such as a gestational age of about 24 weeks, 25 weeks, 26 weeks, 27 weeks, 28 weeks, 29 weeks, 30 weeks, 31 weeks, 32 weeks, 33 weeks, or 34 weeks). The invention additionally provides methods of synthesizing (3S)-3-({[(2S)-3-(biphenyl-4-ylsulfonyl)-1,3-thiazolidin-2-yl]carbonyl}-amino)-3-(4-fluorophenyl)propyl L-valinate, as well as processes for preparing salt forms and crystal polymorphs thereof. The invention further encompasses methods of treating preterm labor in a subject by administering an alpha-amino ester of the invention to a subject in need of treatment, such as a subject experiencing preterm labor or a subject at risk of undergoing preterm labor, optionally in combination with one or more additional therapeutic agents as described herein.

In addition to the above, the invention encompasses compositions and methods relating to 3-([1,1'-biphenyl]-4-ylsulfonyl)-N-[1-(4-fluorophenyl)-3-hydroxypropyl]-1,3-thiazolidine-2-carboxamide. As described herein, this compound may be provided to a subject (e.g., a mammalian subject, such as a human) that is undergoing or is at risk of undergoing labor at an early gestational age, e.g., prior to 38 weeks (e.g., from about 20 to about 37 weeks, such as a gestational age of about 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, or 37 weeks, preferably from about 24 to about 34 weeks, such as a gestational age of about 24 weeks, 25 weeks, 26 weeks, 27 weeks, 28 weeks, 29 weeks, 30 weeks, 31 weeks, 32 weeks, 33 weeks, or 34 weeks), optionally in combination with one or more additional therapeutic agents as described herein.

(3S)-3-({[(2S)-3-(biphenyl-4-ylsulfonyl)-1,3-thiazolidin-2-yl]carbonyl}-amino)-3-(4-fluorophenyl)propyl L-valinate (Compound I)

The invention is based on the discovery that compound I ((3S)-3-({[(2S)-3-(biphenyl-4-ylsulfonyl)-1,3-thiazolidin-2-yl]carbonyl}-amino)-3-(4-fluorophenyl)propyl L-valinate, represented by formula I, below) and salts thereof are converted in vivo to 3-([1,1'-biphenyl]-4-ylsulfonyl)-N-[1-(4-fluorophenyl)-3-hydroxypropyl]-1,3-thiazolidine-2-carboxamide (represented by formula II, below). Compound II, previously described in U.S. Pat. No. 8,415,480, is an antagonist of the prostaglandin F receptor, as this compound exhibits an inhibition constant (Ki) of 6 nM for human FP-R as determined by competitive radioligand binding assays (experimental details of competitive radioligand binding assays useful for the determination of Ki values are described, e.g., in U.S. Pat. No. 8,415,480, Example 51). Following administration to a subject, compound I has been found to be de-esterified in vivo so as to form compound II due to the activity of endogenous esterases, such as those present in the gastrointestinal tract.

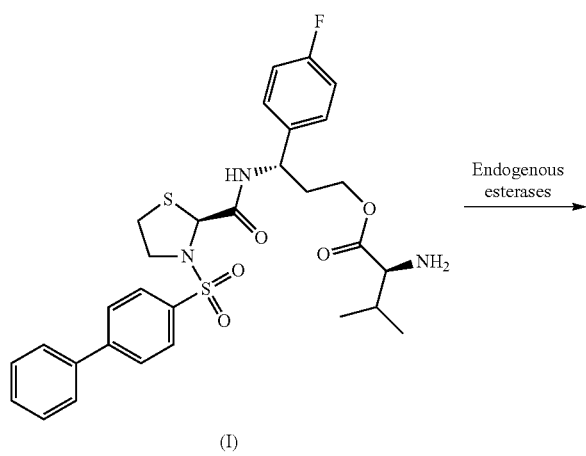

(I)

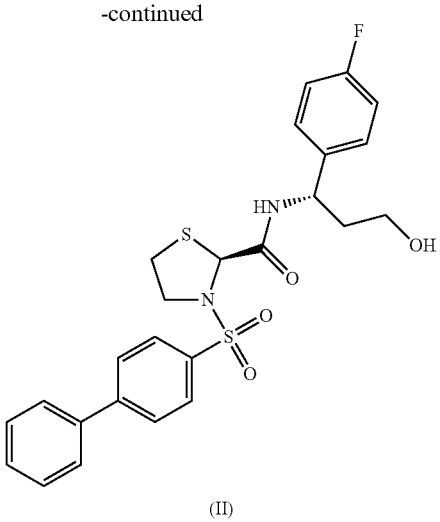

(II)

It has been discovered that compound I is an inhibitor of the prostaglandin F receptor, as compound I inhibits human FP-R with a Ki of 1 nM. Compound I exhibits improvements in several physicochemical characteristics relative to compound II, including solubility in water as well as in media that simulate the small intestinal contents in the fed (FeSSIF) and fasted (FaSSIF) states. These data are summarized in Table 2, below.

TABLE 2

Comparison of physicochemical properties of compound I and compound II

| Parameter | Compound I | Compound II |
|---|---|---|
| Solubility in water (µg/mL) | 380 | 0.4 |
| Solubility in FaSSIF (µg/mL) pH 6.5 | 70 | 0.4 |
| Solubility in FeSSIF (µg/mL) pH 5.0 | 90 | 10 |
| Human FP-R Ki (nM) | 1 | 6 |

In addition to exhibiting enhanced aqueous solubility, compound I and salts thereof feature a surprising and beneficial absorption mechanism. As described in the Examples below, compound I is de-esterified by ambient esterases in the small intestine and subsequently penetrates the small intestinal epithelium passively. Surprisingly, compound I and salts thereof are not substrates for the Pept1 transporter protein, a proton-coupled co-transporter that mediates the absorption of peptidic nutrients. This discovery represents an unexpected and pharmacologically beneficial property. Pept1 is known to mediate the absorption of a variety of valinate esters, as described, for example, in Vig et al., Adv. Drug Deliv. Rev. 65:1370-1385 (2013), the disclosure of which is incorporated herein by reference. Pept1 exhibits broad substrate specificity, as evidenced by the structural diversity of compounds that are transported across the intestinal epithelium by this protein. Despite the presence the valinate ester functionality, compound I and salts thereof are not dependent upon this transporter for absorption across the small intestinal epithelium. This is an advantageous property, as compound I and salts thereof (for instance, compound III) thus do not compete with natural substrates of Pept1, such as peptidic nutrients, for binding to and transport by this protein. Rather, compound I and salts thereof are converted in vivo to a form that is readily absorbed in a manner independent of energy and local proton gradient. This unexpected property, coupled with the high aqueous solubility of compound I and salts thereof, collectively provide a beneficial pharmacokinetic profile by which compounds of the invention readily dissolve in an aqueous environment and are in turn converted into a form capable of transporter-independent absorption.

(3S)-3-({[(2S)-3-(biphenyl-4-ylsulfonyl)-1,3-thiazolidin-2-yl]carbonyl}-amino)-3-(4-fluorophenyl)propyl L-valinate hydrochloride (Compound III)

It has been discovered that the chloride salt of compound I ((3S)-3-({[(2S)-3-(biphenyl-4-ylsulfonyl)-1,3-thiazolidin-2-yl]carbonyl}-amino)-3-(4-fluorophenyl)propyl L-valinate hydrochloride, designated as formula III below) is readily crystallized using a several distinct experimental procedures, as described in the Examples below. Compound III assumes a single, reproducible crystal form upon crystallization from a variety of media and under different ambient conditions. Moreover, this crystal form of compound III exhibits extended stability under ambient conditions and in the presence of elevated relative humidity. As is described in further detail in the Examples presented below, compound III exhibits a low hygroscopicity and thus does not demonstrate a propensity to absorb moisture from the local atmosphere. Compound III therefore exhibits a resistance to chemical changes, such as hydrolysis, as well as a resistance to the incorporation of impurities. For instance, impurities associated with atmospheric water are not readily integrated into the crystalline form of compound III. Compound III can be administered to a subject, such as a pregnant female human subject, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). Compound ill also be administered to a subject, such as a pregnant female human subject, in order to alleviate one or more symptoms associated with labor, such as vaginal bleeding and rupture of uterine membranes.

(III)

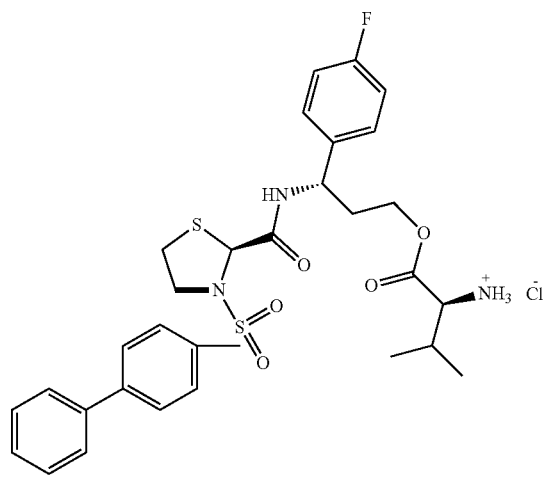

Compound I, or a pharmaceutically acceptable salt thereof, such as compound III, may be administered alone or in combination with one or more additional agents, such as an additional therapeutic agent. Exemplary additional therapeutic agents include additional tocolytic agents, such as an oxytocin receptor antagonist described herein, including, e.g., atosiban, retosiban, barusiban, epelsiban, and nolasiban, which is (3Z, 5S)-5-(hydroxymethyl)-1-[(2'-methyl-1, 1'-biphenyl-4-yl)carbonyl]pyrrolidin-3-one O-methyl oxime, or a variant, formulation, crystalline form, or derivative thereof. By suppressing oxytocin signal transduction, oxytocin receptor antagonists may synergize with the prostaglandin F2α receptor antagonists described herein to slow or halt uterine contractions, for instance, in a patient undergoing or at risk of undergoing (e.g., presenting with one or more symptoms of) preterm labor. Exemplary additional tocolytic agents include betamimetics, such as terbutaline, ritodrine, hexoprenaline, albuterol, fenoterol, nylidrin, and orciprenaline, which may function to inactive myosin light-chain kinase and/or to deplete myometrial $Ca^{2+}$ reserves by upregulation of cAMP, thereby suppressing uterine contractility. Calcium channel inhibitors, such as dihydropyridines (e.g., nifedipine and nicardipine), can additionally or alternatively be administered in conjunction with a compound of the invention, for instance, to modulate myometrial $[Ca^{2+}]$ and suppress $Ca^{2+}$-mediated activation of myosin filaments that leads to myometrial contractions. Magnesium salts, such as magnesium sulfate, can additionally or alternatively be administered on conjunction with a compound of the invention, for instance, to hyperpolarize the plasma membrane and/or to compete with $Ca^{2+}$ for binding to the myosin light-chain. Additionally or alternatively, nitric oxide donors, such as nitroglycerine, can be administered in conjunction with a compound described herein, for instance, to augment myometrial cyclic guanosine monophosphate levels, thereby inactivating myosin light-chain filaments.

A compound of the invention, such as compound I or a pharmaceutically acceptable salt thereof, such as compound III, can additionally or alternatively be administered in conjunction with progesterone or a variant or derivative thereof, such as 17-α-hydroxyprogesterone, to suppress uterine contractility in a subject undergoing or at risk of (e.g., presenting with one or more symptoms of) preterm labor.

Additionally or alternatively, a compound of the invention can be administered in conjunction with a corticosteroid described herein or known in the art, for instance, to promote fetal lung maturation so as to prevent the occurrence of respiratory distress syndrome, among other infantile disorders.

Additionally, compound III may be formulated into a pharmaceutical composition, such as a pharmaceutical composition formulated as described below.

Methods of Treatment

Compound I, as well as salts thereof, represent robust inhibitors of the prostaglandin F receptor and can be used to antagonize the interaction between prostaglandin F family members, such as prostaglandin F2α, with the corresponding prostaglandin F receptor in vivo in order to attenuate uterine contractions. Compound I and salts thereof can be administered to a subject, such as a pregnant human female subject, in order to treat or prevent preterm labor. Endogenous prostaglandin F2α is synthesized in and released by uterine epithelial cells in response to the signal transduction cascades initiated by oxytocin. Upon binding of PGF2α to PGF2α-R on the extracellular surface of a uterine myocyte, phospholipase C cleaves phosphatidylinositol-4,5-bisphosphate ($PIP_2$) to yield diacylglycerol (DAG) and inositol-1,4,5-trisphosphate ($IP_3$). $IP_3$ in turn potentiates the release of intracellular calcium ($Ca^{2+}$) sarcoplasmic reticula. The sudden increase in calcium stores ultimately leads to uterine muscle contractions and a necrosis of endothelial cells of the corpus luteum, a progesterone-secreting structure that supports a developing fetus. The aberrant initiation of uterine contractions and degradation of the corpus luteum caused by dysregulation of PGF2α secretion can lead to preterm labor. Compound I and salts thereof, such as compound III, may attenuate the phospholipase C-mediated formation of IP3, and the subsequent mobilization of intracellular calcium stores, by inhibiting the association of PGF2α with the PGF2αR. Compound I or a salt thereof, such as compound III, can thus be administered to subjects, such as pregnant female human subjects, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). For instance, compound I or a salt thereof, such as compound III, can be administered to a subject in order to prevent labor prior to cesarean delivery. Additionally, compound I or a salt thereof, such as compound III, can be administered to a subject for the prophylaxis and/or treatment of dysmenorrhea. Compound I or a salt thereof, such as compound III, can also be administered to a subject, such as a pregnant female human subject, in order to alleviate one or more symptoms associated with labor, such as vaginal bleeding and rupture of uterine membranes.

Additionally, compounds of the invention can be used to treat endometriosis in a patient (e.g., a human patient). Prostaglandin F2α receptor overexpression has been correlated with aberrant endometrial growth. As antagonists of prostaglandin F2α receptor activity, the compounds of the invention (e.g., compound (I) or a salt thereof, such as compound (III)) can be administered to a patient suffering from endometriosis in order to treat this indication. The compounds of the invention can also be administered to a patient in order to alleviate one or more symptoms of endometriosis, such pain symptoms including dysmenorrhea, dyspareunia, chronic pelvic pain, dysuria, and dyschezia during and/or apart from menstruation. Successful treatment of endometriosis by administration of a compound of the invention to a patient can be indicated by, e.g., a reduction in the growth of endometrial tissue, and/or a reduction in pain symptoms during and/or apart from menstruation.

In addition to the above, the present invention provides methods of therapeutic treatment by providing compound II to a subject in need of treatment for the conditions described herein. For instance, compound II can be provided to a subject, such as a pregnant human female subject, in order to treat or prevent preterm labor. Compound II is a competent antagonist of the PGF2α receptor and can thus inhibit the association of this receptor with PGF2α. Compound II can thus be provided to subjects, such as pregnant female human subjects, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). For instance, compound II can be provided to a subject in order to prevent labor prior to cesarean delivery. Additionally, compound II can be provided to a subject for the prophylaxis and/or treatment of dysmenorrhea. Compound II can also be provided to a subject, such as a pregnant female human subject, in order to alleviate one or more symptoms associated with labor, such as vaginal bleeding and rupture of uterine membranes.

Additionally, compound II can be provided to a subject to treat endometriosis in a patient (e.g., a human patient). As a PGF2α receptor antagonist, compound II can be provided to a patient suffering from endometriosis in order to treat this indication. Compound II can be provided to a patient in order to alleviate one or more symptoms of endometriosis, such pain symptoms including dysmenorrhea, dyspareunia, chronic pelvic pain, dysuria, and dyschezia during and/or apart from menstruation. Successful treatment of endometriosis by providing compound II to the subject can be indicated by, e.g., a reduction in the growth of endometrial tissue, and/or a reduction in pain symptoms during and/or apart from menstruation.

Combination Therapy

Though the processes involved in the onset of labor are not yet fully defined, there is increasing evidence supporting the significance of inflammation in both term and preterm parturition. During the onset of labor, there is a systemic increase in a number of pro-inflammatory factors including prostaglandins, cytokines, and manganese superoxide dismutase. In addition, inflammation has been strongly implicated in infection-driven preterm labor.

Oxytocin is thought to initiate labor by exerting two distinct effects: directly inducing contraction of the uterine myometrium, and enhancing the synthesis and release of contractile prostaglandins from the uterine endometrium/decidua. By inhibiting oxytocin signal transduction, the direct (contractile) and indirect (enhanced prostaglandin synthesis) effects of oxytocin on the uterus may be achieved. Additionally, treatment of human decidua with oxytocin results in the stimulation of prostaglandin F2α production. This suggests that a complimentary role for oxytocin signaling in uterine tissues exists, whereby oxytocin can interact not only both directly with the myometrium in stimulating uterine contractions, but also indirectly via the formation of prostaglandins in other tissues.

There is recent evidence correlating the activity of the contractile prostaglandin F receptor with the onset and during the progression of labor. Recent reports also indicate that oxytocin induces production of prostaglandins in human myometrial cells via potentiation of cyclooxygenase 2 (COX-2). Such a mechanism may explain the sustained release of prostaglandins in uterine tissue that promotes labor. A combination therapy including a prostaglandin F2α receptor antagonist, such as compound I or a salt thereof (e.g., compound III) and an oxytocin receptor antagonist may therefore be useful for the treatment and/or prevention or preterm labor. Additionally, the combination of an oxytocin receptor antagonist and a prostaglandin F2α receptor antagonist may be more efficacious for treating preterm labor than current regimens. Synergistic effects may be observed, and are described herein, in the prevention of both contractile and inflammatory processes that underlie preterm labor, as the dose(s) of an oxytocin receptor antagonist administered to a patient may be lower when administered in combination with a prostaglandin F receptor antagonist relative to the doses that may be administered to a patient receiving an oxytocin receptor antagonist alone.

Compound I or a salt thereof, such as compound III, can be administered with one or more additional agents, such as an oxytocin receptor antagonist, in order to reduce the occurrence of uterine contractions and to delay the onset of labor. For instance, compound I or a salt thereof, such as compound III, can be administered simultaneously with, admixed with, or administered separately from an oxytocin receptor antagonist. Exemplary oxytocin receptor antagonists for use in conjunction with the compositions and methods of the invention include atosiban, retosiban, barusiban, epelsiban, and nolasiban, or a variant, formulation, crystalline form, or derivative thereof. For instance, compound I or a salt thereof, such as compound III, may be administered prior to, after, or simultaneously with nolasiban, or a variant, formulation, crystalline form, or derivative thereof, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, a compound of the invention (e.g., compound I or a pharmaceutically acceptable salt thereof, such as compound III) can be administered to a patient undergoing or at risk of (e.g., displaying one or more symptoms of) preterm labor in conjunction with a betamimetic. Betamimetics, such as terbutaline, ritodrine, hexoprenaline, albuterol, fenoterol, nylidrin, and orciprenaline, may function to deplete intracellular $Ca^{2+}$ levels (e.g., intracellular myometrial $Ca^{2+}$ levels) through potentiation of β-2 adrenergic receptors, thereby upregulating cAMP and exhausting intracellular $Ca^{2+}$ reserves that would otherwise be available to stimulate uterine contractility. Exemplary betamimetics for use in conjunction with the compositions and methods described herein, as well as exemplary methods for the administration of betamimetics in conjunction with the compositions and methods described herein, are described, for example, in Gyetvai et al. Obstet. Gynecol. 94:869-877 (1999), the disclosure of which is incorporated herein by reference.

Additionally or alternatively, a compound of the invention (e.g., compound I or a pharmaceutically acceptable salt thereof, such as compound III) can be administered to a patient undergoing or at risk of (e.g., displaying one or more symptoms of) preterm labor in conjunction with a calcium channel inhibitor, such as an L-type calcium channel inhibitor. Calcium channel inhibitors, including dihydropyridines, such as nifedipine and nicardipine, may function by suppressing the release of $Ca^{2+}$ from sarcoplasmic reticula, thereby preventing the mobilization of $Ca^{2+}$ that stimulates uterine muscle contractions. Exemplary calcium channel inhibitors for use in conjunction with the compositions and methods described herein, as well as exemplary methods for the administration of calcium channel inhibitors in conjunction with the compositions and methods described herein, are described, for example, in Wojcieszek et al. Cochrane Database Syst. Rev. 6:CD002255 (2014), the disclosure of which is incorporated herein by reference.

Additionally or alternatively, a compound of the invention (e.g., compound I or a pharmaceutically acceptable salt thereof, such as compound III) can be administered to a patient undergoing or at risk of (e.g., displaying one or more symptoms of) preterm labor in conjunction with a magnesium salt, such as magnesium sulfate. Magnesium salts, such as magnesium sulfate, can modulate uterine contractility through multiple mechanisms, such as by inducing hyperpolarization of the plasma membrane and/or by competing with $Ca^{2+}$ for binding to the myosin light-chain, thereby suppressing contraction of myosin filaments in uterine myocytes.

Additionally or alternatively, a compound of the invention (e.g., compound I or a pharmaceutically acceptable salt thereof, such as compound III) can be administered to a patient undergoing or at risk of (e.g., displaying one or more symptoms of) preterm labor in conjunction with a nitric oxide donor. Nitric oxide, a vasodilator that is essential for the maintenance of normal smooth-muscle tone, is produced in a variety of cells. Nitric oxide is synthesized during the oxidation of L-arginine to L-citrulline. This reaction is catalyzed by nitric oxide synthase, which exists in several isoforms. Both inducible (type 2) and brain (type 1) nitric oxide synthases are expressed in myometrial cells and blood-vessel endothelial cells, whereas endothelial (type 3) nitric oxide synthase is expressed exclusively in blood-vessel endothelial cells. The interaction between nitric oxide and soluble guanylyl cyclase, which is present in nearby effector cells, represents a widespread signal transduction mechanism that couples diverse extracellular stimuli of nitric oxide formation to the synthesis of cyclic guanosine monophosphate (cGMP) in target cells. The increase in cGMP content in smooth-muscle cells, such as uterine myocytes, inactivates myosin light-chain kinases, leading to smooth-muscle relaxation. The tocolytic effects of nitric oxide donors, such as nitroglycerine, are described, for instance, in Simhan et al. New Engl. J. Med. 357:477-487 (2007), the disclosure of which is incorporated herein by reference.

Additionally or alternatively, a compound of the invention (e.g., compound I or a pharmaceutically acceptable salt thereof, such as compound III) can be administered to a patient undergoing or at risk of (e.g., displaying one or more symptoms of) preterm labor in conjunction with progesterone or a variant thereof, such as 17-α-hydroxyprogesterone caproate. Progesterone is a steroid hormone secreted by the corpus luteum and by the placenta after about 8 weeks of gestation. Progesterone and variants thereof, such as 17-α-hydroxyprogesterone caproate, may regulate uterine quiescence by directly modulating myometrial $[Ca^{2+}]$ and prostaglandin synthesis, as described, for instance, in Muglia et al. New Engl. J. Med. 362:529-535 (2010); Simhan et al. New Engl. J. Med. 357:477-487 (2007); Smith et al. Eur. J. Obstet. Gynecol. Reprod. Biol. 142:3-11 (2009); Bernal. Sem. Cell Dev. Biol. 18:340-347 (2007); and Hubinont et al. J. Pregnancy. 941057 (2011), the disclosures of each of which are incorporated herein by reference.

Additionally or alternatively, a compound of the invention (e.g., compound I or a pharmaceutically acceptable salt thereof, such as compound III) can be administered to a patient undergoing or at risk of (e.g., displaying one or more symptoms of) preterm labor in conjunction with a corticosteroid. Antenatal corticosteroids, such as betamethasone, dexamethasone, and hydrocortisone, represent a class of therapeutic agents that can be administered to a subject, such as a pregnant female subject during preterm labor or to a subject at risk of preterm labor (e.g., a subject exhibiting one or more symptoms of preterm labor, such as vaginal bleeding and rupture of uterine membranes) to accelerate fetal lung maturation. Treatment with antenatal corticosteroids is associated with an overall reduction in neonatal death, respiratory distress syndrome, intraventricular hemorrhage, necrotizing enterocolitis, respiratory support, intensive care admissions, and systemic infections in the first 48 h of life. Additionally, antenatal corticosteroid therapy is effective in women with premature rupture of membranes (PROM) and pregnancy-related hypertension syndromes. There is evidence to suggest benefit across a wide range of gestational ages, such as from about 26 to about 34 weeks, among others (Miracle et al. J. Perinat. Med. 36:191-196 (2008), the disclosure of which is incorporated herein by reference).

In addition to the above, according to the methods described herein, compound II can be provided (for instance, by direct administration or by administration of a prodrug thereof) to a subject in need of treatment (e.g., a human subject undergoing or at risk of undergoing preterm labor, or a human subject suffering from dysmenorrhea or endometriosis) with one or more additional agents, such as an oxytocin receptor antagonist, for example, in order to reduce the occurrence of uterine contractions and to delay the onset of labor. For instance, compound II can be provided simultaneously with, admixed with, or provided separately from an oxytocin receptor antagonist. Exemplary oxytocin receptor antagonists for use in conjunction with the compositions and methods of the invention include atosiban, retosiban, barusiban, epelsiban, and nolasiban, or a variant, formulation, crystalline form, or derivative thereof. For instance, compound II may be provided prior to, after, or simultaneously with nolasiban, or a variant, formulation, crystalline form, or derivative thereof, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, compound II can be provided to a patient undergoing or at risk of (e.g., displaying one or more symptoms of) preterm labor in conjunction with a betamimetic. As described above, betamimetics, such as terbutaline, ritodrine, hexoprenaline, albuterol, fenoterol, nylidrin, and orciprenaline, may function to deplete intracellular $Ca^{2+}$ levels (e.g., intracellular myometrial $Ca^{2+}$ levels) through potentiation of β-2 adrenergic receptors, thereby upregulating cAMP and exhausting intracellular $Ca^{2+}$ reserves that would otherwise be available to stimulate uterine contractility. Exemplary betamimetics for use in conjunction with the compositions and methods described herein, as well as exemplary methods for the administration of betamimetics in conjunction with the compositions and methods described herein, are described, for example, in Gyetvai et al. Obstet. Gynecol. 94:869-877 (1999), the disclosure of which is incorporated herein by reference.

Additionally or alternatively, compound II can be provided to a patient undergoing or at risk of (e.g., displaying one or more symptoms of) preterm labor in conjunction with a calcium channel inhibitor, such as an L-type calcium channel inhibitor. As described above, calcium channel inhibitors, including dihydropyridines, such as nifedipine and nicardipine, may function by suppressing the release of $Ca^{2+}$ from sarcoplasmic reticula, thereby preventing the mobilization of $Ca^{2+}$ that stimulates uterine muscle contractions. Exemplary calcium channel inhibitors for use in conjunction with the compositions and methods described herein, as well as exemplary methods for the administration of calcium channel inhibitors in conjunction with the compositions and methods described herein, are described, for example, in Wojcieszek et al. Cochrane Database Syst. Rev. 6:CD002255 (2014), the disclosure of which is incorporated herein by reference.

Additionally or alternatively, compound II can be provided to a patient undergoing or at risk of (e.g., displaying one or more symptoms of) preterm labor in conjunction with a magnesium salt, such as magnesium sulfate. As described above, magnesium salts, such as magnesium sulfate, can modulate uterine contractility through multiple mechanisms, such as by inducing hyperpolarization of the plasma membrane and/or by competing with $Ca^{2+}$ for binding to the myosin light-chain, thereby suppressing contraction of myosin filaments in uterine myocytes.

Additionally or alternatively, compound II can be provided to a patient undergoing or at risk of (e.g., displaying one or more symptoms of) preterm labor in conjunction with a nitric oxide donor. As described above, nitric oxide, a vasodilator that is essential for the maintenance of normal smooth-muscle tone, is produced in a variety of cells, and the nitric oxide-induced increase in cGMP content in smooth-muscle cells, such as uterine myocytes leads to smooth-muscle relaxation. The tocolytic effects of nitric oxide donors, such as nitroglycerine, are described, for instance, in Simhan et al. New Engl. J. Med. 357:477-487 (2007), the disclosure of which is incorporated herein by reference.

Additionally or alternatively, compound II can be provided to a patient undergoing or at risk of (e.g., displaying one or more symptoms of) preterm labor in conjunction with progesterone or a variant thereof, such as 17-α-hydroxyprogesterone caproate. As described above, progesterone and variants thereof, such as 17-α-hydroxyprogesterone caproate, may regulate uterine quiescence by directly modulating myometrial $[Ca^{2+}]$ and prostaglandin synthesis, as described, for instance, in Muglia et al. New Engl. J. Med. 362:529-535 (2010); Simhan et al. New Engl. J. Med. 357:477-487 (2007); Smith et al. Eur. J. Obstet. Gynecol. Reprod. Biol. 142:3-11 (2009); Bernal. Sem. Cell Dev. Biol. 18:340-347 (2007); and Hubinont et al. J. Pregnancy. 941057 (2011), the disclosures of each of which are incorporated herein by reference.

Additionally or alternatively, compound II can be provided to a patient undergoing or at risk of (e.g., displaying one or more symptoms of) preterm labor in conjunction with a corticosteroid. As described above, antenatal corticosteroids, such as betamethasone, dexamethasone, and hydrocortisone, represent a class of therapeutic agents that can be administered to a subject, such as a pregnant female subject during preterm labor or to a subject at risk of preterm labor (e.g., a subject exhibiting one or more symptoms of preterm labor, such as vaginal bleeding and rupture of uterine membranes) to accelerate fetal lung maturation, and treatment with antenatal corticosteroids is associated with an overall reduction in neonatal death, respiratory distress syndrome, intraventricular hemorrhage, necrotizing enterocolitis, respiratory support, intensive care admissions, and systemic infections in the first 48 h of life.

Pharmaceutical Compositions

Compound I or a salt thereof, such as compound III, can be formulated into a pharmaceutical composition for administration to a subject, such as a pregnant female human subject, in a biologically compatible form suitable for administration in vivo. Accordingly, in one aspect, the present invention provides a pharmaceutical composition containing compound I or a salt thereof, such as compound III, in admixture with a suitable diluent, carrier, or excipient. Compound I or a salt thereof, such as compound III, can be administered, for example, orally or by intravenous injection.

The present invention additionally provides pharmaceutical compositions containing compound II. Such compositions may include compound II in admixture with a suitable diluent, carrier, or excipient.

Under ordinary conditions of storage and use, a pharmaceutical composition may contain a preservative, e.g., to prevent the growth of microorganisms. Conventional procedures and ingredients for the selection and preparation of suitable formulations are described, for example, in Remington: The Science and Practice of Pharmacy (2012, 22$^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a subject in need of treatment.

A pharmaceutical composition may be administered to a subject, e.g., a human subject, alone or in combination with pharmaceutically acceptable carriers, as noted herein, the proportion of which may be determined by the solubility and/or chemical nature of the compound, chosen route of administration, and standard pharmaceutical practice.

Compositions for Combination Therapy

Compound I or a salt thereof, such as compound III, can be used alone or in combination with one or more additional agents useful for the inhibition of uterine contractions and/or luteolysis, such as atosiban, retosiban, barusiban, epelsiban, and nolasiban, or a variant, formulation, crystalline form, or derivative thereof, among other therapeutic agents (e.g., tocolytic agents) described herein. Compound I or a salt thereof, such as compound III, can be admixed with an additional active agent, such as an oxytocin receptor antagonist, betamimetic, calcium channel inhibitor, magnesium salt, nitric oxide donor, progesterone or variant thereof, or corticosteroid described herein, and administered to a patient in a single composition, or compound I or a salt thereof, such as compound III, can be administered to a patient separately from an additional active agent. For instance, compound I or a salt thereof, such as compound III, and an additional active agent can be sequentially administered to a patient.

In addition to the above, compound II can be provided to a subject alone or in combination with one or more additional agents useful for the inhibition of uterine contractions and/or luteolysis, such as atosiban, retosiban, barusiban, epelsiban, and nolasiban, or a variant, formulation, crystalline form, or derivative thereof, among other therapeutic agents (e.g., tocolytic agents) described herein. Compound II can be admixed with an additional active agent, such as an oxytocin receptor antagonist, betamimetic, calcium channel inhibitor, magnesium salt, nitric oxide donor, progesterone or variant thereof, or corticosteroid described herein, and administered to a patient in a single composition, or compound II can be provided to a patient separately from an additional active agent. For instance, compound II and an additional active agent can be sequentially provided to a patient, for example, by providing compound II to the patient followed by administration of the additional active agent to the patient.

A composition for combination therapy described herein, such as a pharmaceutical composition described herein, may be administered to a subject to delay the onset of labor in the subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks). In some embodiments, the subject is undergoing preterm labor. In some embodiments, the pharmaceutical composition is administered to the subject (e.g., a human subject) prior to the initiation of preterm labor. A pharmaceutical composition of the invention can be administered to a subject (e.g., a human subject) to prevent labor prior to cesarean delivery. A pharmaceutical composition of the invention can be administered to a subject (e.g., a human subject) for the treatment or prevention of dysmenorrhea. A pharmaceutical composition of the invention can be administered to a subject, such as a pregnant female human subject, in order to alleviate one or more symptoms associated with labor, such as vaginal bleeding and rupture of uterine membranes.

An additional therapeutic agent present within a composition for combination therapy may be, for instance, another tocolytic agent. The additional tocolytic agent may be, for instance, an oxytocin receptor antagonist, such as atosiban, retosiban, barusiban, epelsiban, and nolasiban, as well as one or more variants, formulations, crystalline forms, or derivatives thereof. For example, atosiban and variants thereof are described in, e.g., U.S. Pat. Nos. 4,504,469 and 4,402,942, the disclosures of each of which are incorporated herein by reference. Retosiban and variants thereof are described, e.g., in U.S. Pat. Nos. 7,514,437; 8,367,673; 8,541,579; 8,071,594; 8,357,685; 8,937,179; and US 2016/0074413, the disclosures of each of which are incorporated herein by reference. Barusiban and variants thereof are described, e.g., in U.S. Pat. Nos. 6,143,722; 7,091,314; 7,816,489; and US 2016/0175283, the disclosures of each of which are incorporated herein by reference. Epelsiban and variants thereof are described, e.g., in U.S. Pat. Nos. 7,514,437; 8,367,673; 8,541,579; 7,550,462; 7,919,492; 8,202,864; 8,742,099; 9,408,851; 8,716,286; and 8,815,856, the disclosures of each of which are incorporated herein by reference. Nolasiban and variants, formulations, and crystalline forms thereof are described, e.g., in U.S. Pat. No. 7,115,754 and US Patent Application Publication No. 2015/0073032; 2015/0164859; and 2016/0002160, the disclosures of each of which are incorporated herein by reference.

In some embodiments, the additional tocolytic agent is a betamimetic, such as terbutaline, ritodrine, hexoprenaline, albuterol, fenoterol, nylidrin, or orciprenaline. In some embodiments, the additional tocolytic agent is a calcium channel inhibitor, such as a dihydropyridine, such as nifedipine or nicardipine. In some embodiments, the additional tocolytic agent is a magnesium salt, such as magnesium sulfate. In some embodiments, the additional tocolytic agent is a nitric oxide donor, such as nitroglycerine.

In some embodiments, the additional therapeutic agent is progesterone or a variant or derivative thereof, such as 17-α-hydroxyprogesterone caproate.

In some embodiments, the additional therapeutic agent is a corticosteroid. In some embodiments, the corticosteroid is betamethasone. In some embodiments, the corticosteroid is dexamethasone. In some embodiments, the corticosteroid is hydrocortisone.

In combination treatments, the dosages of one or more of the therapeutic compounds may be reduced from standard dosages when administered alone. For example, doses may be determined empirically from drug combinations and permutations or may be deduced by a physician of skill in the art.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example 1. Preparation of Compounds I and III

Compound I, and the chloride salt thereof (compound III), were prepared according to Scheme 1, shown below. This Example will describe each of the stages carried out to synthesize compound I, designated Stages 1-6.

Scheme 1. Preparation of compound I and the chloride salt thereof
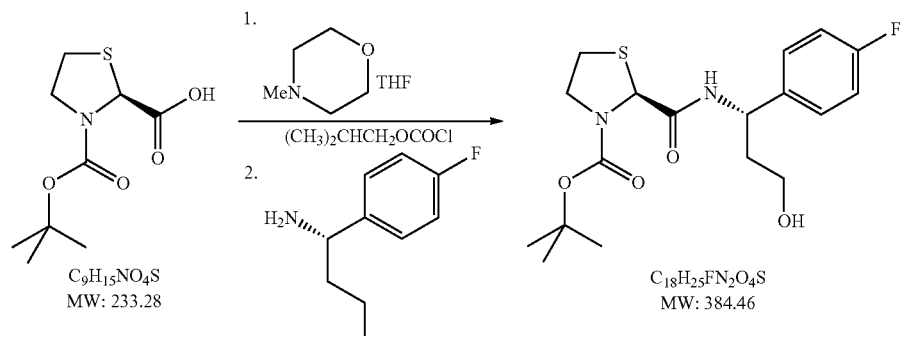
Stage 1
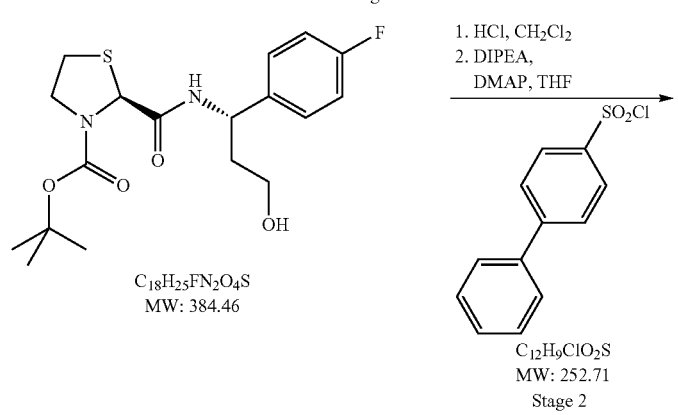
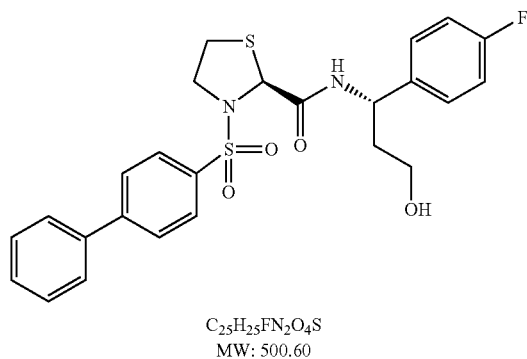
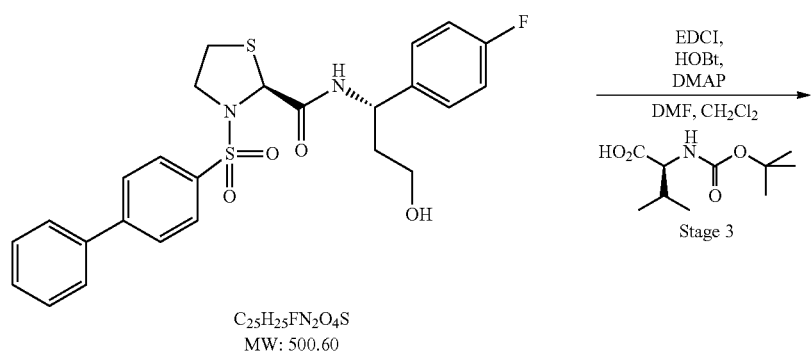
Stage 3

-continued
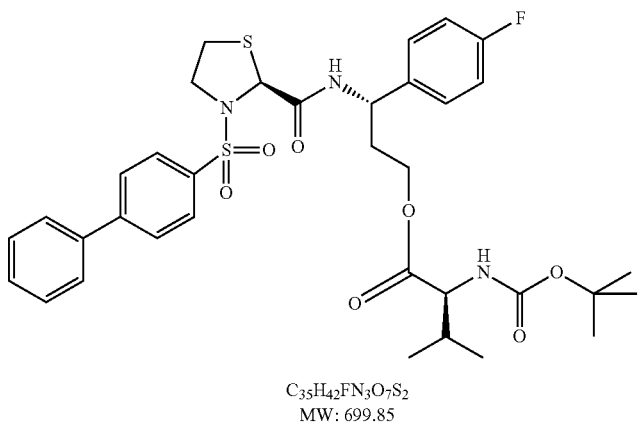
C$_{35}$H$_{42}$FN$_3$O$_7$S$_2$
MW: 699.85
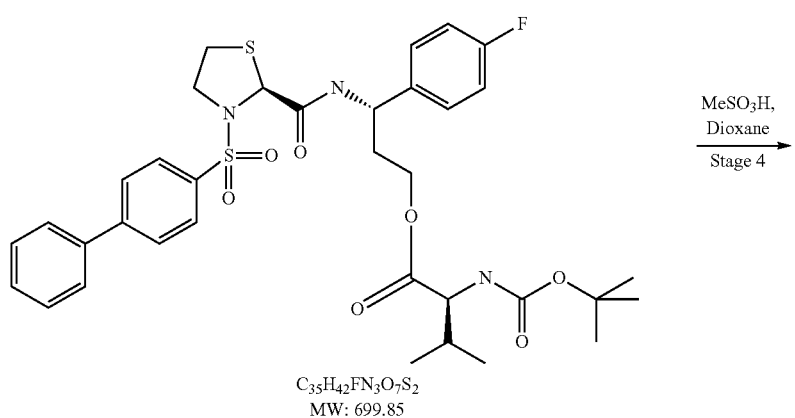
C$_{35}$H$_{42}$FN$_3$O$_7$S$_2$
MW: 699.85
MeSO$_3$H,
Dioxane
———————→
Stage 4
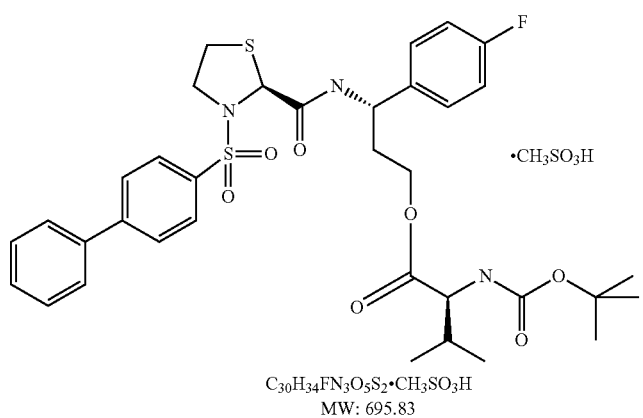
•CH$_3$SO$_3$H
C$_{30}$H$_{34}$FN$_3$O$_5$S$_2$•CH$_3$SO$_3$H
MW: 695.83
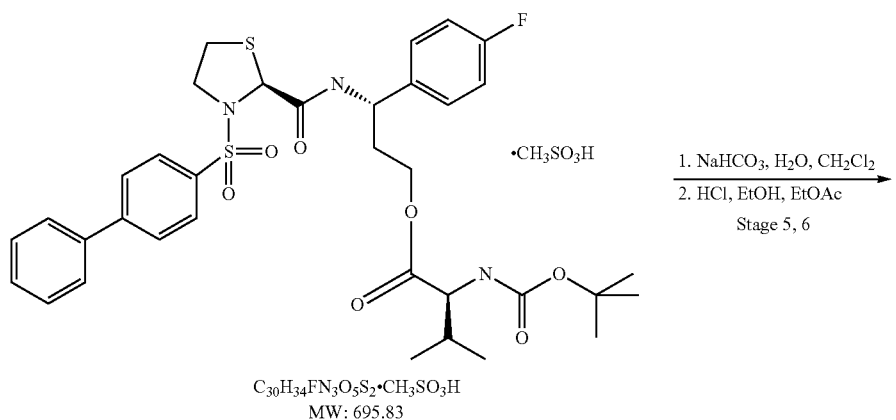
•CH$_3$SO$_3$H
1. NaHCO$_3$, H$_2$O, CH$_2$Cl$_2$
2. HCl, EtOH, EtOAc
———————————→
Stage 5, 6
C$_{30}$H$_{34}$FN$_3$O$_5$S$_2$•CH$_3$SO$_3$H
MW: 695.83

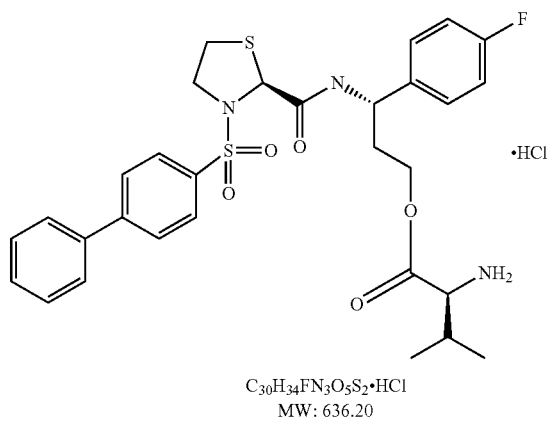

C₃₀H₃₄FN₃O₅S₂•HCl
MW: 636.20

Stage 1: Preparation of 2-[1-(4-fluorophenyl)-3-hydroxypropylcarbamoyl]thiazolidine-3-carboxylic acid tert-butyl ester

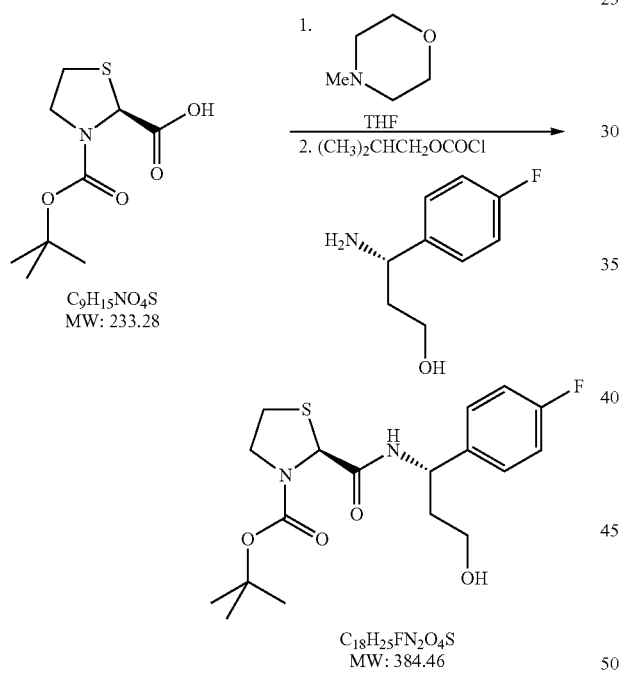

to warm to 15° C. to 25° C. over a period of 1 h to 24 h. The reaction mixture was stirred at 15° C. to 25° C. until the reaction was observed to be complete. The reaction mixture was concentrated to dryness, and ethyl acetate was subsequently added to the residue, followed by saturated aqueous ammonium chloride. The organic phase was separated and washed with saturated aqueous ammonium chloride solution. The organic phase was then separated and washed with saturated aqueous sodium hydrogen carbonate solution. The organic phase was then dried over sodium sulfate, filtered, and the filtrate concentrated at 35° C. to 40° C. until the ethyl acetate content was ≤10% by weight (w/w) to yield 2-[1-(4-fluorophenyl)-3-hydroxypropylcarbamoyl]thiazolidine-3-carboxylic acid tert-butyl ester.

Stage 2: Preparation of 3-(biphenyl-4-sulfonyl)thiazolidine-2-carboxylic acid [1-(4-fluorophenyl)-3-hydroxypropyl]-amide

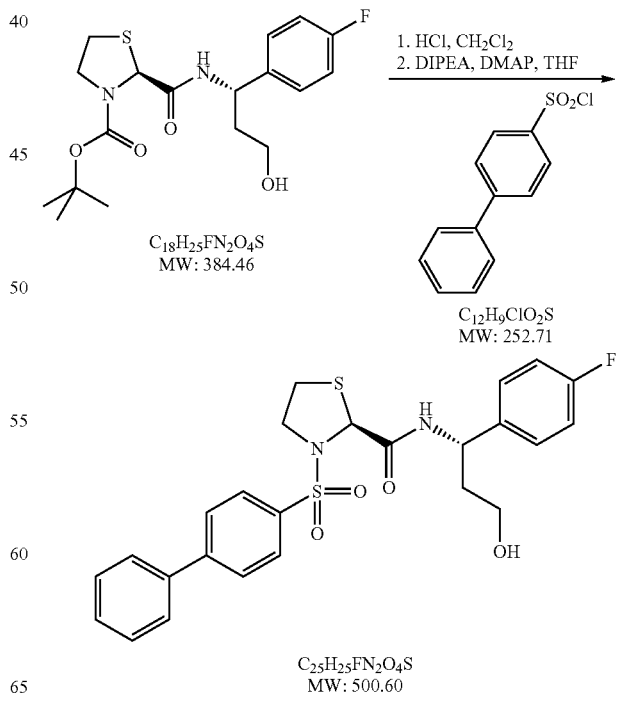

To a suitably sized flask (vessel A), 3-(butoxycarbonyl)-1,3-thiazolidine-(2S)-carboxylic acid (1 wt) was added, followed by tetrahydrofuran and the flask contents were subsequently cooled to −35° C. to about −45° C. N-methylmorpholine (1.18 vol) were then added to the flask while maintaining the temperature between −30° C. and −40° C. Isobutyl chloroformate (0.58 vol) were then added to the flask while maintaining the temperature between −30° C. and −40° C.

To a separate vessel (vessel B), (3S)-amino-3-(4-fluorophenyl)propan-1-ol (0.76 wt) and THF were added and the vessel was mixed thoroughly until the bulk solids dissolved.

The (3S)-amino-3-(4-fluorophenyl)propan-1-ol solution of vessel B was then added to the reaction vessel A while maintaining the temperature between −30° C. and −40° C. The flask contents were then allowed To a suitably sized flask (vessel A), 2-[1-(4-fluorophenyl)-3-hydroxypropylcarbamoyl]thiazolidine-3-carboxylic acid tert-butyl ester (1 wt) was added, followed by dichloromethane. The flask contents were subsequently cooled to −15° C. to −20° C. Hydrochloric acid (3.3 vol) was then added to the flask while maintaining the temperature between −15° C. and −20° C. until the reaction was observed to be complete. The reaction mixture was then cooled to −35° C. to −40° C. and tetrahydrofuran was added to the mixture while maintaining the temperature between −30° C. and −40° C. N,N-diisopropylethylamine was then added to the mixture (8.16 vol) while maintaining the temperature between −15° C. and −45° C. 4-dimethylaminopyridine (0.032 wt) was then added to the vessel while maintaining the temperature between −15° C. and −45° C.

In a separate vessel (vessel B), 4-biphenylsulfonyl chloride (0.85 wt) was added, followed by THF.

The 4-biphenylsulfonyl chloride solution from vessel B was added to the reaction vessel A while maintaining the temperature between −15° C. and −45° C. The contents of the reaction mixture were then allowed to warm to 15° C. to 25° C. over a period of 1 h to 24 h. Ethyl acetate was subsequently added to the flask, followed by saturated aqueous ammonium chloride solution. The organic phase was separated and washed with saturated aqueous ammonium chloride solution followed by saturated aqueous hydrogen carbonate solution. The organic phase was then dried over sodium sulfate and filtered. The filtrate was concentrated at 35° C. to 40° C. until a solid residue was obtained. Dichloromethane was then added to the residue and mixed at 30° C. to 35° C. After evaporation, ethyl acetate was then added to the residue, and the slurry was transferred to a suitable vessel. The stirred slurry was then warmed to reflux, and then cooled to 0° C. to 5° C. The precipitated solid was collected by filtration. The filter cake was washed with ethyl acetate followed by tert-butyl methyl ether and the filter cake was pulled dry for 1 h to 24 h under nitrogen to yield 3-(biphenyl-4-sulfonyl)thiazolidine-2-carboxylic acid [1-(4-fluorophenyl)-3-hydroxypropyl]-amide.

Stage 3A: Preparation of 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester

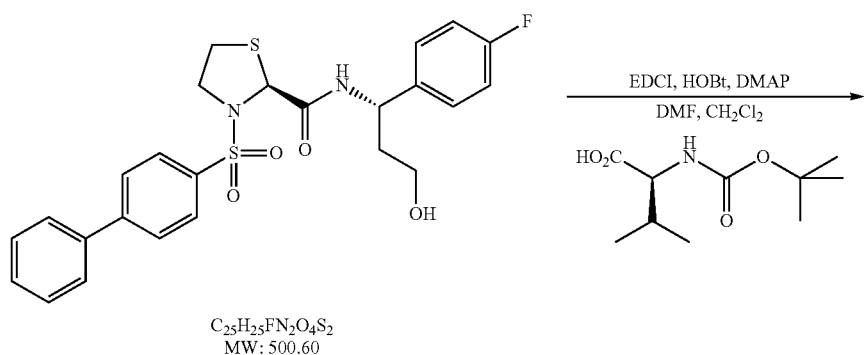

$C_{25}H_{25}FN_2O_4S_2$
MW: 500.60

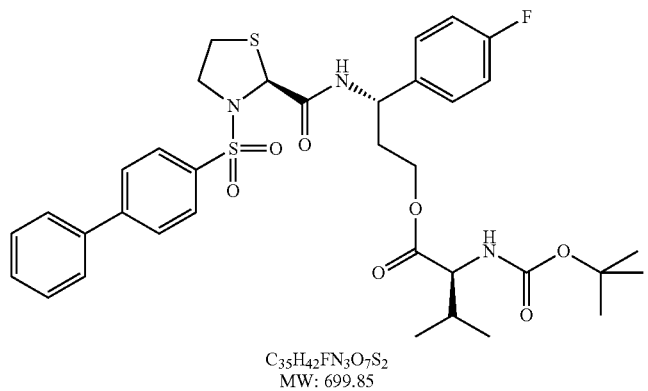

$C_{35}H_{42}FN_3O_7S_2$
MW: 699.85

To a suitably sized flask (vessel A), Boc-L-valine (0.48 wt), dichloromethane, and N,N-dimethylformamide were added and the mixture was subsequently stirred under nitrogen at 15° C. to 25° C. 1-hydroxybenzotriazole (HOBt, 0.3 wt) and 1-(3-dimethylaminopropyl)-3-ethylcarbodiimide hydrochloride (EDCI, 0.42 wt) were then added to the vessel while maintaining the temperature at 15° C. to 25° C. The mixture was subsequently stirred at 15° C. to 25° C. until the bulk solids dissolved in order to yield solution A.

To a separate vessel (vessel B), 3-(biphenyl-4-sulfonyl)thiazolidine-2-carboxylic acid [1-(4-fluorophenyl)-3-hydroxypropyl]amide (1.0 wt), dichloromethane, and N,N-dimethylformamide were added, and the mixture was subsequently stirred at 15° C. to 25° C. under nitrogen. 4-dimethylaminopyridine (0.27 wt) was then added to the vessel while maintaining the temperature between 15° C. to 25° C. The mixture was stirred at this temperature until the bulk solids dissolved (typically 5 to 15 minutes) to yield solution B.

Solution A was then added to solution B while maintaining the temperature between 15° C. and 30° C. The mixture was stirred at this temperature until the reaction was observed to be complete. The reaction mixture was concentrated to remove volatile solvents. Ethyl acetate was subsequently added to the flask, followed by 10% w/w aqueous citric acid solution. The aqueous phase was separated and extracted with ethyl acetate. The combined organic phases were washed with a mixture of 10% w/w aqueous citric acid solution and saturated aqueous sodium chloride solution were added, followed by saturated aqueous ammonium chloride solution, saturated aqueous sodium hydrogen carbonate and saturated aqueous sodium chloride solution. The organic phase was then dried over magnesium sulfate, filtered, and the filter cake washed with ethyl acetate. The filtrates were concentrated until a solid residue was obtained to yield crude 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester.

Stage 3B: Purification of 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester

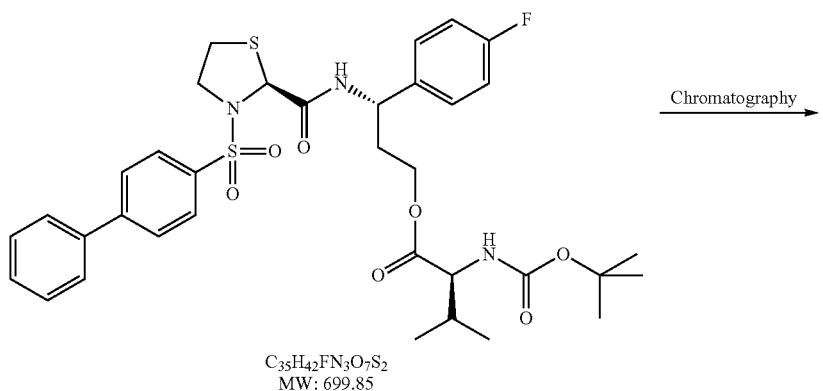

C35H42FN3O7S2
MW: 699.85

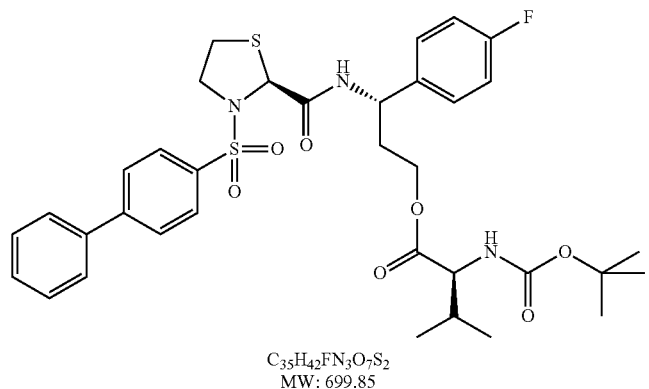

C35H42FN3O7S2
MW: 699.85

To purify 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester, the crude product (1 wt) and dichloromethane were mixed in a vessel until the bulk solids dissolved. The solution was then loaded on to silica followed by the addition of dichloromethane. The product was eluted with ethyl acetate:heptanes. Fractions containing the product were combined and concentrated to dryness under vacuum at a water bath temperature of 35° C. to 40° C. to yield purified 2-tert-butoxycarbonylamino-3-methylbutyric acid 3-([3-(biphenyl-4-sulfonyl)thiazolidine-2-carbonyl]amino)-3-(4-fluorophenyl)-3-propyl ester.

Stage 4: Preparation of 2-amino-3-methylbutyric acid 3-{[3-(biphenyl-4-sulfonyl)thiazolidine-2-carbonyl]amino}-3-(4-fluorophenyl) propyl ester methanesulfonate To a suitably sized flask, 2-tert-butoxycarbonylamino-3-methylbutyric acid 3-{[3-(biphenyl-4-sulfonyl)thiazolidine-2-carbonyl]amino}-3-(4-fluorophenyl)-3-propyl ester (1 wt) was added, followed by 1,4-dioxane and the mixture was stirred under nitrogen. Methanesulfonic acid (0.18 wt) was subsequently added, and the flask contents were heated to 68° C. to 73° C. The reaction was stirred at this temperature until the reaction was observed to be complete by $^1$H NMR analysis. The reaction mixture was subsequently cooled to 35° C. to 40° C. and concentrated to dryness at this temperature. The residue was then dissolved in THF and concentrated to dryness at 35° C. to 40° C. This azeo-drying cycle was repeated until the 1,4-dioxane content was less than 1.0% w/w to yield 2-amino-3-methylbutyric acid 3-{[3-(biphenyl-4-sulfonyl)thiazolidine-2-carbonyl]amino}-3-(4-fluorophenyl) propyl ester methanesulfonate.

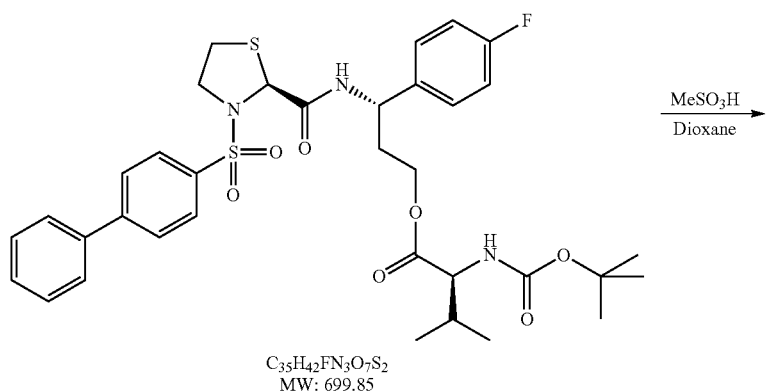

$C_{35}H_{42}FN_3O_7S_2$
MW: 699.85

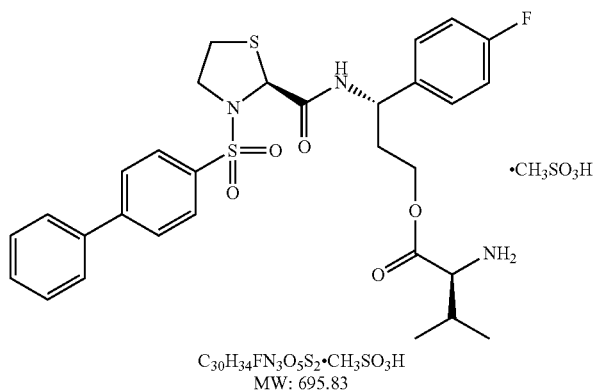

$C_{30}H_{34}FN_3O_5S_2 \cdot CH_3SO_3H$
MW: 695.83

Stage 5: Preparation of 2-amino-3-methylbutyric acid 3-{[3-(biphenyl-4-sulfonyl)thiazolidine-2-carbonyl]amino}-3-(4-fluorophenyl) propyl ester (Compound I)

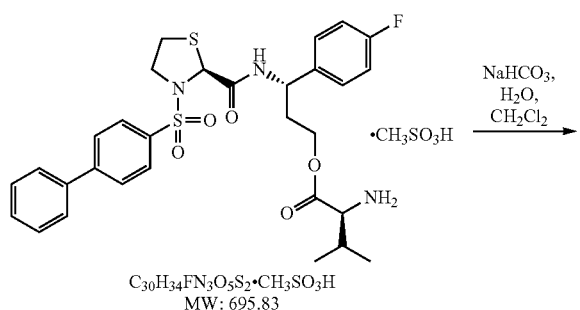

C$_{30}$H$_{34}$FN$_3$O$_5$S$_2$·CH$_3$SO$_3$H
MW: 695.83

↓ NaHCO$_3$, H$_2$O, CH$_2$Cl$_2$

C$_{30}$H$_{34}$FN$_3$O$_5$S$_2$
MW: 599.75

To a suitably sized flask, 2-amino-3-methylbutyric acid 3-{[3-(biphenyl-4-sulfonyl)thiazolidine-2-carbonyl]amino}-3-(4-fluorophenyl) propyl ester methanesulfonate (1 wt) was added, followed by dichloromethane. The flask contents were subsequently cooled to 5° C. to 15° C. Aqueous sodium hydrogen carbonate solution was added to the mixture while maintaining the temperature between 5° C. and 25° C. The phases were subsequently separated, and the organic phase was re-added to the vessel, followed by saturated aqueous sodium hydrogen carbonate solution while maintaining the temperature at 5° C. to 25° C. The aqueous and organic layers were then separated, and the organic phase was dried over magnesium sulfate, filtered, and the filter cake washed with dichloromethane. The combined organic layers were then concentrated to dryness at 40° C. to 45° C. until the dichloromethane content was 2% w/w to yield 2-amino-3-methylbutyric acid 3-{[3-(biphenyl-4-sulfonyl)thiazolidine-2-carbonyl]amino}-3-(4-fluorophenyl) propyl ester (compound I).

Stage 6: Preparation of 2-amino-3-methylbutyric acid 3-{[3-(biphenyl-4-sulfonyl)thiazolidine-2-carbonyl]amino}-3-(4-fluorophenyl) propyl ester hydrochloride (Compound III)

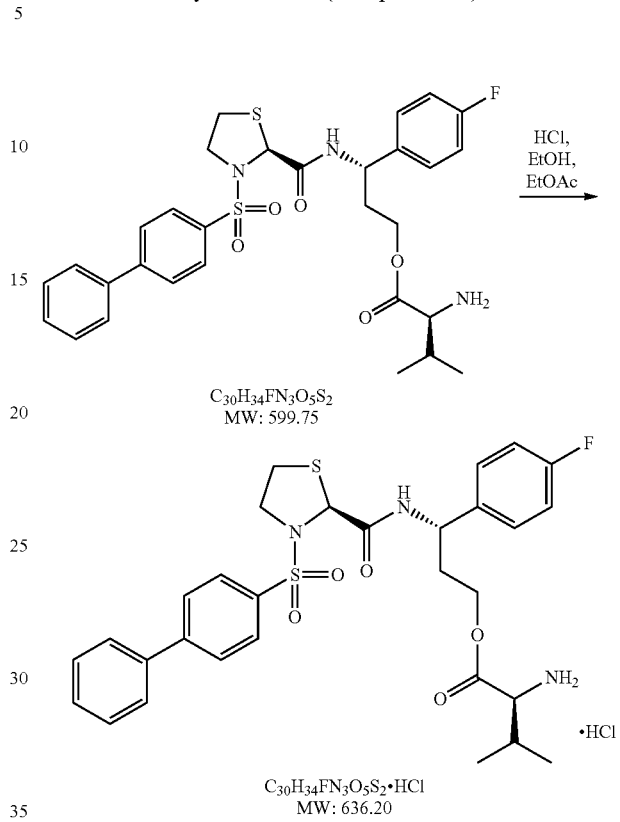

C$_{30}$H$_{34}$FN$_3$O$_5$S$_2$
MW: 599.75

↓ HCl, EtOH, EtOAc

C$_{30}$H$_{34}$FN$_3$O$_5$S$_2$·HCl
MW: 636.20

To a suitably sized flask, water (1.66 vol) was added, followed by hydrochloric acid (0.18 vol), and the temperature of the mixture was adjusted to 15° C. to 25° C. The solution was then filtered, and the filtered solution was added to a suitably sized flask (vessel A) followed by ethanol and ethyl acetate. The resulting mixture was stirred under nitrogen at 15° C. to 25° C. for at least 5 minutes.

In a suitably sized vessel (vessel B), 2-amino-3-methylbutyric acid 3-{[3-(biphenyl-4-sulfonyl)thiazolidine-2-carbonyl]amino}-3-(4-fluorophenyl) propyl ester (1 wt) was added, followed by ethanol. The contents of the flask were subsequently mixed to dissolve the bulk solids and clarify the solution.

The solution of vessel B was then added to vessel A while maintaining the temperature at 15° C. to 25° C. The stirred mixture was cooled to 0° C. to 5° C. and stirred at this temperature for 50 to 70 minutes. The solid was collected by filtration and the filter cake pulled dry under nitrogen for at least 12 hours to yield crude 2-amino-3-methylbutyric acid 3-{[3-(biphenyl-4-sulfonyl)thiazolidine-2-carbonyl]amino}-3-(4-fluorophenyl) propyl ester hydrochloride.

Example 2. Pharmacodynamic Properties of Compound I and Salts Thereof

Non-Clinical Pharmacology

Compound I and salts thereof are rapidly converted to compound II following gastro-intestinal tract administration. Compound II is a competitive and reversible prostaglandin F2α receptor antagonist (human FP2α receptor $K_i$=6 nM) that is under development for the management of preterm labor by inhibition of premature uterine contractions. Efficacy pharmacology (tocolytic effect) has been demonstrated in a model of spontaneous uterine activity in late-term pregnant rats.

In Vitro Pharmacology

The potency of inhibition of compound I and compound II on prostaglandin F2α receptor was assessed by analyzing the affinity of these compounds for recombinant FP receptor expressed in HEK293-EBNA cells. The results show high binding affinity of compound I and compound II to the human receptor (see Table 2).

Selectivity of compound II was tested against all eight prostaglandin receptor subtypes. Selectivity was approximately 10-fold versus prostaglandin E receptor 2 (EP2) and higher than 100-fold against other receptors. Testing the effect of 1 μM compound II against a panel of 50 receptors, channels and enzymes binding sites showed high selectivity for FP.

The functional characterization of compound II on human FP was performed in transfected HEK293-EBNA cells. Compound II was able to dose-dependently inhibit the synthesis of IP3 with $IC_{50}$ value 60 nM. When added alone to FP/HEK293-EBNA cells, compound II tested up to 10 μM did not induce any synthesis of IP3, indicating that the compound is devoid of agonist activity.

In Vivo Pharmacology

The tocolytic effects of compound I and compound II were investigated in a model of spontaneous uterine activity in late-term (19-21 days of gestation) anaesthetized pregnant rat (Kawarabayashi et al. Am. J. Obstet. Gynecol. 175:1348-1355 (1996) and Shinkai et al. J. Pharm. Pharmacol. 52:1417-1423 (2000)). Briefly, late-term pregnant female rats were anaesthetized with urethane. One pregnant uterine horn was exposed and a polyethylene catheter bearing on the tip a latex balloon filled with saline was inserted into the lumen. The catheter was connected to an amplifying/recording system via a pressure-transducer. Increasing doses of compound I (as mesylate salt) or compound II were orally administered or injected by a 10-min i.v. infusion. For the i.v. administration the uterine contractile activity was quantified by calculating the AUC during the 10 min injection period.

The percent variation of the AUC values relative to the spontaneous uterine response observed after each compound administration was calculated in comparison to the value recorded before the first dose-administration (basal value). The effect of compound I or compound II was evaluated by comparing pre- and post-treatment luminal uterine pressure values. For the oral administration the same computation procedure was applied at different time points after treatment. Statistical differences between treatment groups at each time-point were determined by using one-way ANOVA followed by Tukey test. Both compounds intravenously or orally administered were able to markedly reduce spontaneous uterine contractions by around 40-50% (maximal effect obtained at 30 mg/kg by i.v. route and 60 mg/kg by oral route). The intravenous activity was comparable or slightly higher than that of the tocolytic drug atosiban licensed in the European Union.

Figure 3:
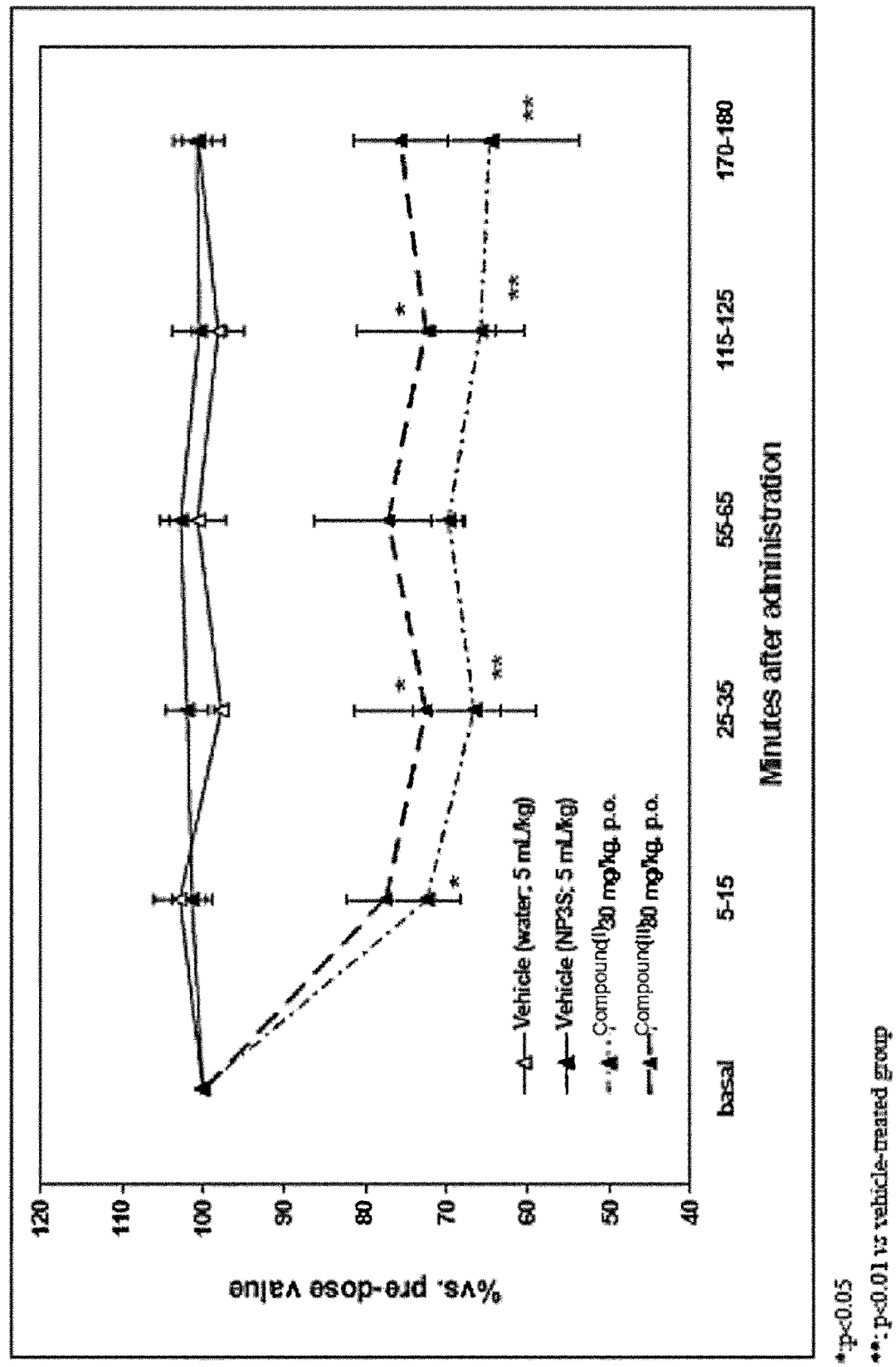
FIG. 3 is a graph demonstrating the effect of compound II and compound III on spontaneous uterine contractility in late-term pregnant rats following oral administration.
Figure 12:
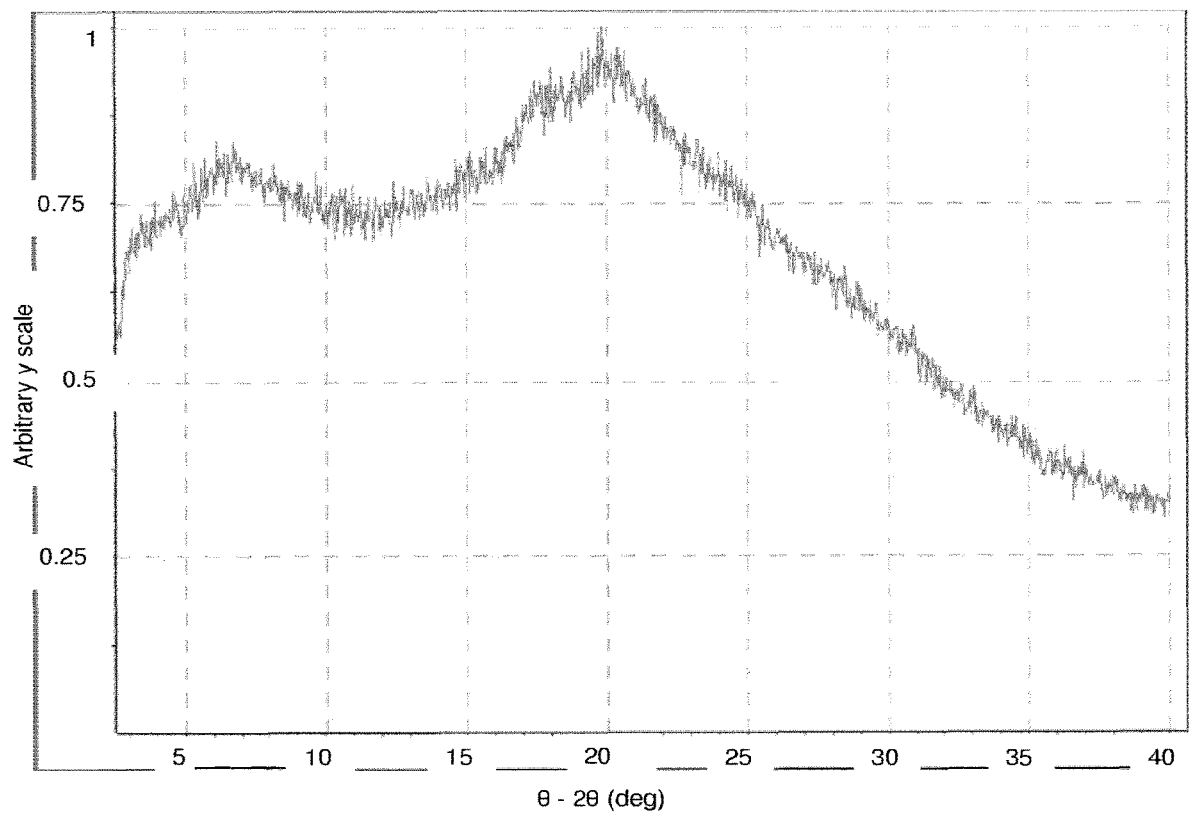
FIG. 12 shows an XRPD spectrum of the mesylate salt of compound I.

The inhibitory effect following the oral administration appeared with a fast onset (5-15 min after administration) and remained at sustained level up to the end of the observation period of 3 h. (FIG. 3)

By single oral dose, significant inhibition of uterine contractions are achieved at 30 mg/kg.

In vitro pharmacology studies thus showed the high affinity of compound I and compound II for the human FP receptor. When administered by the intravenous or oral route, these compounds were able to markedly reduce spontaneous uterine contractions by around 40-50% when investigated in a model of spontaneous uterine activity in late-term (19-21 days of gestation) anaesthetized pregnant rats.

Example 3. Crystal Screens of Compound I Salts

This example describes experiments conducted to generate and characterize crystalline salt forms of compound I.

Summary

The mesylate salt of compound I was determined to be amorphous by XRPD. Attempts to crystallize the material were not successful. The free base was synthesized from the mesylate salt and was used in the preparation of a variety of salts. A crystalline hydrosulfate salt was obtained directly from the salt synthesis. Three salts were crystallized using different solvent mixtures and crystallization techniques: hydrochloride, fumarate and dihydrophosphate. The hydrochloride salt appeared to exhibit low hygroscopicity, extended stability at elevated relative humidity (RH), and assumes a single crystal form when crystallized from a variety of distinct experimental conditions.

The crystalline HCl salt was obtained in two evaporation experiments and a slurry experiment. The same XRPD pattern was observed in each case. Based on thermal data, the material had some residual solvent; a probable melting point was approximately 146-147° C. Partial decomposition likely occurred during the melt. The hydrochloride salt was non-hygroscopic based on moisture balance data.

The crystalline hydrosulfate salt was likely solvated and decomposed above approximately 100° C. The material was stable at relative humidities up to approximately 65%.

The crystalline dihydrophosphate and fumarate salt were hygroscopic at approximately 65% RH. Attempts to scale up the salts were not successful due to high laboratory humidity. Thus, only partial characterization was available for these salts.

The hydrochloride, hydrosulfate, and fumarate salt showed comparable aqueous solubilities (below 1 mg/mL, see FIG. 8).

Experimental

X-ray powder diffraction analyses described herein were carried out on a Shimadzu XRD-6000 X-ray powder diffractometer using Cu Kα radiation. The instrument is equipped with a long fine focus X-ray tube. The tube voltage and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed each day to check the instrument alignment. Samples were analyzed with a silicon sample holder.

X-ray powder diffraction analyses described herein were also performed on an Inel XRG-3000 diffractometer, equipped with a curved position-sensitive detector with a 2θ range of 120°. Real time data was collected using Cu Kα radiation starting at approximately 4° 2θ at a resolution of 0.03° 2θ. The tube voltage and amperage were set to 40 kV and 30 mA, respectively. The monochromator slit was set at 5 mm by 160 μm. Patterns are displayed from 2.5 to 40° 2θ. Samples were prepared for analysis by packing them into thin-walled glass capillaries. Each capillary was mounted onto a goniometer head that is motorized to permit spinning of the capillary during data acquisition. The samples were analyzed for 5 or 10 min. Instrument calibration was performed daily using a silicon reference standard.

The DSC analyses described herein were carried out on a TA Instruments differential scanning calorimeter 2920. The instrument was calibrated using indium as the reference material. Samples were placed into a standard aluminum DSC pan, the pan was crimped, and the weight accurately recorded. The samples were equilibrated at 25° C. and heated under a nitrogen purge at a rate of 10° C./min up to 350° C. Indium metal was used as calibration standard.

The TG analyses described herein were carried out on a TA Instruments 2950 thermogravimetric analyzer. The calibration standards were nickel and ALUMEL™. Samples were placed in an aluminum sample pan and inserted into the TG furnace. The samples were first equilibrated at 25° C., then heated under a stream of nitrogen at a heating rate of 10° C./min up to 350° C.

The solution $^1$H nuclear magnetic resonance (NMR) spectra described herein were acquired at ambient temperature with a Varian UNITYINOVA-400 spectrometer at a $^1$H Larmor frequency of 399.8 MHz. Samples were dissolved in methanol-d4, methylene chloride-d2, or chloroform-d3. The spectra were acquired with a $^1$H pulse width of 7.8 or 8.6 μs, a 2.50 second acquisition time, a 5 second delay between scans, a spectral width of 4095 or 6400 Hz with 20474 or 32000 data points, and 16 or 40 co-added scans. The free induction decay (FID) was processed using the Varian VNMR 6.1C software with 65536 points and an exponential line broadening factor of 0.2 Hz to improve the signal-to-noise ratio. The spectra were referenced to internal tetramethylsilane (TMS) at 0.0 ppm or the residual solvent peak.

The FT-Raman spectra described herein were acquired on a FT-Raman 960 or 860 spectrometer (Thermo Nicolet). This spectrometer uses an excitation wavelength of 1064 nm. Approximately 0.5-0.7W of Nd:YVO$_4$ laser power was used to irradiate the samples. The Raman spectra were measured with an indium gallium arsenide (InGaAs) detector. The samples were prepared for analysis by placing the material in a glass capillary and then into a gold-coated capillary holder in the accessory. A total of 256 sample scans were collected from 3600 to 100 cm-1 at a spectral resolution of 4 cm-1, using Happ-Genzel apodization. Wavelength calibration was performed using sulfur and cyclohexane.

Moisture sorption/desorption (MB) data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Preparation of Compound I

Figure 15:
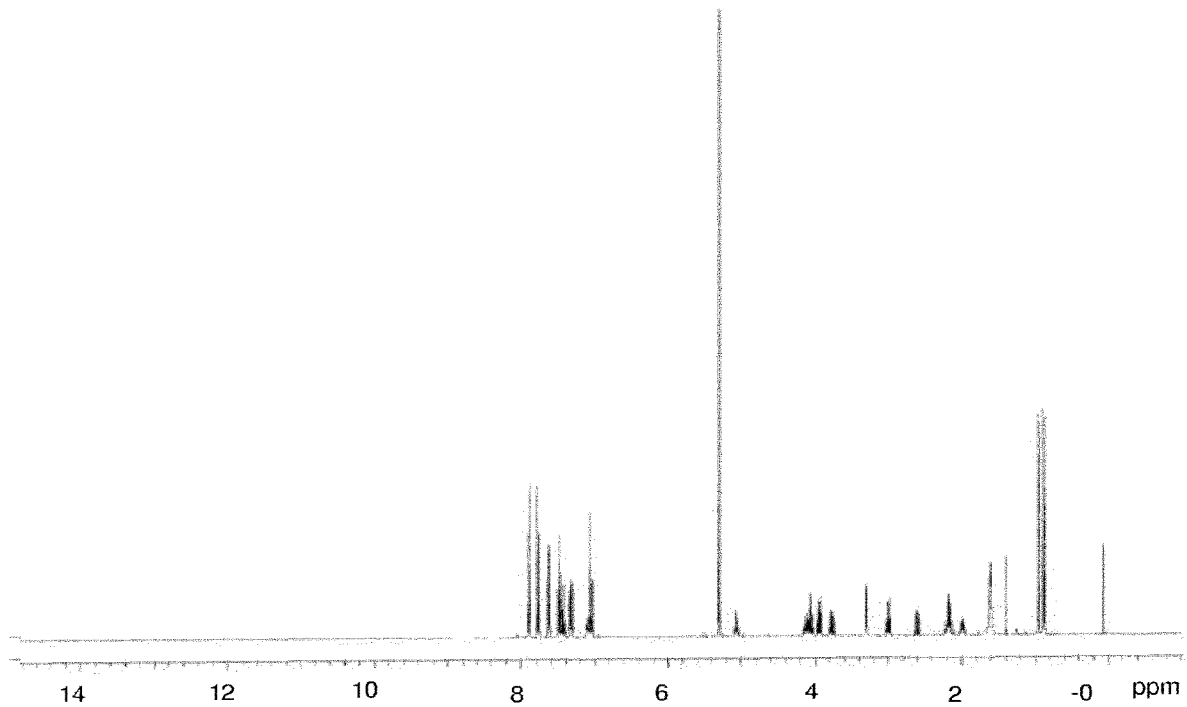
FIG. 15 shows a $^1$H NMR spectrum of the free base of compound I.
Figure 16:
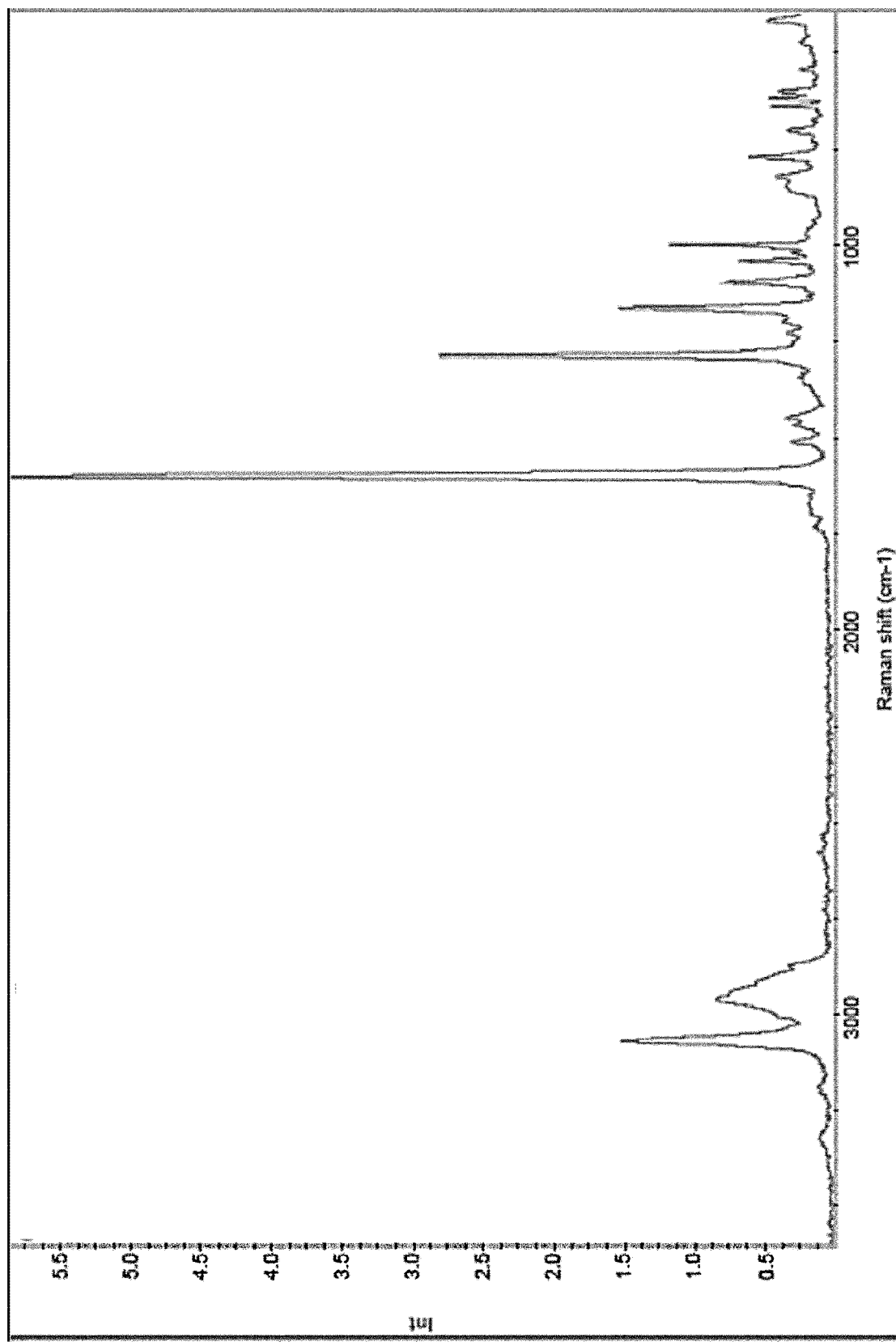
FIG. 16 shows a Raman infrared spectrum of the free base of compound I.
Figure 17:
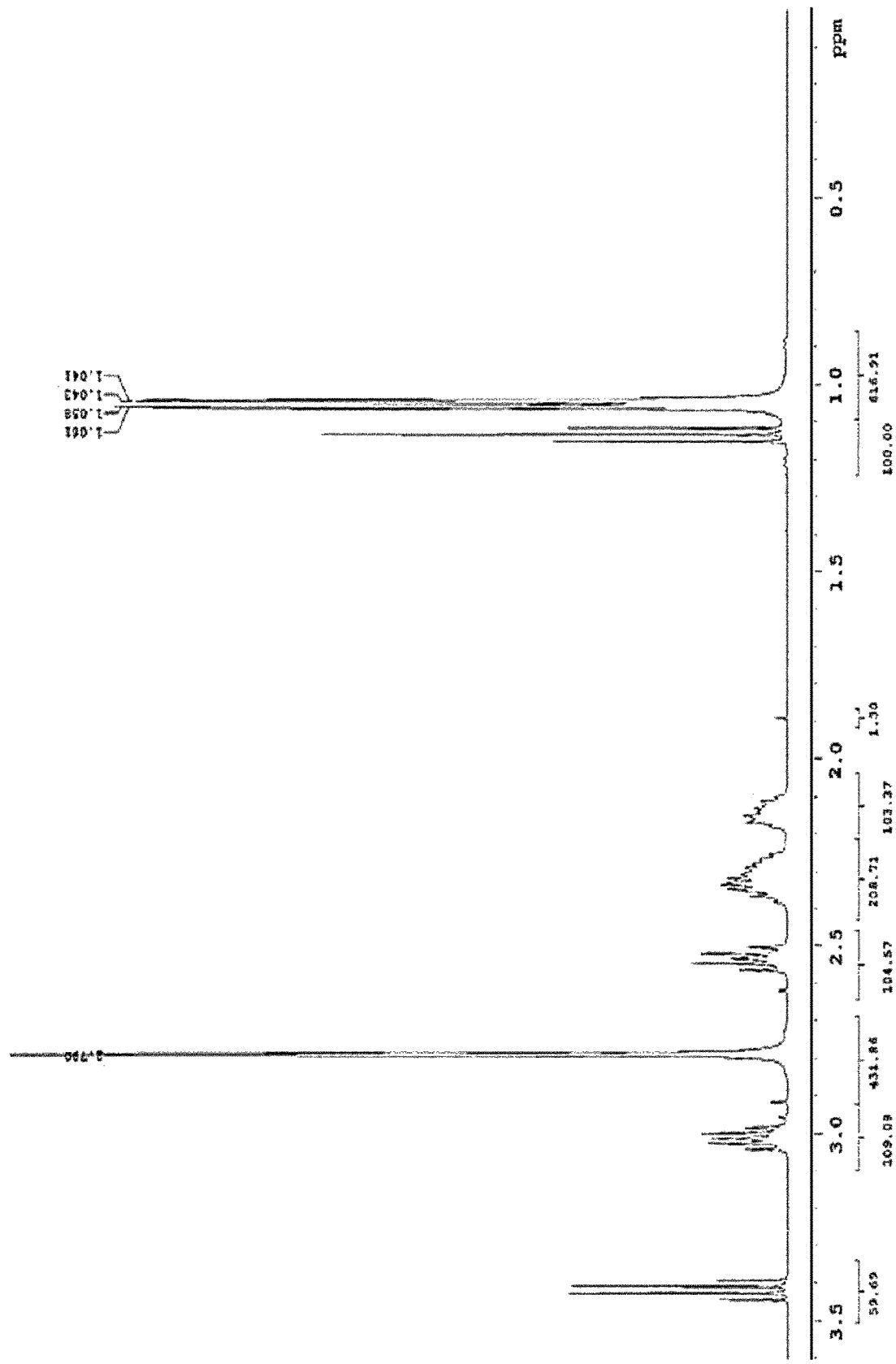
FIG. 17 shows a $^1$H NMR spectrum of the mesylate salt of compound I. The mesylate salt was prepared by addition of methanesulfonic acid to a solution of the free base of compound I in diethyl ether.

Multiple attempts were made to generate the free base of compound I from the mesylate salt, the results of which are described in FIG. 4. Initially, one equivalent of sodium hydroxide was used per equivalent of the salt. Proton NMR indicated presence of methanesulfonic acid peaks. A complete reaction was achieved when the mesylate salt in methylene chloride and a NaOH solution in water were mixed at a 1:2 salt:base ratio. The organic layer was separated after several washes and evaporated. The resulting paste-like or viscous oily material was dried in vacuum to yield an amorphous solid. The free base was analyzed by $^1$H NMR and Raman spectroscopy (FIG. 15 and FIG. 16, respectively). Subsequent salt screen studies used the free base as the starting material (summarized in FIGS. 5-7).

Salt Screen of Compound I

Twelve salts of compound I were prepared. A crystalline hydrosulfate salt was precipitated by addition of approximately 25 molar excess of sulfuric acid to a free base solution in acetone. The other salts from the synthesis step appeared to be non-birefringent by microscopy or amorphous by XRPD (FIGS. 5-7). The benzenesulfonate, citrate, ethanesulfonate, hydrochloride, hydrosulfate and sulfate salts were analyzed by proton NMR.

Crystallization experiments on the compound I salts are summarized in FIGS. 5-7. The following salts were crystallized: hydrochloride, fumarate, and dihydrophosphate.

The chloride salt was crystallized from a 1:1 mixture of acetone:toluene, a mixture of methylene chloride:ethyl ether, and an acetone slurry. The same XRPD pattern was observed in all the experiments and was designated as form A (FIG. 7). The crystalline fumarate salt was obtained from slow evaporation of a 1:1 methanol:toluene solution. The X-ray pattern was designated as pattern B. The hydrosulfate and dihydrophosphate salt exhibited very similar XRPD patterns (designated as pattern X). The counterions HSO$_4^-$ and H$_2$PO$_4^-$ are similar in size and small compared to the free base molecule, therefore, similar crystal structures are likely for the hydrosulfate and dihydrophosphate salt. Attempts to crystallize the mesylate salt yielded viscous or glassy solid materials.

Characterization of the Free Base and Mesylate Salt of Compound I

Figure 13:
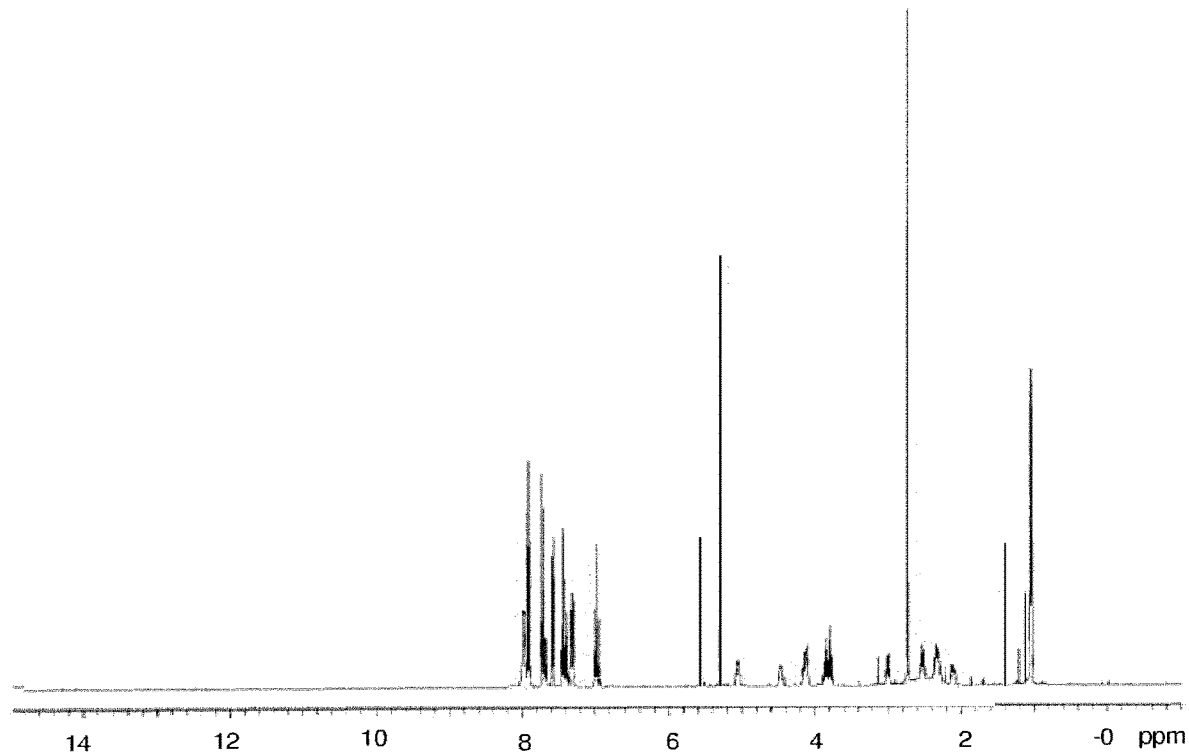
FIG. 13 shows a $^1$H NMR spectrum of the mesylate salt of compound I.
Figure 14:
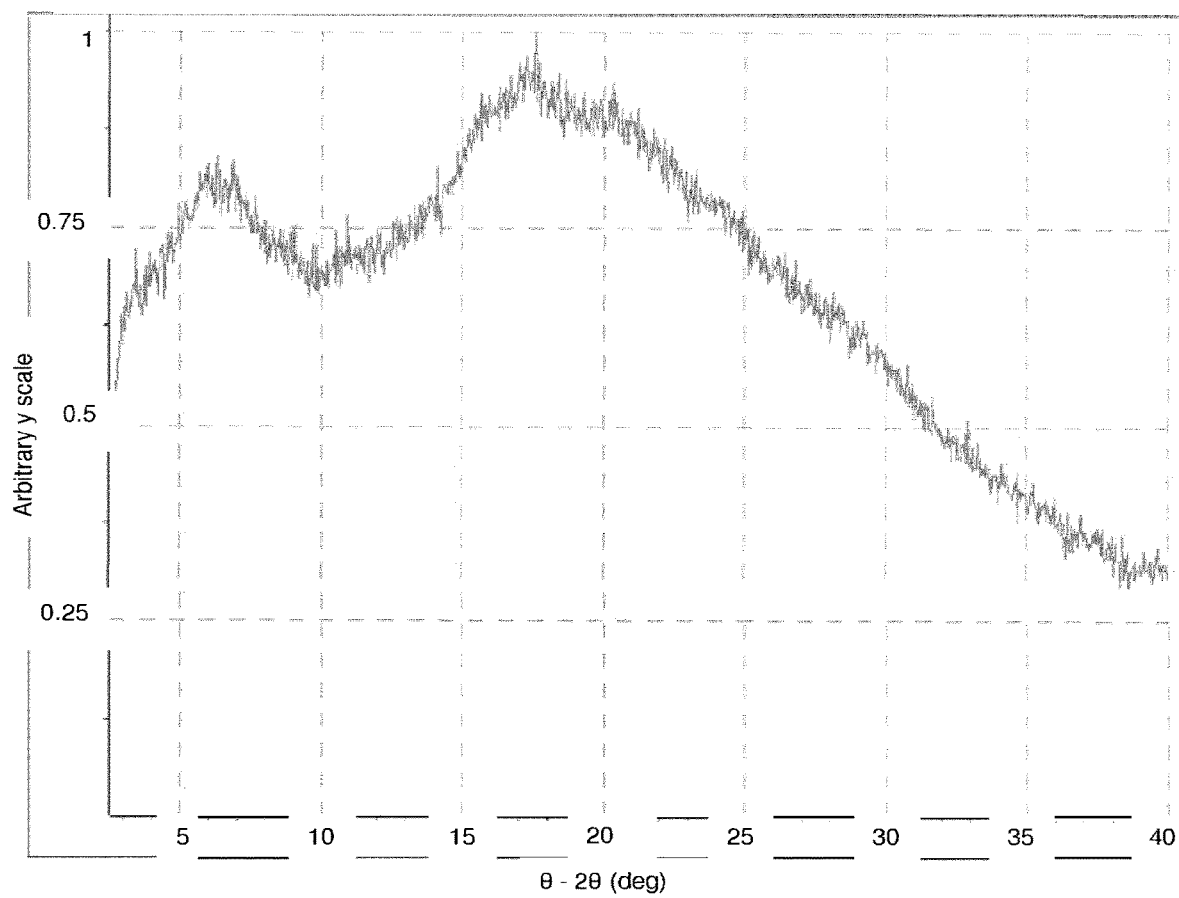
FIG. 14 shows an XRPD spectrum of the free base of compound I.
Figure 21:
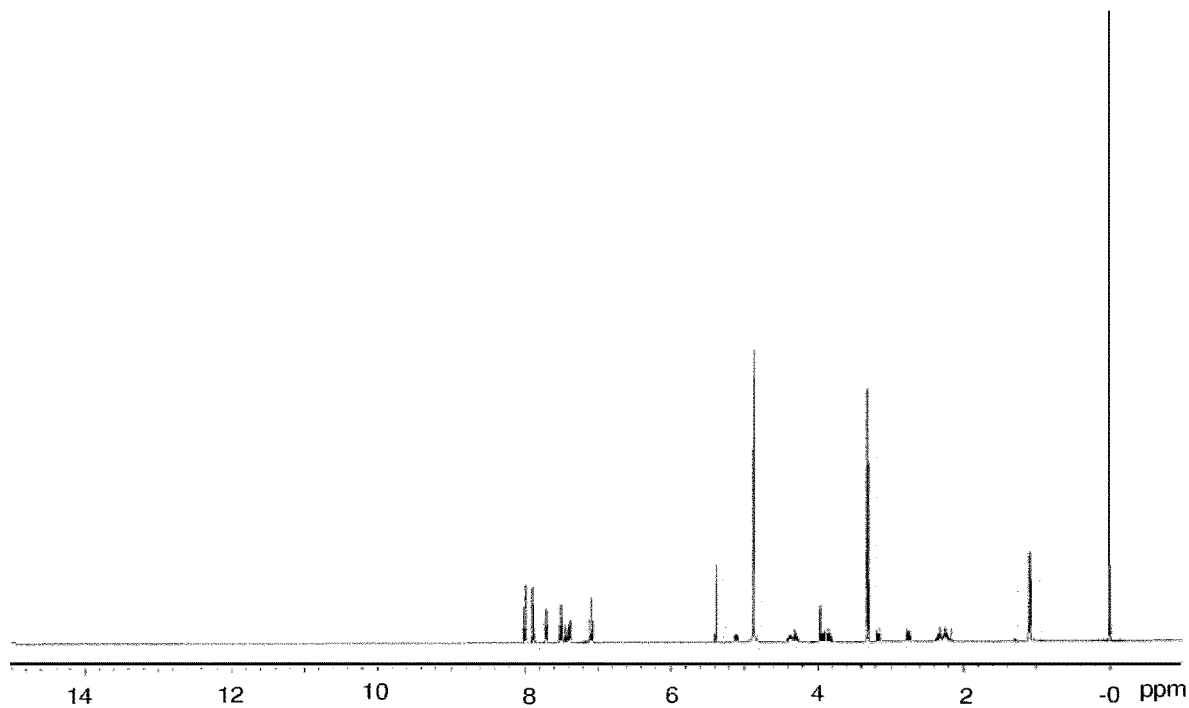
FIG. 21 shows a $^1$H NMR spectrum of the chloride salt of compound I as produced from a 1:1 acetone:toluene mixture.
Figure 21:
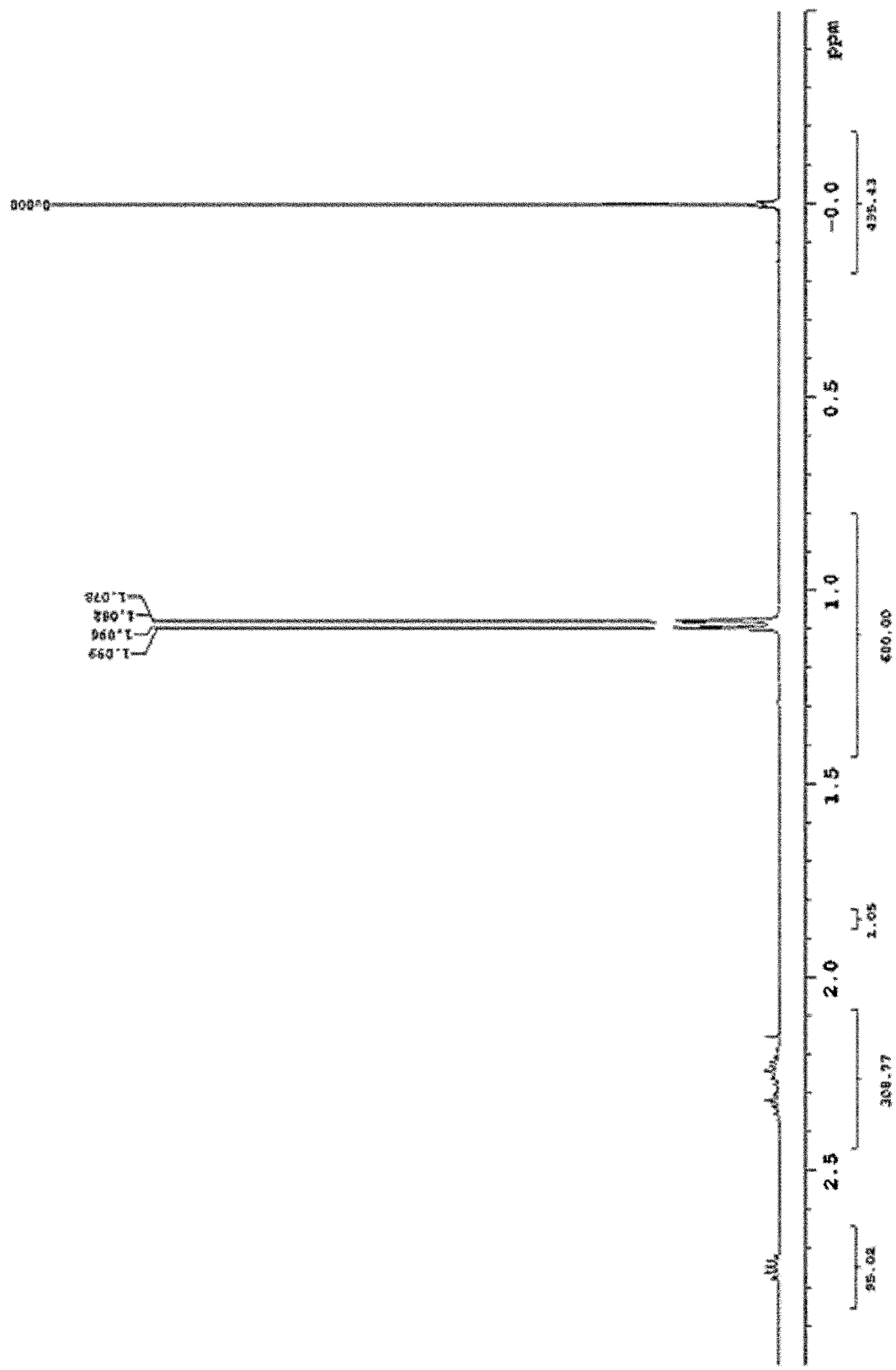
Figure 21:
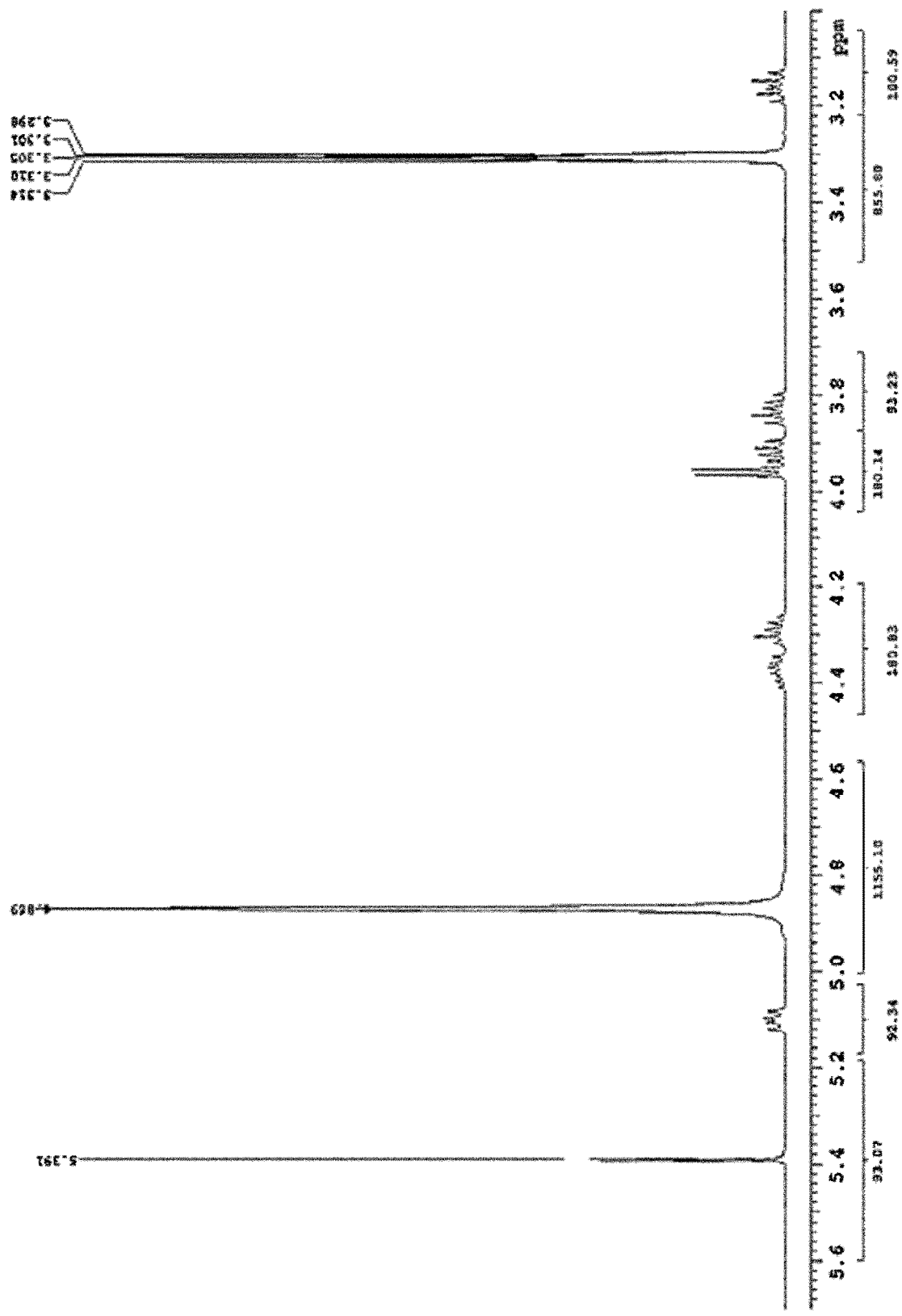
Figure 21:
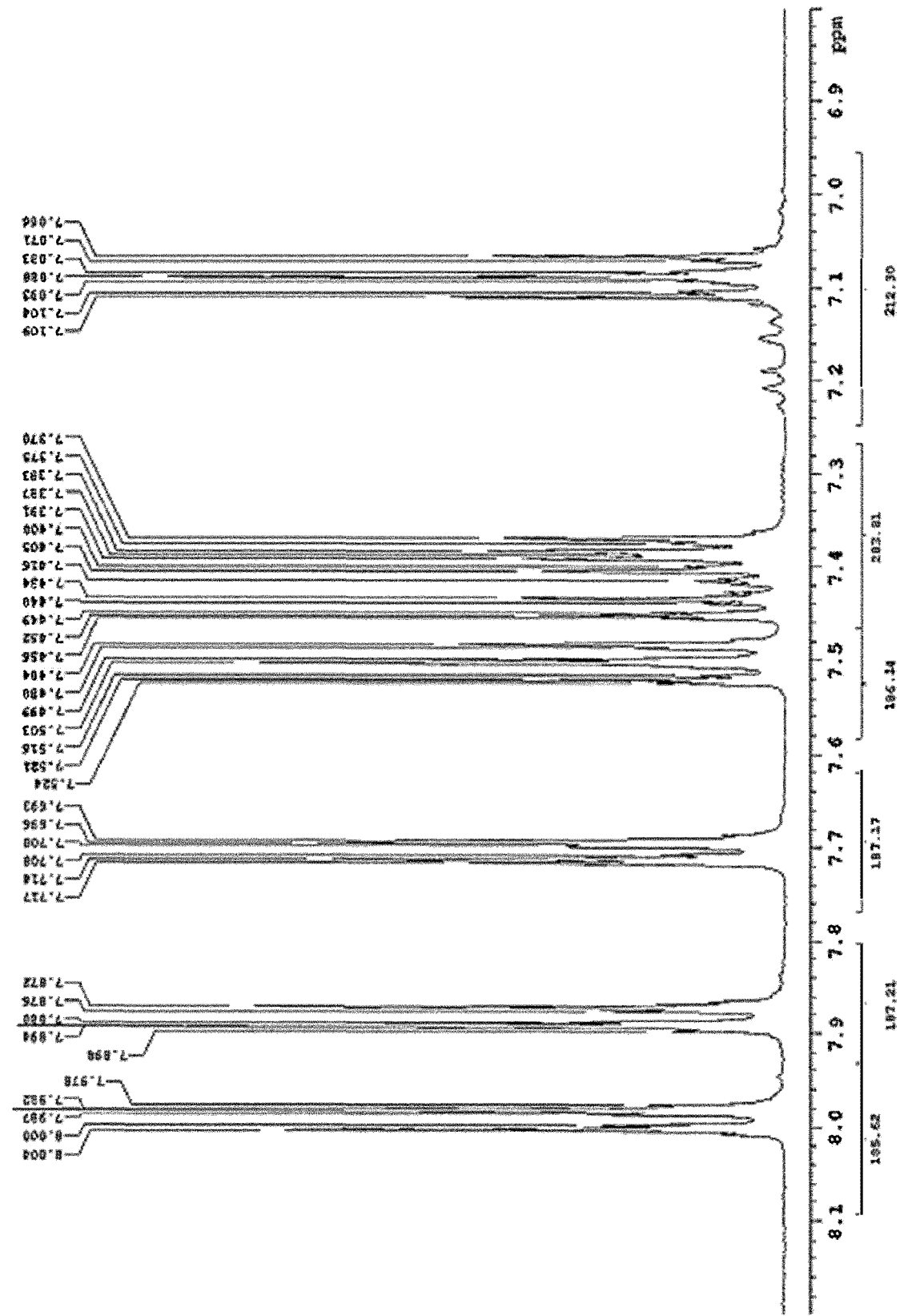

The proton NMR spectrum of the free base showed two doublets at approximately 1 ppm corresponding to the methyl groups of the valine fragment. The methyl groups are at the chiral carbon center and, therefore, are not equivalent in proton NMR. Two doublets for the methyl groups were observed for the following compound I salts: besylate, citrate, esylate, hydrosulfate (more overlapped) and sulfate (more overlapped). In the $^1$H NMR spectra of the mesylate salt and the chloride salt, the doublet at ~1 ppm corresponding to six hydrogen atoms resulted from a complete overlap of two doublets of the methyl groups (FIG. 13 and FIG. 21).

Figure 18:
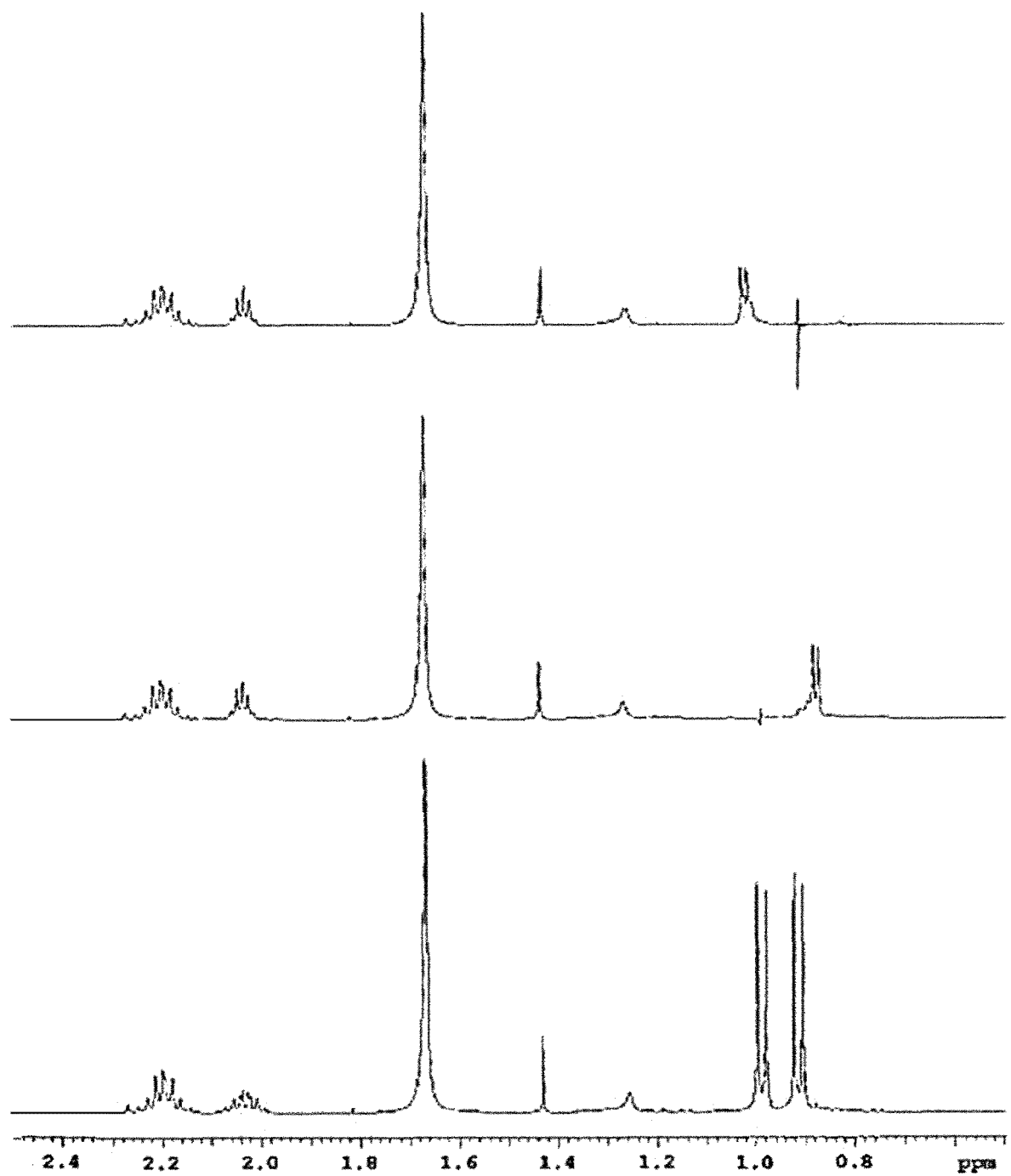
FIG. 18 shows a series of $^1$H NMR spectra of the free base of compound I recorded during homonuclear decoupling experiments.
Figure 19:
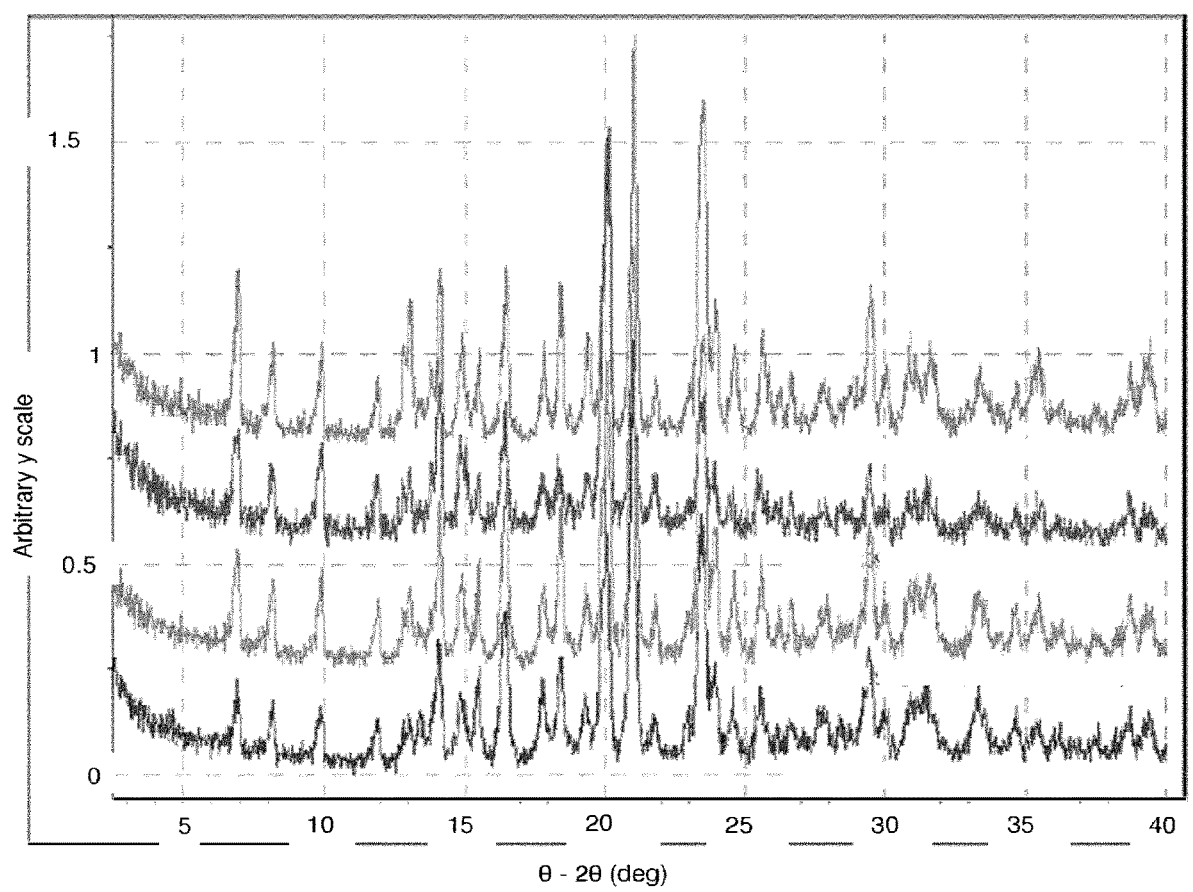
FIG. 19 shows a series of XRPD spectra of the chloride salt of compound I as produced from an acetone slurry (top), from evaporation of a methylene chloride:ethyl ether mixture (second from top), and from slow evaporation of a 1:1 acetone:toluene mixture (second from bottom and bottom).

A homonuclear decoupling $^1$H NMR experiment on the free base confirmed the methyne (CH) hydrogen multiplet at approximately 2 ppm (FIG. 18). A $^1$H NMR spectrum of the free base recorded in the absence of pre-irradiation of either methyl group is shown at the bottom of FIG. 18. Irradiation of each methyl group (top, middle) resulted in a simplified methyne multiplet with the same number of lines (5). If the two doublets corresponded to different diastereoisomers, two types of multiplets, the original and the simplified, would be observed.

Characterization of the Chloride Salt of Compound I (Compound III)

Figure 20:
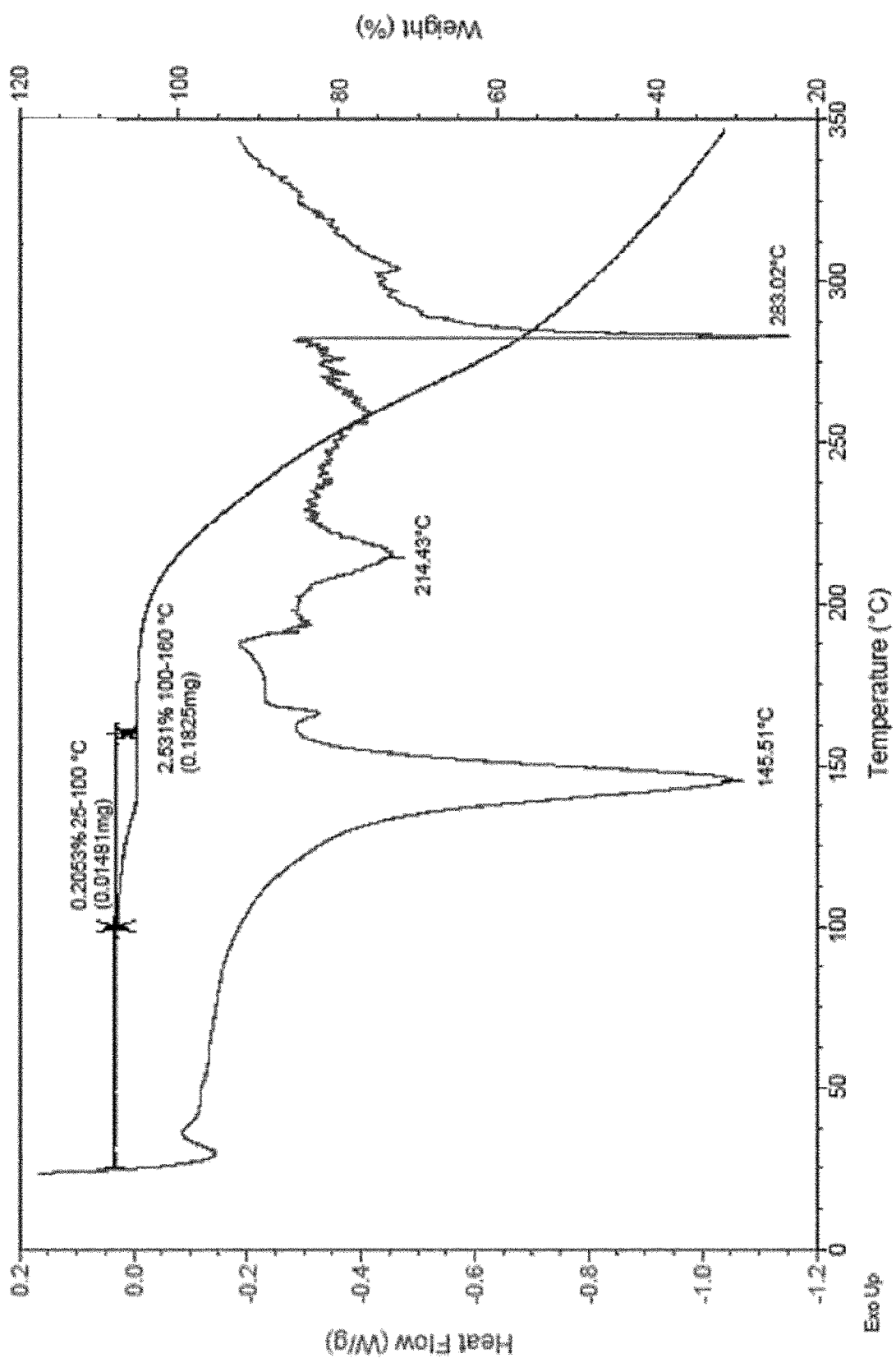
FIG. 20 shows an overlay of a differential scanning calorimetry curve (ranging from about −0.5 to about 1.3 W/g) and a thermogravimetric analysis curve (ranging from about 0% to about 100% by weight) recorded for the chloride salt of compound I as produced from an acetone slurry.
Figure 22:
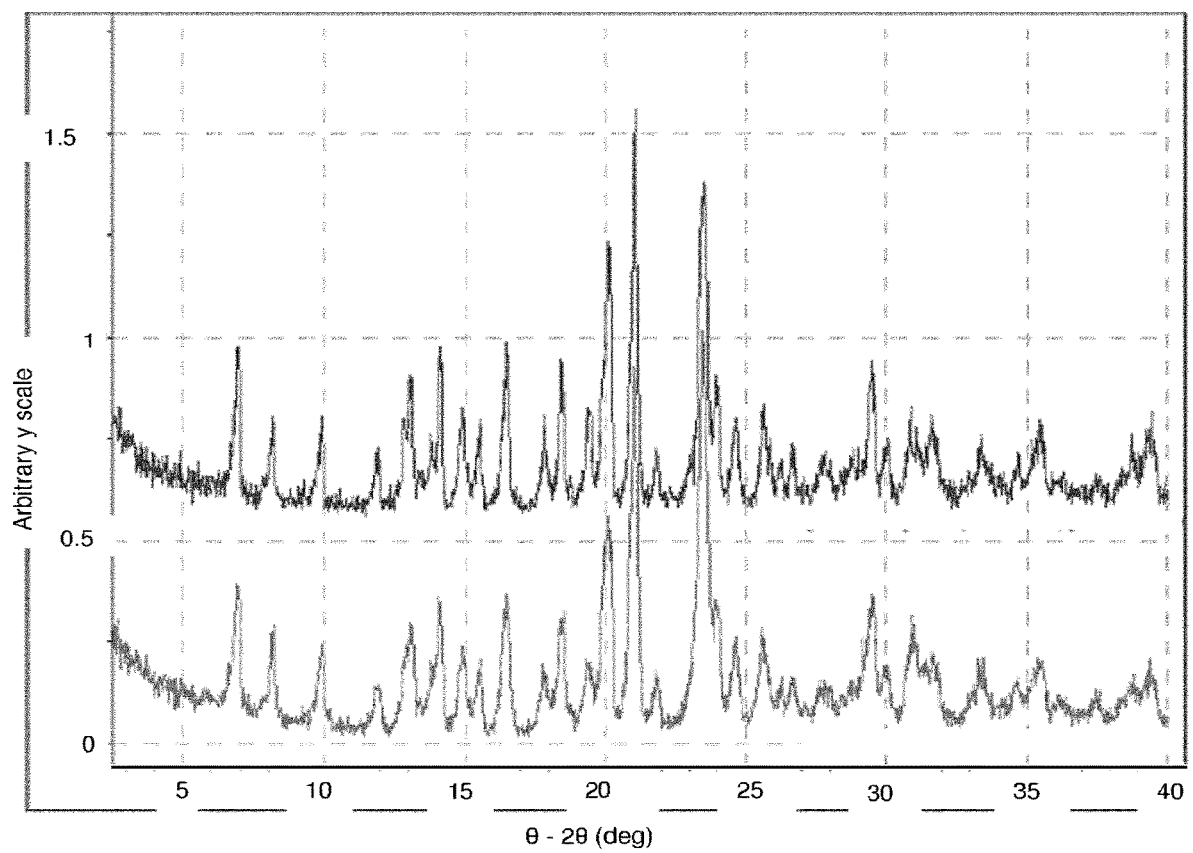
FIG. 22 shows a series of XRPD spectra of the chloride salt of compound I as produced from an acetone slurry (top) and after being vacuum-dried at about 50° C. for 1 day (bottom).
Figure 23:
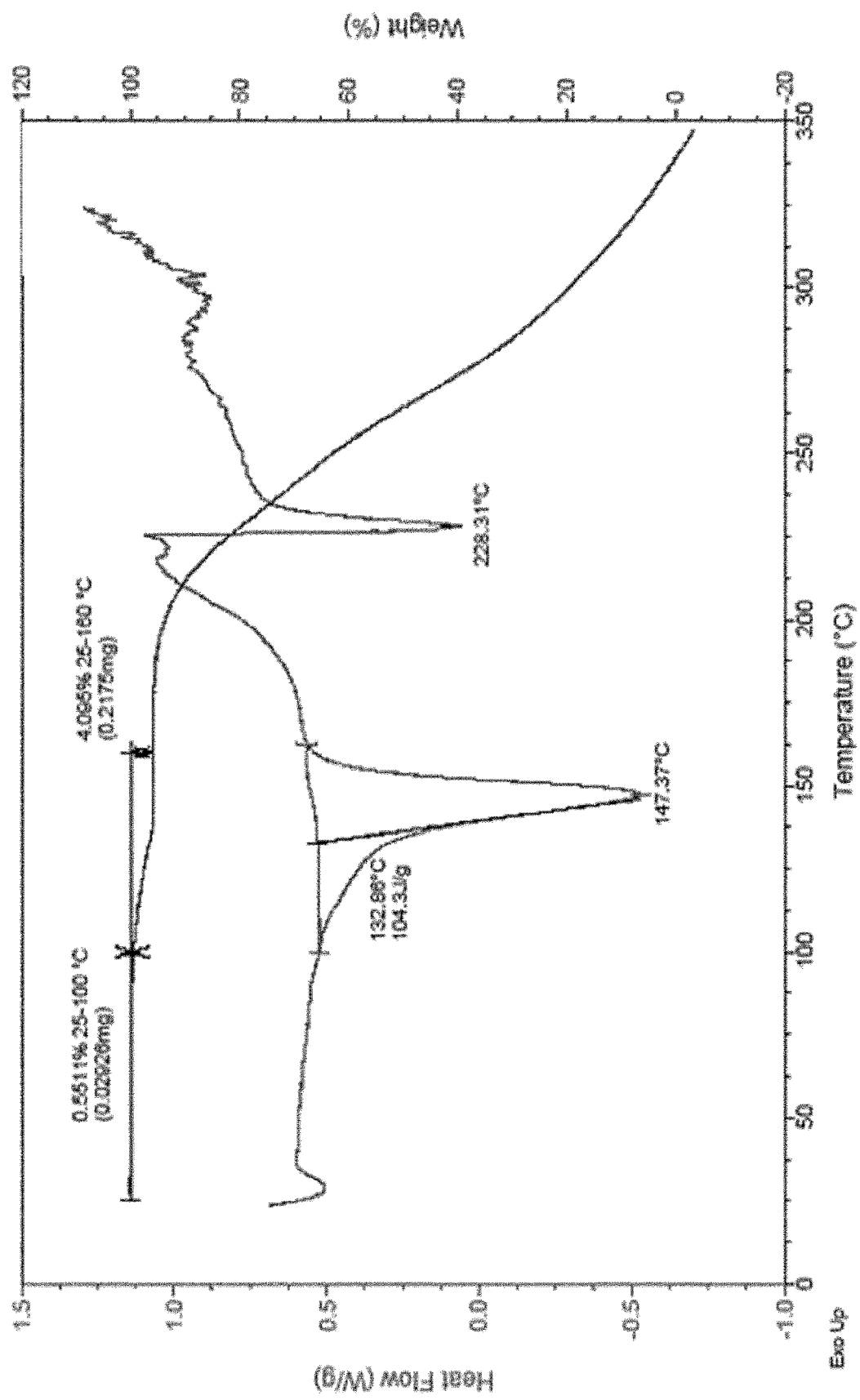
FIG. 23 shows an overlay of a differential scanning calorimetry curve (ranging from about −1.0 to about 0.2 W/g) and a thermogravimetric analysis curve (ranging from about 30% to about 100% by weight) recorded for the chloride salt of compound I after being vacuum-dried at about 50° C. for 1 day.
Figure 24:
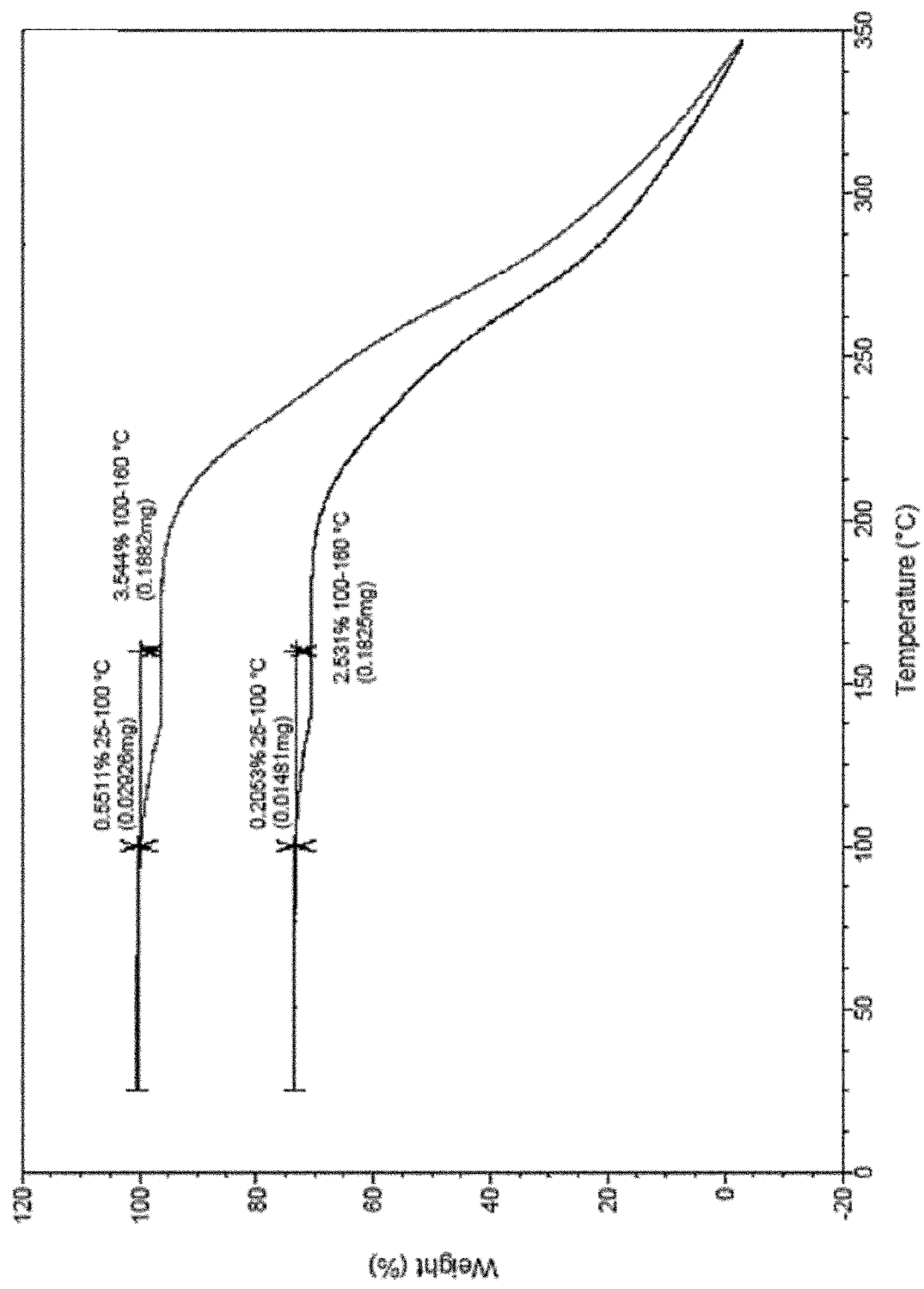
FIG. 24 shows an overlay of thermogravimetric analysis curves of the chloride salt of compound I as produced from an acetone slurry (top) and after being vacuum-dried at about 50° C. for 1 day (bottom).
Figure 25:
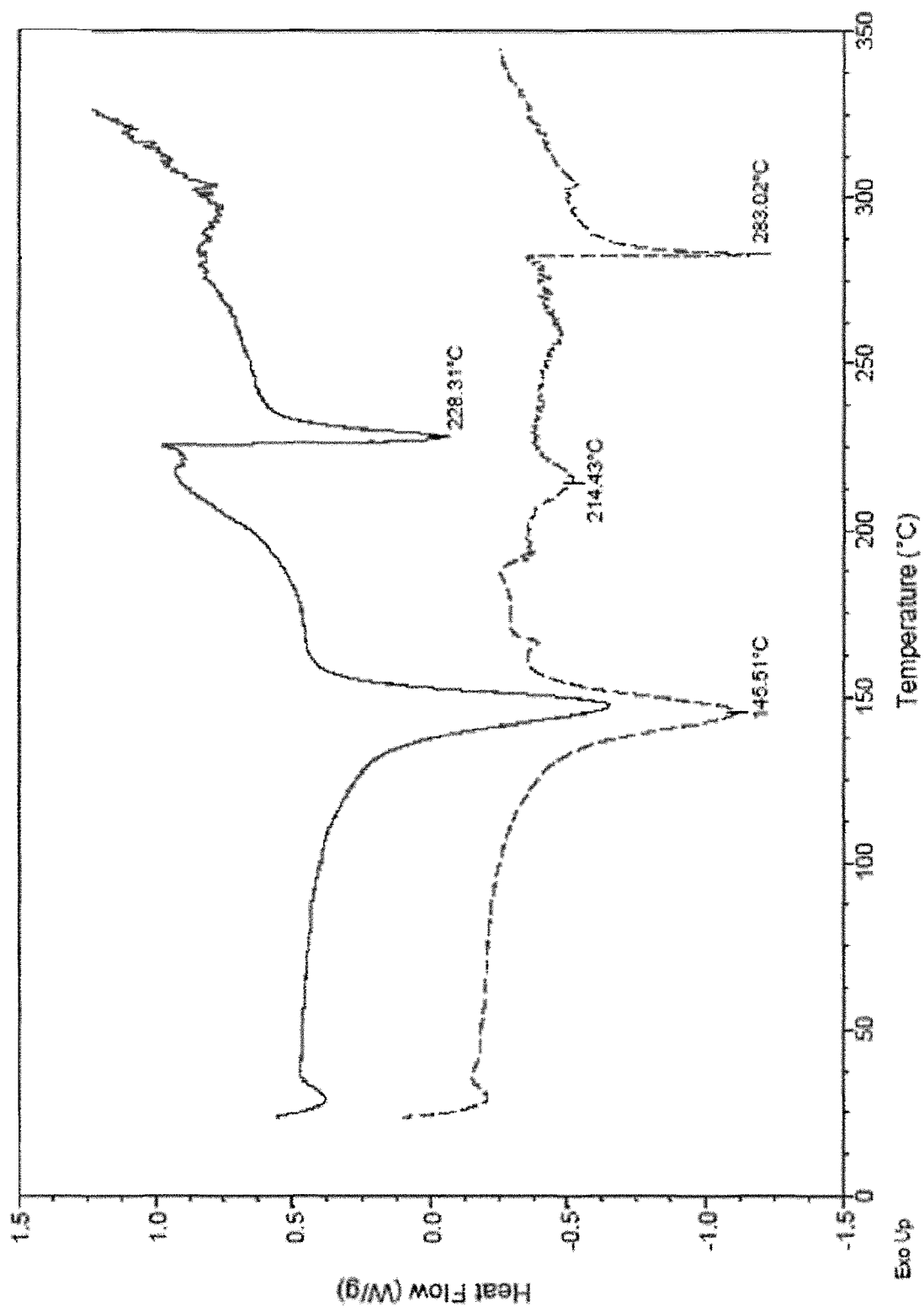
FIG. 25 shows an overlay of differential scanning calorimetry curves recorded for the chloride salt of compound I as produced from an acetone slurry (top) and after being vacuum-dried at about 50° C. for 1 day (bottom).

The crystalline chloride salt was analyzed by thermal techniques, $^1$H NMR and automated moisture sorption/desorption analysis. The endotherm at approximately 147° C. in DSC appeared broader than what is typically observed for the melting endotherm. A weight loss of approximately 4% was observed from 25 to 160° C. (acetone slurry sample analyzed, FIG. 20). The $^1$H NMR of the chloride salt was consistent with the structure (FIG. 21). However, the data cannot be correlated with the weight loss in the thermal analyses because a different sample was analyzed (slow evaporation of a 1:1 acetone:toluene mixture). The chloride salt from an acetone slurry was vacuum-dried at approximately 50° C. for 1 day. The resulting sample was similar to the original salt by XRPD (FIG. 22). The thermal data are presented in FIG. 23. Based on comparison of the thermal data, the dried material had lower weight losses between 25 and 100° C. (0.2% vs. 0.6% for the original chloride salt) and 100 and 160° C. (2.5% vs. 3.5%) (FIG. 24). This indicated that some solvent had been removed on vacuum drying. However, the endotherm at approximately 146-147° C. in DSC was still broad (FIG. 25). Partial decomposition probably occurred during the melt (note the degrading baseline and the corresponding weight loss in TG).

Figure 26:
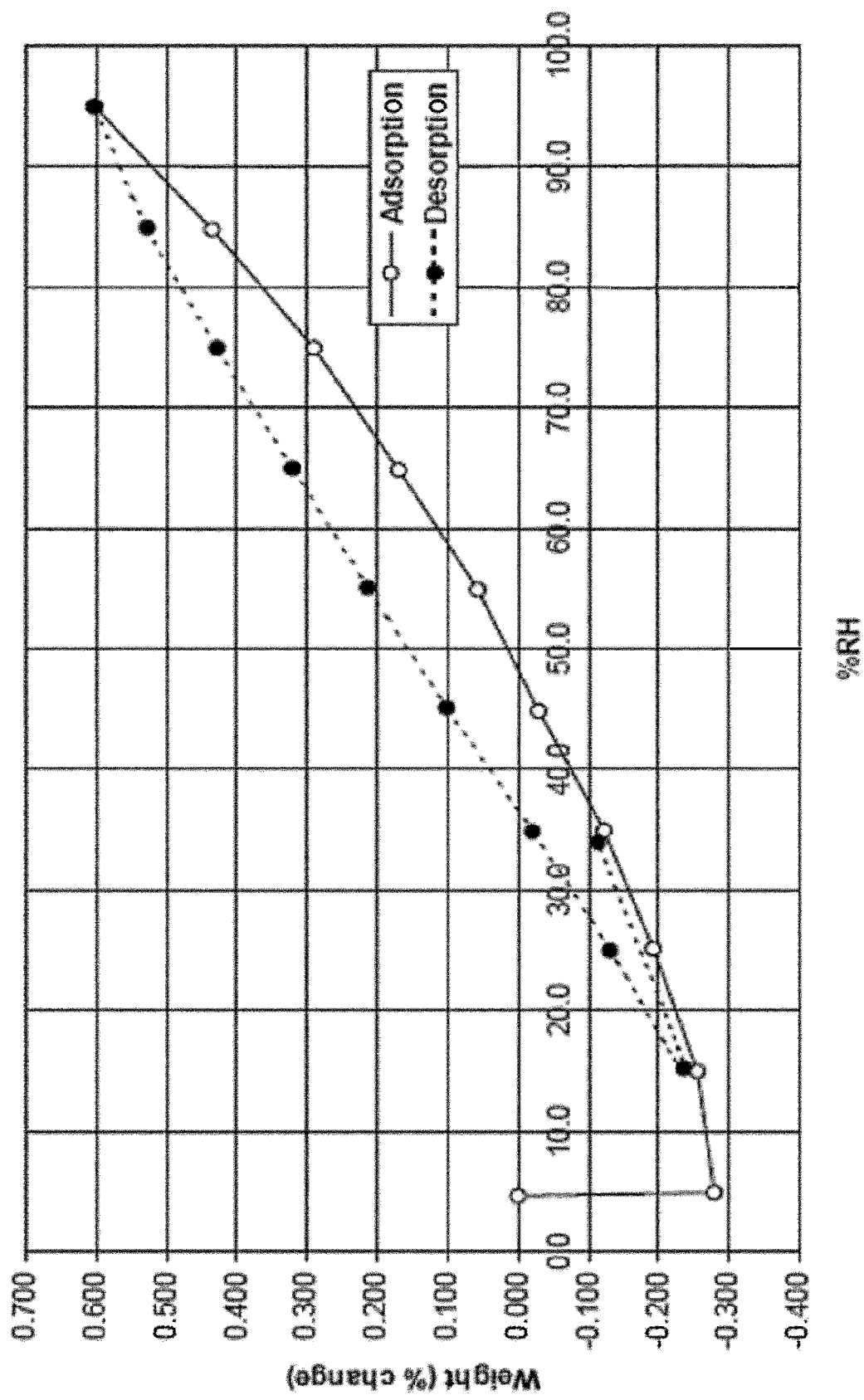
FIG. 26 shows a moisture sorption/desorption curve recorded for the chloride salt of compound I. Values on the y-axis show the percent change in the weight of the chloride salt as a function of the relative humidity (RH) in the atmosphere surrounding the salt.
Figure 28:
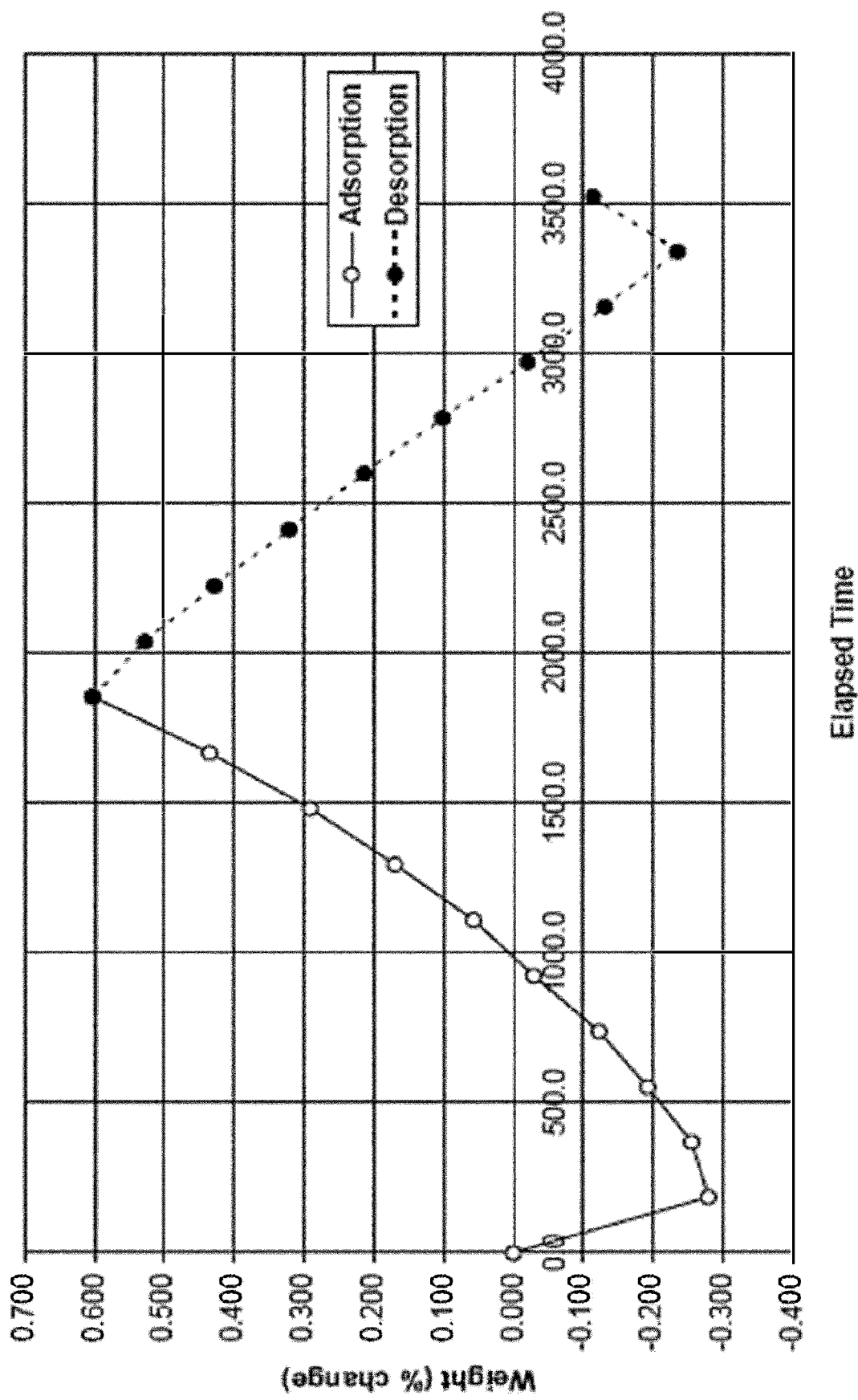
FIG. 28 shows a moisture sorption/desorption curve recorded for the chloride salt of compound I. Values on the y-axis show the percent change in the weight of the chloride salt as a function of the time over which the relative humidity in the atmosphere surrounding the salt was altered.
Figure 29:
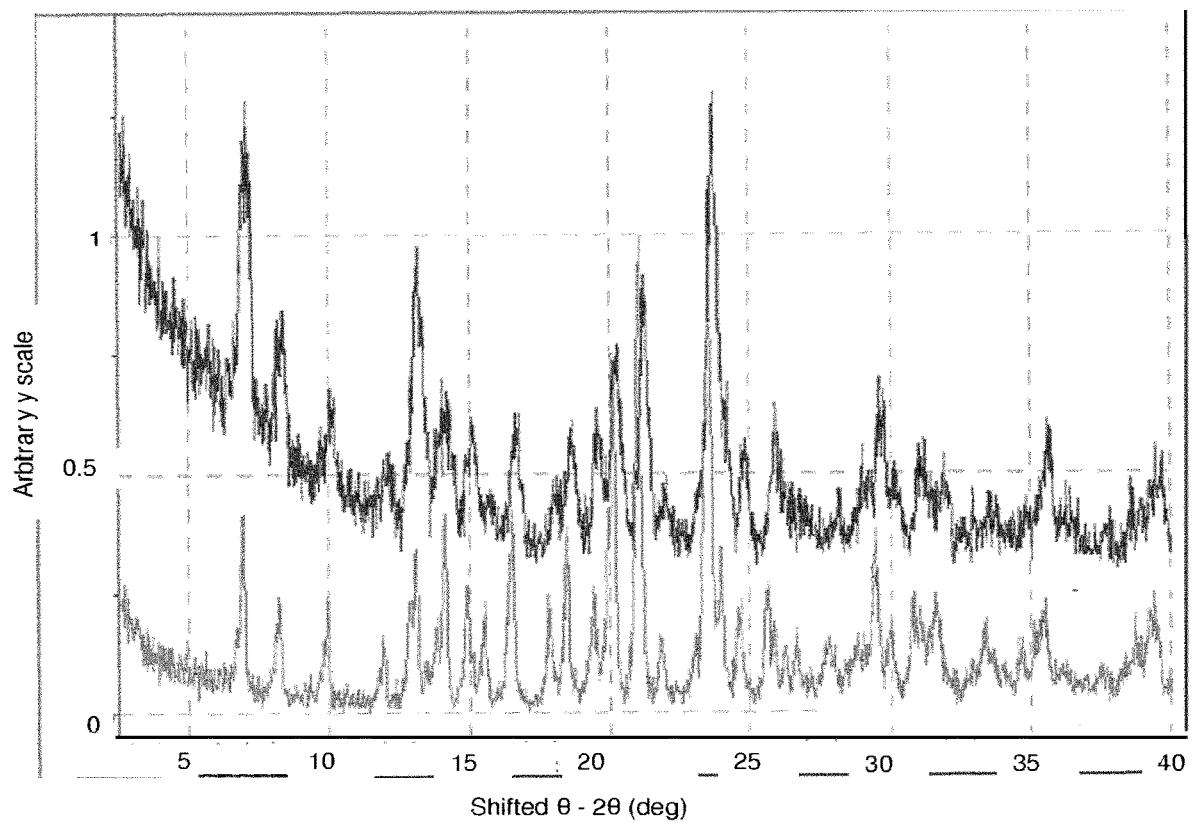
FIG. 29 shows an overlay of XRPD spectra of the chloride salt of compound I following (top) and prior to performing (bottom) moisture sorption/desorption experiments.
Figure 30:
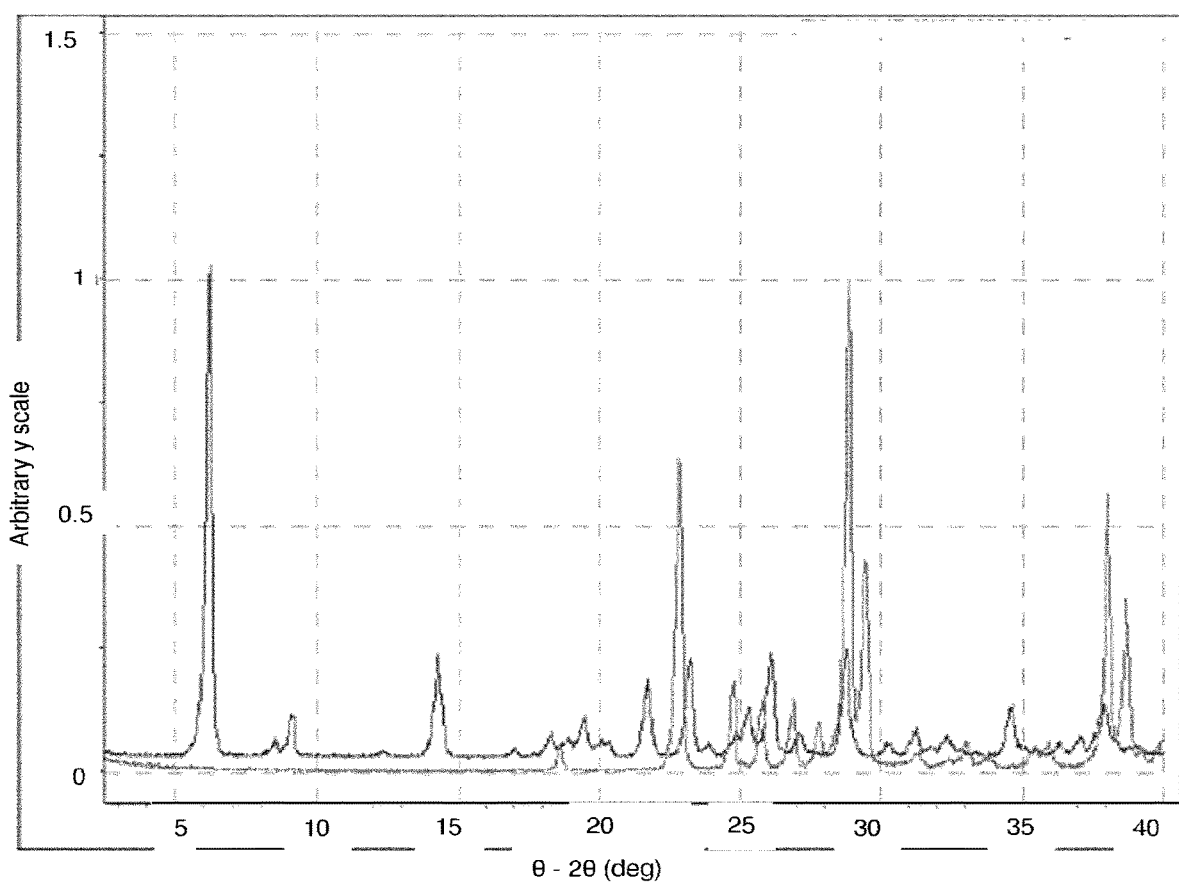
FIG. 30 shows an overlay of an XRPD spectrum of the fumarate salt of compound I produced by slow evaporation of a 1:1 methanol:toluene mixture (top) and an XRPD of fumaric acid (bottom).
Figure 31:
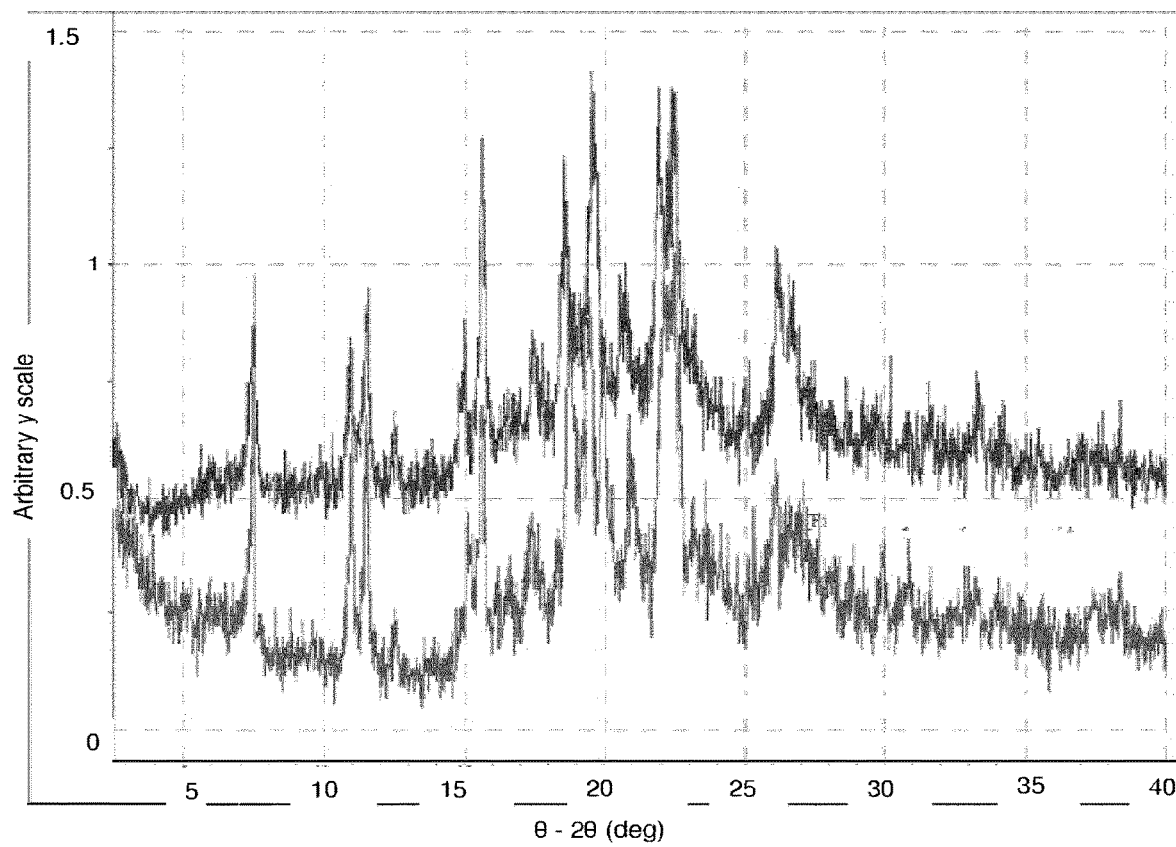
FIG. 31 shows an overlay of an XRPD spectrum of the dihydrophosphate salt of compound I (top) and an XRPD of the hydrosulfate salt of compound I (bottom).

The chloride salt of compound I did not deliquesce after 2 days at approximately 95% RH. Moisture sorption/desorption data are summarized in FIG. 27 and displayed in FIGS. 26 and 28. Minimal weight loss was observed on equilibration at 5% RH. Approximately 0.9% weight gain occurred on sorption from 5 to 95% relative humidity. The sample displayed approximately 0.7% weight loss upon desorption. XRPD analysis on the post-MB sample exhibited an X-ray pattern similar to that for the starting material (FIG. 29).

Characterization of the Hydrosulfate and Sulfate Salts of Compound I

Figure 32:
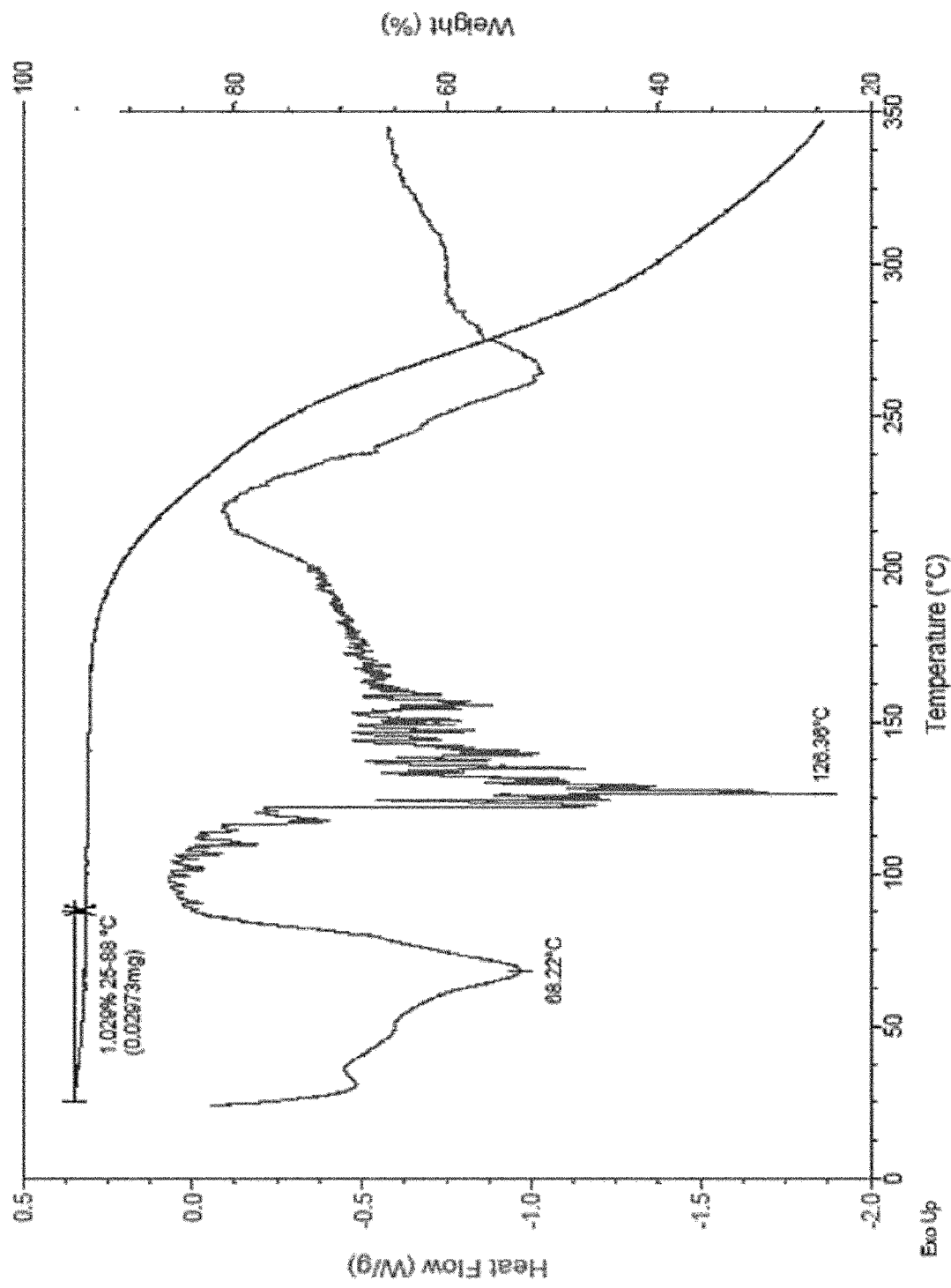
FIG. 32 shows an overlay of a differential scanning calorimetry curve (ranging from about −1.9 to about 0 W/g) and a thermogravimetric analysis curve (ranging from about 25% to about 95% by weight) recorded for the hydrosulfate salt of compound I.
Figure 33:
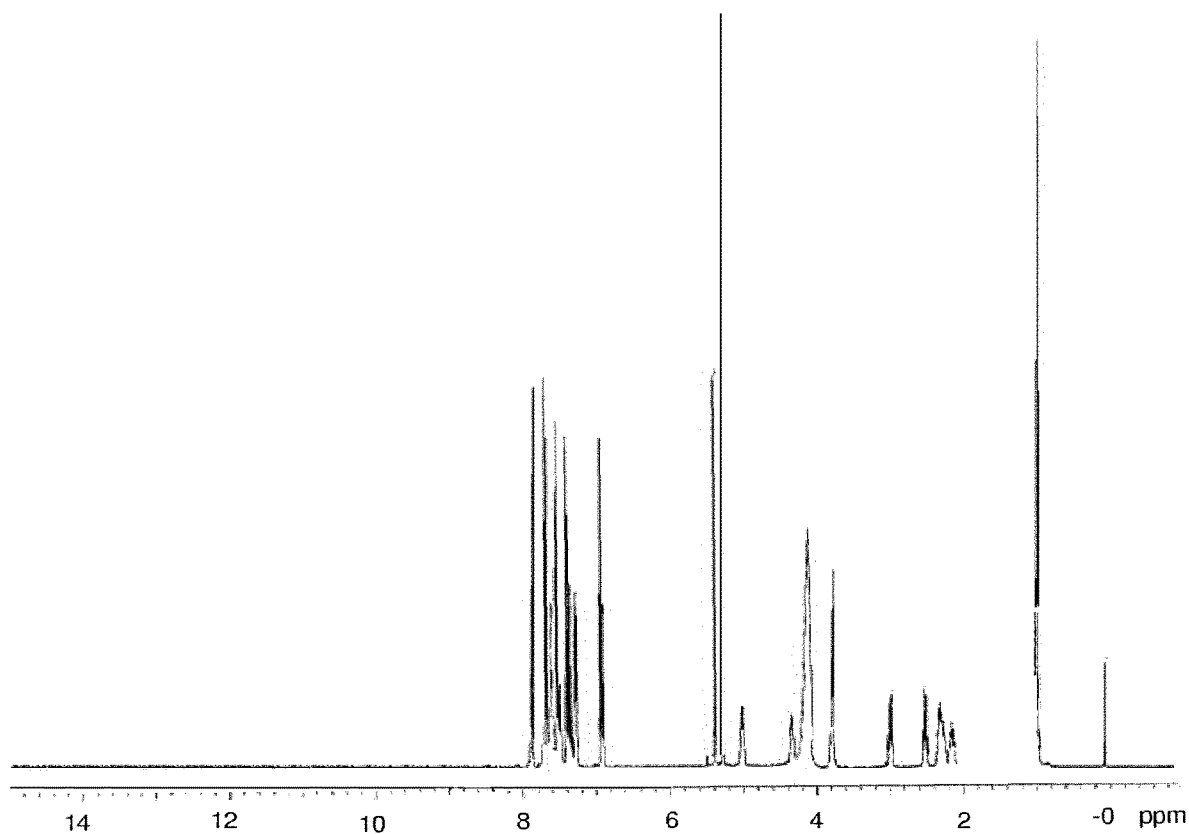
FIG. 33 shows a $^1$H NMR spectrum of the hydrosulfate salt of compound I.
Figure 34:
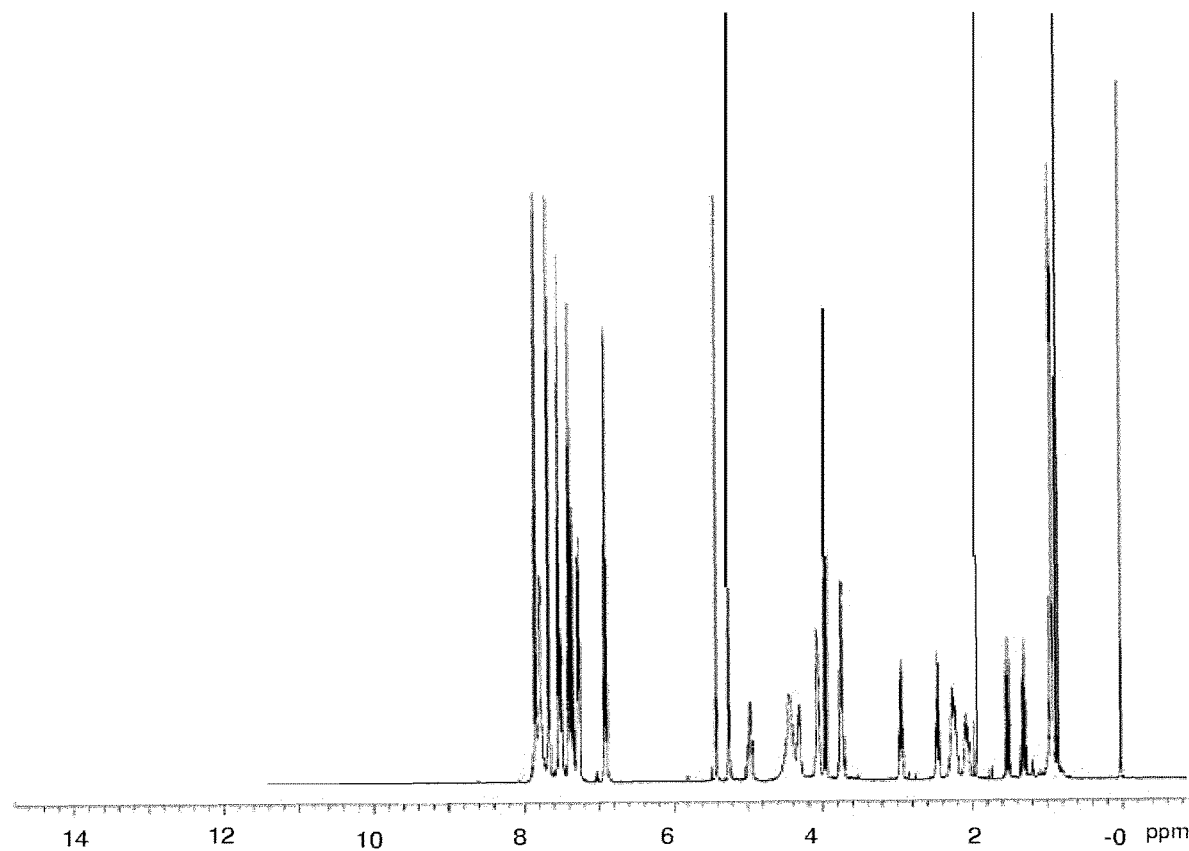
FIG. 34 shows a $^1$H NMR spectrum of the sulfate salt of compound I.
Figure 35:
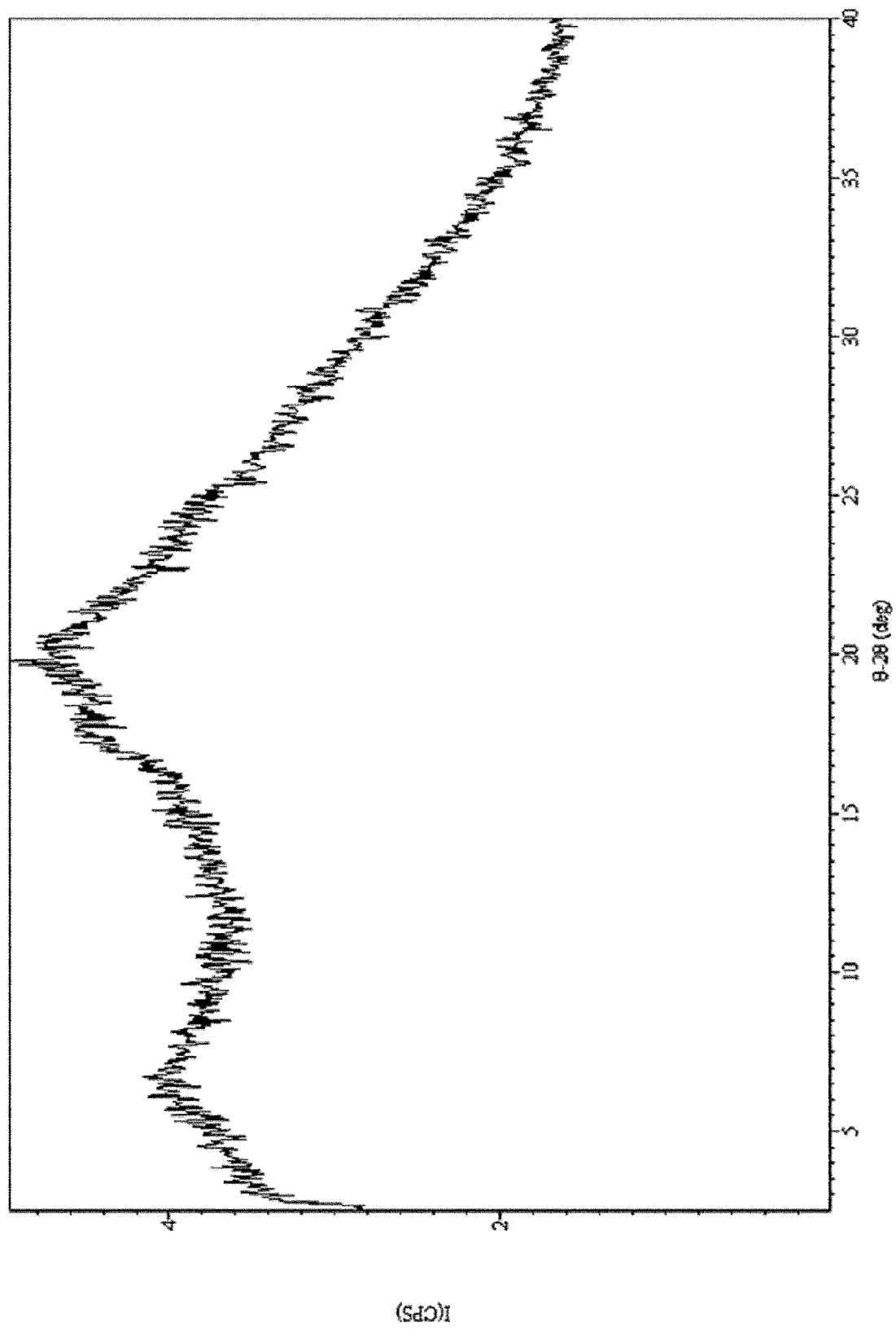
FIG. 35 shows an XRPD spectrum of the mesylate salt of compound I.
Figure 36:
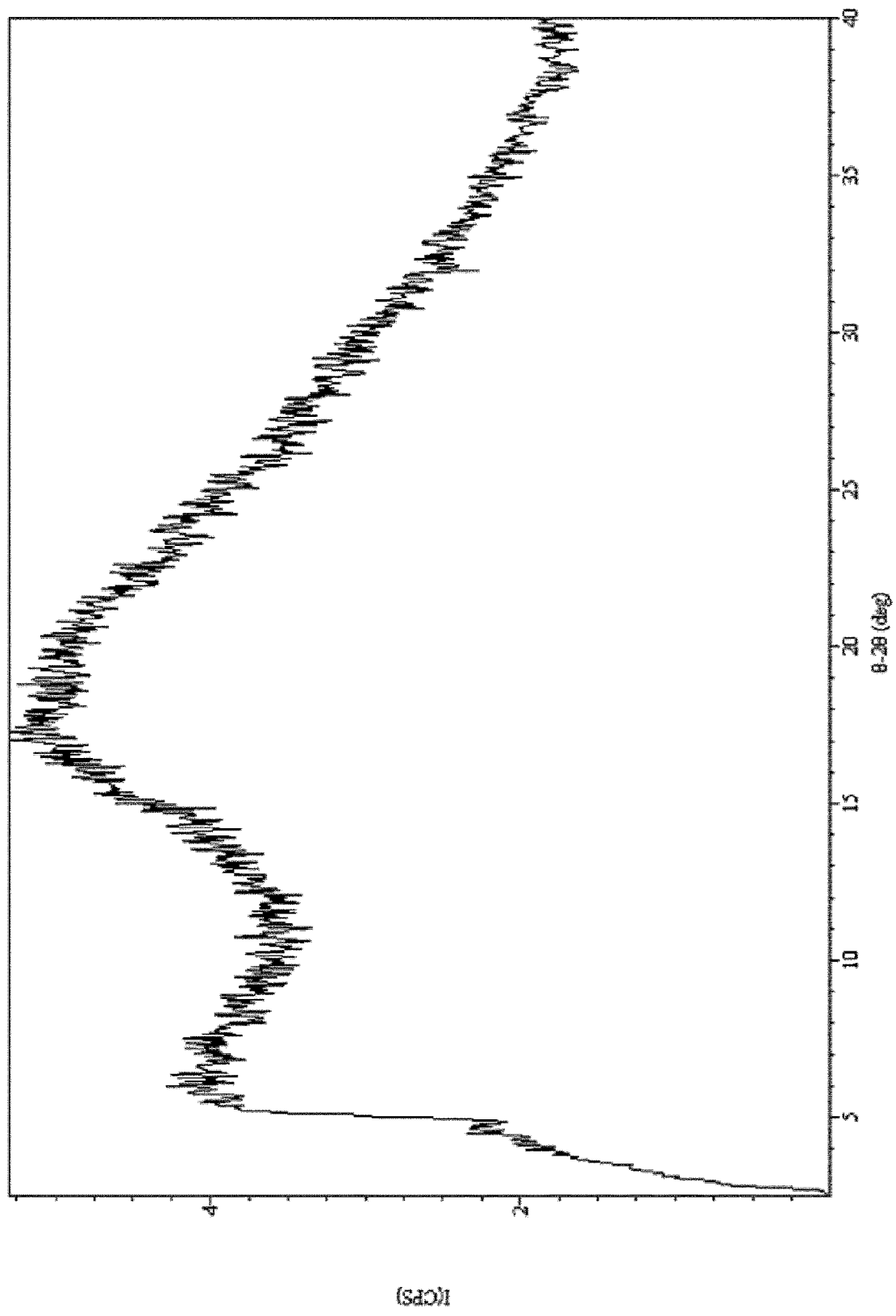
FIG. 36 shows an XRPD spectrum of the citrate salt of compound I.
Figure 37:
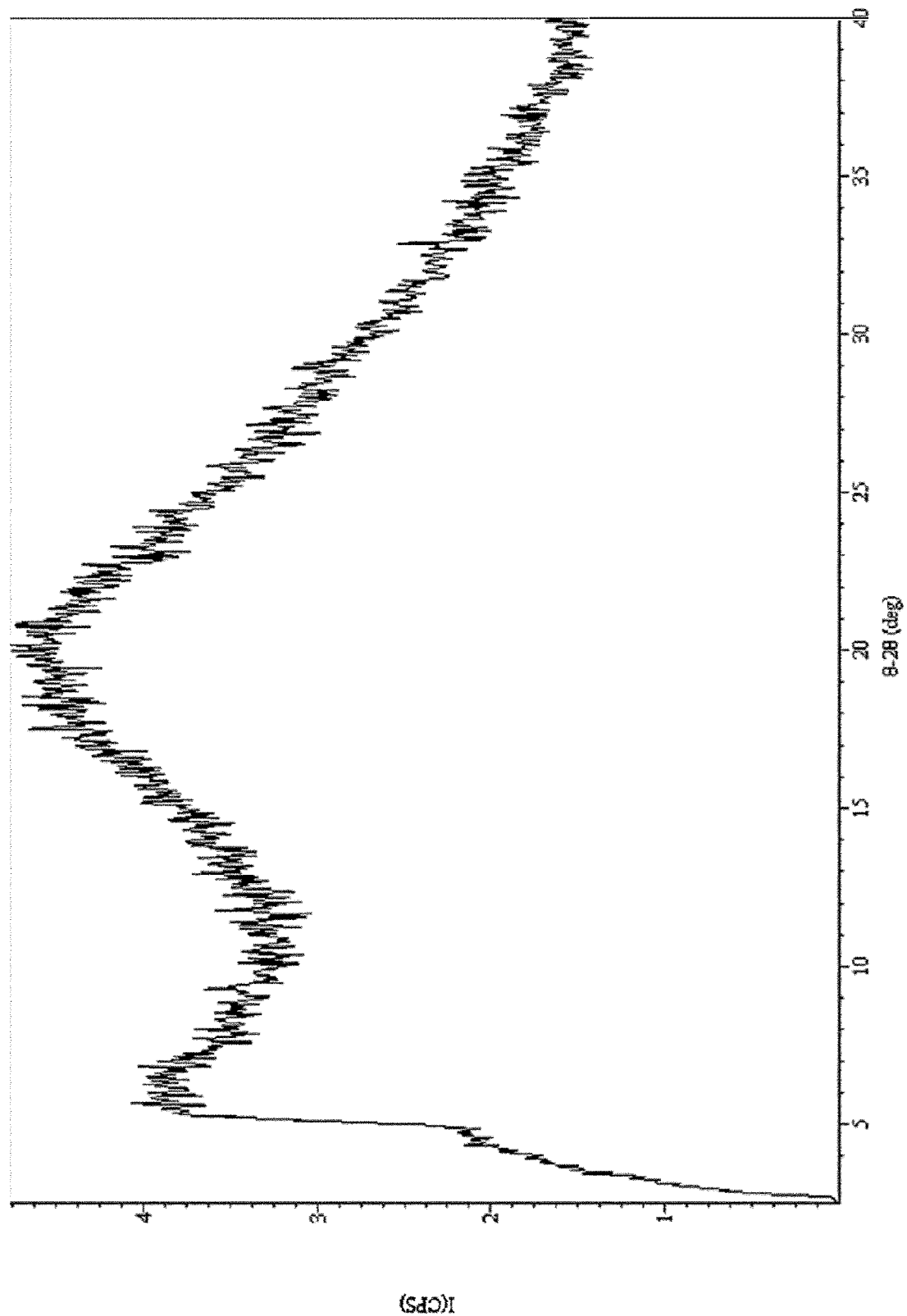
FIG. 37 shows an XRPD spectrum of the edisylate salt of compound I.
Figure 38:
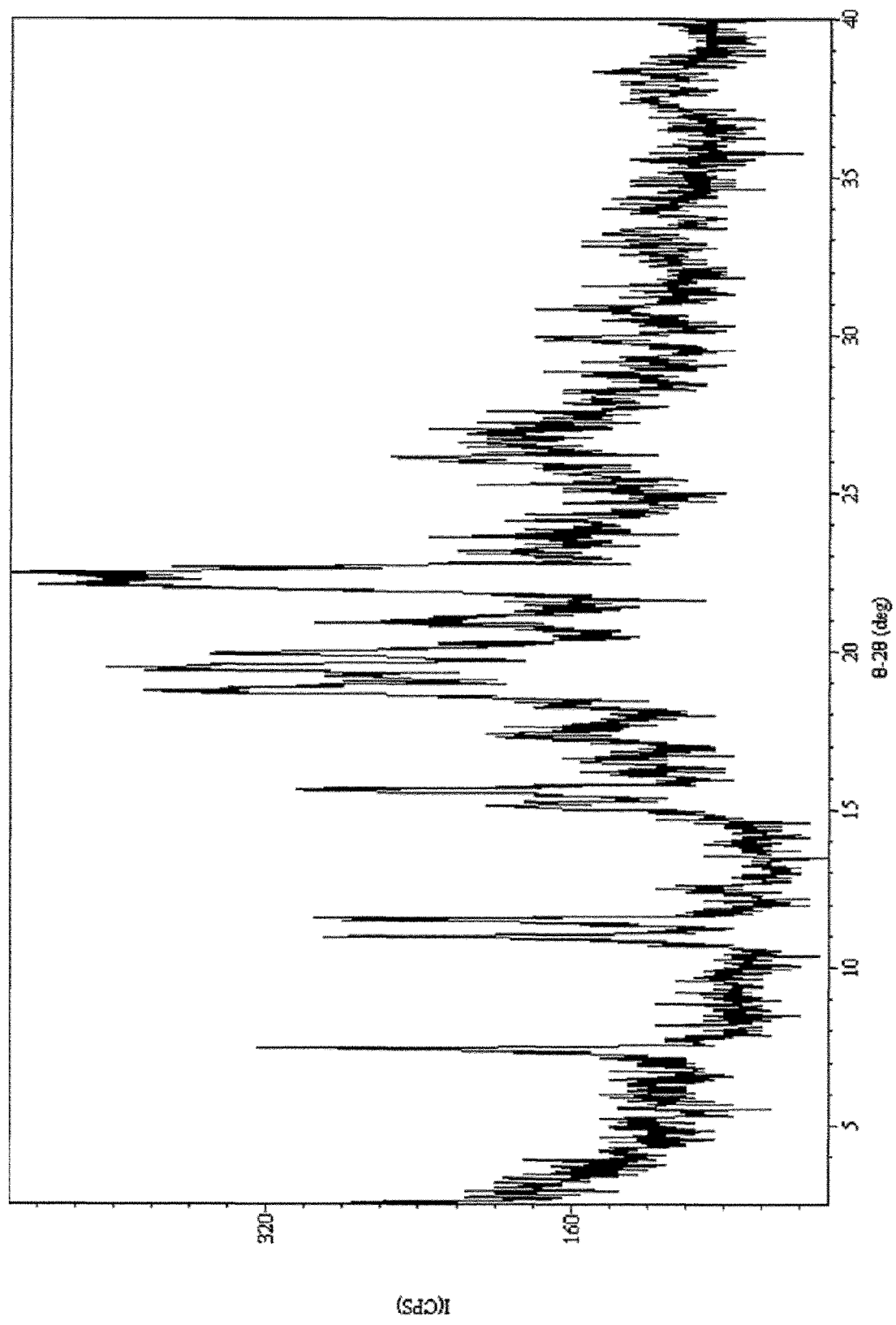
FIG. 38 shows an XRPD spectrum of the hydrosulfate salt of compound I.
Figure 39:
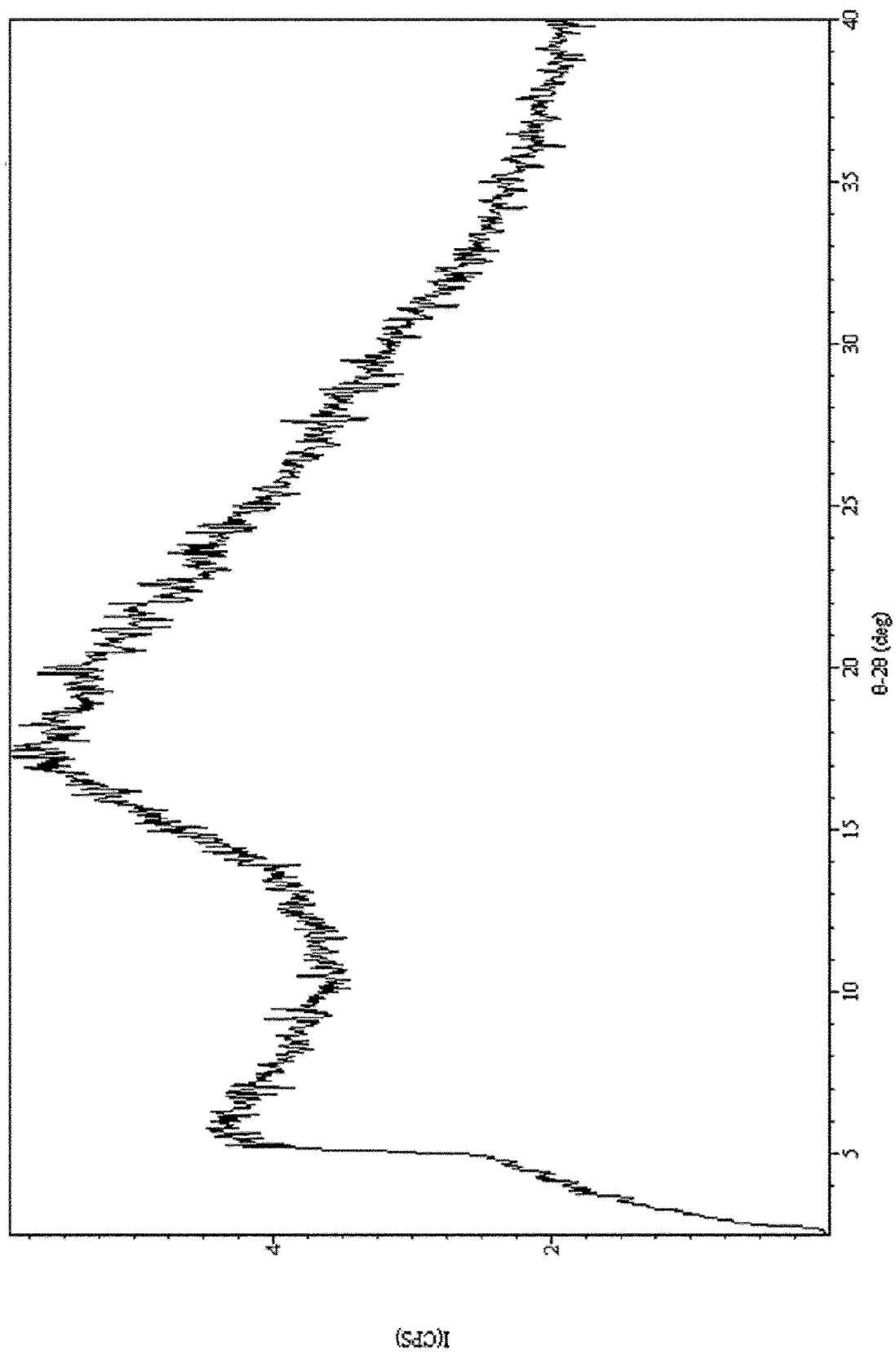
FIG. 39 shows an XRPD spectrum of the citrate salt of compound I as produced by slow evaporation of a 1:2 methanol:toluene mixture.
Figure 40:
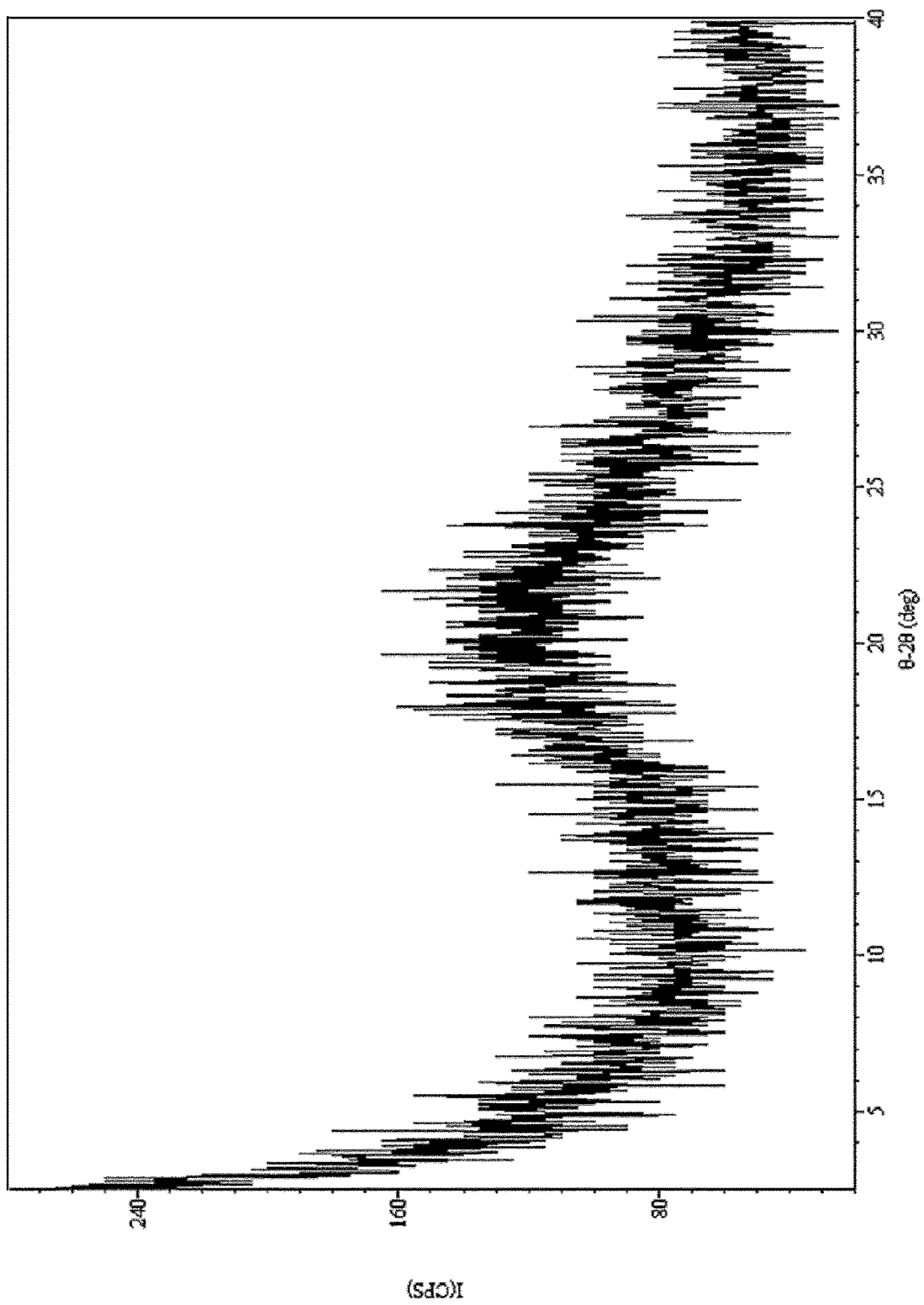
FIG. 40 shows an XRPD spectrum of the hydrosulfate salt of compound I as produced by slow evaporation of a 6:1 ethyl acetate:heptane mixture.
Figure 41:
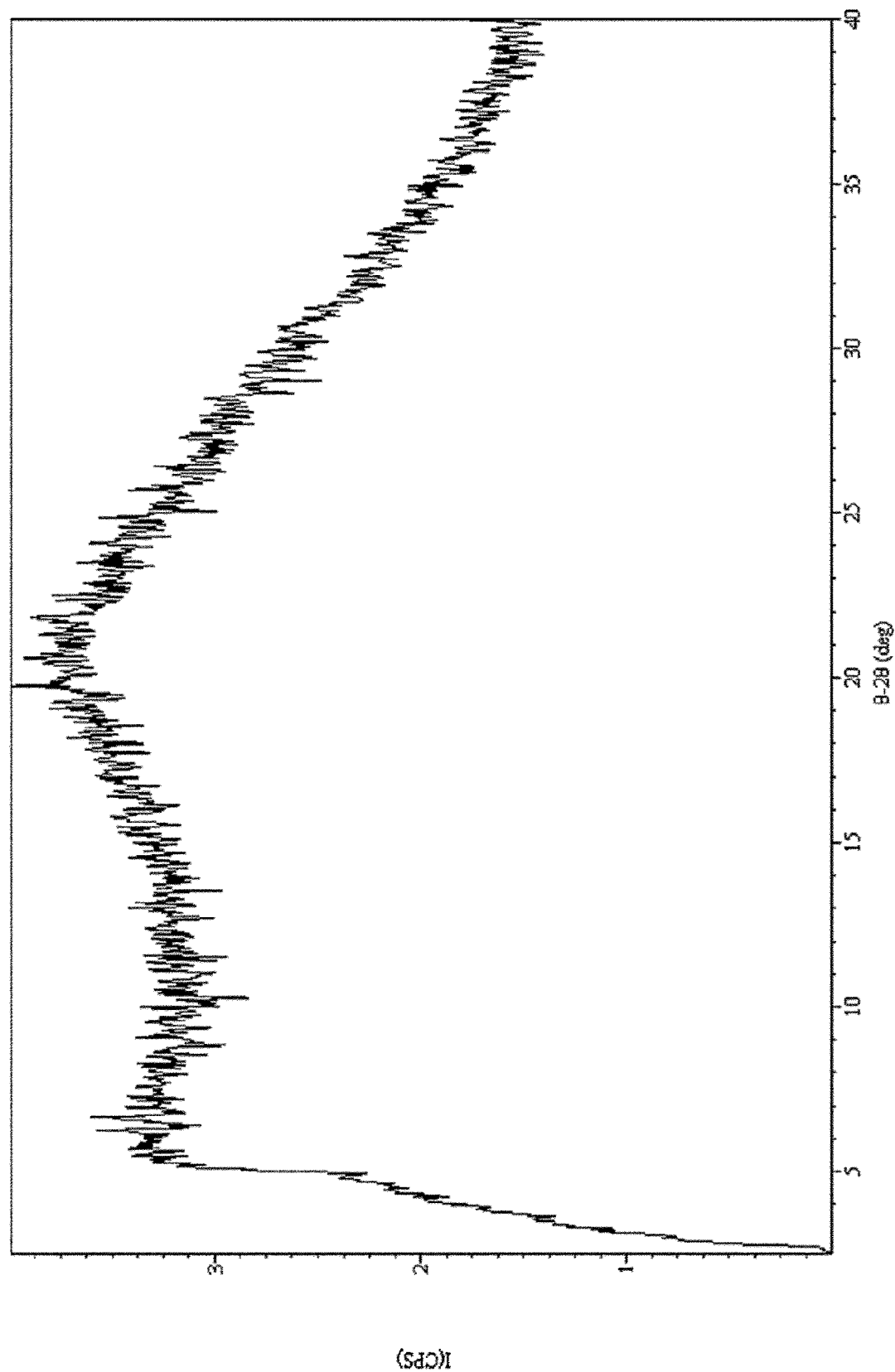
FIG. 41 shows an XRPD spectrum of the hydrosulfate salt of compound I as produced by slow evaporation of an ethyl acetate mixture.
Figure 42:
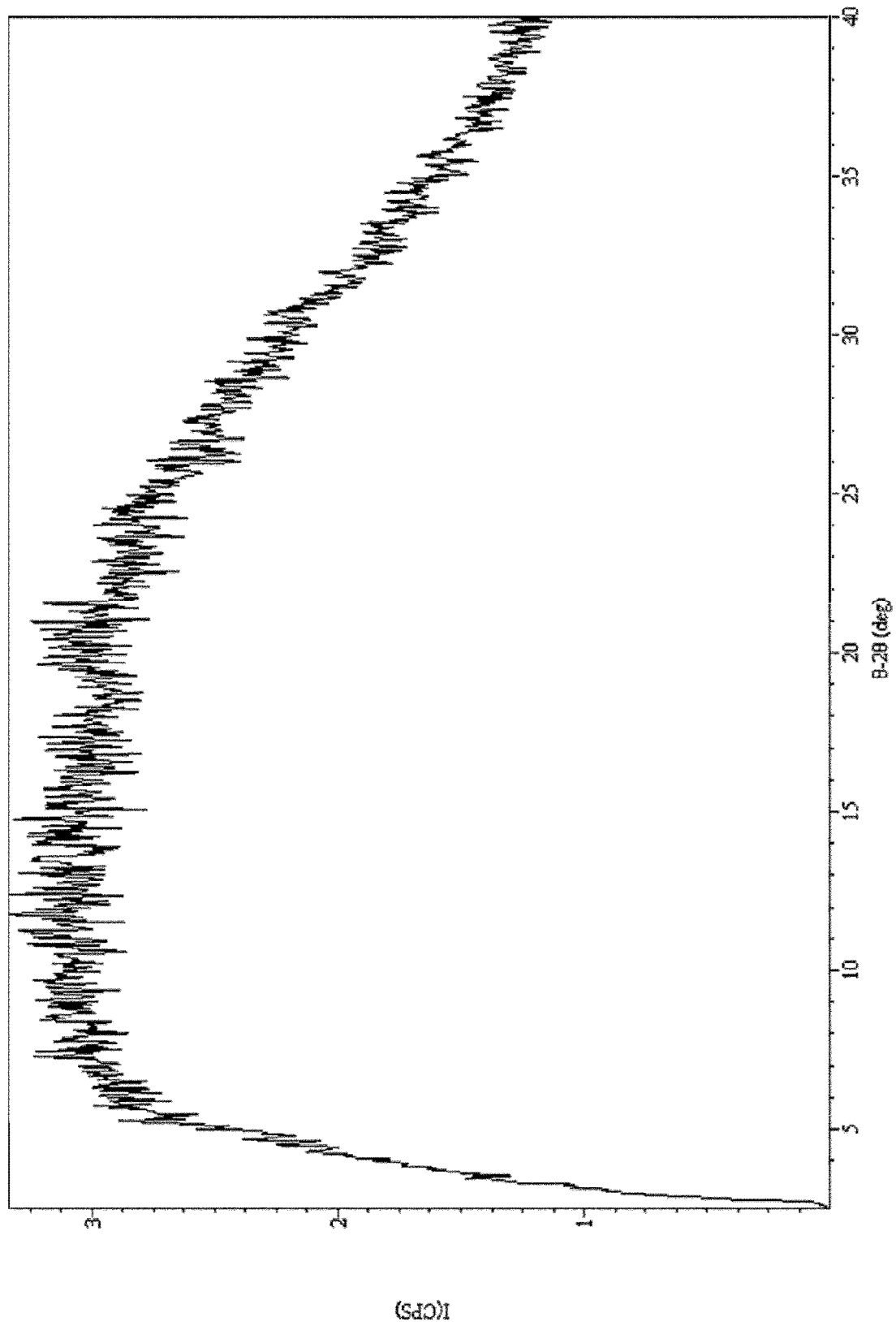
FIG. 42 shows an XRPD spectrum of the dihydrophosphate salt of compound I as produced by slow evaporation of a 1:2 methanol:acetonitrile mixture.

Both the hydrosulfate and sulfate salt of compound I were prepared. The hydrosulfate salt was precipitated from an acetone solution of the free base by addition of approximately 25 molar excess of sulfuric acid. The precipitate was found to be crystalline by XRPD (FIG. 38). Thermal data for the hydrosulfate salt are given in FIG. 32. A broad endotherm at approximately 68° C. corresponded to a weight loss of approximately 1% and was likely due to desolvation (dehydration). Decomposition occurred at higher temperatures. It did not deliquesce after 3 days at approximately 65% RH (FIG. 32). The sulfate salt was prepared using two equivalents of the free base per one equivalent of the acid. Attempts to crystallize the sulfate salt of compound I were not successful (FIGS. 5-7). The hydrosulfate and the sulfate salt were analyzed by proton NMR (FIG. 33 and FIG. 34). Differences were noted in the NMR spectra. For example, the methyl groups of the valine fragment appeared to have different coupling.

Characterization of the Dihydrophosphate Salt of Compound I

Figure 43:
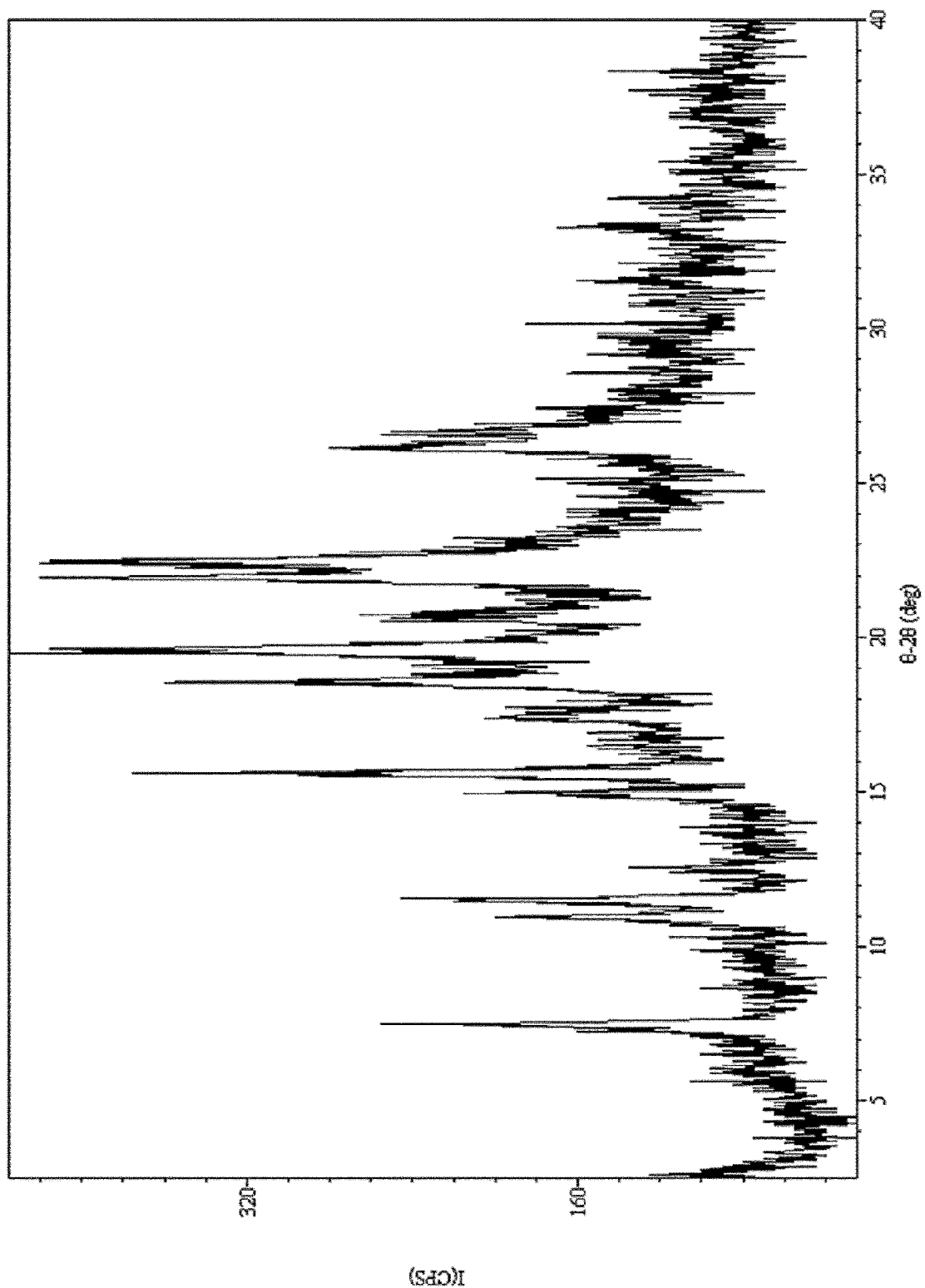
FIG. 43 shows an XRPD spectrum of the dihydrophosphate salt of compound I as produced by slow evaporation of a 1:1 methyl ethyl ketone:n-butyl acetate mixture.
Figure 44:
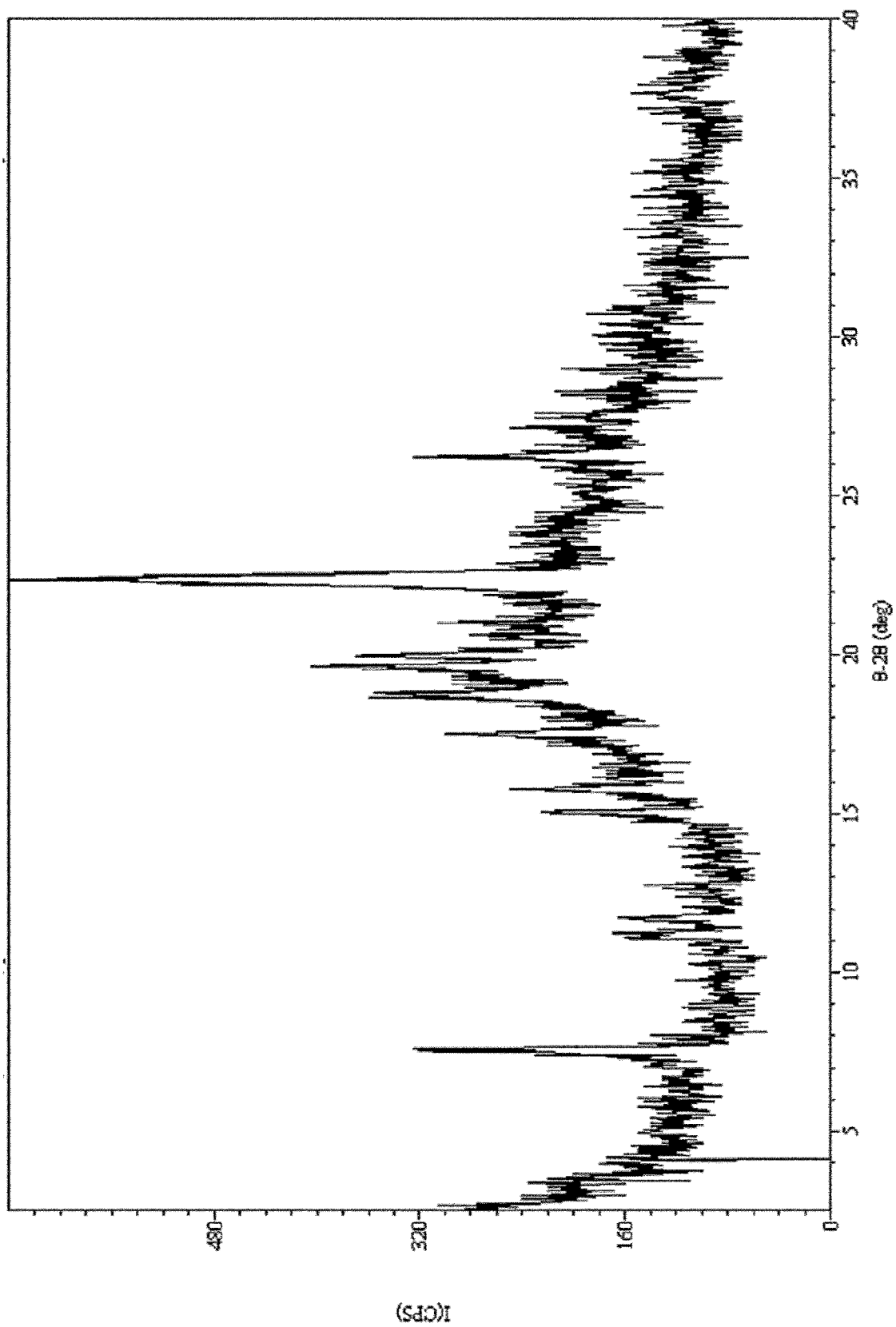
FIG. 44 shows an XRPD spectrum recorded from a duplicate XRPD experiment of the dihydrophosphate salt of compound I as produced by slow evaporation of a 1:1 methyl ethyl ketone:n-butyl acetate mixture.
Figure 45:
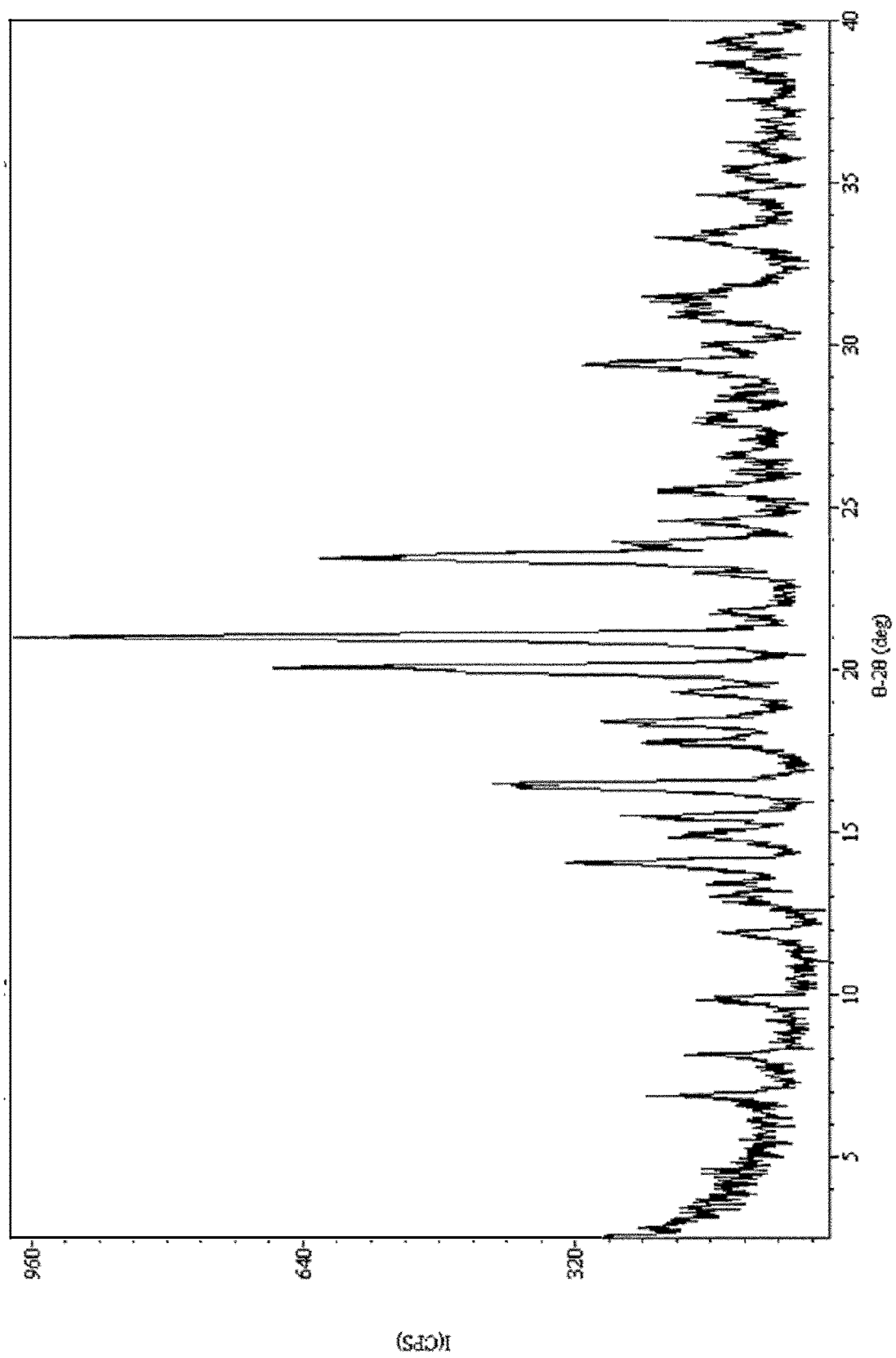
FIG. 45 shows an XRPD spectrum of the chloride salt of compound I as produced by slow evaporation of a 1:1 acetone:toluene mixture.
Figure 46:
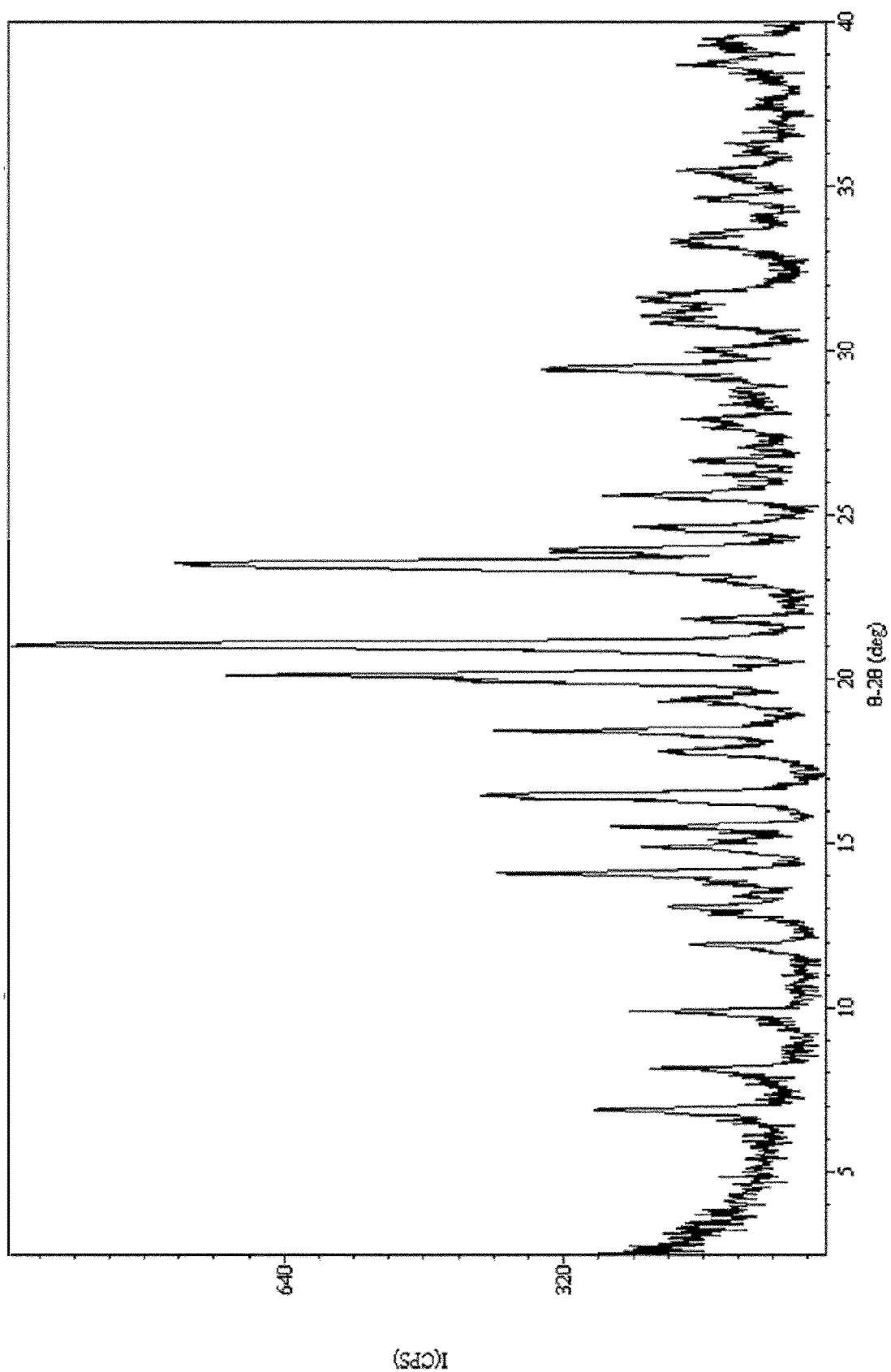
FIG. 46 shows an XRPD spectrum recorded from a duplicate XRPD experiment of the chloride salt of compound I as produced by slow evaporation of a 1:1 acetone:toluene mixture.
Figure 47:
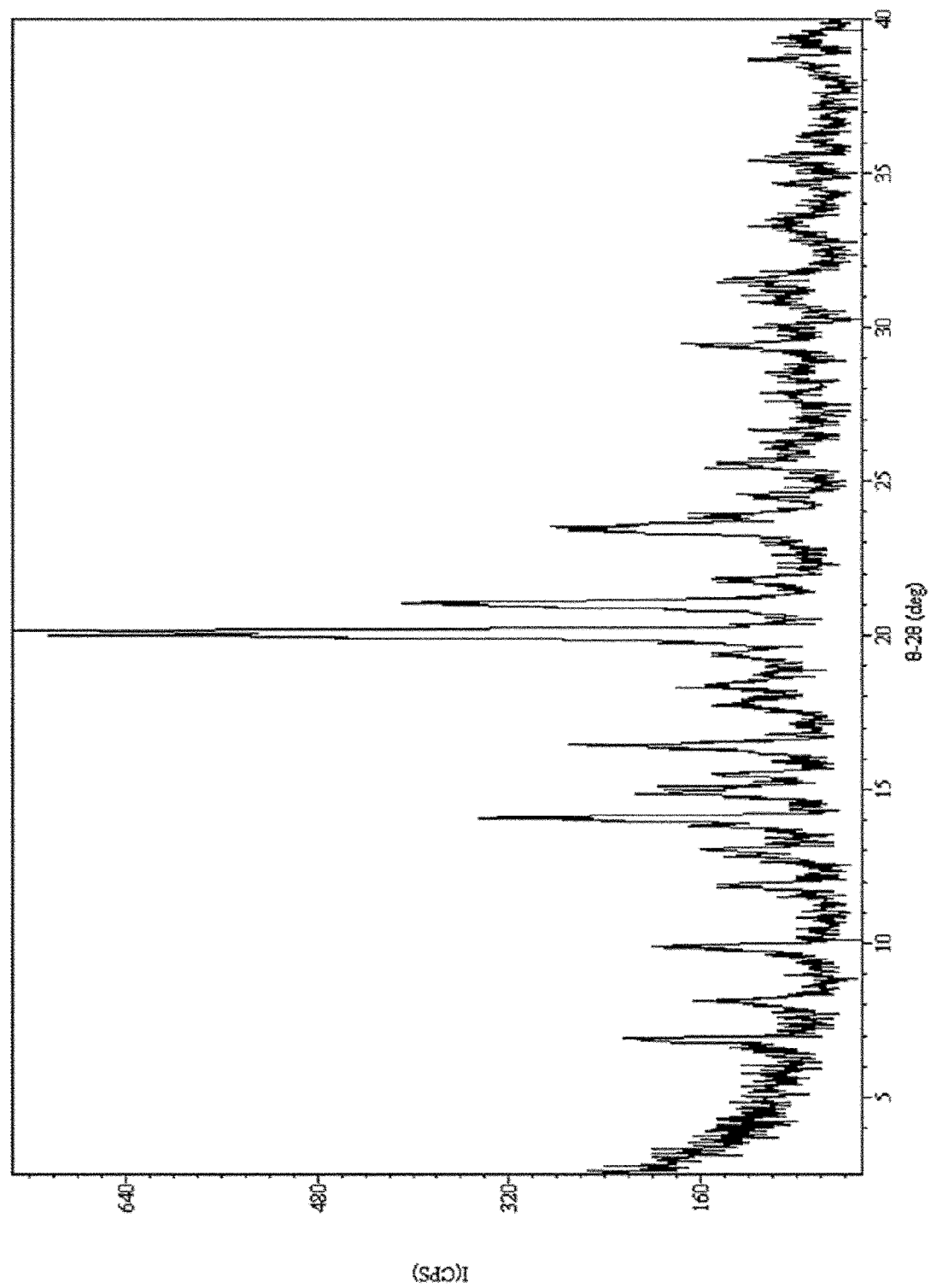
FIG. 47 shows an XRPD spectrum of the chloride salt of compound I as produced by slow evaporation of a diethyl ether:methylenechloride mixture.
Figure 48:
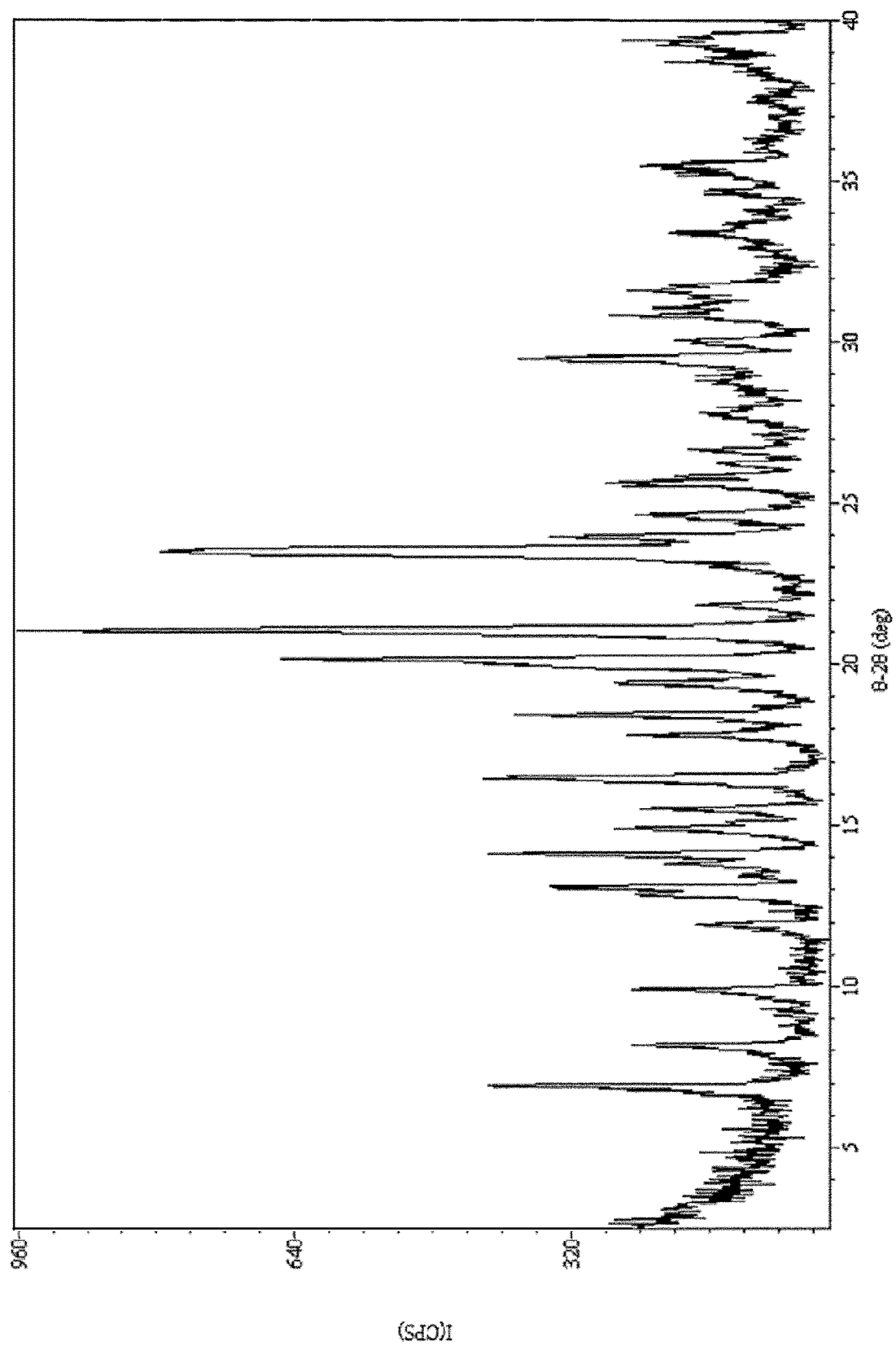
FIG. 48 shows an XRPD spectrum of the chloride salt of compound I as produced from an acetone slurry.
Figure 49:
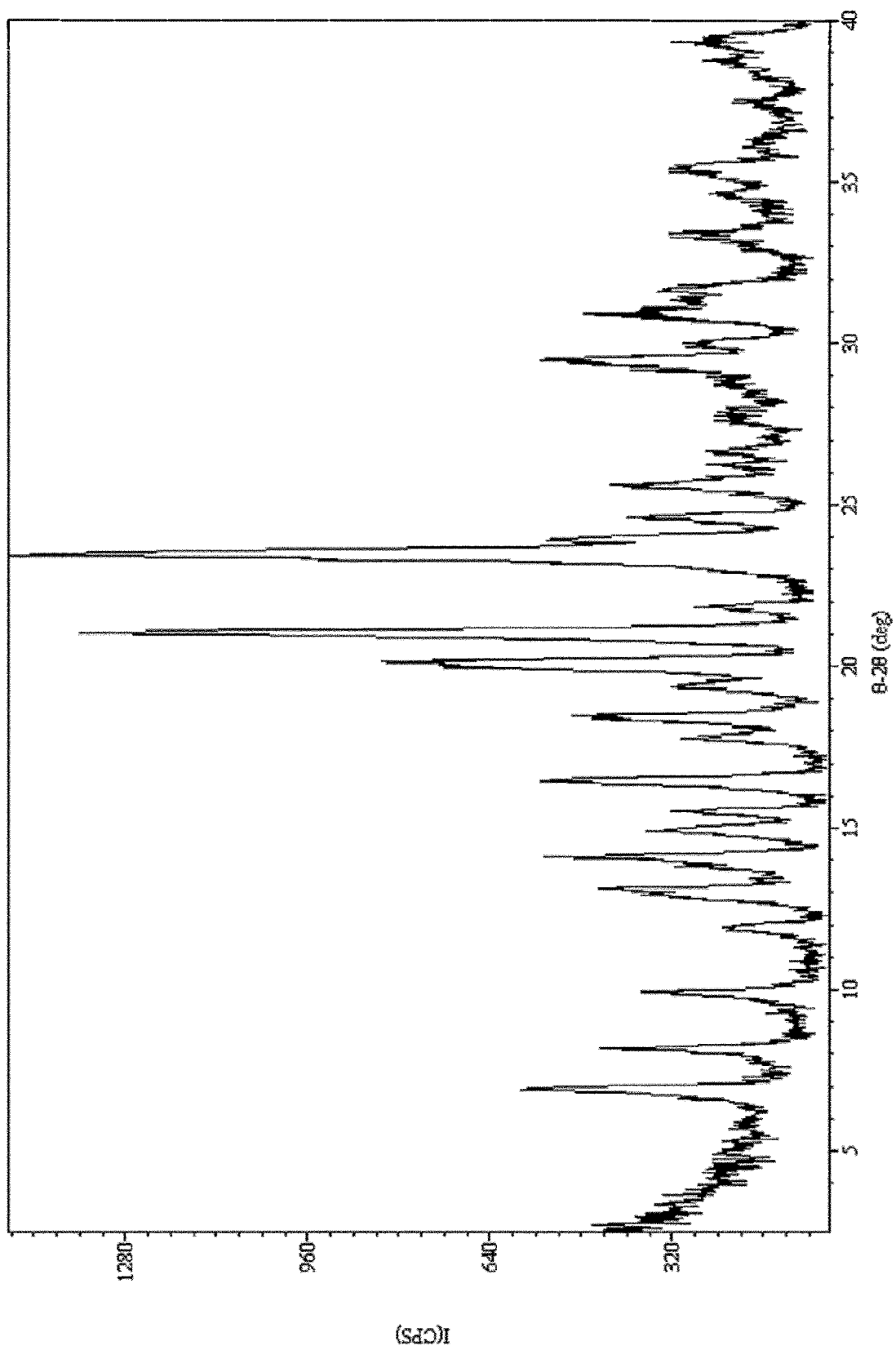
FIG. 49 shows an XRPD spectrum of the chloride salt of compound I after being vacuum dried.
Figure 50:
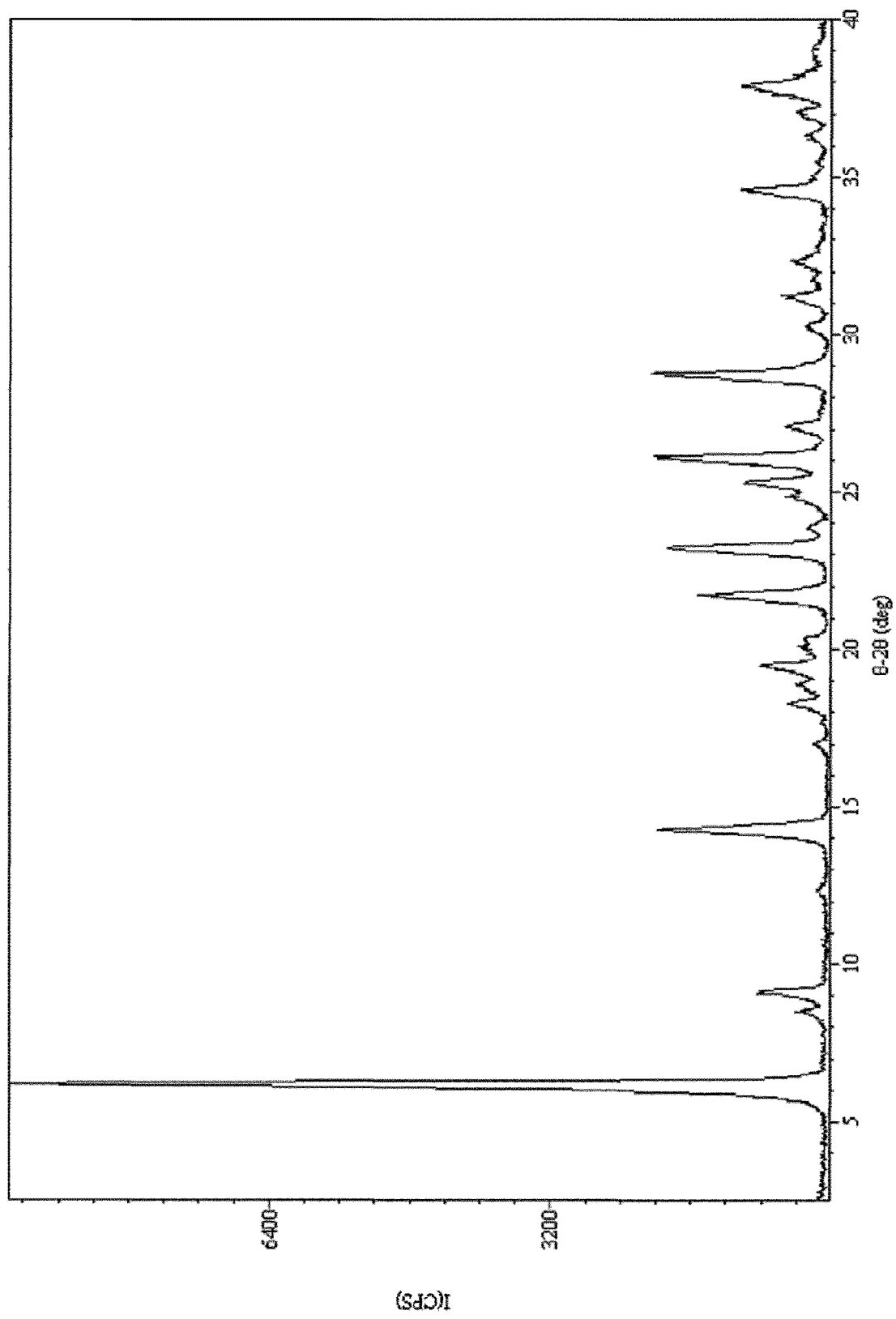
FIG. 50 shows an XRPD spectrum of the fumarate salt of compound I as produced by slow evaporation of a 1:1 methanol:toluene mixture.
Figure 51:
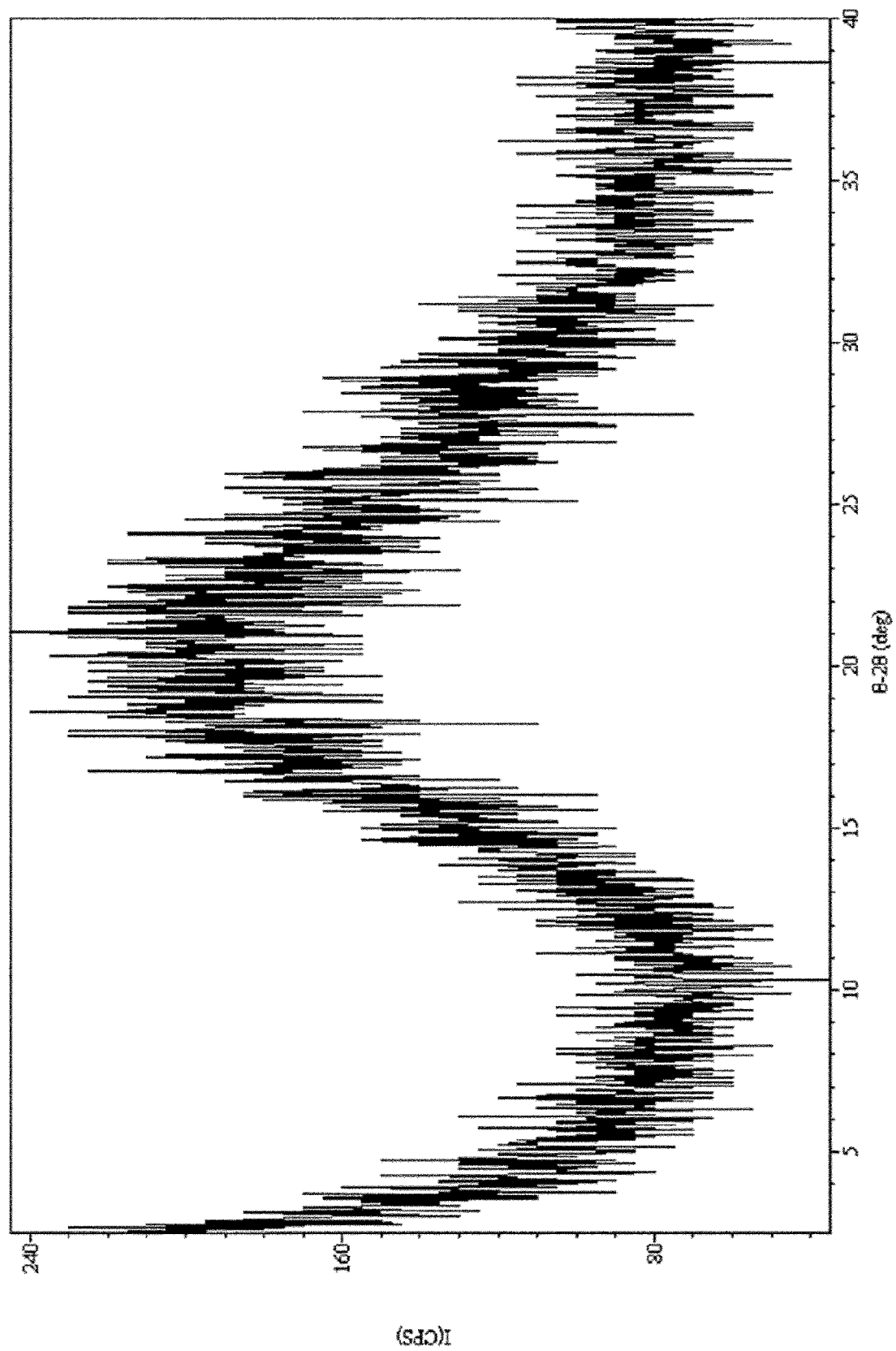
FIG. 51 shows an XRPD spectrum of the fumarate salt of compound I as produced by slow evaporation of a 1:1 methanol:ethyl acetate mixture.
Figure 52:
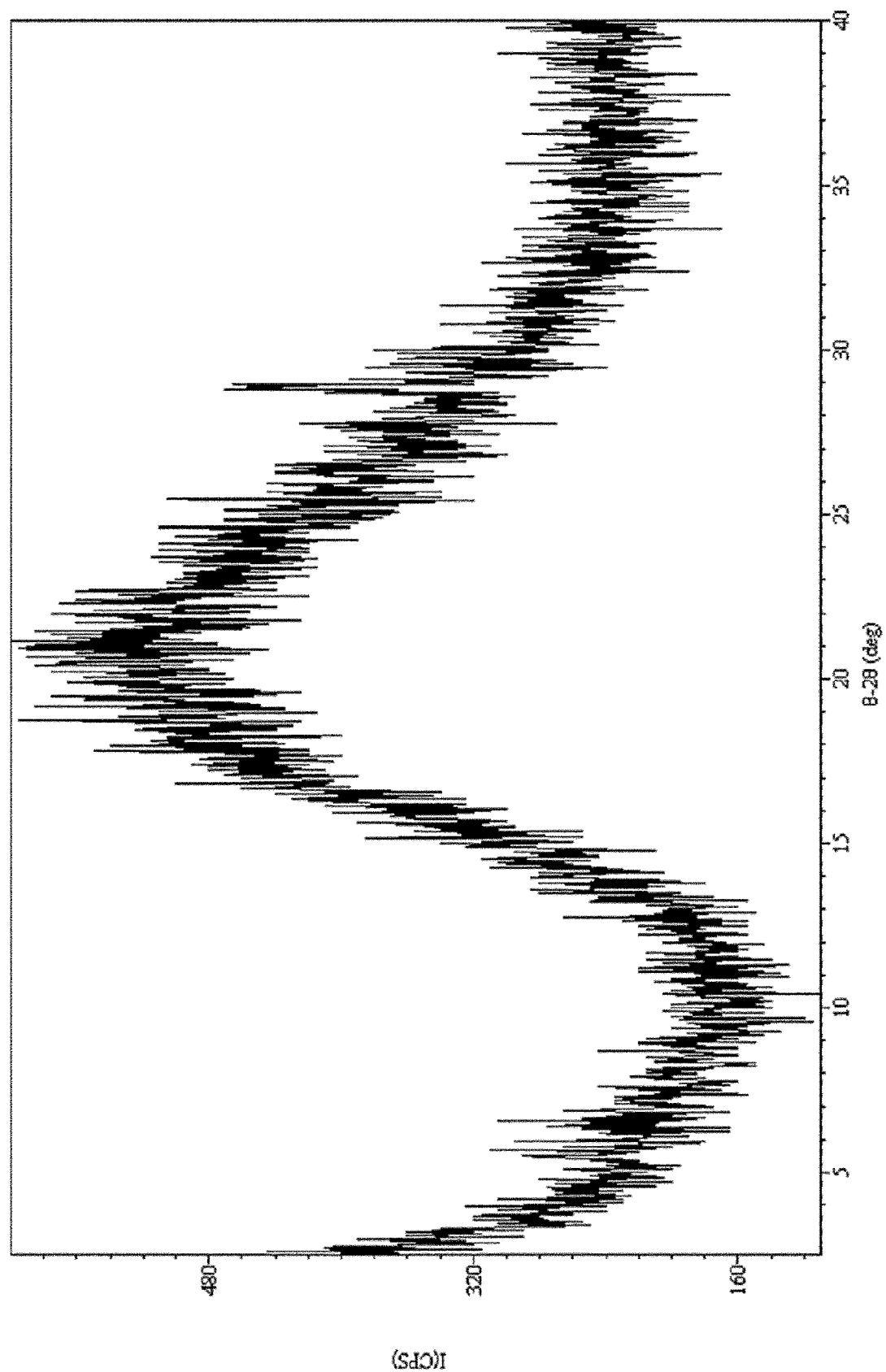
FIG. 52 shows an XRPD spectrum of the fumarate salt of compound I as produced by vacuum drying a 1:1 methanol:toluene mixture.
Figure 53:
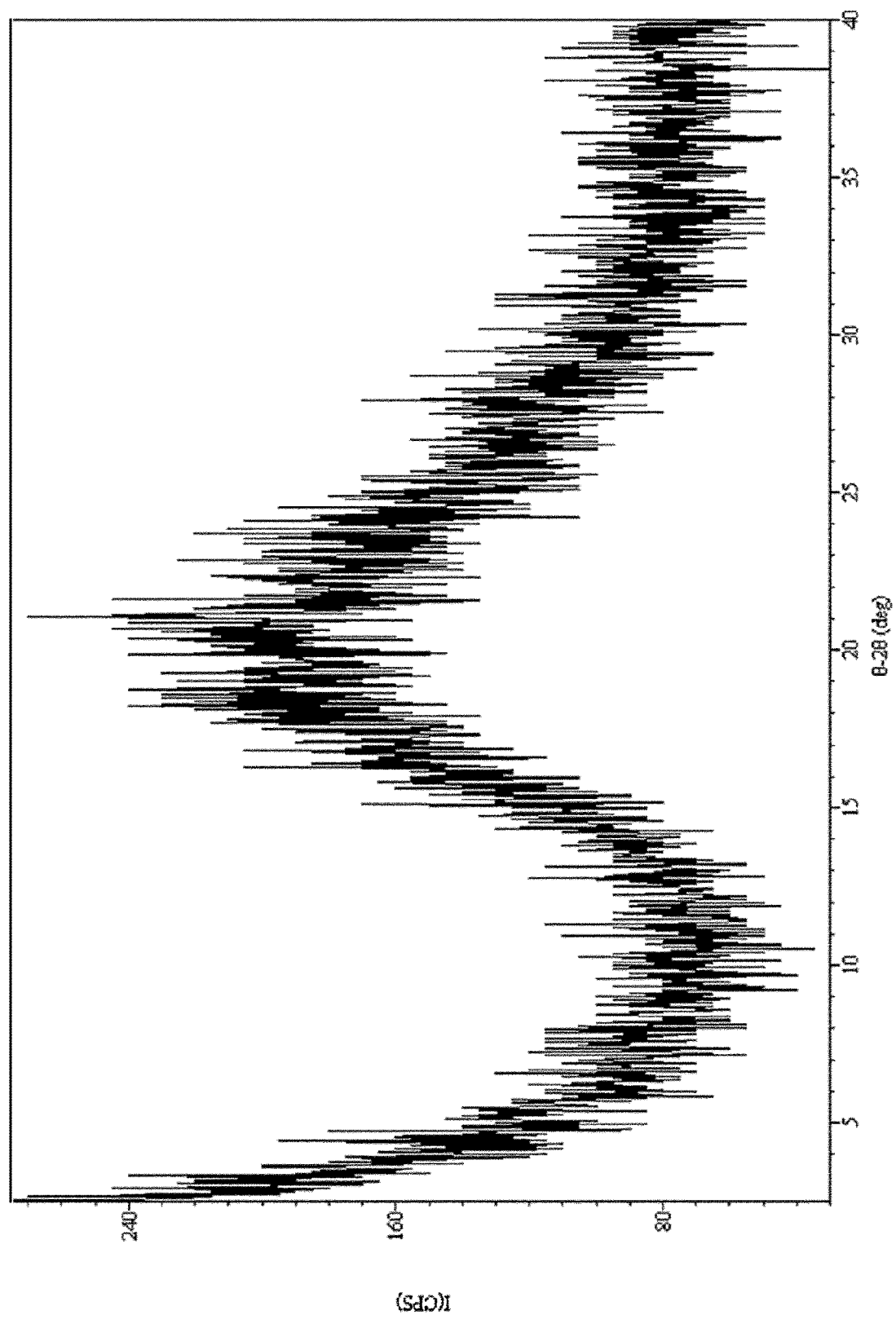
FIG. 53 shows an XRPD spectrum of the edisylate salt of compound I as produced by slow evaporation of a 1:1:1 methanol:methyl ethyl ketone:toluene mixture.
Figure 54:
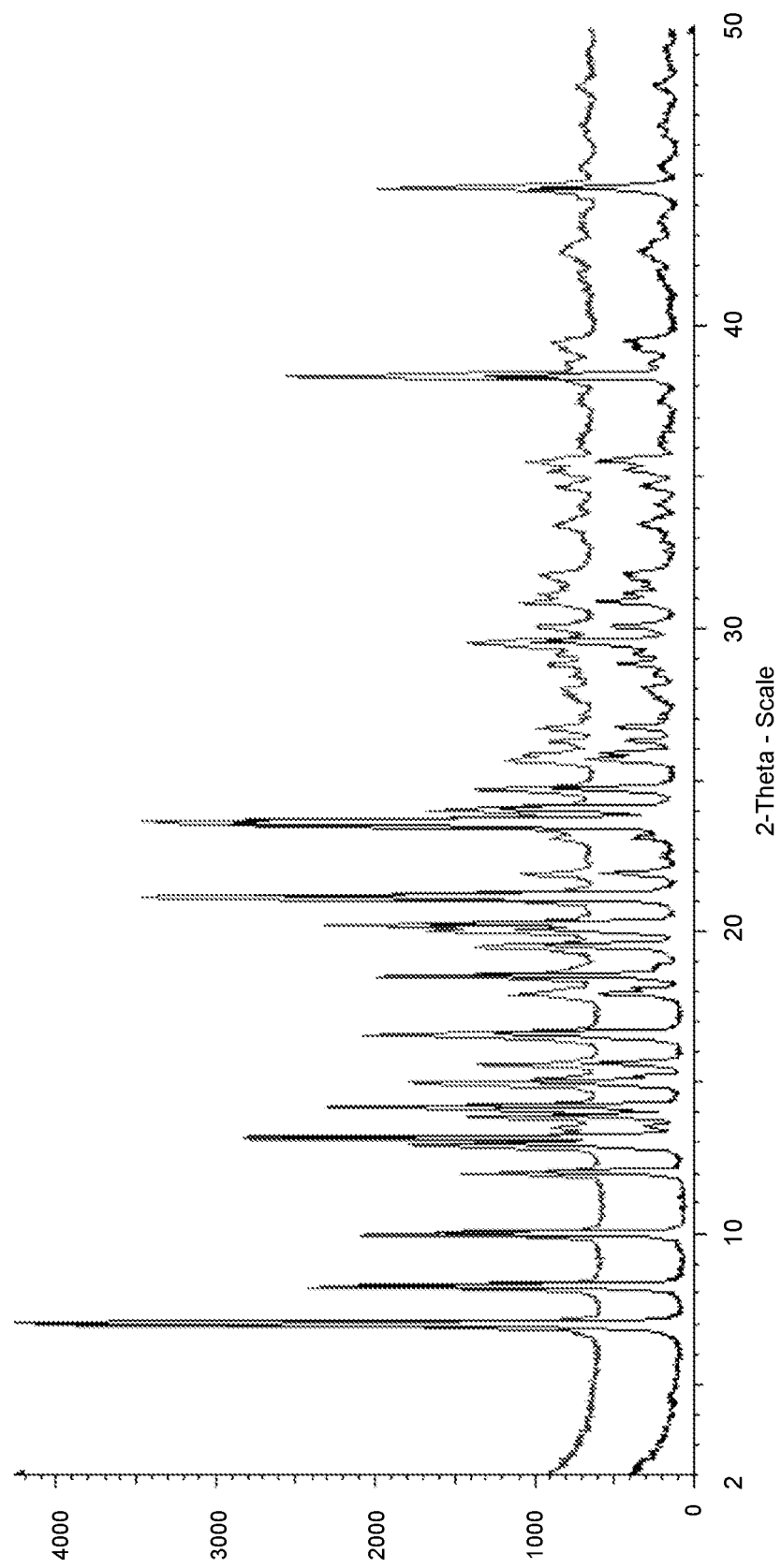
FIG. 54 shows an overlay of XRPD spectra of the chloride salt of compound I prior to (bottom) and following (top) storage at 40° C. and 75% relative humidity.
Figures 56A, 56B, 56C:
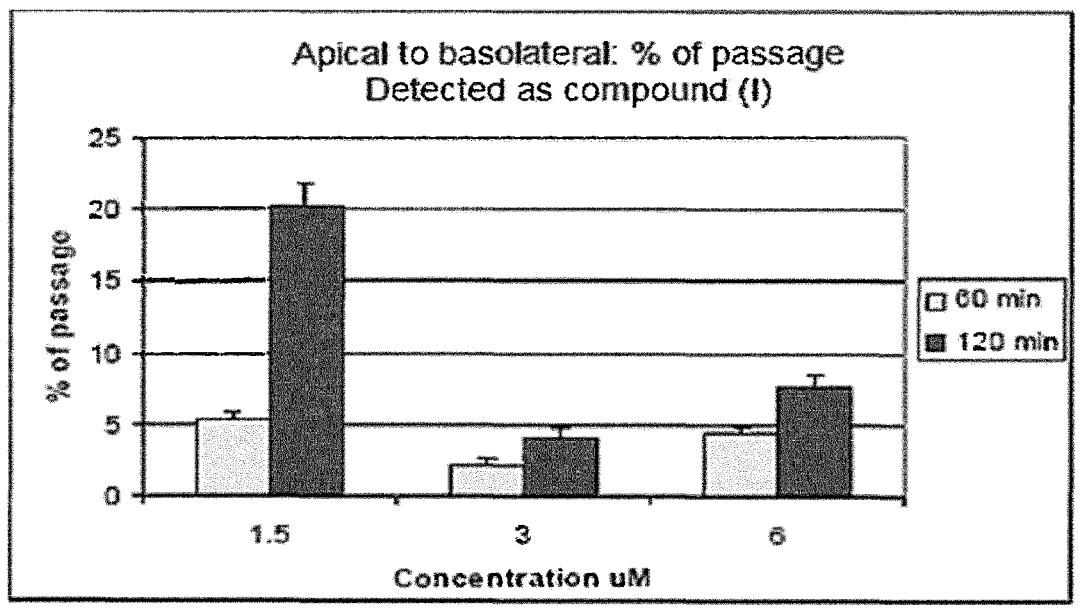
FIG. 56a is a table reporting data obtained from analysis of the ability of the mesylate salt of compound I to pass from the apical to the basolateral compartment of a transwell coated with a Caco-2 cell monolayer. Cultured Caco-2 cells were incubated with the indicated concentration of the mesylate salt of compound I in the apical compartment of the transwell, and aliquots from the basolateral compartment were sampled at the indicated sampling times in order to determine the presence of compound I or compound II. The data reports the concentration of compound II in the basolateral compartment as a percentage of the indicated initial concentration of the mesylate salt of compound I.
FIG. 56b is a table reporting data obtained from analysis of the ability of the mesylate salt of compound I to pass from the basolateral to the apical compartment of a transwell coated with a Caco-2 cell monolayer. Cultured Caco-2 cells were incubated with the indicated concentration of the mesylate salt of compound I in the basolateral compartment of the transwell, and aliquots from the apical compartment were sampled at the indicated sampling times in order to determine the presence of compound I or compound II. The data reports the concentration of compound II in the basolateral compartment as a percentage of the indicated initial concentration of the mesylate salt of compound I.
FIG. 56c is a graph showing the relative concentration of compound II in the basolateral compartment as a percentage of the initial concentration of the mesylate salt of compound I in the apical compartment.
Figures 56D, 56E:
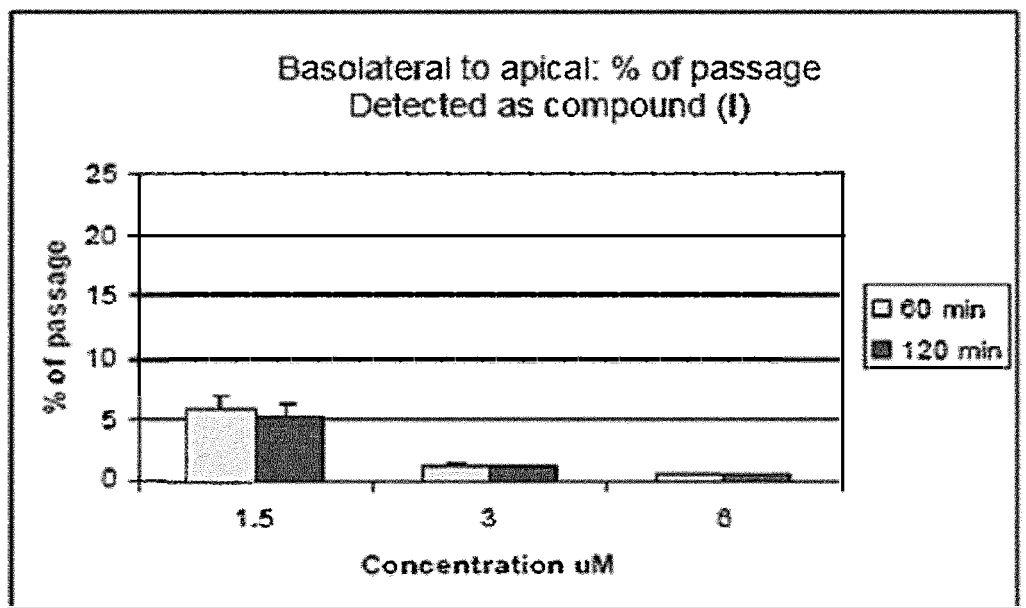
FIG. 56d is a graph showing the relative concentration of compound II in the apical compartment as a percentage of the initial concentration of the mesylate salt of compound I in the basolateral compartment. Compound I was not detected in the basolateral compartment following 60 or 120 minutes of incubation in the apical compartment. Additionally, compound I was not detected in the apical compartment following 60 or 120 minute of incubation in the basolateral compartment. Rather, compound II was detected in each case.
FIG. 56e is a table showing the recovery of compound I in the apical compartment following 120 minutes of incubation. The initial compound was primarily recovered in the form of the de-esterified variant, compound II.
Figure 57D:
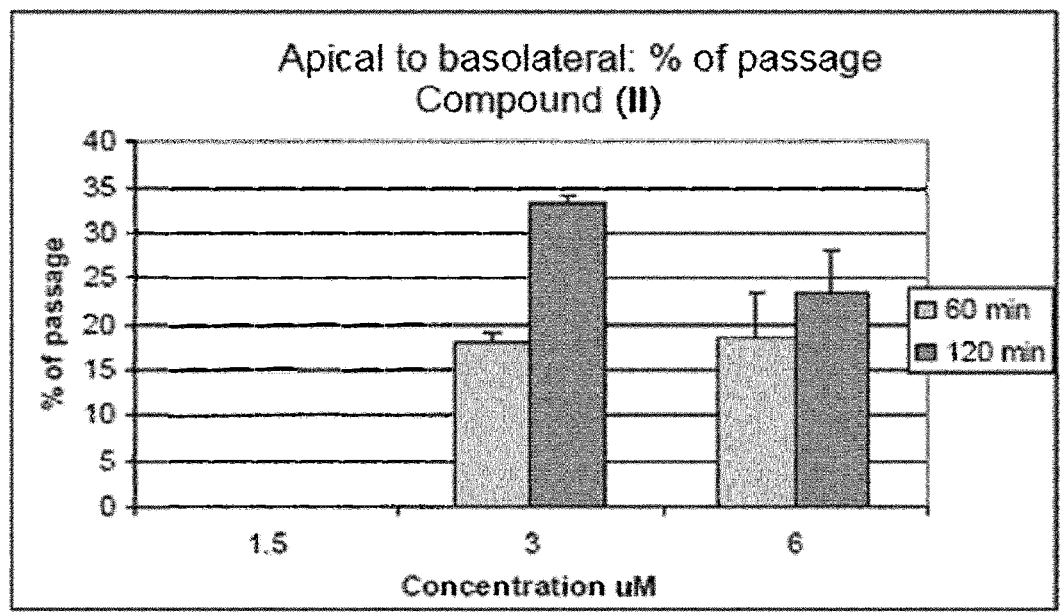
FIG. 57d is a graph showing the relative concentration of compound II in the basolateral compartment as a percentage of the initial concentration of compound II in the apical compartment.
Figure 57E:
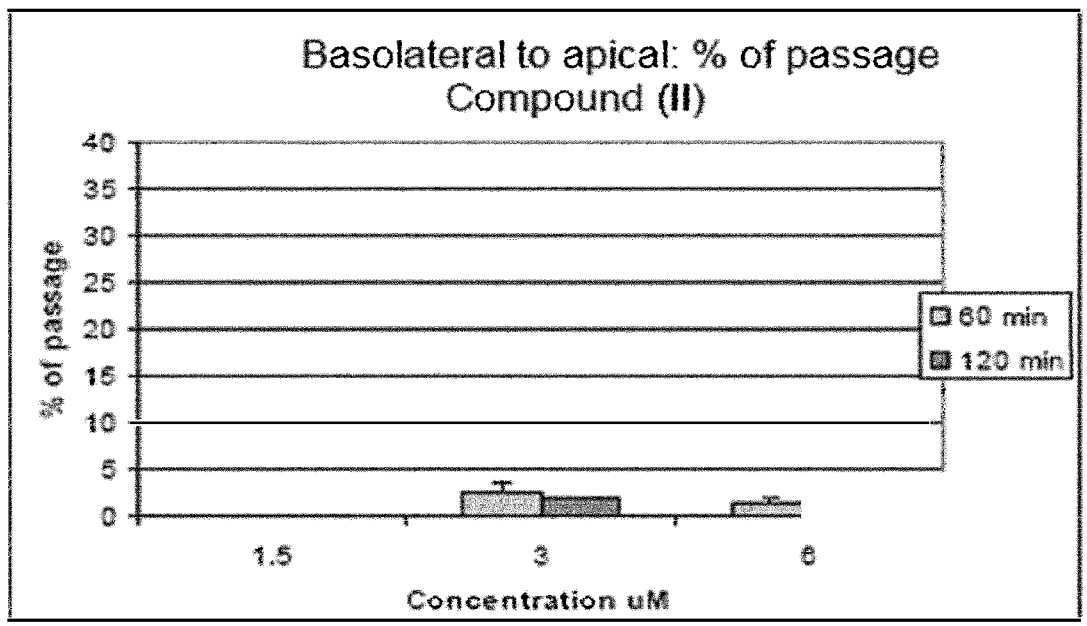
FIG. 57e is a graph showing the relative concentration of compound II in the apical compartment as a percentage of the initial concentration of compound II in the basolateral compartment.

The dihydrophosphate salt was crystallized from a 1:1 methyl ethyl ketone:n-butyl acetate mixture (FIGS. 5-7). It exhibited an X-ray pattern similar to that of the hydrosulfate salt (FIG. 43). Characterization of the dihydrophosphate salt was limited to XRPD due to sample loss during the analysis. Attempts to prepare additional quantities of the crystalline salt were not successful. A low crystalline material was generated during the first attempt (FIGS. 5-7). A recrystallization of the low crystalline salt yielded a viscous solid. The material remained viscous after it had been dried in vacuum. The laboratory humidity was approximately 62% RH during the scale-up crystallization and likely affected the material due to its hygroscopicity. No further attempts to crystallize the dihydrophosphate salt were undertaken.

Characterization of the Fumarate Salt of Compound I

A small amount of the fumarate salt was crystallized from a methanol:toluene 1:1 mixture (FIGS. 5-7). Attempts to scale up the crystalline salt were carried out at the laboratory humidity of approximately 62% RH and were not successful. Mostly oily materials resulted, although some crystalline solid was present by microscopy. Drying the viscous solid in vacuum yielded mostly amorphous material. The originally prepared crystalline salt was used for seeding experiments. However, no crystalline materials were generated. The hygroscopic nature of the fumarate salt was confirmed in relative humidity studies.

The fumarate salt appeared to be moisture sensitive. The crystalline salt was stable at approximately 43 and 53% relative humidities, and began to deliquesce within the first day at approximately 65% RH. Yellow oil formed after 3 days at 65% RH (approximately 4% of moisture gained).

Conclusions

The mesylate salt of compound I was found to be amorphous by XRPD. Attempts to crystallize the material were not successful.

The free base of compound I was synthesized from the mesylate salt and used in preparation of 12 salts. A crystalline hydrosulfate salt was obtained directly from the salt synthesis. Three salts were crystallized using different solvent mixtures and crystallization techniques: hydrochloride, fumarate and dihydrophosphate. The chloride salt appeared to be the best candidate for further development. The crystalline hydrosulfate salt was likely solvated and decomposed above approximately 100° C. The material was stable at relative humidities up to approximately 65%. The crystalline HCl salt was obtained in two evaporation experiments and a slurry experiment. The same XRPD pattern was observed. Based on thermal data, the material had some residual solvent; a probable melting point was approximately 146-147° C. Partial decomposition likely occurred during the melt. The chloride salt was non-hygroscopic based on moisture balance data. The crystalline dihydrophosphate and fumarate salt were hydroscopic at approximately 65% RH. Attempts to scale up the salts were not successful due to high laboratory humidity. Thus, only partial characterization was available for these salts.

Example 4. Monitoring Caco-2 Cell Permeability of the Mesylate Salt of Compound I The bioavailability of orally administered drugs depends to a great extent on the capability of being transported across the intestinal barriers. Caco-2 cells, derived from a human colon adenocarcinoma, established by J. Fogh for its ability to achieve a higher degree of enterocytic differentiation, can be used as an in vitro model for the investigation of transport of drugs through the intestinal epithelium. These cells form a monolayer of polarized epithelial cells when grown onto collagen-coated polycarbonate membrane. The monolayer of differentiated cells represents a relevant model for the small intestinal epithelium. The process of differentiation starting at cell confluence leads to the formation of a brush border with well-developed microvilli, tight apical junctions, and a polarized distribution of membrane components, including enzymes, receptors, transport systems, ion channels and lipid molecules.

The purpose of the study was in a first step to assess the non-specific binding of compound I in the Caco-2 cell test system (without cells) and, in a second step, to assess the conversion of compound I into compound II and to determine if the transport of compound I across Caco-2 cell monolayers is mediated by the PepT1 transporter protein.

Materials

Caco-2 cell line (human colon adenocarcinoma cells) was obtained from controlled cell Banks (Biosearch S.p.A, Gerenzano-Italy). Dulbecco's modified Eagles's Medium (DMEM), Fetal Bovine Serum, Non essential amino acids solution, L-Glutamine 200 mM, Penicillin/Streptomycin Solution, Trypsin-EDTA solution without Calcium and Magnesium were purchased from Celbio (Milan, Italy). HEPES, Hank's Balanced Salt Solution (HBSS), Dulbecco's Phosphate Buffered Saline (PBS), Dimethyl Sulphoxide (DMSO), Glycine-Sarcosine (Gly-Sar) were purchased from Sigma (Milan, Italy).

Experimental

The Caco-2 cells were cultured in DMEM supplemented with 10% Fetal Bovine Serum, 2% L-Glutamine 200 mM and 1% non-essential amino acids solution.

The cells were stored frozen in cryotubes under liquid nitrogen, as 1 mL volumes of cell suspension in Fetal Bovine Serum containing 10% DMSO. Cells used for the experiments will be kept in culture for no longer than one month.

When necessary, frozen vials of Caco-2 cells were rapidly thawed at 37° C. in a water bath by gently swirling up to semi-complete thawing. Then the cell suspension was added drop by drop to 10 mL of culture medium. The cell suspension was then centrifuged for 7 minutes at 900-1000 rpm, the supernatant was removed and the cell pellet reconstituted in the medium and distributed into 75 $cm^2$ flasks containing medium. The flasks were incubated at 37° C. in an atmosphere of 5% $CO_2$. The cells were serially subcultured when near-confluent monolayers were obtained. The medium of each flask was removed and the monolayer was washed with 10-15 mL of Dulbecco's Phosphate Buffer Saline (PBS).

Trypsin-EDTA solution was added to the cell monolayer, incubated at 37° C. and tapped gently at intervals to dislodge the cells. Complete detachment and disaggregation of the cell monolayer was confirmed by microscopy examination. The cells were then re-suspended in 10 mL of complete medium and centrifuged for 7 minutes at 900-1000 rpm. The supernatant was discarded; the cells were resuspended in culture medium and plated at 2.5×105 cell/mL in 175 cm2 flasks.

The cells from flasks of near-confluent cultures were detached and disaggregated by treatment with trypsin as described above. The cells were resuspended in culture medium and counted. The cell suspension was diluted with medium to give about 1×10$^6$ cells/mL and 300 μL of cell suspension was put onto the apical compartment of each Transwell (6.5 mm diameter, 0.4 μm pore size). 600 μL of culture medium were put into the basolateral compartment. The plates were incubated at 37° C. in a humidified atmosphere of 5% CO2 in air for 15-21 days, changing the medium every 48-72 hours.

The integrity of each Caco-2 cell monolayer was evaluated by Transepithelial Electrical resistance (TEER), both pre-experiment and at the end of the incubation time. TEER, expressed as ohms×$cm^2$, was measured in the Transwells using the Millicell-ERS (Millipore). The monolayer is considered well differentiated when TEER value is higher than 800 ohms×$cm^2$.

The integrity of each Caco-2 cell monolayer was evaluated at the end of the incubation time by Lucifer Yellow. Post experiment the Transwells were washed twice with transport buffer. 200 μL of Lucifer Yellow at the concentration of 100 μM in HBSS were distributed in the apical compartment, while 400 μL of HBSS were added to the basolateral compartment. The transwells were incubated at 37° C. for 1 hour. The amount of Lucifer Yellow was quantitated in the basolateral compartment at 535 nm wavelength against a standard Lucifer Yellow curve in the same saline solution, using a Microplate Spectrofluorometer (EG & G WAL-LAC). The monolayer is considered not damaged if <1% Lucifer Yellow is detected in the basolateral compartment.

Assessment of Non-Specific Binding to Cell-Free Transwells

Non-specific binding and recovery was assessed across cell-free transwells.

Compound I was tested at 1.5, 3 and 6 μM in duplicate cell-free transwells. The test was performed in a pH gradient between the apical and the basolateral compartment. The apical compartment (donor) had a buffer pH of 6.5 while the basolateral compartment (receiver) had a buffer pH of 7.4. The following sampling times were performed: 60 and 120 min for the basolateral compartment (receiver) and 120 min for the apical compartment (donor). Samples obtained were analyzed by LC-MS, both compound I and compound II were monitored in order to assess percent of recovery.

Assessment of Stability of Compound I and Compound II

Stability of both compound I and compound II was assessed during the test. These compounds were dissolved in HBSS buffer (1% DMSO final concentration) at the concentrations of 1.5, 3 and 6 μM. An aliquot of each solution was sampled at time zero (t=0) to assess the starting concentrations of the compounds. The solutions were incubated at 37° C. for the duration of the transport experiment. An aliquot of each solution was sampled at the end of experiment (t=120) to assess the final concentrations of compound I and compound II. Samples were analyzed by LC-MS.

Assessment of Bidirectional Permeability of Compound I

Compound I was dissolved in HBSS buffer (1% DMSO final concentration) at the concentrations of 1.5, 3 and 6 μM. Each concentration/sampling time was run in duplicate well. The test was performed in a gradient pH: the apical compartment (mucosal) was at pH 6.5, the basolateral compartment (serosal) was at pH 7.4.

Apical to basolateral (A→B, mucosal to serosal) transport: 200 μL of each concentration of compound I was added to the apical compartment and 400 μL of HBSS was added to the basolateral compartment. The plates were incubated at 37° C. An aliquot of the basolateral compartment was sampled after 60 and 120 min (t=60 and t=120). An aliquot of the apical compartment was sampled at the starting time (t=0) and after 120 min. (t=120).

Basolateral to apical (B→A, serosal to mucosal) transport: 400 μL of each concentration of compound I was added to the basolateral compartment and 200 μL of HBSS was added to the apical compartment. The plates were incubated at 37° C. An aliquot of the apical compartment was sampled after 60 and 120 min (t=60 and t=120). An aliquot of the basolateral compartment was sampled at the starting time (t=0) and after 120 min. (t=120). All samples were analyzed by LC/MS monitoring both compound I and the appearance of compound II.

Assessment of Bidirectional Permeability of Compound II

Compound II was dissolved in HBSS buffer (1% DMSO final concentration) at the concentrations of 1.5, 3 and 6 μM. Each concentration/sampling time was run in duplicate well. The test was performed in a gradient pH: the apical compartment (mucosal) was at pH 6.5, the basolateral compartment (serosal) was at pH 7.4.

Apical to basolateral (A→B, mucosal to serosal) transport: 200 μL of each concentration of compound II was added to the apical compartment and 400 μL of HBSS was added to the basolateral compartment. The plates were incubated at 37° C. An aliquot of the basolateral compartment was sampled after 60 and 120 min (t=60 and t=120). An aliquot of the apical compartment was sampled at the starting time (t=0) and after 120 min. (t=120).

Basolateral to apical (B→A, serosal to mucosal) transport: 400 μL of each concentration of compound II was added to the basolateral compartment and 200 μL of HBSS was added to the apical compartment. The plates were incubated at 37° C. An aliquot of the apical compartment was sampled after 60 and 120 min (t=60 and t=120). An aliquot of the basolateral compartment was sampled at the starting time (t=0) and after 120 min. (t=120). All samples were analyzed by LC/MS monitoring compound II.

Inhibition of Mucosal-to-Serosal Transport of Compound I by PepT1 Substrate (Gly-Sar)

The differentiated cells were pre-treated for 30 min. with 10 mM of Gly-Sar in order to block the active transporter PepT1.

Compound I was dissolved in HBSS buffer (1% DMSO final concentration) at the concentrations of 1.5, 3 and 6 NM. Each concentration/sampling time was run in duplicate well. The test was performed in a gradient pH: the apical compartment (mucosal) was at pH 6.5, the basolateral compartment (serosal) was at pH 7.4.

Apical to basolateral (A→B, mucosal to serosal) transport: 200 µL of each concentration of compound I was added to the apical compartment and 400 µL of HBSS was added to the basolateral compartment. The plates were incubated at 37° C. An aliquot of the basolateral compartment was sampled after 60 and 120 min (t=60 and t=120). An aliquot of the apical compartment was sampled at the starting time (t=0) and after 120 min. (t=120). All samples were analyzed by LC/MS monitoring both compound I and the appearance of compound II.

Analytical Determinations

The concentrations of compound II and compound I in the post-incubation samples were determined by a high performance liquid chromatography/mass spectrometry (LC/MS) method reported in Appendices (section 7.1) without any further dilution.

Results

Figures 58A, 58B, 58C:
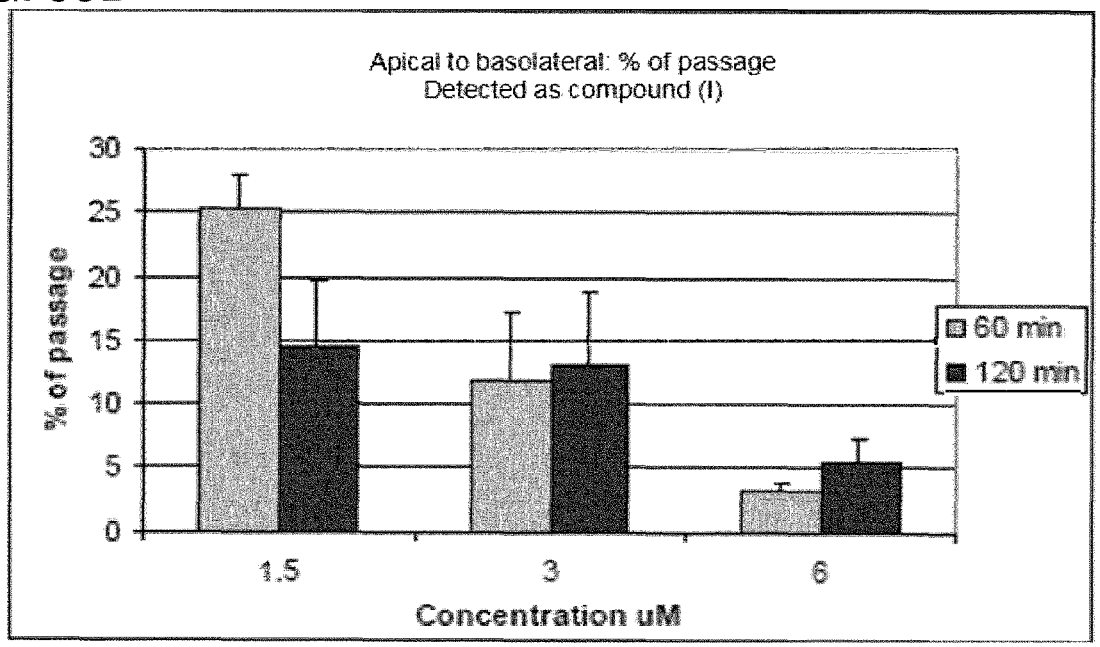
FIG. 58a is a table reporting data obtained from analysis of the ability of the mesylate salt of compound I to pass from the apical to the basolateral compartment of a transwell coated with a Caco-2 cell monolayer. Cultured Caco-2 cells were incubated with the indicated concentration of the mesylate salt of compound I in the apical compartment of the transwell, and aliquots from the basolateral compartment were sampled at the indicated sampling times in order to determine the presence of compound I or compound II. The data reports the concentration of compound II in the basolateral compartment as a percentage of the indicated initial concentration of the mesylate salt of compound I. Compound I was not detected in the basolateral compartment following 60 or 120 minutes of incubation in the apical compartment.
FIG. 58b is a graph showing the relative concentration of compound II in the basolateral compartment as a percentage of the initial concentration of the mesylate salt of compound I in the apical compartment.
FIG. 58c is a table showing the recovery of compound I in the apical compartment following 120 minutes of incubation. The initial compound was primarily recovered in the form of the de-esterified compound variant, compound II.

Pre-experiments TEER values of the Caco-2 cell monolayers used ranged from 850 to 1160 $\Omega \times cm^2$, indicating confluent monolayer with tight junctions. At the end of the experiments TEER values decreased in average of 170 $\Omega \times cm^2$ (from 680 to 990 $\Omega \times cm^2$) with no influence of cell monolayer integrity. The Lucifer Yellow test confirmed the integrity of all monolayers post-experiments, in fact the amount of Lucifer Yellow detected in the basolateral compartments post-experiments was always <1% in all wells. FIG. 55 reports data obtained in the non-specific binding test on compound I. In the test conditions compound I proved to be recovered in the apical compartment at all the doses tested. Compound I was not detected in the basolateral compartment at any dose tested. Non-specific binding of compound I was excluded. Compound II was not detected in any compartment. FIG. 55 reports data obtained in the stability test on compound I and compound II. Both compounds proved to be stable in the test conditions: HBSS buffer (2% DMSO final concentration) at 37° C. for 60 and 120 minutes. FIGS. 56a-56e report data obtained in the bi-directional permeability test on compound I. This compound did not pass through the cell monolayer. In the apical to basolateral test compound I was not detected in the receiving compartment after both 60 and 120 minutes, while increasing concentrations of compound II were detected at the end of the experiment in basolateral compartment. The percentage of passage of compound II is reported in the table. At the end of the apical to basolateral experiment, in the apical compartment low recovery of compound I was observed, while increased concentrations of compound II were detected (high recovery). The increased concentration of compound II after 120 min in the apical compartment could be explained by the presence of extra- and intracellular esterases in the Caco-2 cell able to de-esterify compounds (Kern et al. J. Agric. Food Chem. 51: 7884-7891 (2003)). In the basolateral to apical test compound I was not detected in the receiving compartment, while low concentrations of compound II were detected. Therefore, compound I is likely transferred and transported as compound II through the Caco-2 monolayer. FIGS. 57a-57e report data obtained in the bi-directional permeability test on compound II. This compound showed a good percentage of passage apical to basolateral and a low rate of permeability from basolateral to apical compartment. Papp was calculated because concentration in the donor compartments was known. Compound II has a good passive passage through the Caco-2 monolayer. No efflux was detected. FIGS. 58a-58c report data obtained in the inhibition test, in which the Caco-2 cell monolayer was pre-treated with 10 mM Gly-Sar (in order to saturate PepT1 transporter). Compound I was not detected in the receiving compartment, while a passage of compound II was observed. The percentage of passage was not linear in this test.

Discussion

In this study the non-specific binding of compound I in the Caco-2 cell test system (without cells) was evaluated and excluded. Compound I was stable in the test conditions. The conversion of compound I into compound II was evaluated and confirmed in the bi-directional permeability test. Compound I did not pass through the cell monolayer under the conditions tested. Compound I is therefore likely transferred and transported as de-esterified compound II through the Caco-2 cell monolayer.

In the bi-directional permeability test compound II showed a good passive passage through the Caco-2 cell monolayer. Evidence was not found that compound II might be a substrate for an efflux transporter.

The test with Gly-Sar pre-treatment (in order to saturate PepT1 transporter) showed no passage of compound I and a rate of passage of compound II. The transport of compound I across Caco-2 cell monolayers is likely not mediated by PepT1.

These experiments indicate that intestinal absorption of compound I and salts thereof is not mediated by the Pept1 transporter protein. Instead, the foregoing results demonstrate that compound I is de-esterified by ambient esterases in the small intestine and subsequently penetrates the small intestinal epithelium passively. That compound I and salts thereof are not substrates for Pept1 represents a surprising and pharmacologically beneficial property. Pept1 is a pH-dependent co-transporter known to mediate the absorption of a variety of valinate esters, as described, for example, in Vig et al., Adv. Drug Deliv. Rev. 65:1370-1385 (2013), the disclosure of which is incorporated herein by reference. Pept1 exhibits broad substratespecificity, as evidenced by the structural diversity of compounds that are transported across the intestinal epithelium by this protein. Unexpectedly, despite the presence the valinate ester functionality, compound I and salts thereof are not dependent upon this transporter for absorption across the small intestinal epithelium. This is an advantageous property, as Compound I and salts thereof thus do not compete with natural substrates of Pept1, such as peptidic nutrients, for binding to and transport by this protein. Rather, compound I and salts thereof are converted in vivo to a form that is readily absorbed in a manner independent of energy and local proton gradient. This unexpected property, coupled with the high aqueous solubility of compound I and salts thereof, collectively provide a beneficial pharmacokinetic profile by which these therapeutics readily dissolve in an aqueous environment and are in turn converted into a form capable of transporter-independent absorption.

Example 5. Combination Therapy Including an Additional Tocolytic Agent

Compound I or a salt thereof, such as compound III, can be administered to a subject, such as a human subject, in combination with one or more additional agents, such as an oxytocin receptor antagonist, betamimetic, calcium channel inhibitor, magnesium salt, or nitric oxide donor, for instance, in order to reduce the occurrence of uterine contractions and to delay the onset of labor.

A physician of skill in the art can administer compound I or a salt thereof, such as compound III, simultaneously with, as an admixture with, or separately from an oxytocin receptor antagonist. Exemplary oxytocin receptor antagonists for use in conjunction with the compositions and methods of the invention include atosiban, retosiban, barusiban, epelsiban, and nolasiban, or a variant, formulation, crystalline form, or derivative thereof. For instance, compound I or a salt thereof, such as compound III, may be administered prior to, after, or simultaneously with nolasiban, or a variant, formulation, crystalline form, or derivative thereof, in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, a physician of skill in the art can administer compound I or a salt thereof, such as compound III, simultaneously with, as an admixture with, or separately from a betamimetic, such as a betamimetic described herein. For instance, compound I or a salt thereof, such as compound III, may be administered prior to, after, or simultaneously with a betamimetic described herein or known in the art in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, a physician of skill in the art can administer compound I or a salt thereof, such as compound III, simultaneously with, as an admixture with, or separately from a calcium channel inhibitor, such as a calcium channel inhibitor described herein. For instance, compound I or a salt thereof, such as compound III, may be administered prior to, after, or simultaneously with a calcium channel inhibitor described herein or known in the art in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, a physician of skill in the art can administer compound I or a salt thereof, such as compound III, simultaneously with, as an admixture with, or separately from a magnesium salt, such as magnesium sulfate. For instance, compound I or a salt thereof, such as compound III, may be administered prior to, after, or simultaneously with magnesium sulfate in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, a physician of skill in the art can administer compound I or a salt thereof, such as compound III, simultaneously with, as an admixture with, or separately from a nitric oxide donor, such as nitroglycerine. For instance, compound I or a salt thereof, such as compound III, may be administered prior to, after, or simultaneously with nitroglycerine in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Additionally or alternatively, a physician of skill in the art can administer compound I or a salt thereof, such as compound III, simultaneously with, as an admixture with, or separately from progesterone or a derivative or variant thereof, such as a derivative or variant described herein or known in the art. For instance, compound I or a salt thereof, such as compound III, may be administered prior to, after, or simultaneously with progesterone or a variant or derivative thereof described herein or known in the art in order to delay the onset of labor in a subject, e.g., by one or more days or weeks, such as from about 1 day to about 16 weeks (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or about 1, 2, 3, 4, 5, 6, 7, 8, 9, 10, 11, 12, 13, 14, 15, or 16 weeks).

Example 6. Tocolytic Effects of Compound I and Pharmaceutically Acceptable Salts Thereof in Combination with Nifedipine and Atosiban in Mouse Models of Preterm Labor To investigate the therapeutic effects of compound I in combination with a calcium channel blocker or an oxytocin receptor antagonist in animal models of preterm parturition, primigravid pregnant CD-1 mice were treated with established inducers of labor at an early gestational age of 17 days and were subsequently administered various dosages of the chloride salt of compound I (compound III; 10 mg/kg, 30 mg/kg, or 100 mg/kg, each administered orally) alone or in combination with nifedipine (5 mg/kg, administered orally) or atosiban (300 mg/kg, administered subcutaneously). Tocolytic effects were assessed by measuring the time from induction to delivery of the first pup for each mouse in the treatment and control cohorts, the time from time from induction to completion of delivery among all mice in each cohort, and viability of offspring among mice in each cohort. The inducers of preterm parturition used in this study were RU486 (also referred to as mifepristone), a steroidal antiprogestin that promotes cervical dilatation and provokes enhanced uterine contractility and sensitivity to prostaglandins, and lipopolysaccharide (LPS), a mediator of inflammation.

To induce labor at an early gestational age, a single dose of RU486 was administered to each mouse subcutaneously at 2.5 mg/kg (t=0). Mice treated with LPS received a single intraperitoneal injection of LPS at 2 mg/kg (t=0). Atosiban was administered to CD-1 mice by subcutaneous injection at 300 mg/kg at two distinct sites. These injections were performed at 5 hours (t=5) and 29 hours (t=29) following treatment with the inducing agent RU486 or LPS. Nifedipine was administered to CD-1 mice orally at 5 mg/kg at 5 hours (t=5), 19 hours (t=19), 29 hours (t=29), and 43 hours (t=43) following treatment with the inducing agent RU486 or LPS. Compound III was administered to CD-1 mice orally at either 10 mg/kg, 30 mg/kg, or 100 mg/kg at 5 hours (t=5), 19 hours (t=19), 29 hours (t=29), and 43 hours (t=43)

following treatment with the inducing agent RU486 or LPS. Following induction with RU486 or LPS and subsequent administration of atosiban, nifedipine, and/or compound III, mouse cohorts were subject to continuous visual monitoring to assess the time elapsed between induction and delivery of the first pup for each mouse, as well as the proportion of mice in each cohort that had undergone delivery as a function of time. The viability of pups delivered in each cohort was assessed by galenic hydrostatic pulmonary docimasy.

Figure 60A:
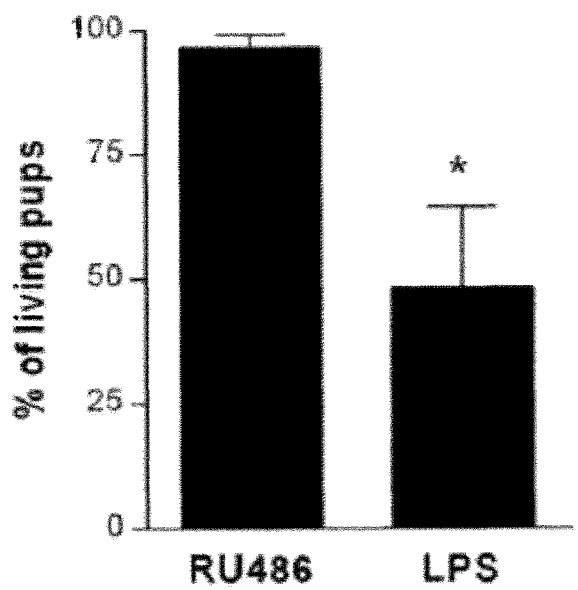
FIG. 60a is a graph illustrating the fractional viability of offspring of CD-1 mice treated with RU486 or lipopolysaccharide (LPS) at a gestational age of 17 days so as to induce parturition. Values represent the mean plus/minus standard error of the mean. Asterisk designates a p value of $p<0.05$. Statistical analyses were conducted using a Mann-Whitney test versus the corresponding group.
Figure 60B:
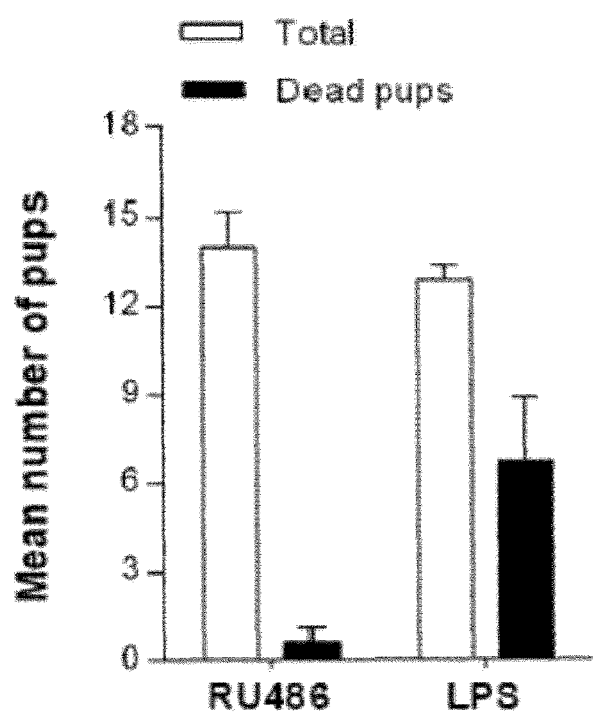
FIG. 60b is a graph illustrating the quantity of viable and non-viable offspring of CD-1 mice treated with RU486 or LPS at a gestational age of 17 days so as to induce parturition.
Figure 61A:
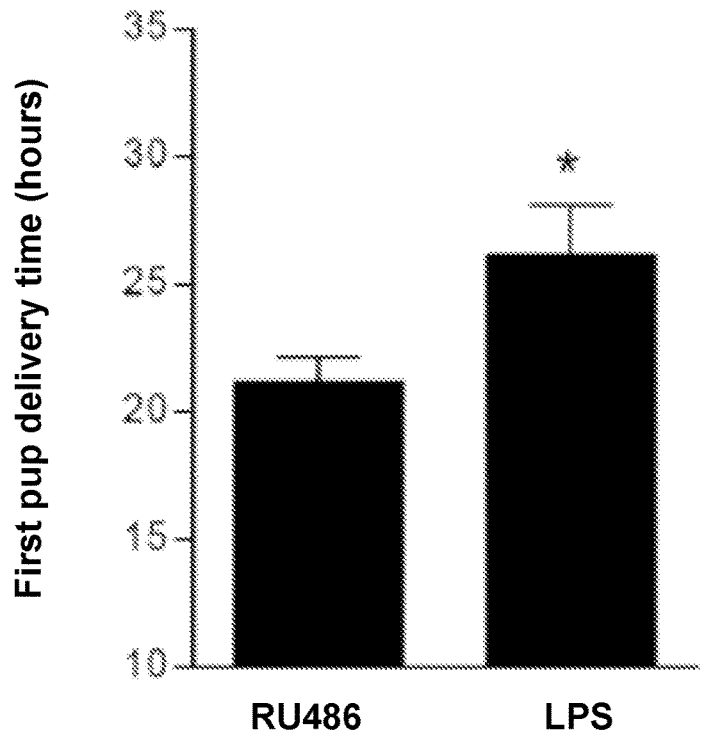
FIG. 61a is a graph illustrating the time from induction to first pup delivery for CD-1 mice treated with RU486 or LPS at a gestational age of 17 days so as to induce parturition. Values represent the mean plus/minus standard error of the mean.
Figure 61B:
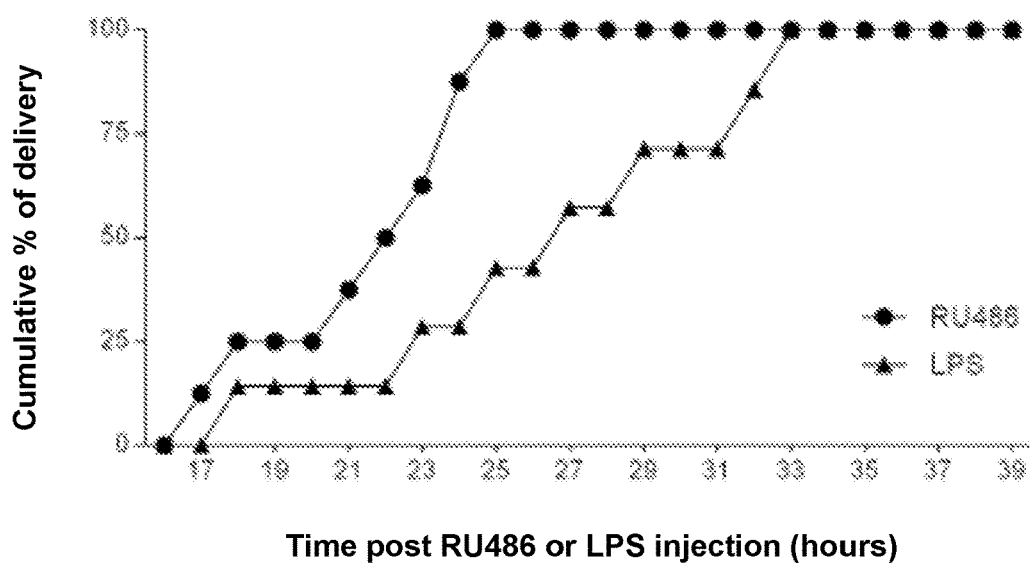
FIGS. 61b and 61c are graphs illustrating the time from induction to completion of delivery among CD-1 mice treated with RU486 or LPS at a gestational age of 17 days so as to induce parturition. Values along the Y-axis denote the proportion of CD-1 mice that have completed labor. In each figure, an asterisk designates a p value of $p<0.05$. Statistical analyses were conducted using a Mann-Whitney test or Log-rank test versus the corresponding group.
Figure 61C:
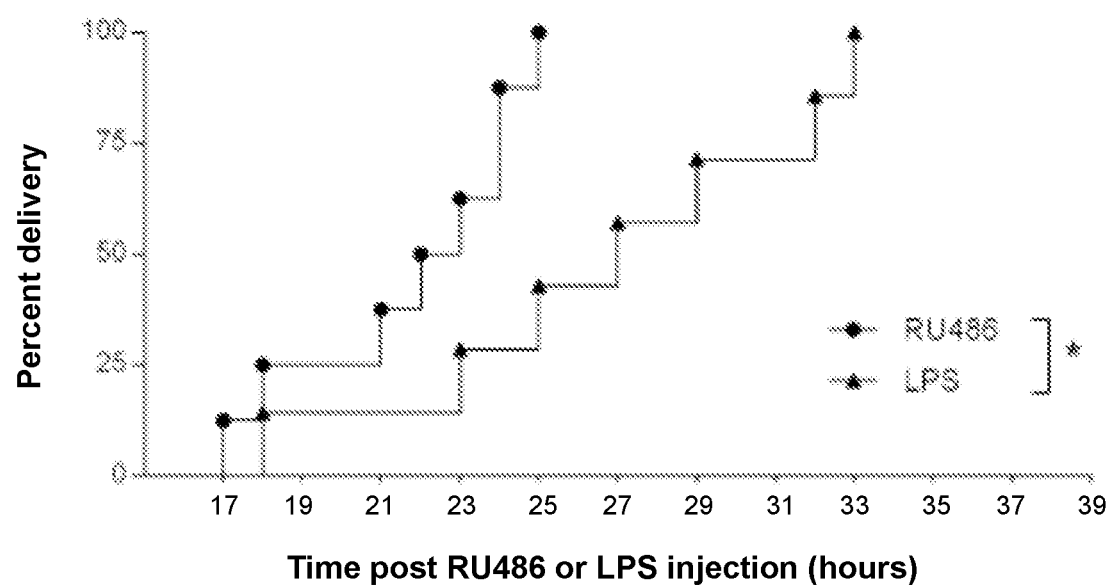
Figure 62A:
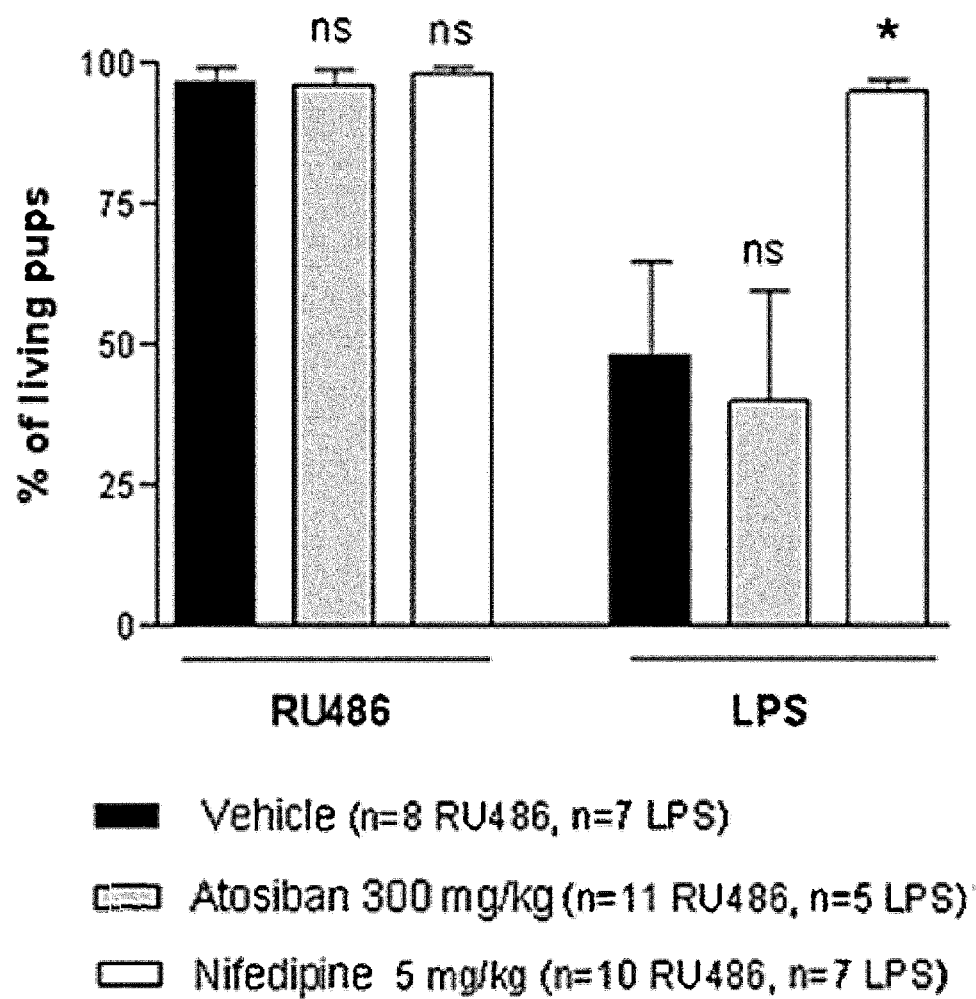
FIG. 62a is a graph demonstrating the effects of atosiban (300 mg/kg, administered subcutaneously) and nifedipine (5 mg/kg, administered orally) on the fractional viability of offspring of CD-1 mice treated with RU486 or lipopolysaccharide (LPS) at a gestational age of 17 days so as to induce parturition. Values represent the mean plus/minus standard error of the mean. Asterisk designates a p value of $p<0.05$; "ns" designates a p value of $p>0.05$. Statistical analyses were conducted using a Mann-Whitney test or unpaired t test versus the corresponding vehicle group.
Figure 62B:
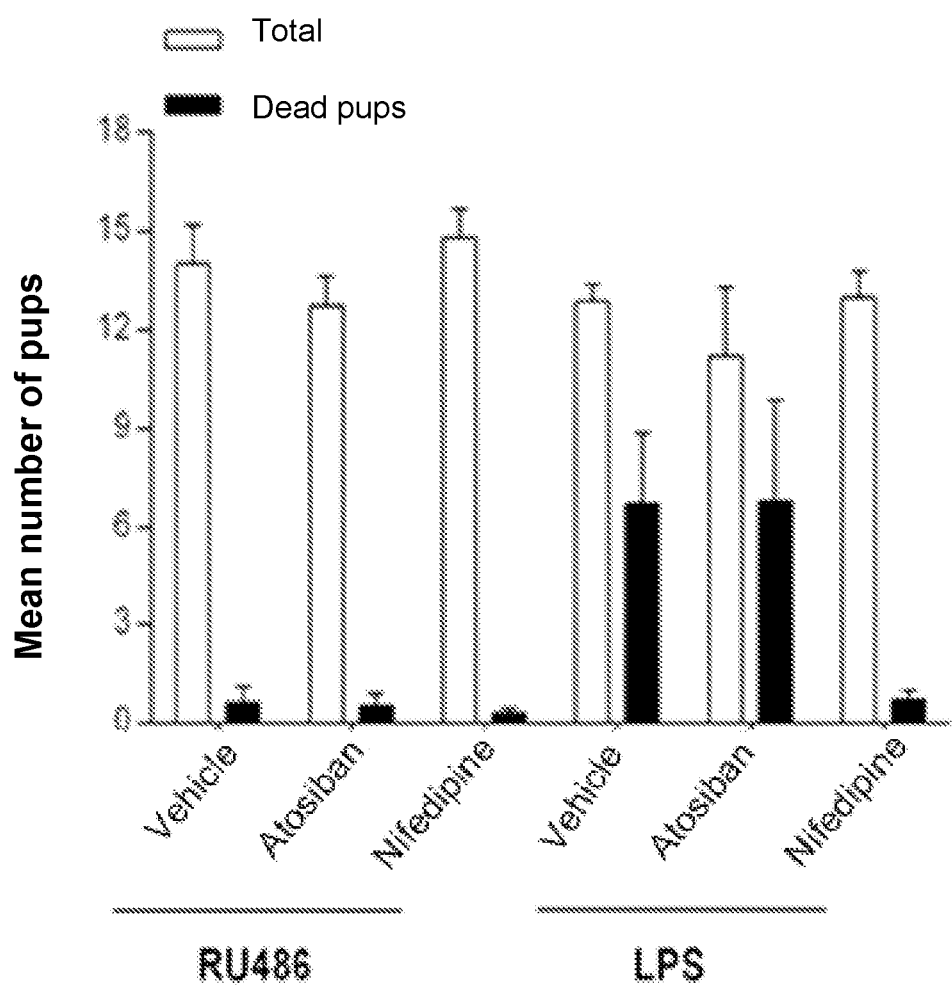
FIG. 62b is a graph demonstrating the effects of atosiban (300 mg/kg, administered subcutaneously) and nifedipine (5 mg/kg, administered orally) on the quantity of viable and non-viable offspring of CD-1 mice treated with RU486 or LPS at a gestational age of 17 days so as to induce parturition.
Figure 63A:
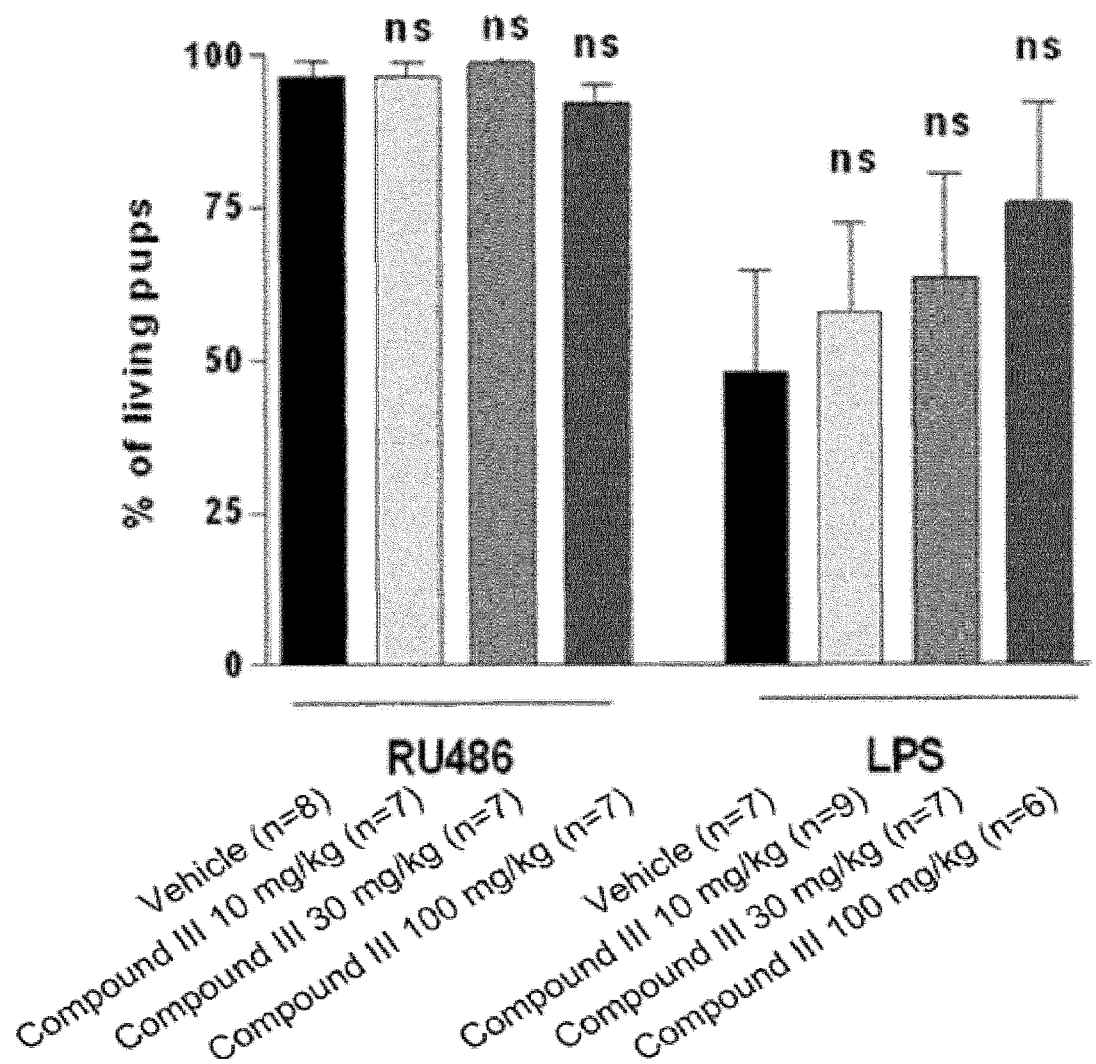
FIG. 63a is a graph demonstrating the effects of compound III (10 mg/kg, 30 mg/kg, and 100 mg/kg, administered orally) on the fractional viability of offspring of CD-1 mice treated with RU486 or LPS at a gestational age of 17 days so as to induce parturition. Values represent the mean plus/minus standard error of the mean. "ns" designates a p value of $p>0.05$. Statistical analyses were conducted using a Mann-Whitney test versus the corresponding vehicle group.
Figure 63B:
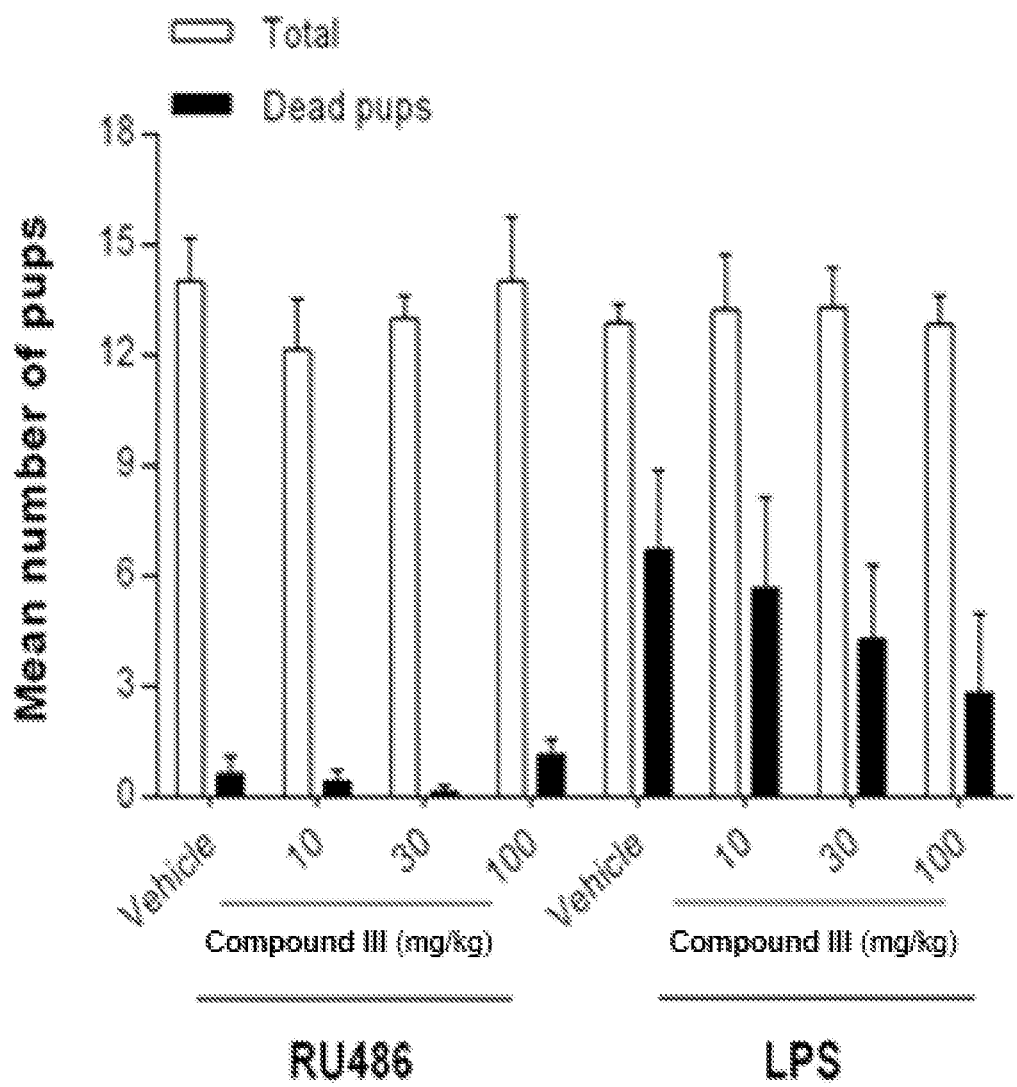
FIG. 63b is a graph demonstrating the effects of compound III (10 mg/kg, 30 mg/kg, and 100 mg/kg, administered orally) on the quantity of viable and non-viable offspring of CD-1 mice treated with RU486 or LPS at a gestational age of 17 days so as to induce parturition.
Figure 64A:
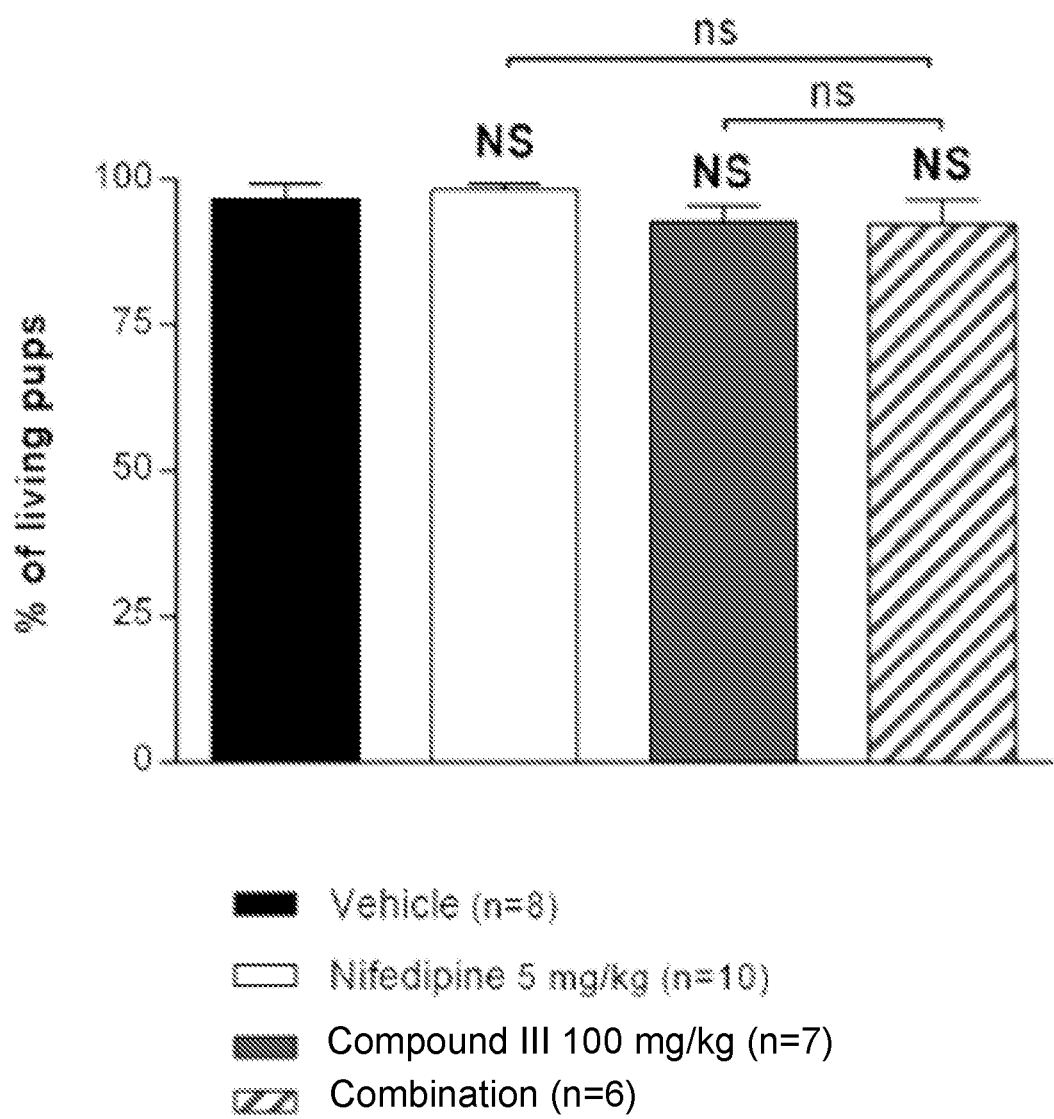
FIG. 64a is a graph demonstrating the effects of nifedipine (5 mg/kg, administered orally), compound III (100 mg/kg, administered orally), and a combination thereof on the fractional viability of offspring of CD-1 mice treated with RU486 at a gestational age of 17 days so as to induce parturition. Values represent the mean plus/minus standard error of the mean. "ns" designates a p value of $p>0.05$ versus the corresponding group; "NS" designates a p value of $p>0.05$ versus the corresponding vehicle group. Statistical analyses were conducted using a Mann-Whitney test versus the corresponding group of interest.
Figure 64B:
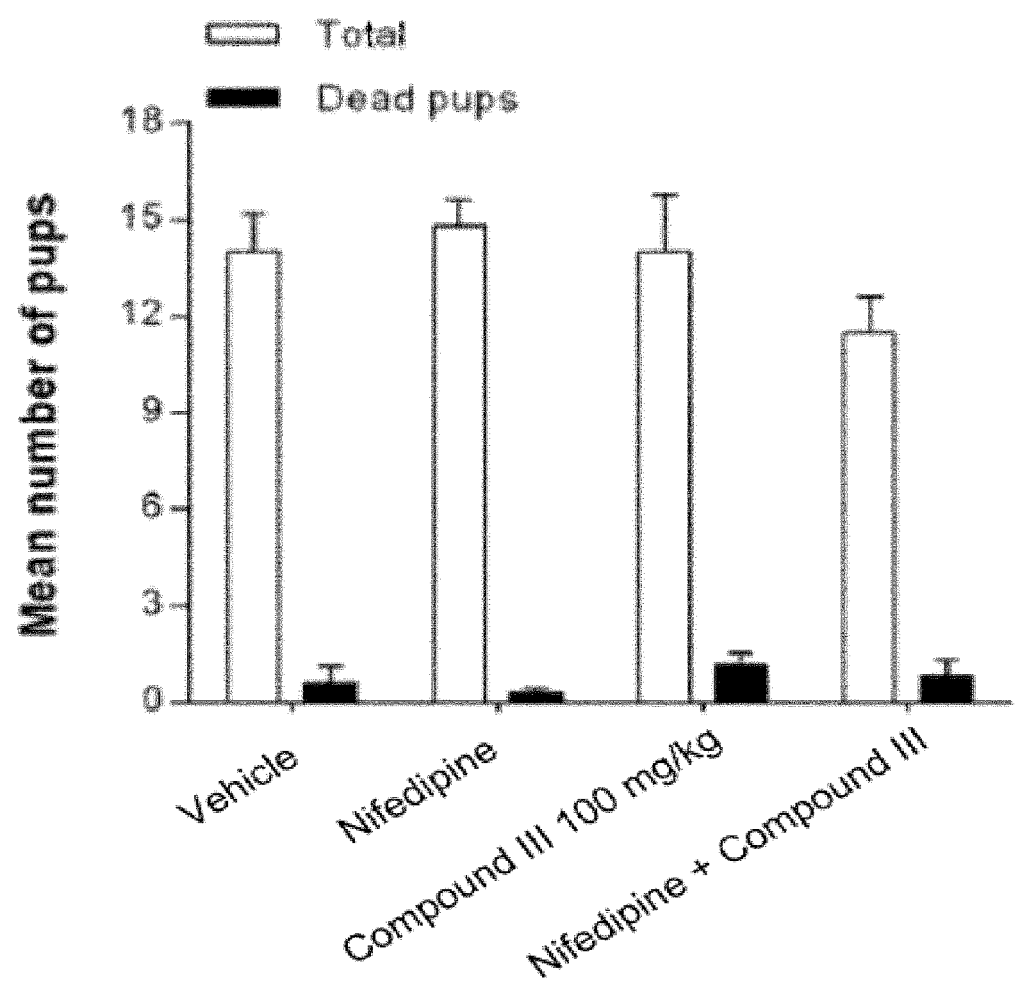
FIG. 64b is a graph demonstrating the effects of nifedipine (5 mg/kg, administered orally), compound III (100 mg/kg, administered orally), and a combination thereof on the quantity of viable and non-viable offspring of CD-1 mice treated with RU486 at a gestational age of 17 days so as to induce parturition.
Figure 65A:
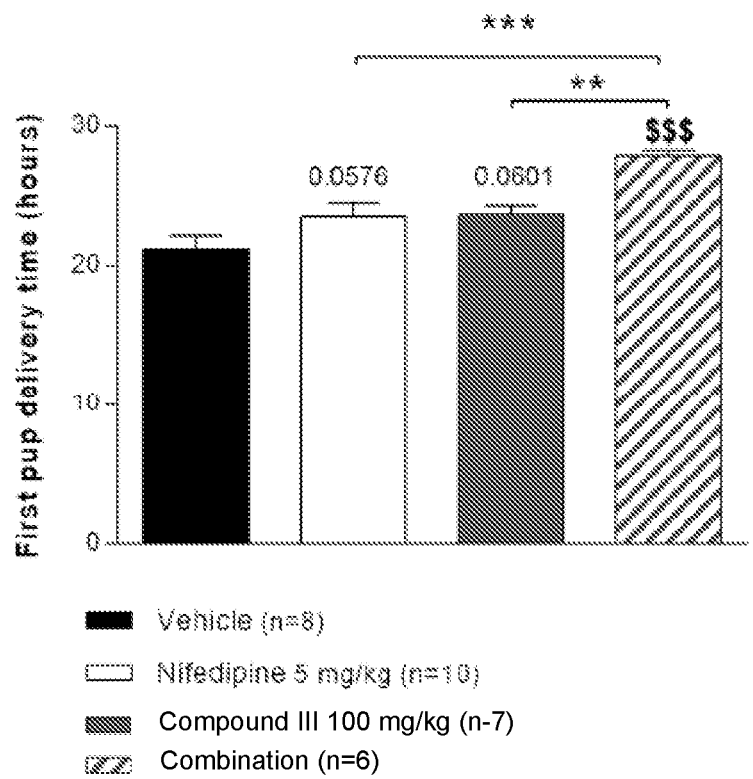
FIG. 65a is a graph demonstrating the effects of nifedipine (5 mg/kg, administered orally), compound III (100 mg/kg, administered orally), and a combination thereof on the time from induction to first pup delivery for CD-1 mice treated with RU486 at a gestational age of 17 days so as to induce parturition. Values represent the mean plus/minus standard error of the mean. Three asterisks designate a p value of $p<0.001$ versus the corresponding group; two asterisks designate a p value of $p<0.01$ versus the corresponding group. Nifedipine, compound III, and combination arms exhibited p values of $p=0.0576$, $p=0.0601$, and $p<0.001$ (indicated by "$$$" symbol), respectively, relative to the group treated with vehicle alone. Statistical analyses were conducted using a Mann-Whitney test or unpaired t test versus the corresponding group of interest.
Figure 65B:
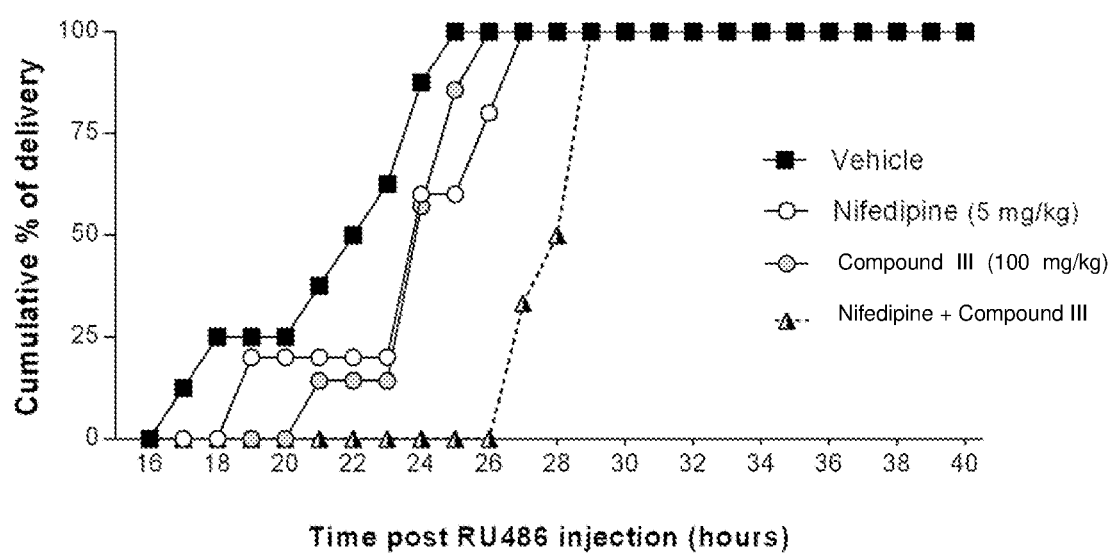
FIG. 65b is a graph demonstrating the effects of nifedipine (5 mg/kg, administered orally), compound III (100 mg/kg, administered orally), and a combination thereof on the time from induction to completion of delivery among CD-1 mice treated with RU486 at a gestational age of 17 days so as to induce parturition. Values along the Y-axis denote the proportion of CD-1 mice that have completed labor.
Figure 65C:
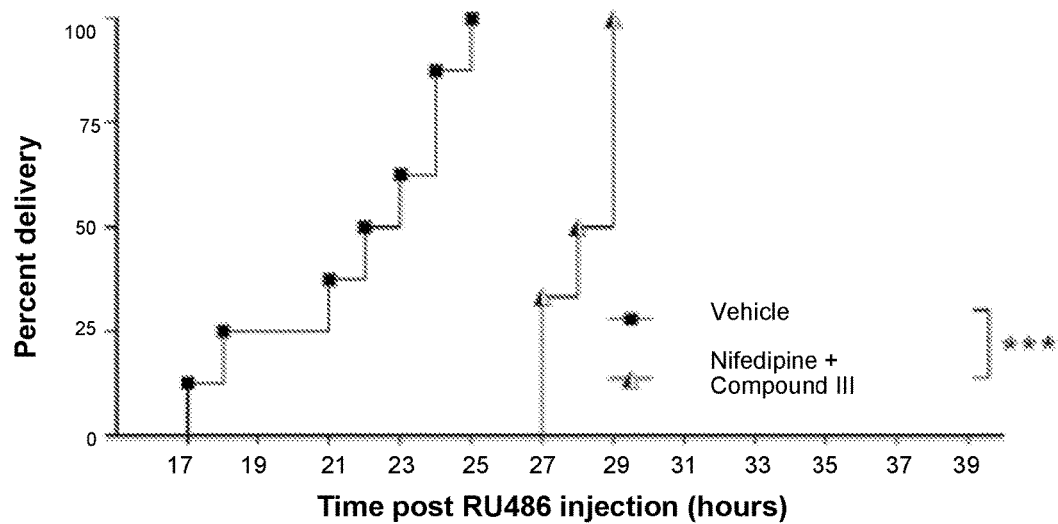
FIG. 65c is a graph showing the time from induction to completion of offspring delivery for the vehicle and combination arms shown in FIG. 65b. Three asterisks designate a p value of p<0.001 versus the corresponding group. Statistical analyses were conducted using a Log-rank test versus the corresponding group of interest.
Figure 65D:
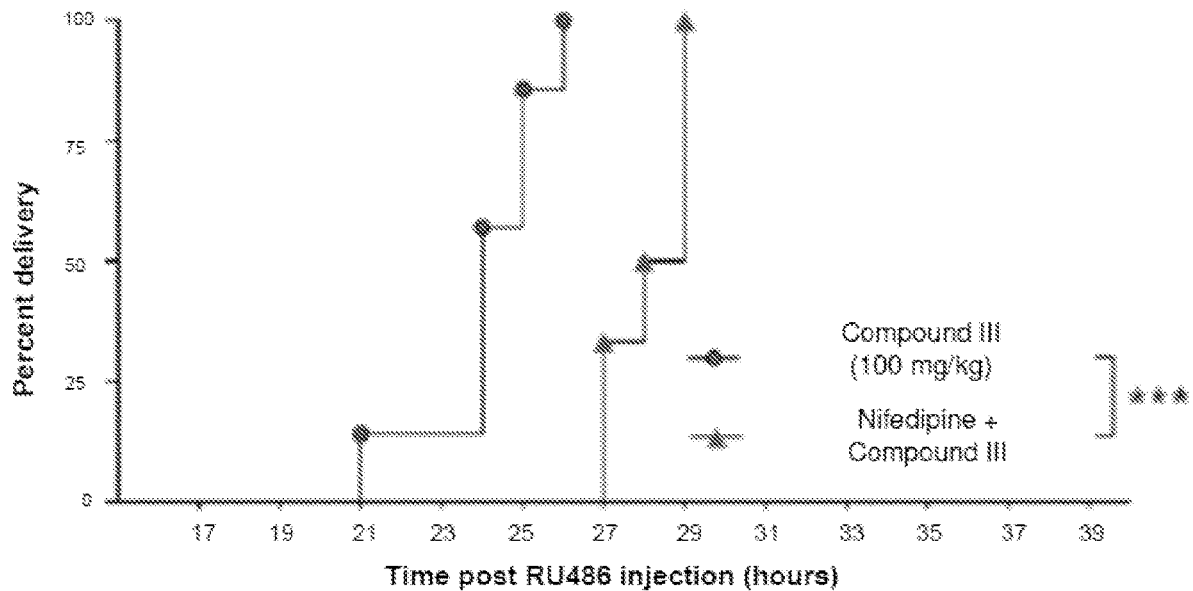
FIG. 65d is a graph showing the time from induction to completion of offspring delivery for the compound III and combination arms shown in FIG. 65b. Three asterisks designate a p value of p<0.001 versus the corresponding group. Statistical analyses were conducted using a Log-rank test versus the corresponding group of interest.
Figure 65E:
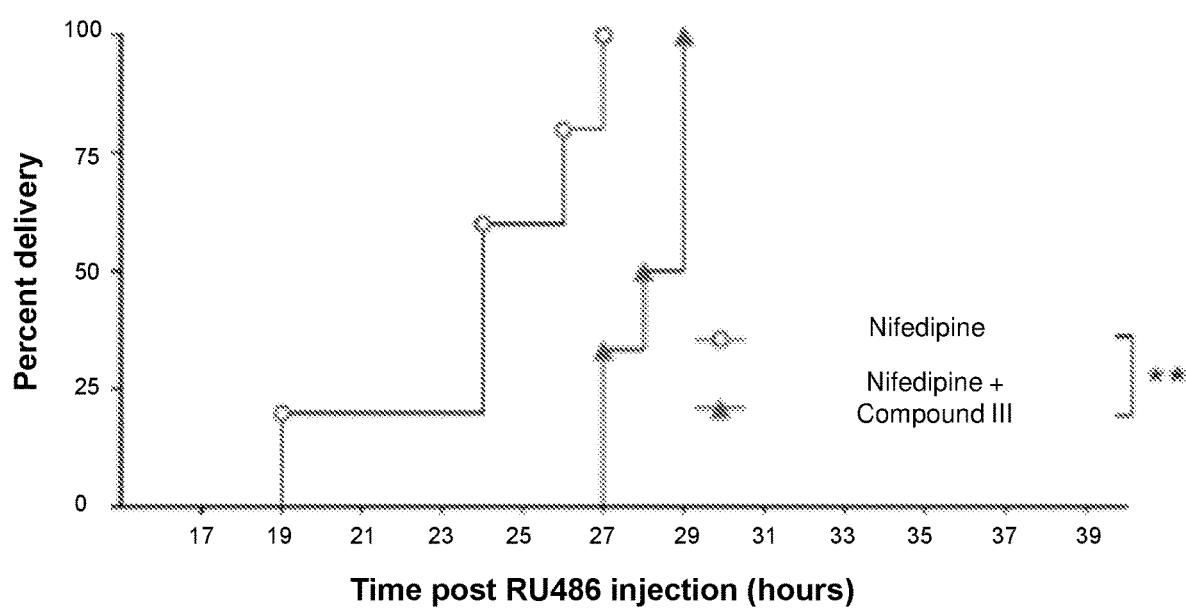
FIG. 65e is a graph showing the time from induction to completion of offspring delivery for the nifedipine and combination arms shown in FIG. 65b. Two asterisks designate a p value of p<0.01 versus the corresponding group. Statistical analyses were conducted using a Log-rank test versus the corresponding group of interest.
Figure 66A:
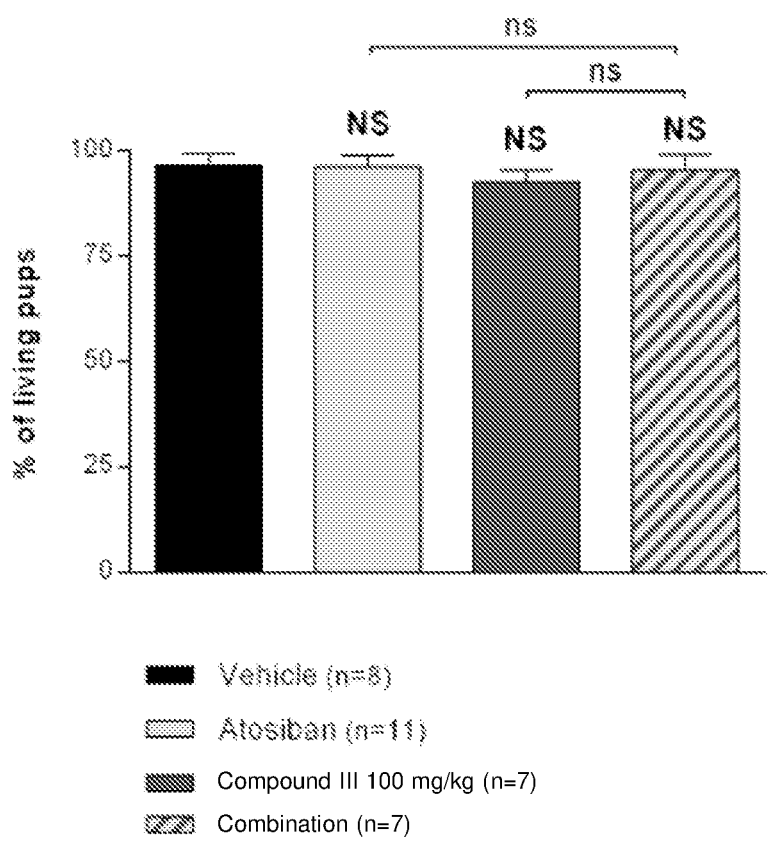
FIG. 66a is a graph demonstrating the effects of atosiban (300 mg/kg, administered subcutaneously), compound III (100 mg/kg, administered orally), and a combination thereof on the fractional viability of offspring of CD-1 mice treated with RU486 at a gestational age of 17 days so as to induce parturition. Values represent the mean plus/minus standard error of the mean. "ns" designates a p value of p>0.05 versus the corresponding group; "NS" designates a p value of p>0.05 versus the corresponding vehicle group. Statistical analyses were conducted using a Mann-Whitney test versus the corresponding group of interest.
Figure 66B:
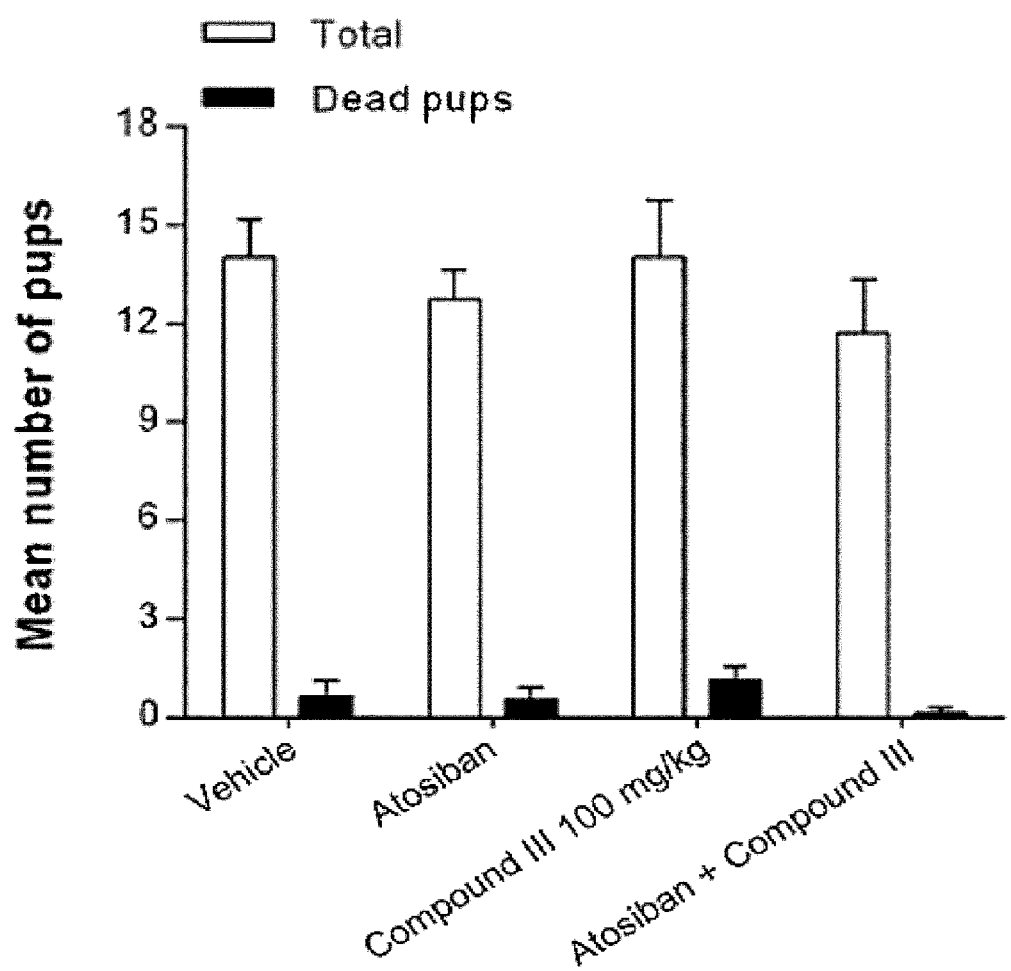
FIG. 66b is a graph demonstrating the effects of atosiban (300 mg/kg, administered subcutaneously), compound III (100 mg/kg, administered orally), and a combination thereof on the quantity of viable and non-viable offspring of CD-1 mice treated with LPS at a gestational age of 17 days so as to induce parturition.
Figure 67A:
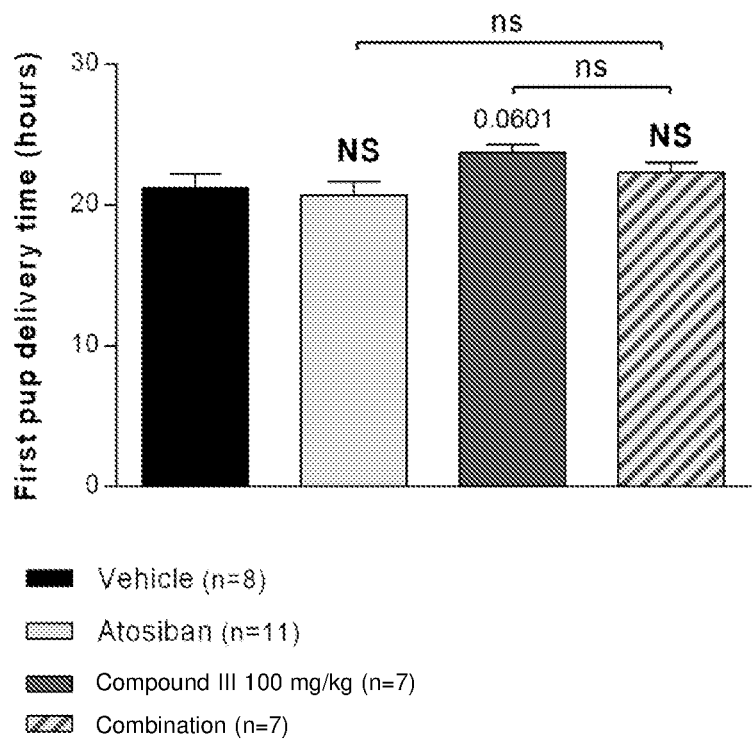
FIG. 67a is a graph demonstrating the effects of atosiban (300 mg/kg, administered subcutaneously), compound III (100 mg/kg, administered orally), and a combination thereof on the time from induction to first pup delivery for CD-1 mice treated with RU486 at a gestational age of 17 days so as to induce parturition. Values represent the mean plus/minus standard error of the mean. "ns" designates a p value of p>0.05 versus the corresponding group; "NS" designates a p value of p>0.05 versus the corresponding vehicle group. Atosiban, compound III, and combination arms exhibited p values of p>0.05, p=0.0601, and p>0.05, respectively, relative to vehicle group. Statistical analyses were conducted using an unpaired t test versus the corresponding group of interest.
Figure 67B:
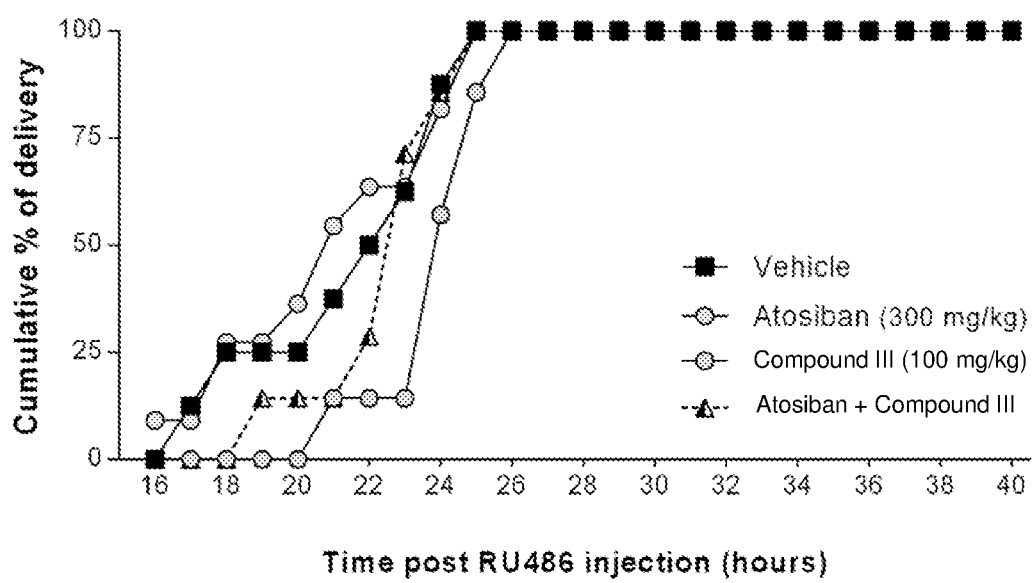
FIG. 67b is a graph demonstrating the effects of atosiban (300 mg/kg, administered subcutaneously), compound III (100 mg/kg, administered orally), and a combination thereof on the time from induction to completion of delivery among CD-1 mice treated with RU486 at a gestational age of 17 days so as to induce parturition. Values along the Y-axis denote the proportion of CD-1 mice that have completed labor.
Figure 67C:
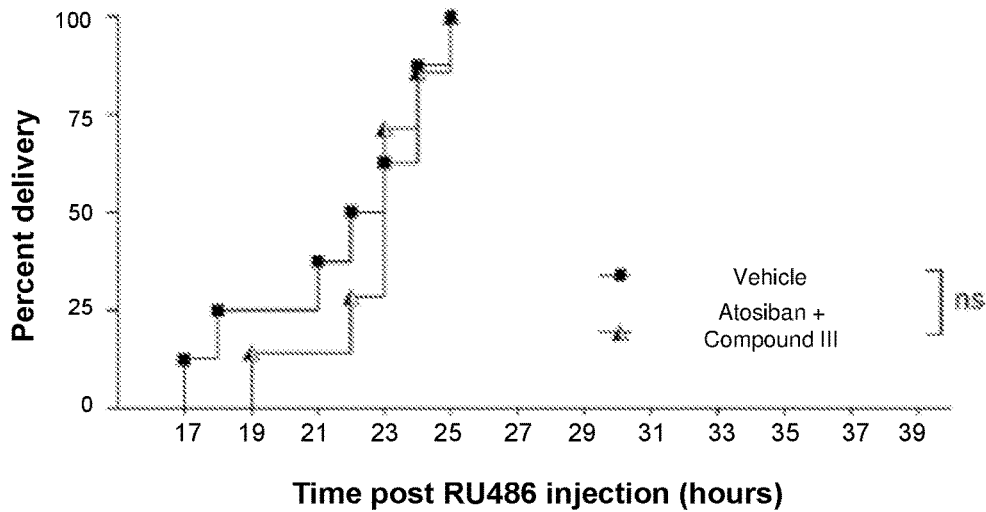
FIG. 67c is a graph showing the time from induction to completion of offspring delivery for the vehicle and combination arms shown in FIG. 67b. "ns" designates a p value of p>0.05 versus the corresponding group. Statistical analyses were conducted using a Log-rank test versus the corresponding group of interest.
Figure 67D:
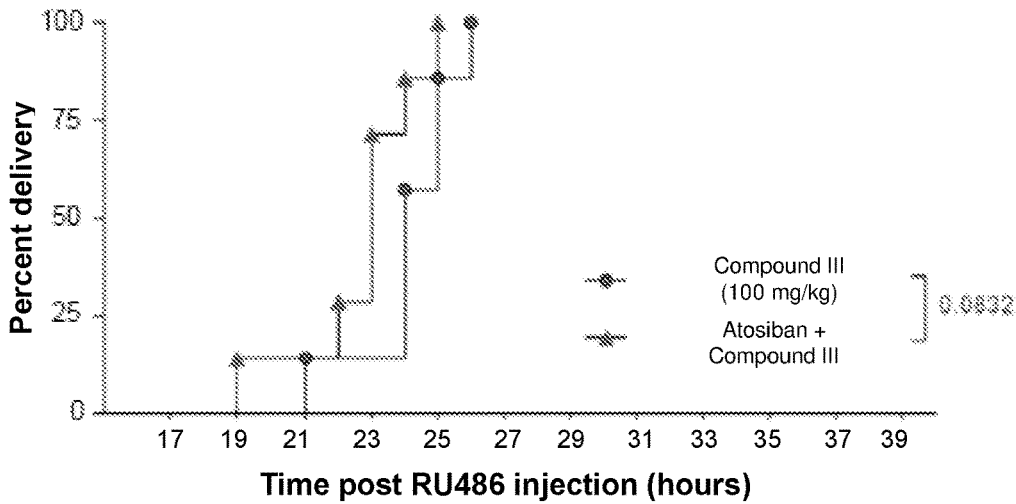
FIG. 67d is a graph showing the time from induction to completion of offspring delivery for the compound III and combination arms shown in FIG. 67b. The combination arm exhibited a p value of p=0.0832 relative to the compound III arm. Statistical analyses were conducted using a Log-rank test versus the corresponding group of interest.
Figure 67E:
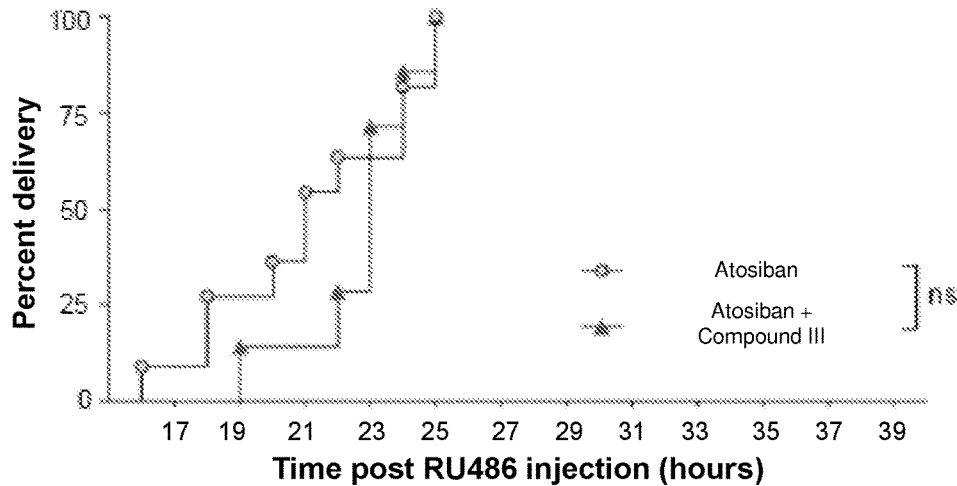
FIG. 67e is a graph showing the time from induction to completion of offspring delivery for the atosiban and combination arms shown in FIG. 67b. "ns" designates a p value of p>0.05 versus the corresponding group. Statistical analyses were conducted using a Log-rank test versus the corresponding group of interest.

The ability of RU486 and LPS to induce preterm parturition was confirmed, as treatment of CD-1 mice with RU486 at a gestational age of 17 days resulted in a mean delivery time of about 21 hours following induction (t=21; calculated mean=21±1.00 hours), while CD-1 mice treated with LPS at a gestational age of 17 days exhibited a mean delivery time of about 26 hours following induction (t=26; calculated mean=26±2.34 hours). In contrast, term delivery in CD-1 mice occurs at a gestational age of from about 19 days to about 21 days, more than 50 hours after day 17 of gestation. Among pups delivered from RU486-treated mice, 96% were delivered alive, and 48% of pups delivered to LPS-treated mice were delivered alive (FIGS. 60 and 61). 3% of mice treated with RU486 were excluded from this investigation due to death or sacrifice during the study; 34% of mice treated with LPS were excluded from this investigation due to death or sacrifice during the study.

Figure 68A:
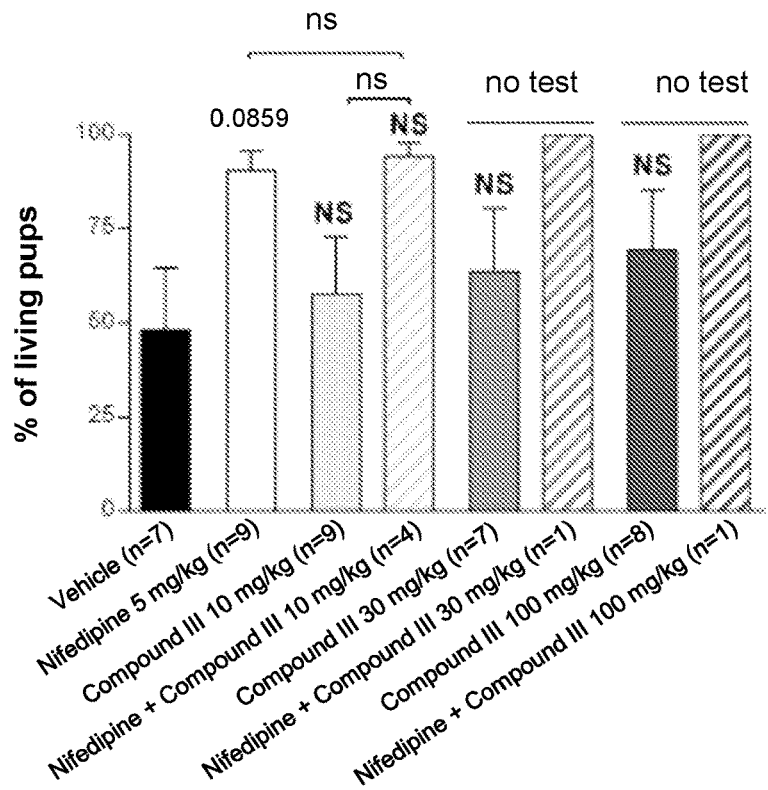
FIG. 68a is a graph demonstrating the effects of nifedipine (5 mg/kg, administered orally), compound III (10 mg/kg, 30 mg/kg, and 100 mg/kg, administered orally), and combinations thereof on the fractional viability of offspring of CD-1 mice treated with LPS at a gestational age of 17 days so as to induce parturition. Values represent the mean plus/minus standard error of the mean. "ns" designates a p value of p>0.05 versus the corresponding group; "NS" designates a p value of p>0.05 versus the corresponding vehicle group. The nifedipine arm exhibited a p value of p=0.0859 relative to the group treated with vehicle alone. Statistical analyses were conducted using a Mann-Whitney test or unpaired t test versus the corresponding group of interest.
Figure 68B:
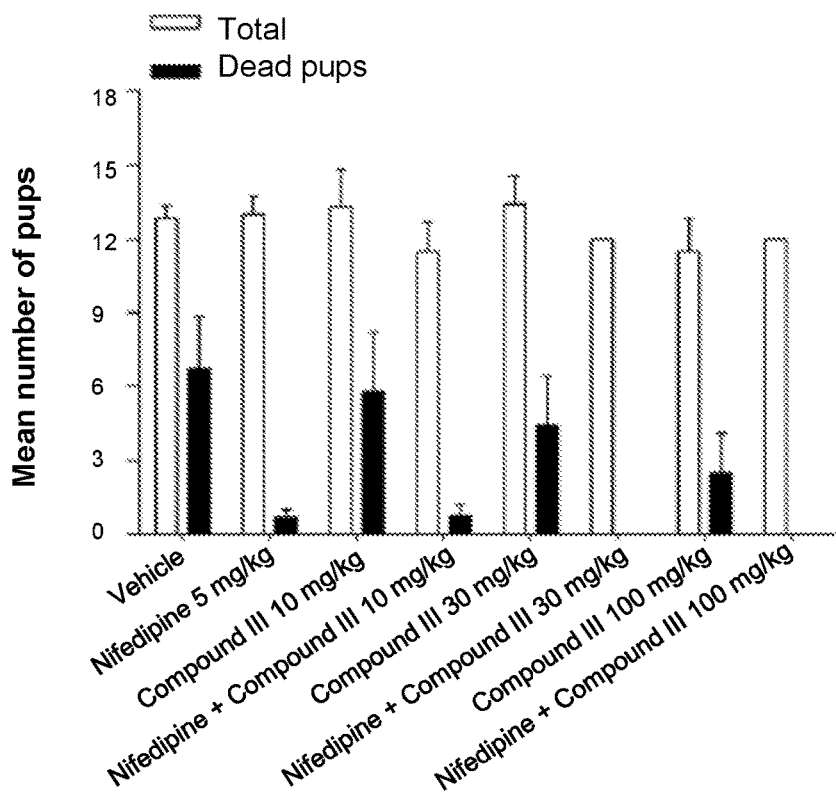
FIG. 68b is a graph demonstrating the effects of nifedipine (5 mg/kg, administered orally), compound III (10 mg/kg, 30 mg/kg, and 100 mg/kg, administered orally), and combinations thereof on the quantity of viable and non-viable offspring of CD-1 mice treated with LPS at a gestational age of 17 days so as to induce parturition.
Figure 69A:
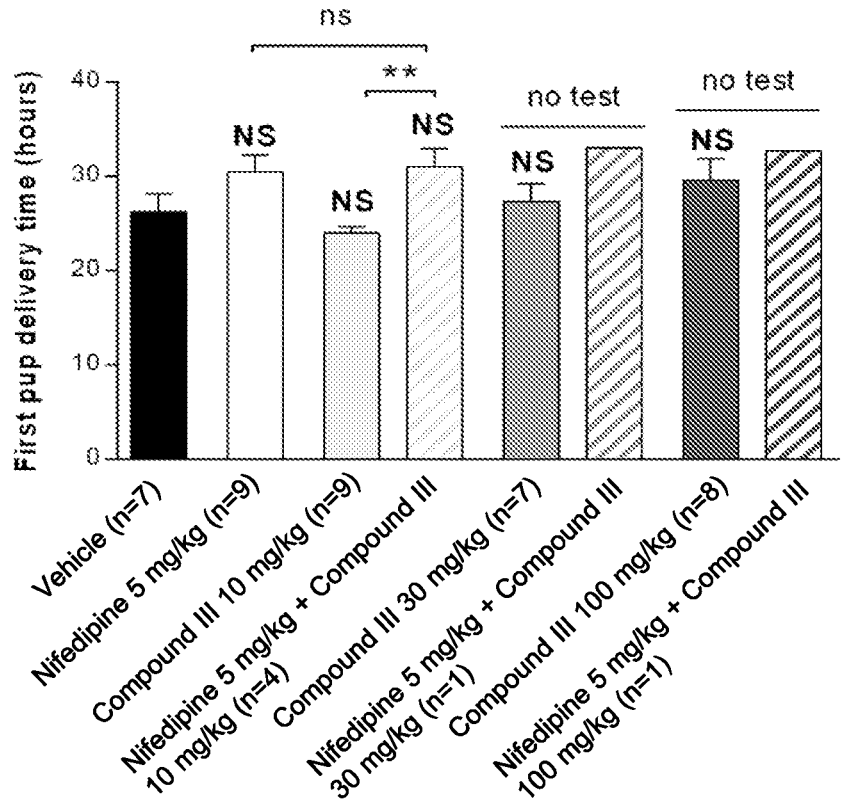
FIG. 69a is a graph demonstrating the effects of nifedipine (5 mg/kg, administered orally), compound III (10 mg/kg, 30 mg/kg, and 100 mg/kg, administered orally), and combinations thereof on the time from induction to first pup delivery for CD-1 mice treated with LPS at a gestational age of 17 days so as to induce parturition. Values represent the mean plus/minus standard error of the mean. Two asterisks designate a p value of p<0.01 versus the corresponding group as assessed by a Mann-Whitney test versus the corresponding group; "ns" designates a p value of p>0.05 versus the corresponding group as assessed by a Mann-Whitney test versus the corresponding group; "NS" designates a p value of p>0.05 versus the corresponding vehicle group as assessed by an unpaired t test versus the corresponding group; "no test" designates that no statistical test was conducted for the indicated pair.
Figure 69B:
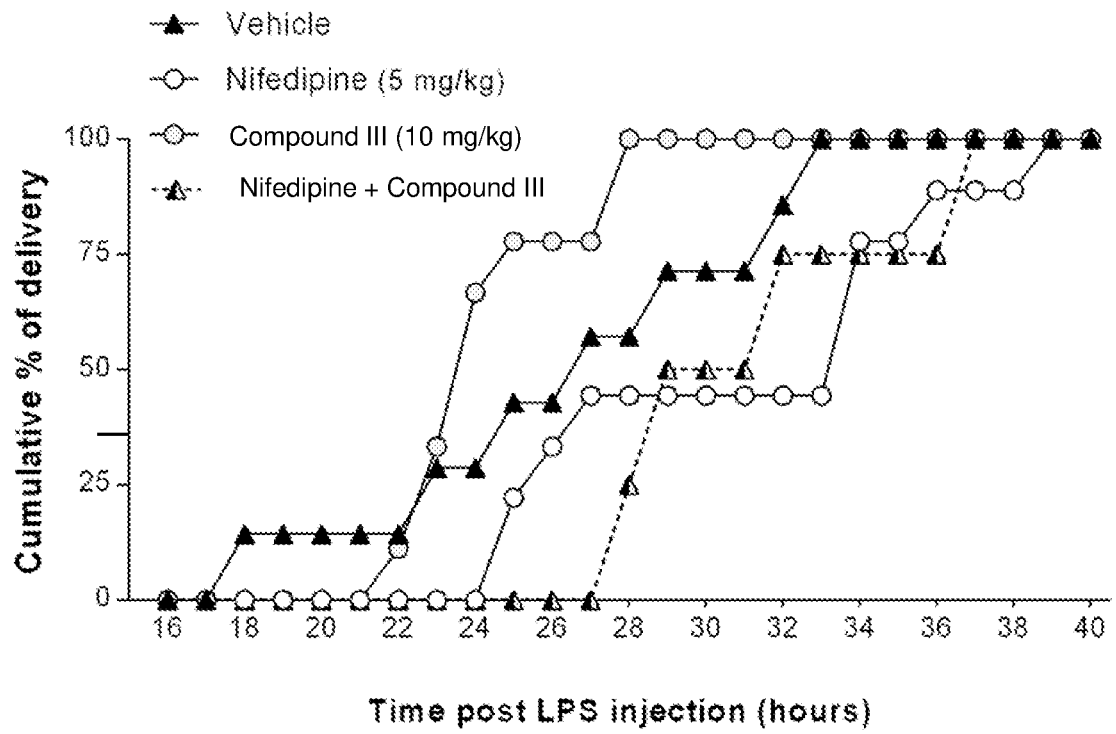
FIG. 69b is a graph demonstrating the effects of nifedipine (5 mg/kg, administered orally), compound III (10 mg/kg, administered orally), and combinations thereof on the time from induction to completion of delivery among CD-1 mice treated with LPS at a gestational age of 17 days so as to induce parturition.
Figure 69C:
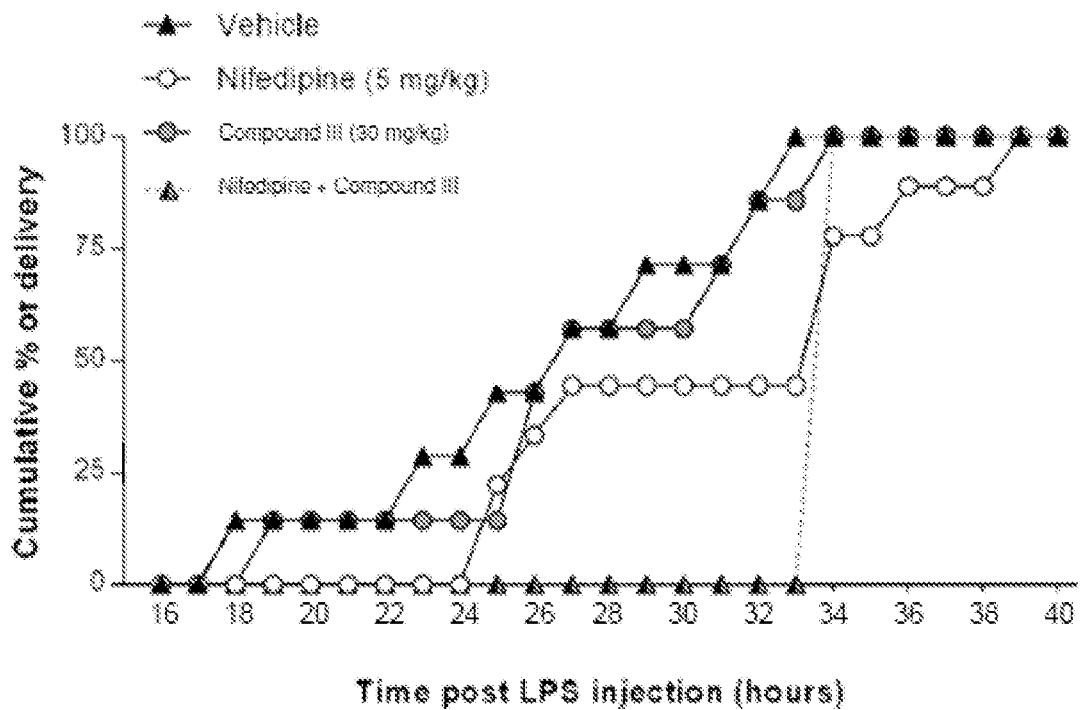
FIG. 69c is a graph demonstrating the effects of nifedipine (5 mg/kg, administered orally), compound III (30 mg/kg, administered orally), and combinations thereof on the time from induction to completion of delivery among CD-1 mice treated with LPS at a gestational age of 17 days so as to induce parturition.
Figure 69D:
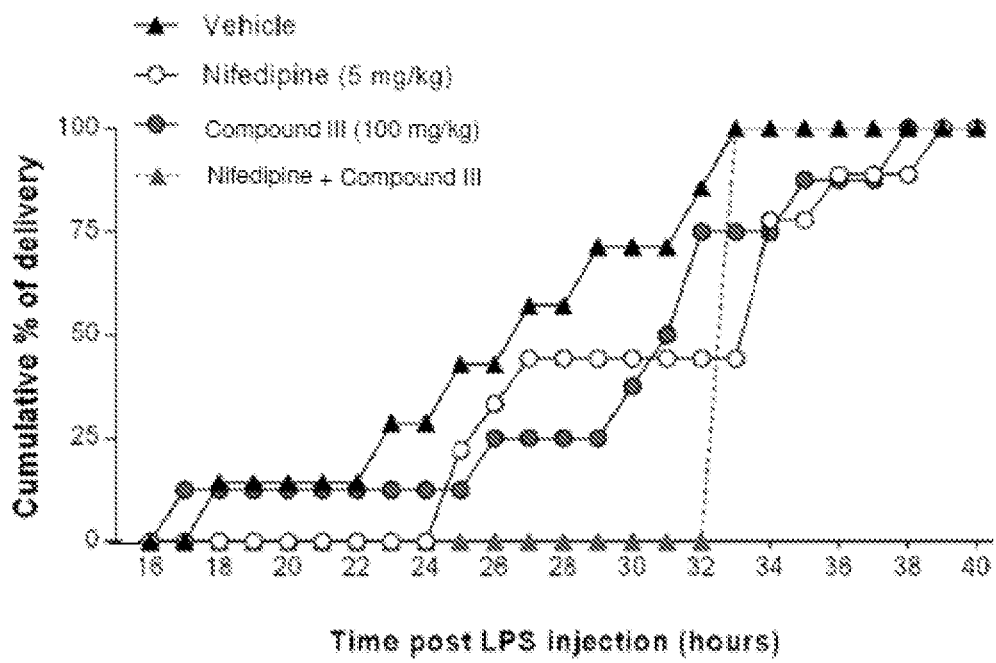
FIG. 69d is a graph demonstrating the effects of nifedipine (5 mg/kg, administered orally), compound III (100 mg/kg, administered orally), and combinations thereof on the time from induction to completion of delivery among CD-1 mice treated with LPS at a gestational age of 17 days so as to induce parturition.
Figure 69E:
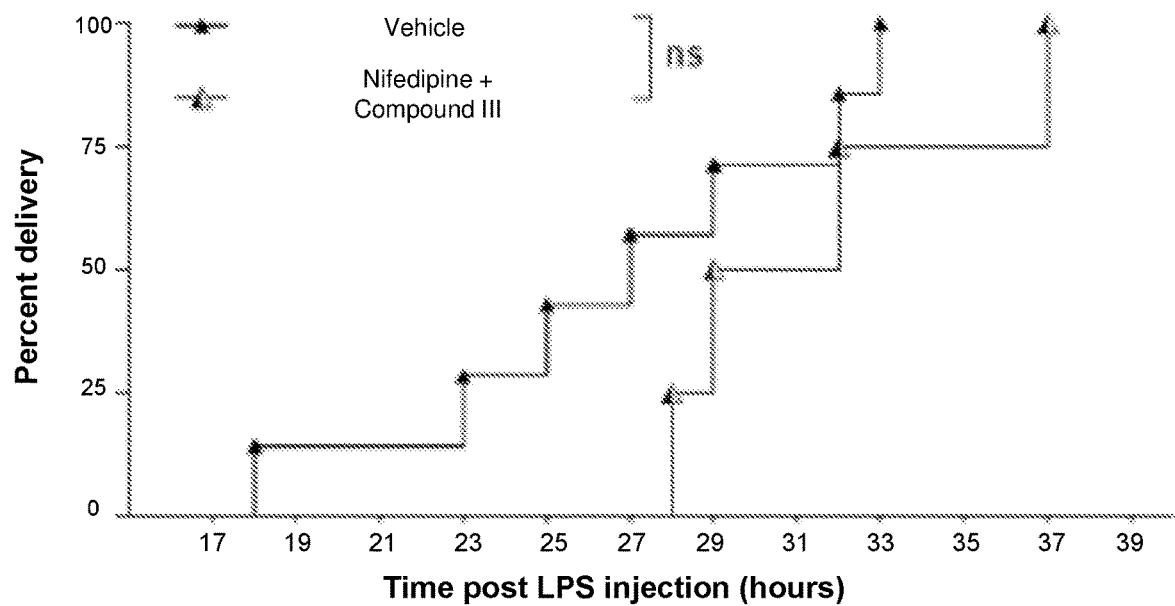
FIG. 69e is a graph showing the time from induction to completion of offspring delivery for the vehicle and combination arms shown in FIG. 69b. "ns" designates a p value of p>0.05 versus the corresponding group. Statistical analyses were conducted using a Log-rank test versus the corresponding group.
Figure 69F:
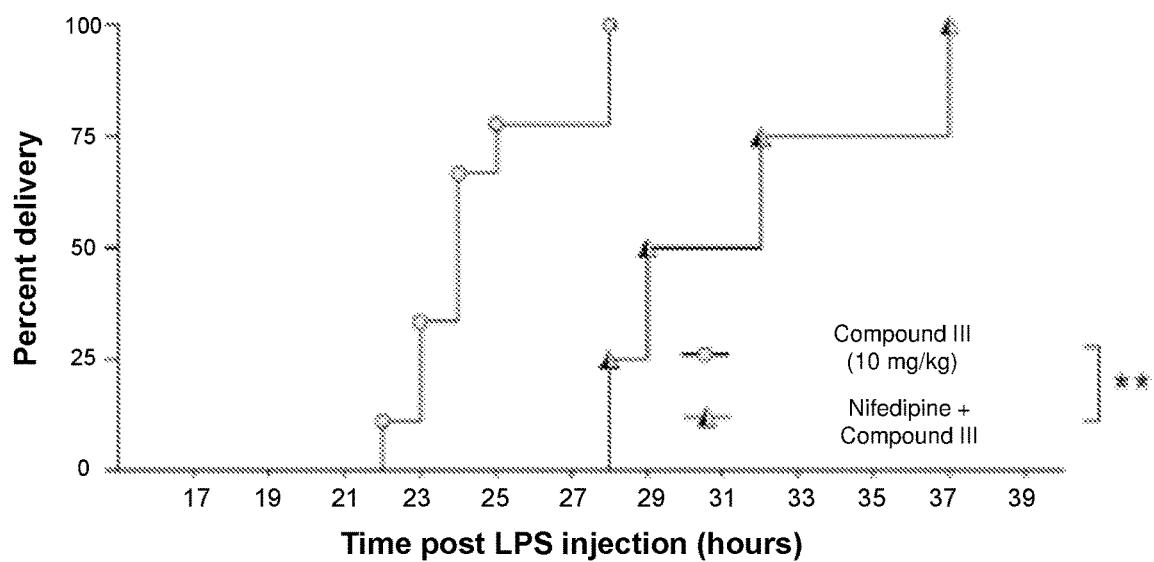
FIG. 69f is a graph showing the time from induction to completion of offspring delivery for the compound III and combination arms shown in FIG. 69b. Two asterisks designate a p value of p<0.01 versus the corresponding group. Statistical analyses were conducted using a Log-rank test versus the corresponding group of interest.
Figure 69G:
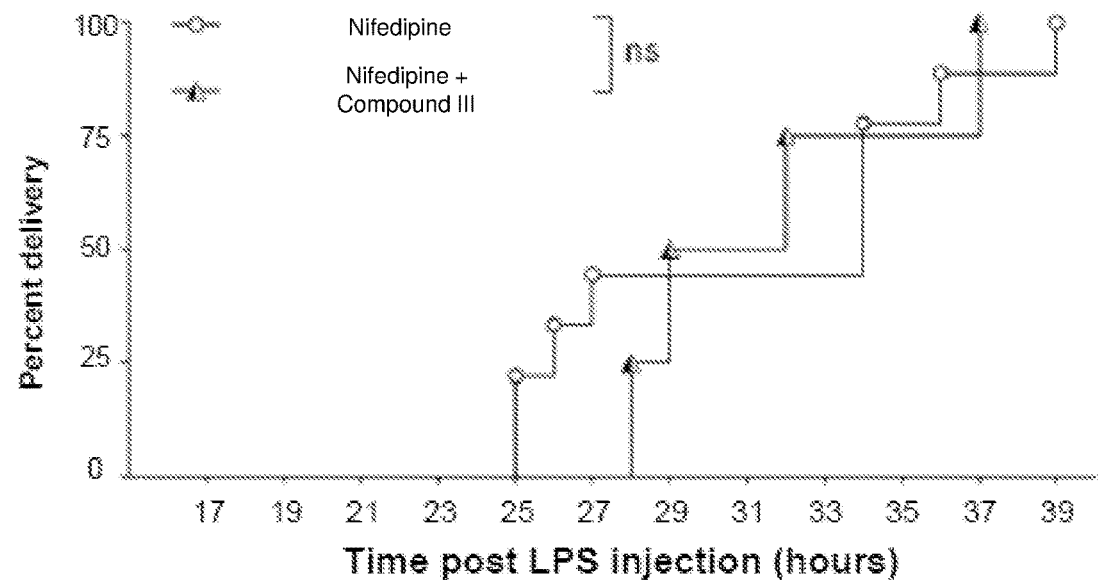
FIG. 69g is a graph showing the time from induction to completion of offspring delivery for the nifedipine and combination arms shown in FIG. 69b. "ns" designates a p value of p>0.05 versus the corresponding group. Statistical analyses were conducted using a Log-rank test versus the corresponding group.
Figure 69H:
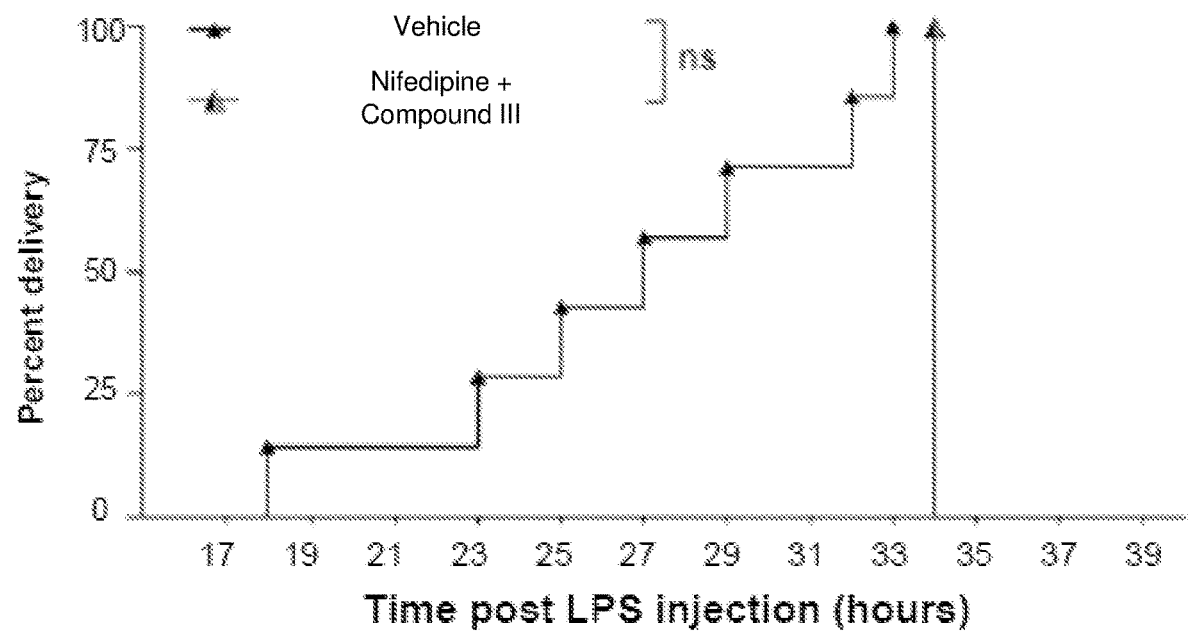
FIG. 69h is a graph showing the time from induction to completion of offspring delivery for the vehicle and combination arms shown in FIG. 69c. "ns" designates a p value of p>0.05 versus the corresponding group. Statistical analyses were conducted using a Log-rank test versus the corresponding group.
Figure 69I:
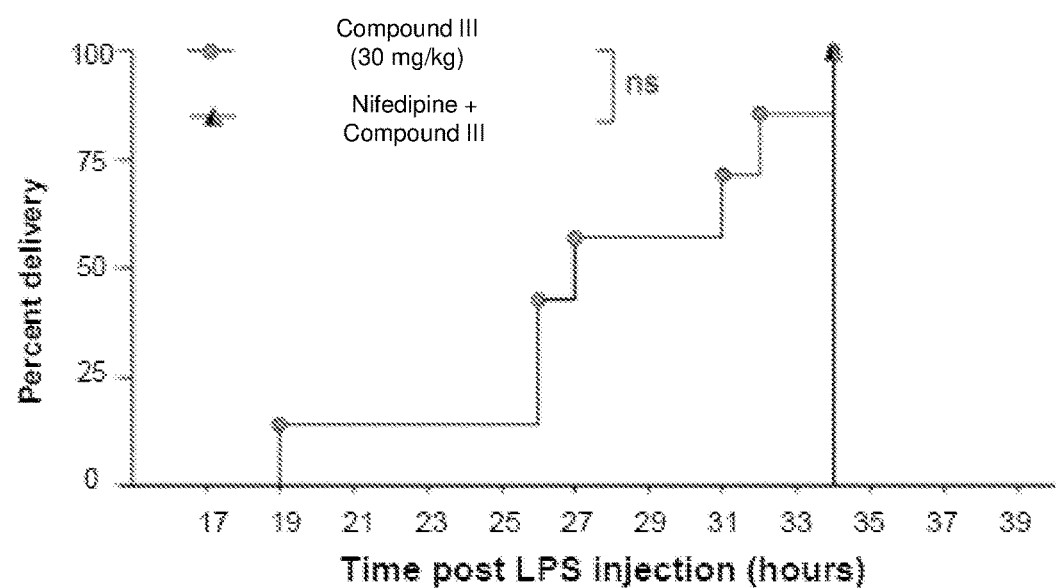
FIG. 69i is a graph showing the time from induction to completion of offspring delivery for the compound III and combination arms shown in FIG. 69c. "ns" designates a p value of p>0.05 versus the corresponding group. Statistical analyses were conducted using a Log-rank test versus the corresponding group.
Figure 69J:
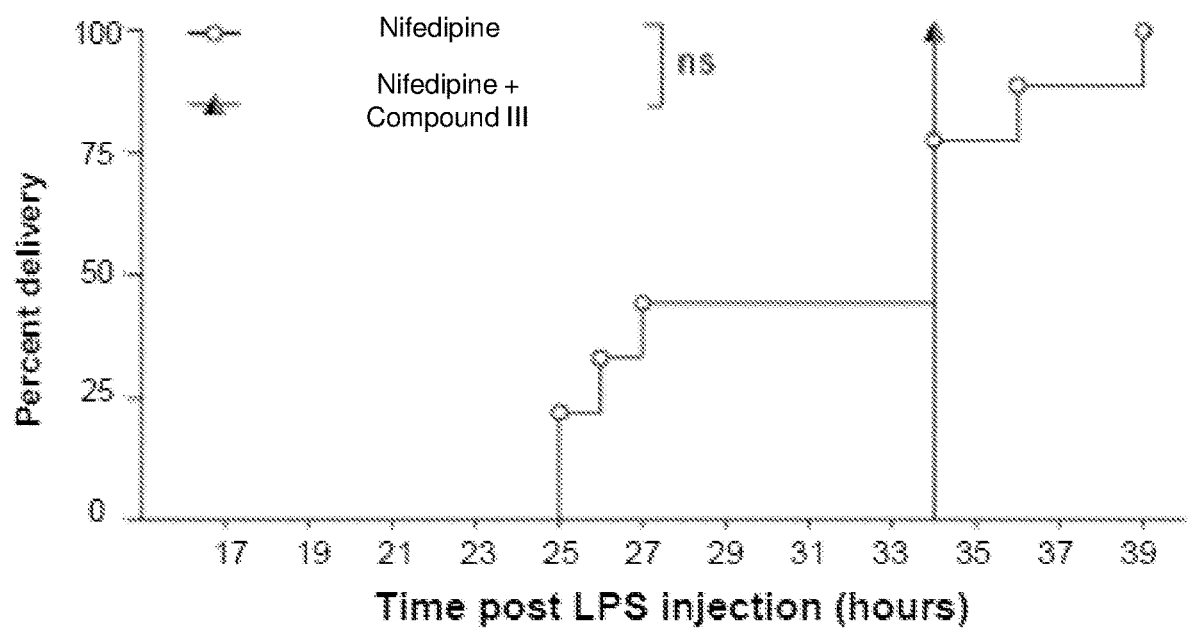
FIG. 69j is a graph showing the time from induction to completion of offspring delivery for the nifedipine and combination arms shown in FIG. 69c. "ns" designates a p value of p>0.05 versus the corresponding group. Statistical analyses were conducted using a Log-rank test versus the corresponding group.
Figure 69K:
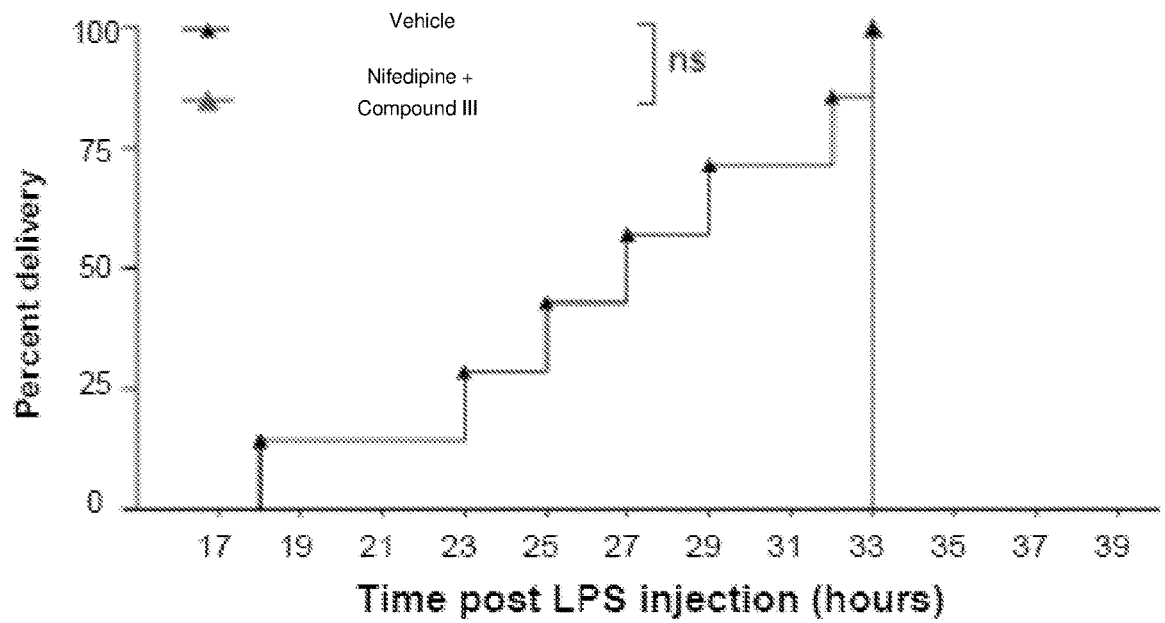
FIG. 69k is a graph showing the time from induction to completion of offspring delivery for the vehicle and combination arms shown in FIG. 69d. "ns" designates a p value of p>0.05 versus the corresponding group. Statistical analyses were conducted using a Log-rank test versus the corresponding group.
Figure 69L:
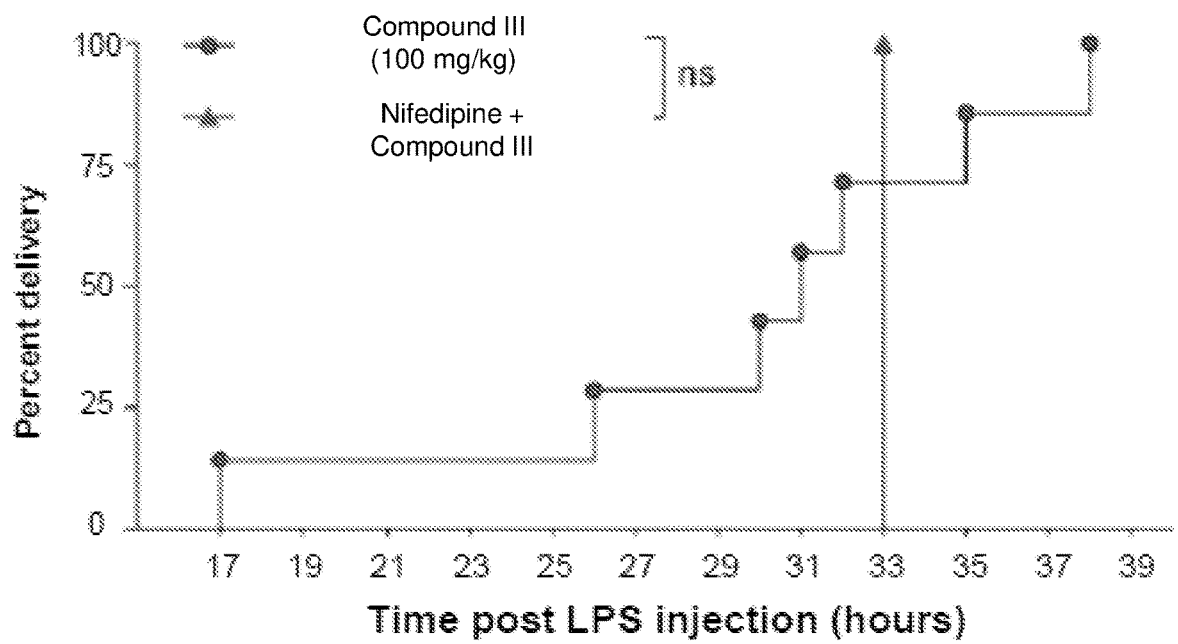
FIG. 69l is a graph showing the time from induction to completion of offspring delivery for the compound III and combination arms shown in FIG. 69d. "ns" designates a p value of p>0.05 versus the corresponding group. Statistical analyses were conducted using a Log-rank test versus the corresponding group.
Figure 69M:
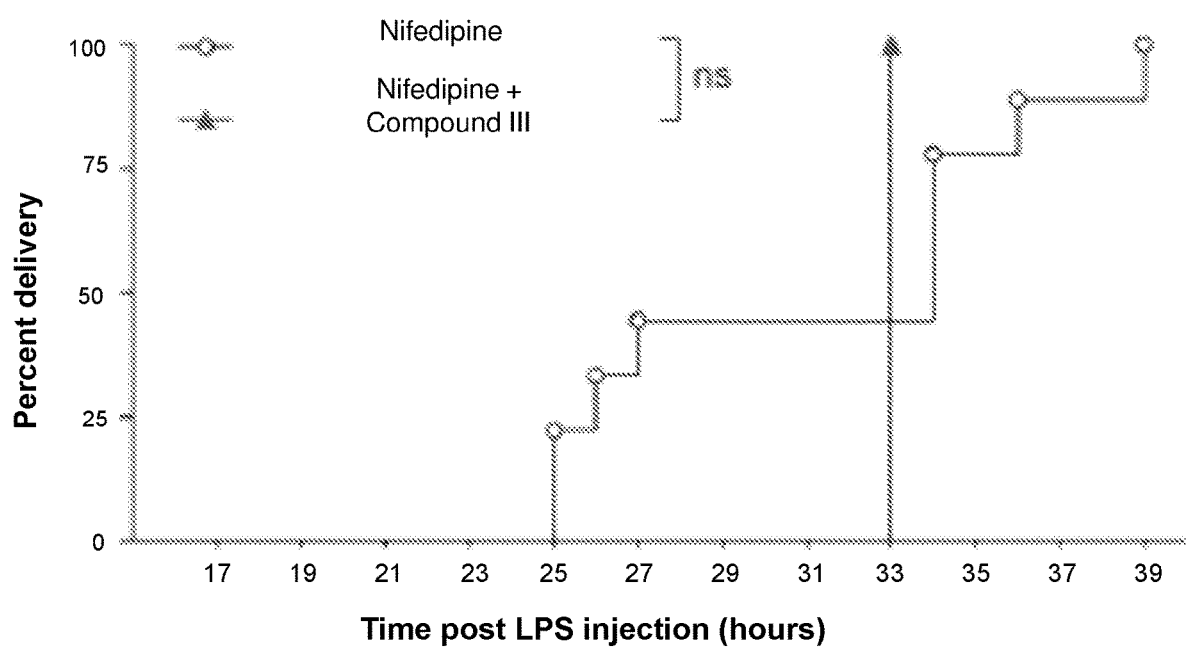
FIG. 69m is a graph showing the time from induction to completion of offspring delivery for the nifedipine and combination arms shown in FIG. 69d. "ns" designates a p value of p>0.05 versus the corresponding group. Statistical analyses were conducted using a Log-rank test versus the corresponding group.
Figure 70A:
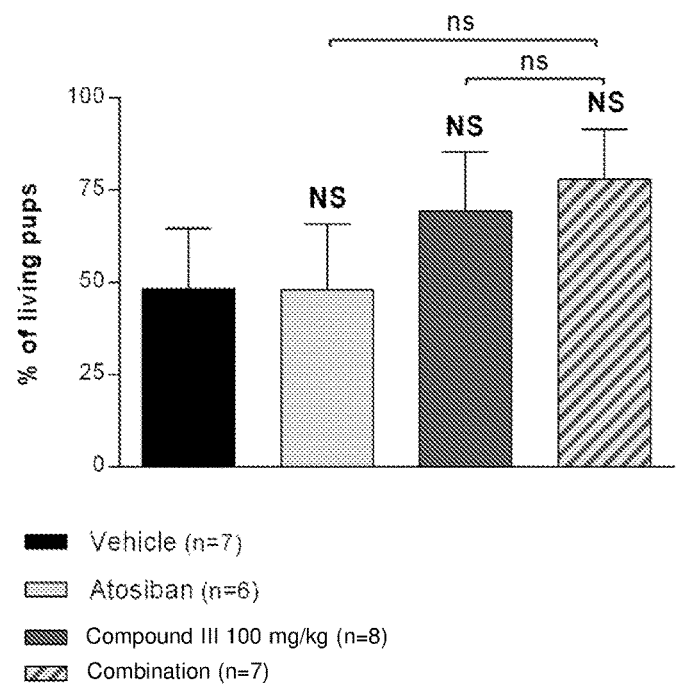
FIG. 70a is a graph demonstrating the effects of atosiban (300 mg/kg, administered subcutaneously), compound III (100 mg/kg, administered orally), and a combination thereof on the fractional viability of offspring of CD-1 mice treated with LPS at a gestational age of 17 days so as to induce parturition. Values represent the mean plus/minus standard error of the mean. "ns" designates a p value of p>0.05 versus the corresponding group; "NS" designates a p value of p>0.05 versus the corresponding vehicle group. Statistical analyses were conducted using a Mann-Whitney test or unpaired t test versus the corresponding group of interest.
Figure 70B:
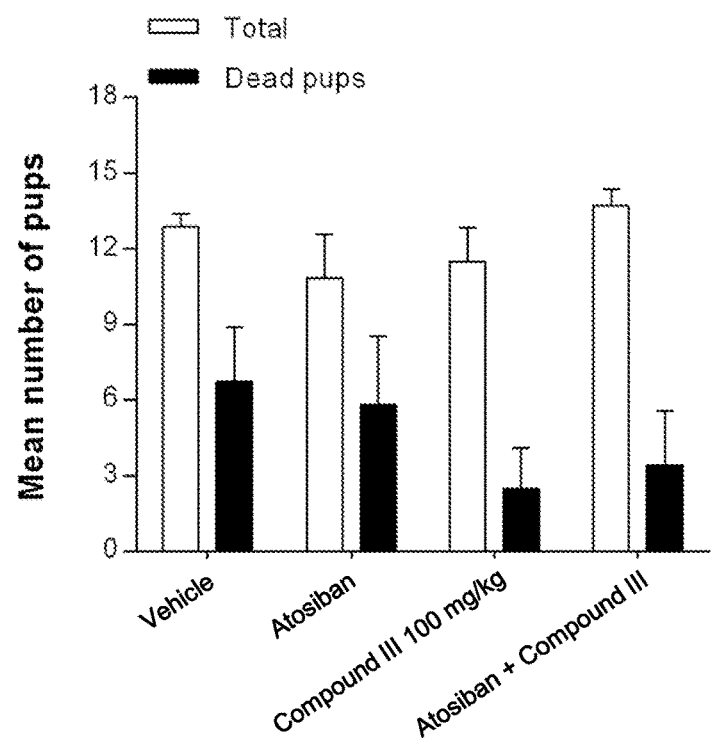
FIG. 70b is a graph demonstrating the effects of atosiban (300 mg/kg, administered subcutaneously), compound III (100 mg/kg, administered orally), and a combination thereof on the quantity of viable and non-viable offspring of CD-1 mice treated with LPS at a gestational age of 17 days so as to induce parturition.
Figure 71A:
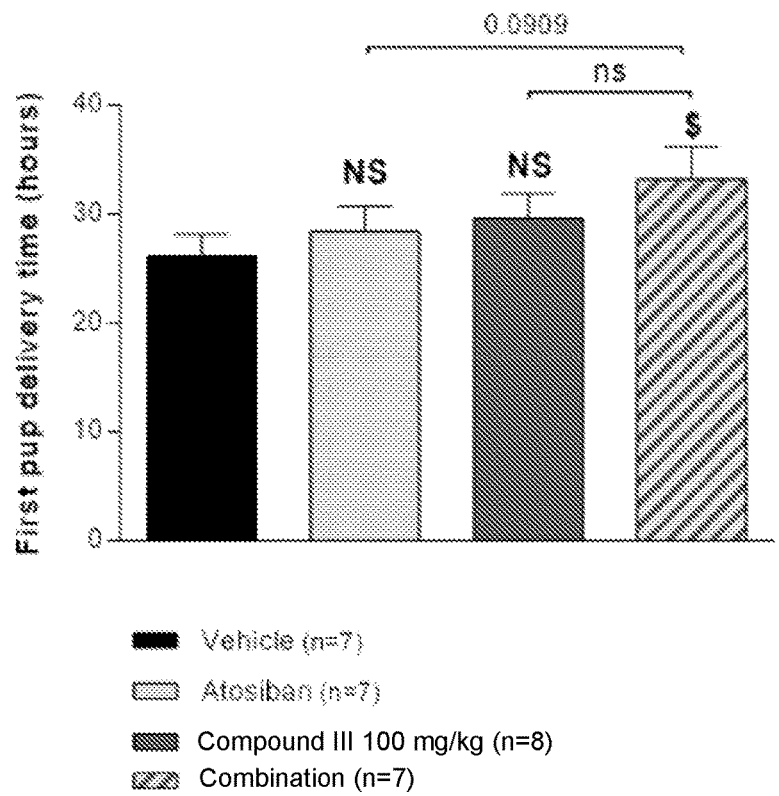
FIG. 71a is a graph demonstrating the effects of atosiban (300 mg/kg, administered subcutaneously), compound III (100 mg/kg, administered orally), and a combination thereof on the time from induction to first pup delivery for CD-1 mice treated with LPS at a gestational age of 17 days so as to induce parturition. Values represent the mean plus/minus standard error of the mean. "ns" designates a p value of p>0.05 versus the corresponding group; "NS" designates a p value of p>0.05 versus the corresponding vehicle group; "$" designates a p value of p<0.05 versus the corresponding vehicle group. The combination arm exhibited a p value of p=0.0909 relative to the arm treated with atosiban alone. Statistical analyses were conducted using a Mann-Whitney test or unpaired t test versus the corresponding group of interest.
Figure 71B:
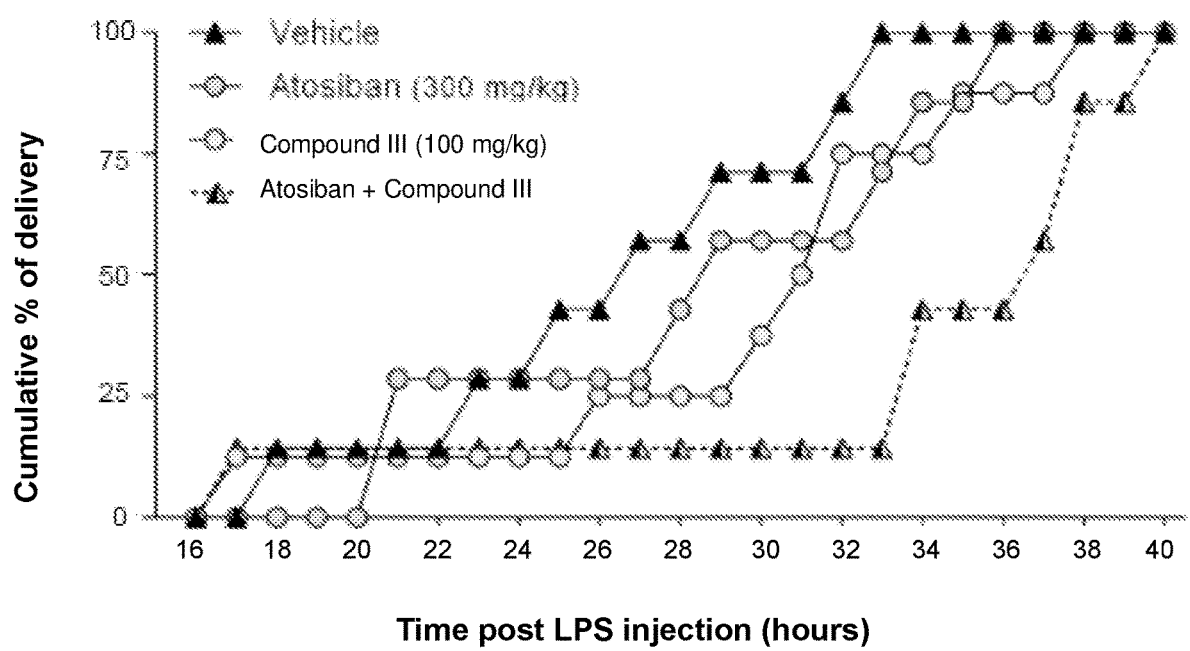
FIG. 71b is a graph demonstrating the effects of atosiban (300 mg/kg, administered subcutaneously), compound III (100 mg/kg, administered orally), and a combination thereof on the time from induction to completion of delivery among CD-1 mice treated with LPS at a gestational age of 17 days so as to induce parturition.
Figure 71C:
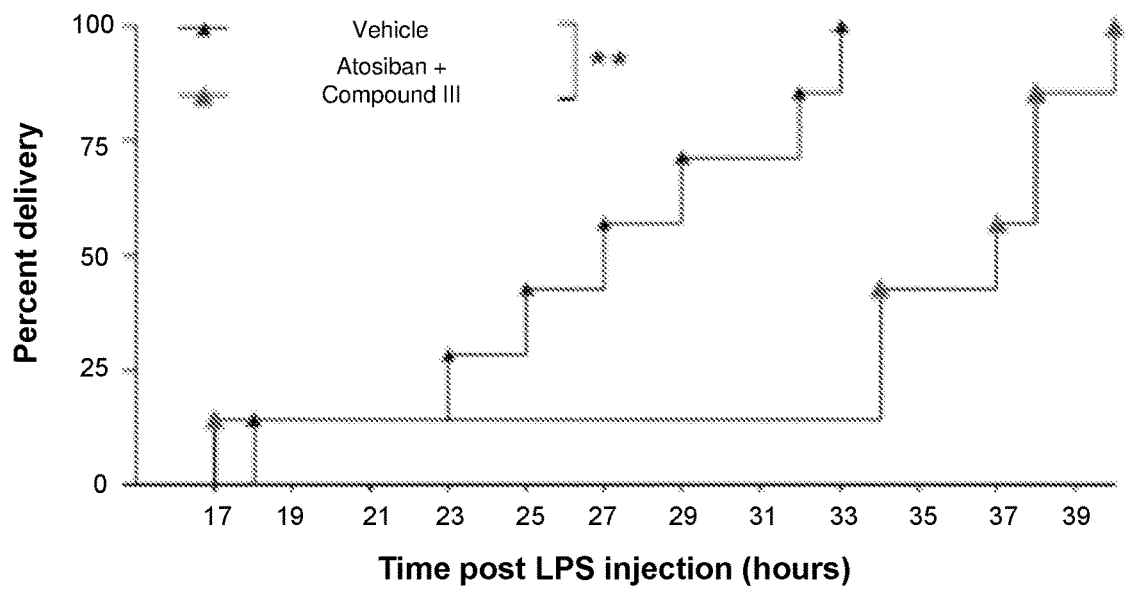
FIG. 71c is a graph showing the time from induction to completion of offspring delivery for the vehicle and combination arms shown in FIG. 71b. Two asterisks designate a p value of p<0.01 versus the corresponding group. Statistical analyses were conducted using a Log-rank test versus the corresponding group of interest.
Figure 71D:
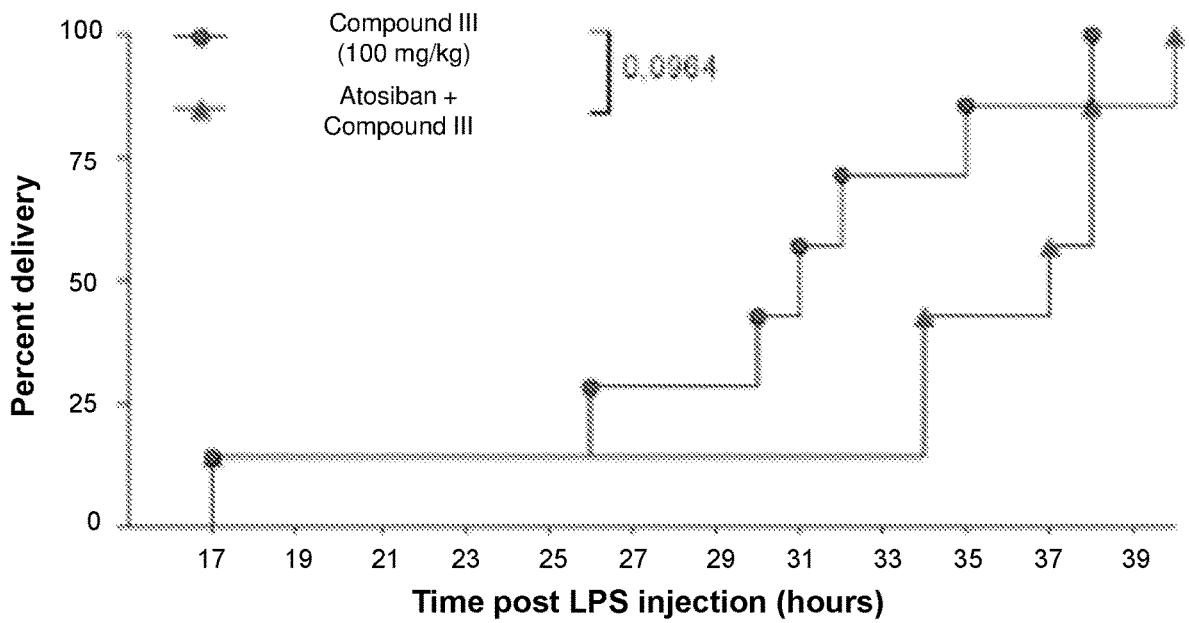
FIG. 71d is a graph showing the time from induction to completion of offspring delivery for the compound III and combination arms shown in FIG. 71b. The combination arm exhibited a p value of p=0.0964 relative to the compound III arm. Statistical analyses were conducted using a Log-rank test versus the corresponding group of interest.
Figure 71E:
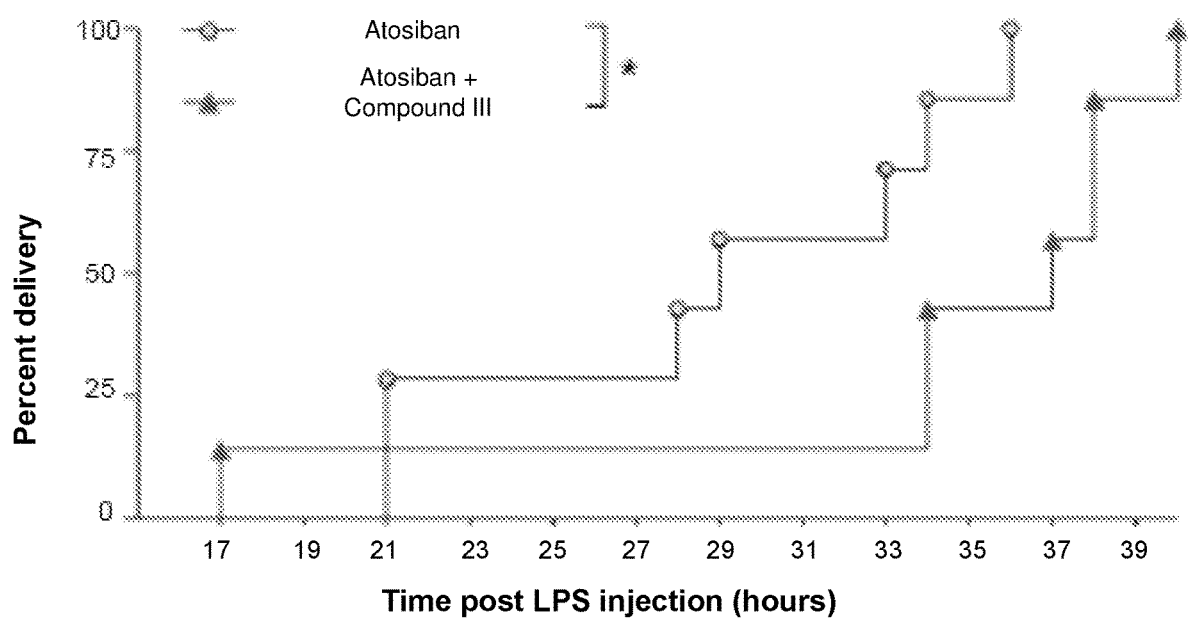
FIG. 71e is a graph showing the time from induction to completion of offspring delivery for the atosiban and combination arms shown in FIG. 71b. Asterisk designates a p value of p<0.05 versus the corresponding group. Statistical analyses were conducted using a Log-rank test versus the corresponding group of interest.
Figure 72A:
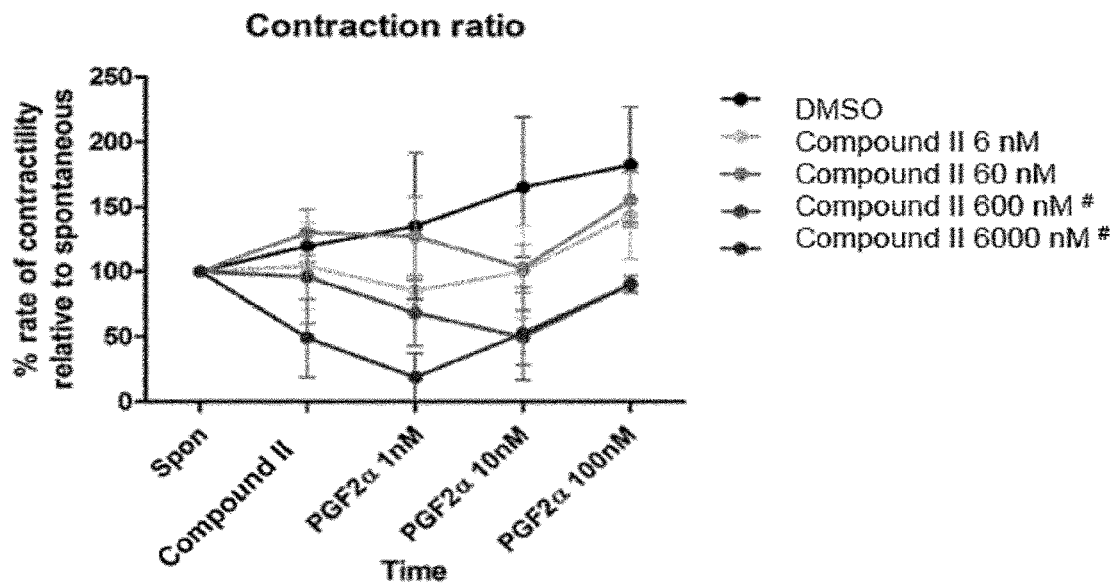
FIG. 72a is a graph demonstrating the effects of varying concentrations of compound II (6 nM, 60 nM, 600 nM, and 6000 nM) on the frequency of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control or compound II was then added to each myometrial sample at the indicated concentrations and the effects of control or compound II on contractile frequency were measured over the ensuing 10-minute period. This time point is represented on the x-axis as "Compound II." The effects of compound II on contractile frequency in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the frequency of contractions as a percentage of the frequency of spontaneous baseline contractions. The "#" symbol designates a p value of p<0.05 versus the DMSO control.
Figure 72B:
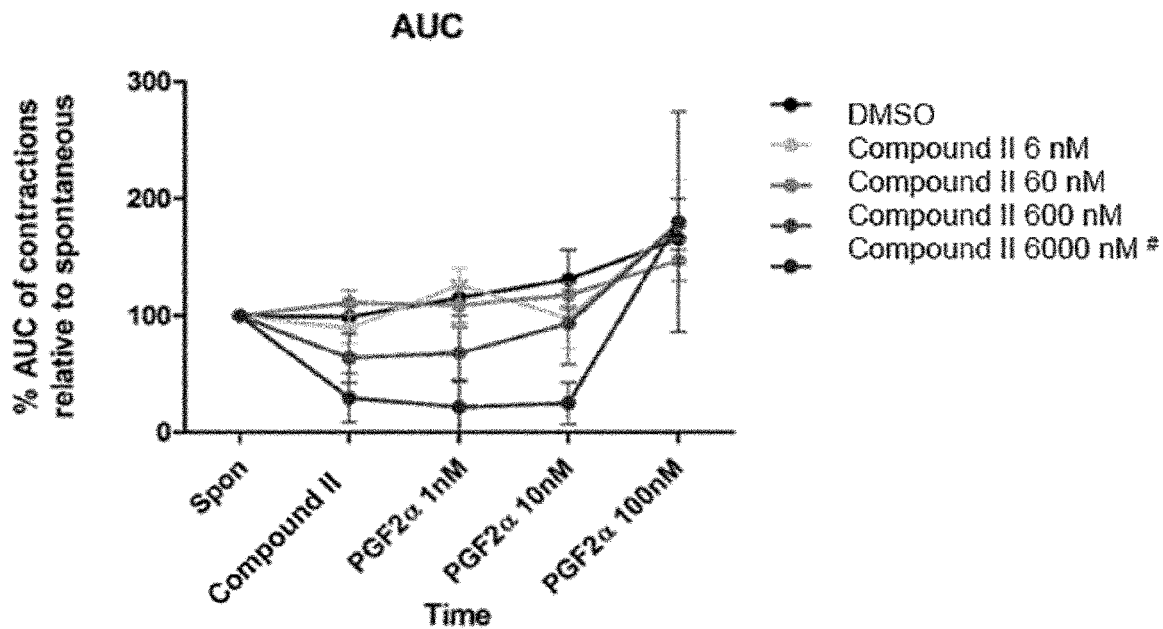
FIG. 72b is a graph demonstrating the effects of varying concentrations of compound II (6 nM, 60 nM, 600 nM, and 6000 nM) on the work done per contraction (area under the curve, or "AUC") of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spon." A DMSO control or compound II was then added to each myometrial sample at the indicated concentrations and the effects of control or compound II on work done per contraction were measured over the ensuing 10-minute period. This time point is represented on the x-axis as "Compound II." The effects of compound II on work done per contraction in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the work done per contraction as a percentage of the work done per contraction for spontaneous baseline contractions. The "#" symbol designates a p value of $p<0.05$ versus the DMSO control.
Figure 72C:
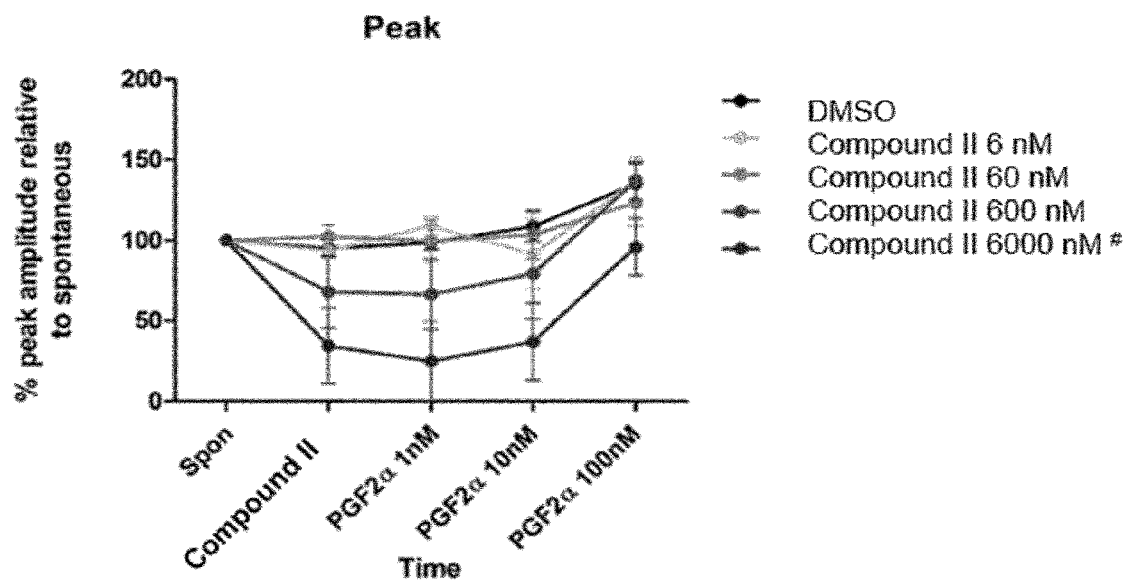
FIG. 72c is a graph demonstrating the effects of varying concentrations of compound II (6 nM, 60 nM, 600 nM, and 6000 nM) on the peak amplitude of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Spon." A DMSO control or compound II was then added to each myometrial sample at the indicated concentrations and the effects of control or compound II on contraction peak amplitude were measured over the ensuing 10-minute period. This time point is represented on the x-axis as "Compound II." The effects of compound II on contraction peak amplitude in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the contraction peak amplitude as a percentage of the peak amplitude of spontaneous baseline contractions. The "#" symbol designates a p value of $p<0.05$ versus the DMSO control.
Figure 72D:
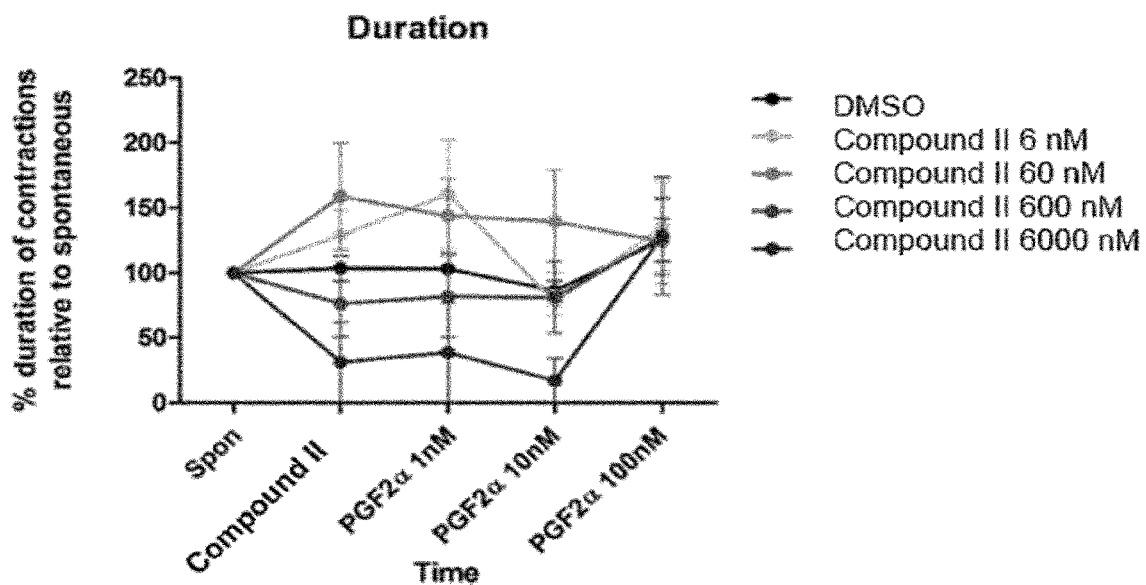
FIG. 72d is a graph demonstrating the effects of varying concentrations of compound II (6 nM, 60 nM, 600 nM, and 6000 nM) on the duration of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Spon." A DMSO control or compound II was then added to each myometrial sample at the indicated concentrations and the effects of control or compound II on contraction duration were measured over the ensuing 10-minute period. This time point is represented on the x-axis as "Compound II." The effects of compound II on contraction duration in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the contraction duration as a percentage of the duration of spontaneous baseline contractions.
Figure 72E:
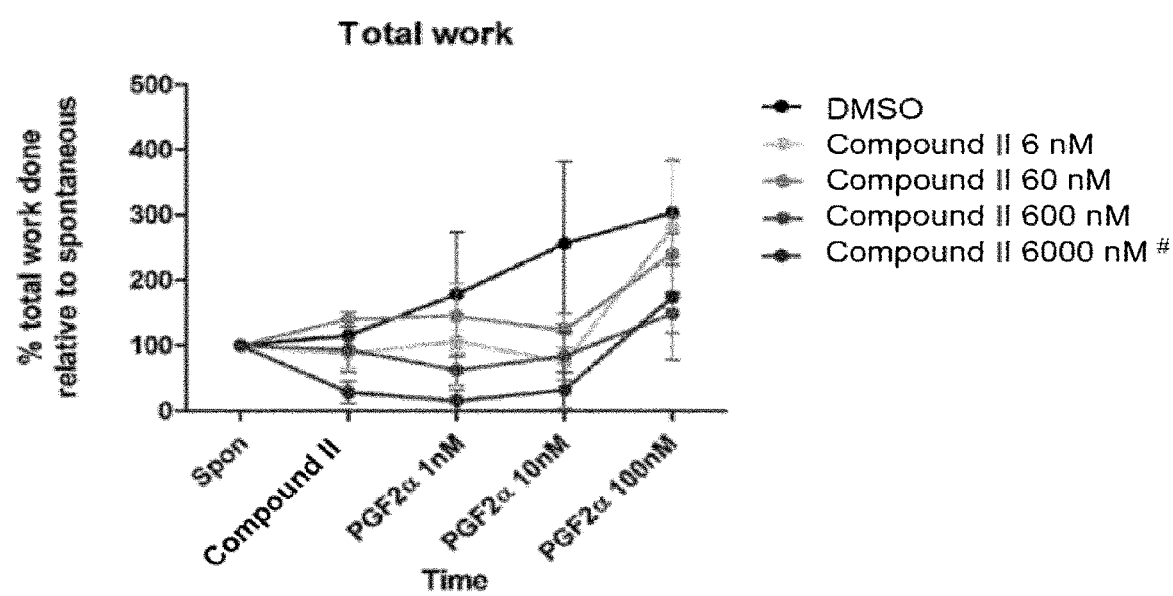
FIG. 72e is a graph demonstrating the effects of varying concentrations of compound II (6 nM, 60 nM, 600 nM, and 6000 nM) on the total work done by all contractions (sum of area under the curve for all contractions) for PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Spon." A DMSO control or compound II was then added to each myometrial sample at the indicated concentrations and the effects of control or compound II on total work done for all subsequent contractions were measured over the ensuing 10-minute period. This time point is represented on the x-axis as "Compound II." The effects of compound II on total work done by contractions in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the total work done by contractions as a percentage of the total work done by spontaneous baseline contractions. The "#" symbol designates a p value of $p<0.05$ versus the DMSO control.
Figure 73A:
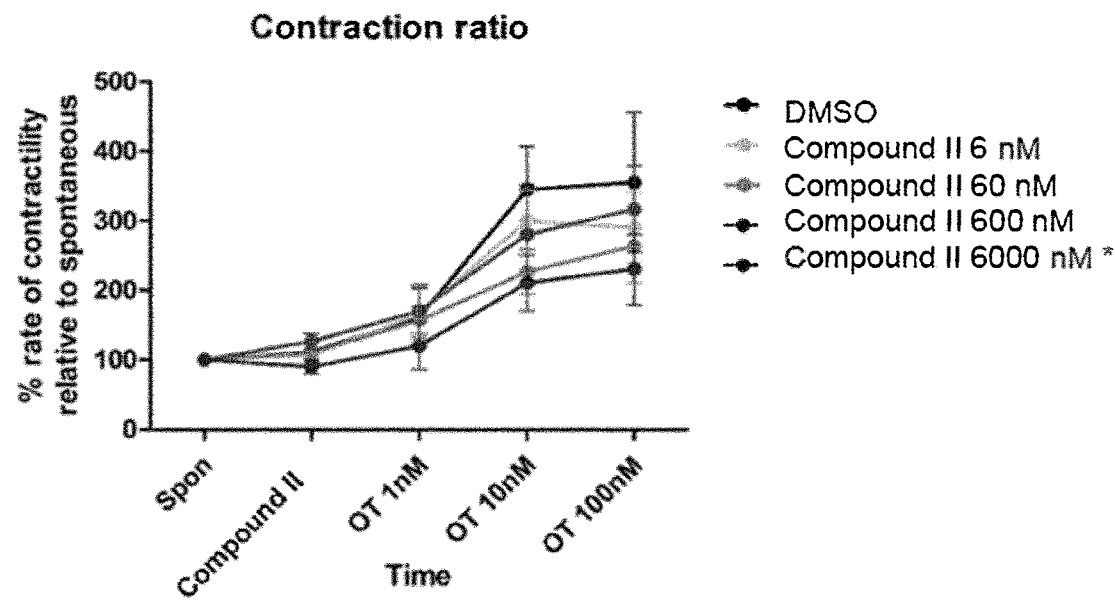
FIG. 73a is a graph demonstrating the effects of varying concentrations of compound II (6 nM, 60 nM, 600 nM, and 6000 nM) on the frequency of oxytocin (OT)-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control or compound II was then added to each myometrial sample at the indicated concentrations and the effects of control or compound II on contractile frequency were measured over the ensuing 10-minute period. This time point is represented on the x-axis as "Compound II." The effects of compound II on contractile frequency in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the frequency of contractions as a percentage of the frequency of spontaneous baseline contractions. Asterisk designates a p value of $p<0.05$ versus the DMSO control.
Figure 73B:
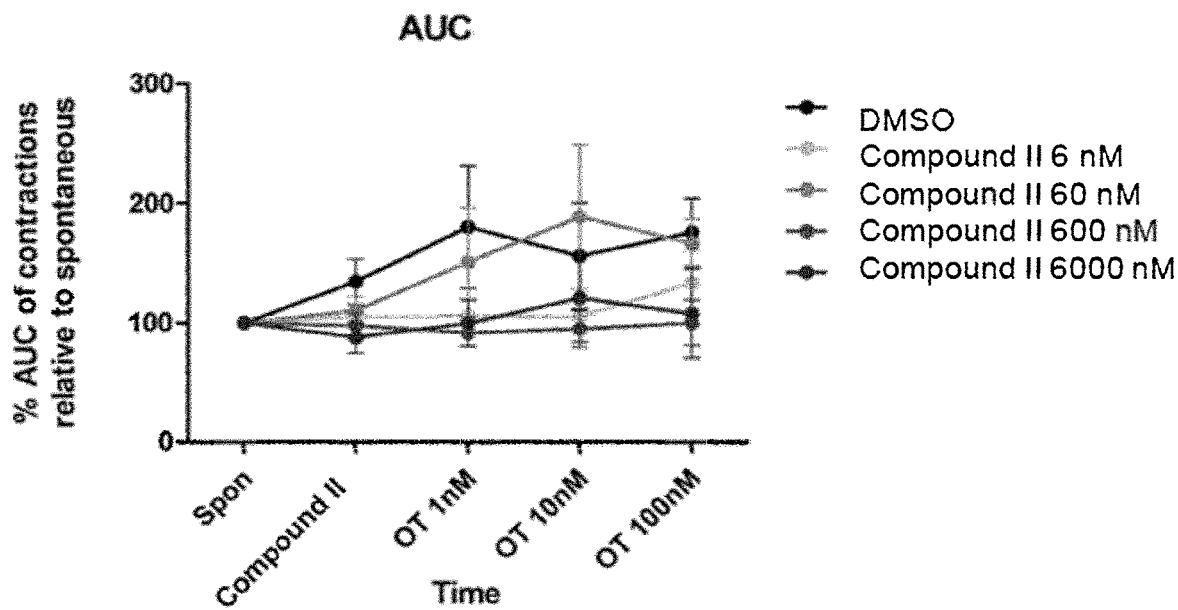
FIG. 73b is a graph demonstrating the effects of varying concentrations of compound II (6 nM, 60 nM, 600 nM, and 6000 nM) on the work done per contraction (area under the curve, or "AUC") of OT-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spon." A DMSO control or compound II was then added to each myometrial sample at the indicated concentrations and the effects of control or compound II on work done per contraction were measured over the ensuing 10-minute period. This time point is represented on the x-axis as "Compound II." The effects of compound II on work done per contraction in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the work done per contraction as a percentage of the work done per contraction for spontaneous baseline contractions.
Figure 73C:
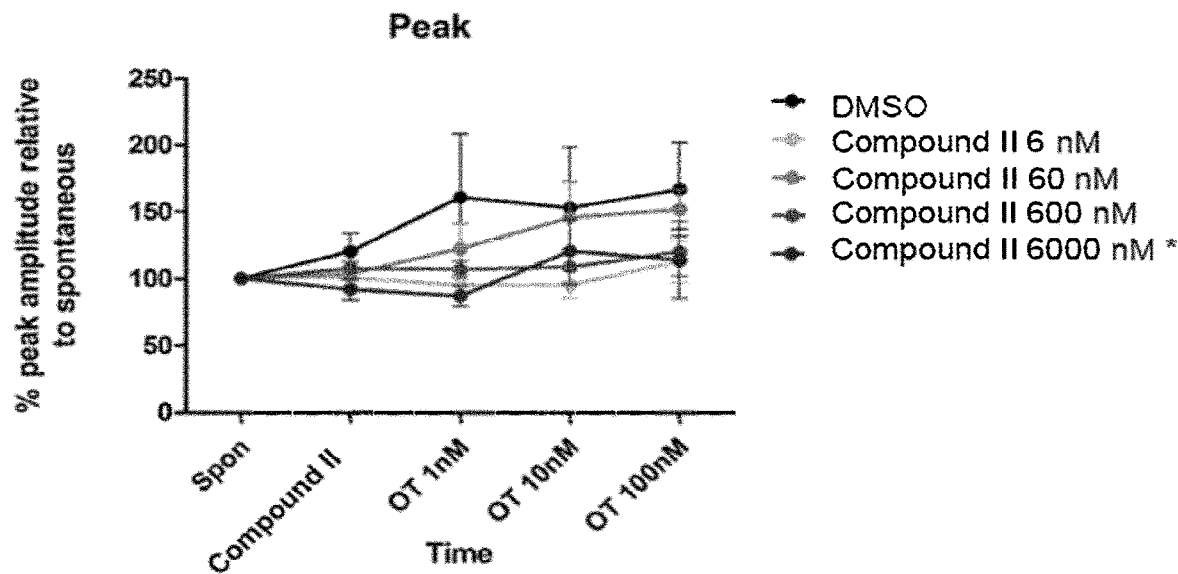
FIG. 73c is a graph demonstrating the effects of varying concentrations of compound II (6 nM, 60 nM, 600 nM, and 6000 nM) on the peak amplitude of OT-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Spon." A DMSO control or compound II was then added to each myometrial sample at the indicated concentrations and the effects of control or compound II on contraction peak amplitude were measured over the ensuing 10-minute period. This time point is represented on the x-axis as "Compound II." The effects of compound II on contraction peak amplitude in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction peak amplitude as a percentage of the peak amplitude of spontaneous baseline contractions. Asterisk designates a p value of $p<0.05$ versus the DMSO control.
Figure 73D:
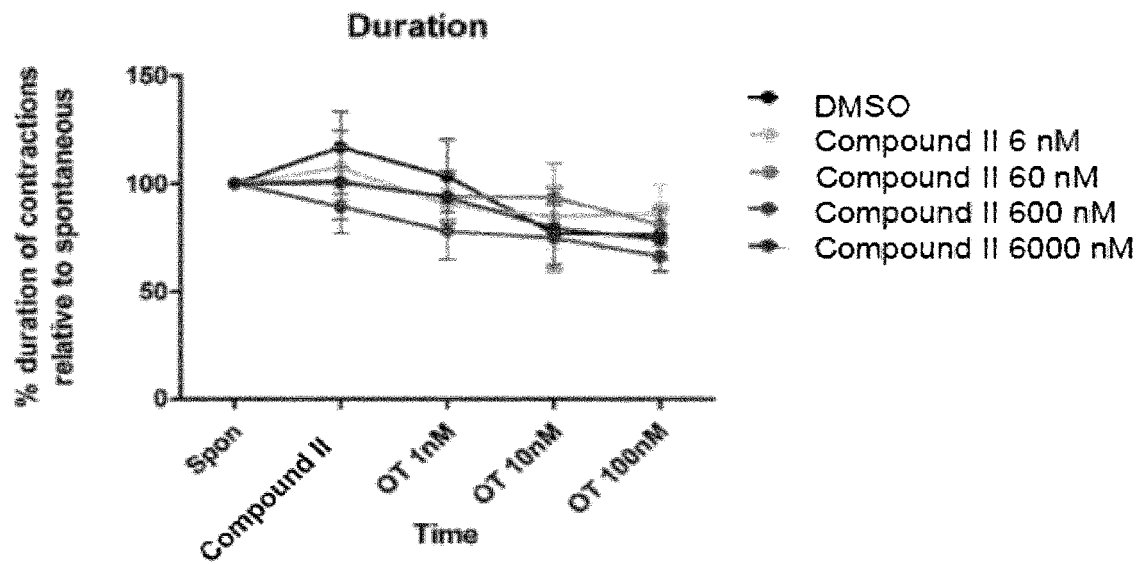
FIG. 73d is a graph demonstrating the effects of varying concentrations of compound II (6 nM, 60 nM, 600 nM, and 6000 nM) on the duration of OT-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Spon." A DMSO control or compound II was then added to each myometrial sample at the indicated concentrations and the effects of control or compound lion contraction duration were measured over the ensuing 10-minute period. This time point is represented on the x-axis as "Compound II." The effects of compound II on contraction duration in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction duration as a percentage of the duration of spontaneous baseline contractions.
Figure 73E:
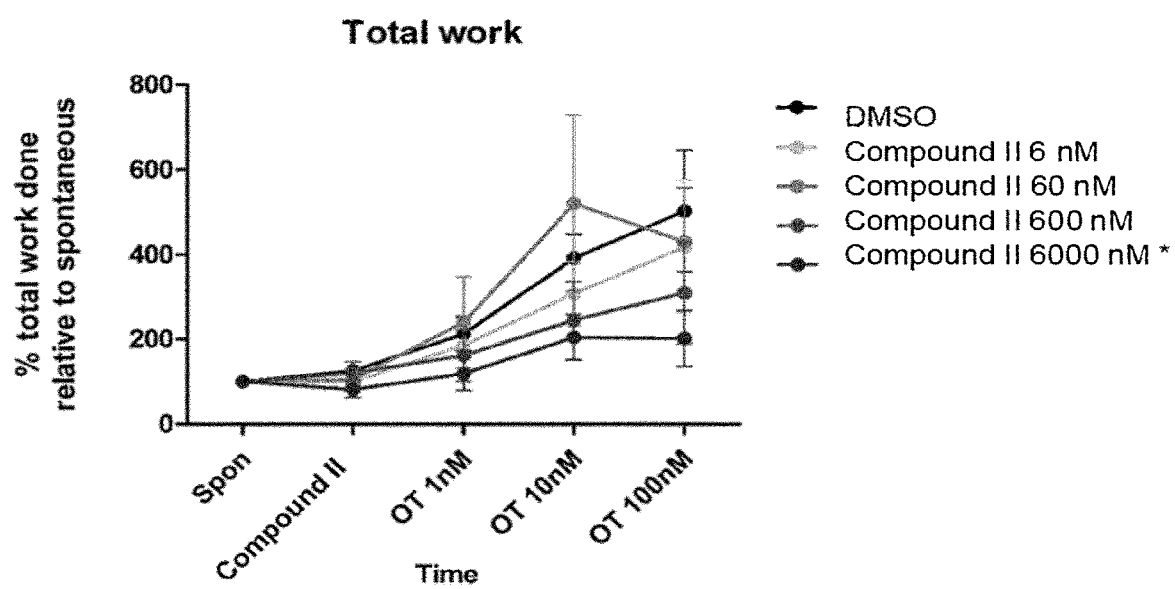
FIG. 73e is a graph demonstrating the effects of varying concentrations of compound II (6 nM, 60 nM, 600 nM, and 6000 nM) on the total work done by all contractions (sum of area under the curve for all contractions) for OT-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Spon." A DMSO control or compound II was then added to each myometrial sample at the indicated concentrations and the effects of control or compound II on total work done for all subsequent contractions were measured over the ensuing 10-minute period. This time point is represented on the x-axis as "Compound II." The effects of compound II on total work done by contractions in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the total work done by contractions as a percentage of the total work done by spontaneous baseline contractions. Asterisk designates a p value of $p<0.05$ versus the DMSO control.
Figure 74A:
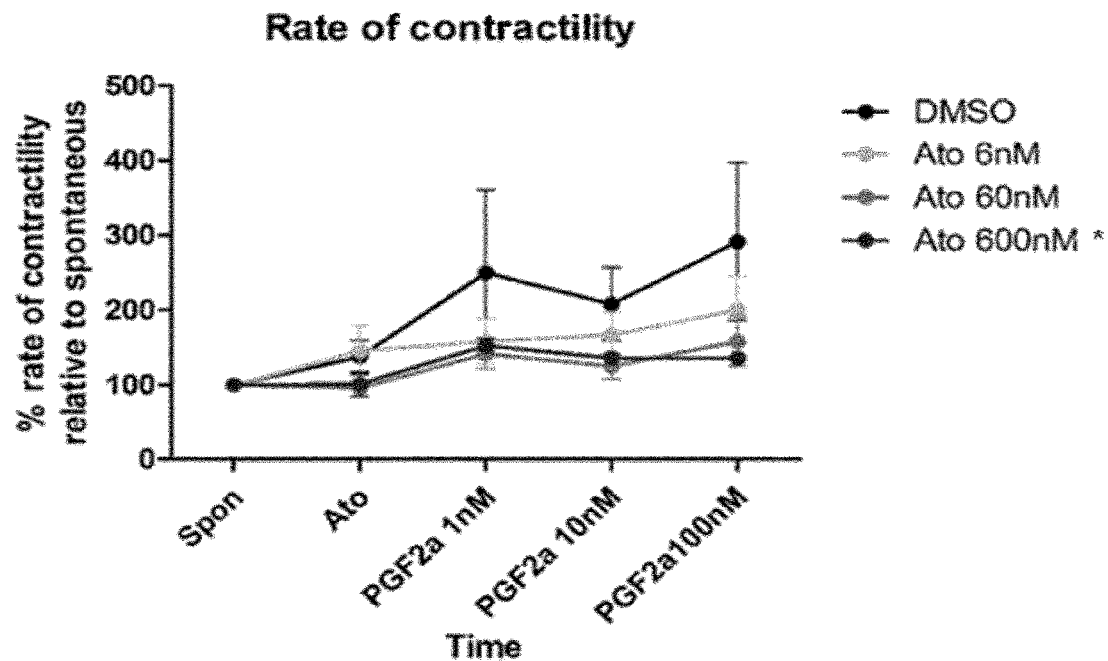
FIG. 74a is a graph demonstrating the effects of varying concentrations of atosiban (6 nM, 60 nM, and 600 nM) on the frequency of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control or atosiban ("Ato") was then added to each myometrial sample at the indicated concentrations and the effects of control or atosiban on contractile frequency were measured over the ensuing 10-minute period. This time point is represented on the x-axis as "Ato." The effects of atosiban on contractile frequency in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the frequency of contractions as a percentage of the frequency of spontaneous baseline contractions. Asterisk designates a p value of $p<0.05$ versus the DMSO control.
Figure 74B:
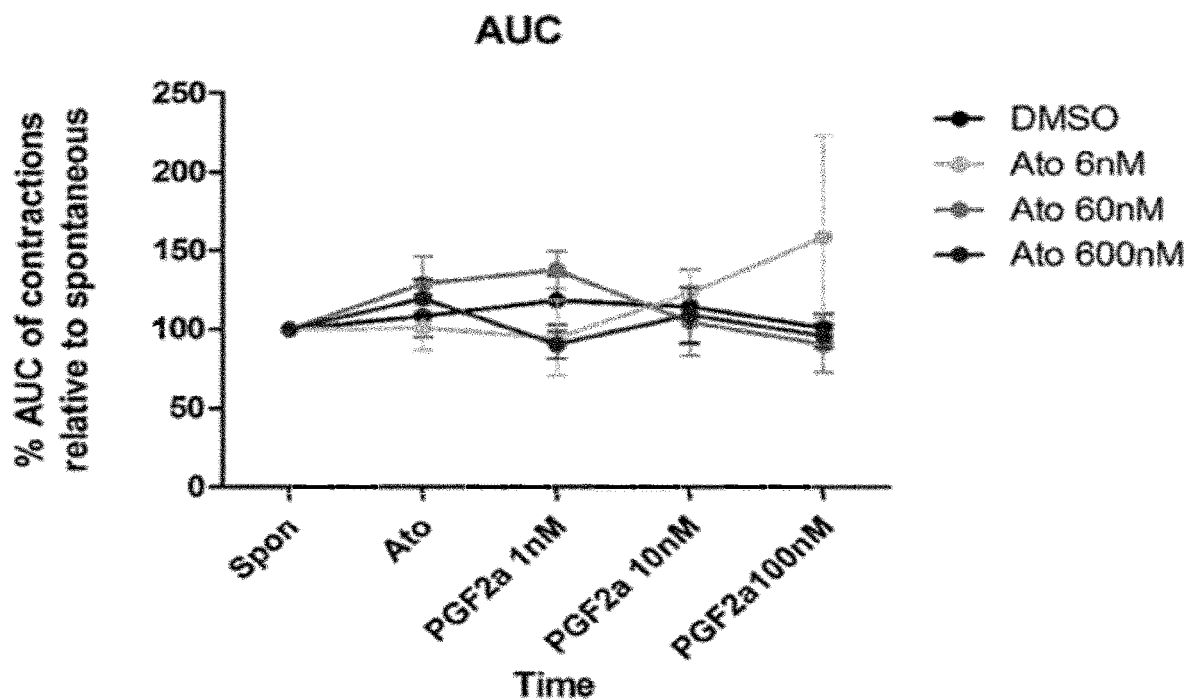
FIG. 74b is a graph demonstrating the effects of varying concentrations of atosiban (6 nM, 60 nM, and 600 nM) on the work done per contraction (area under the curve, or "AUC") of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spon." A DMSO control or atosiban was then added to each myometrial sample at the indicated concentrations and the effects of control or atosiban on work done per contraction were measured over the ensuing 10-minute period. This time point is represented on the x-axis as "Ato." The effects of atosiban on work done per contraction in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the work done per contraction as a percentage of the work done per contraction for spontaneous baseline contractions.
Figure 74C:
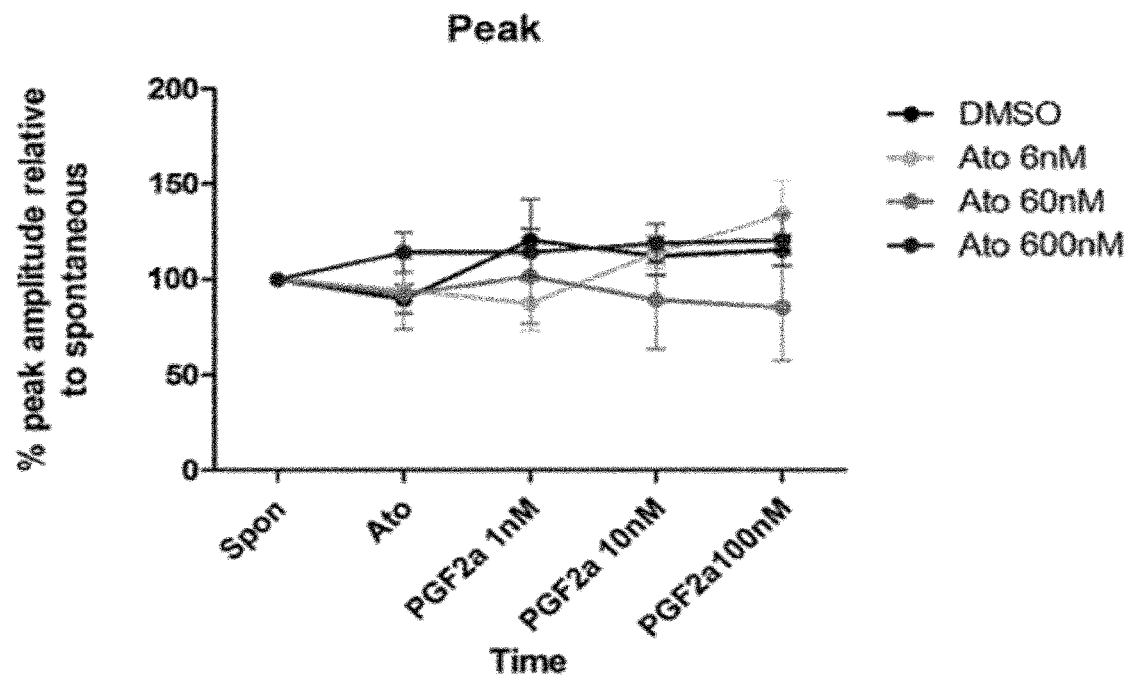
FIG. 74c is a graph demonstrating the effects of varying concentrations of atosiban (6 nM, 60 nM, and 600 nM) on the peak amplitude of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Span." A DMSO control or atosiban was then added to each myometrial sample at the indicated concentrations and the effects of control or atosiban on contraction peak amplitude were measured over the ensuing 10-minute period. This time point is represented on the x-axis as "Ato." The effects of atosiban on contraction peak amplitude in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the contraction peak amplitude as a percentage of the peak amplitude of spontaneous baseline contractions.
Figure 74D:
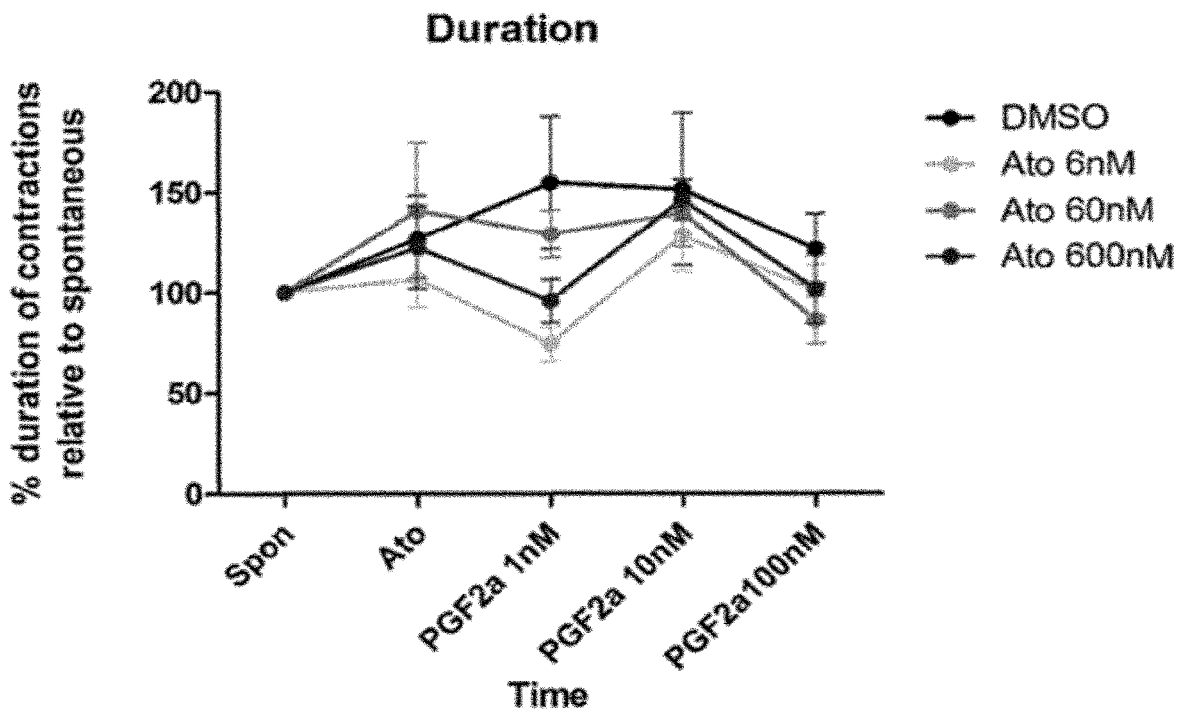
FIG. 74d is a graph demonstrating the effects of varying concentrations of atosiban (6 nM, 60 nM, and 600 nM) on the duration of PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Spon." A DMSO control or atosiban was then added to each myometrial sample at the indicated concentrations and the effects of control or atosiban on contraction duration were measured over the ensuing 10-minute period. This time point is represented on the x-axis as "Ato." The effects of atosiban on contraction duration in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the contraction duration as a percentage of the duration of spontaneous baseline contractions.
Figure 74E:
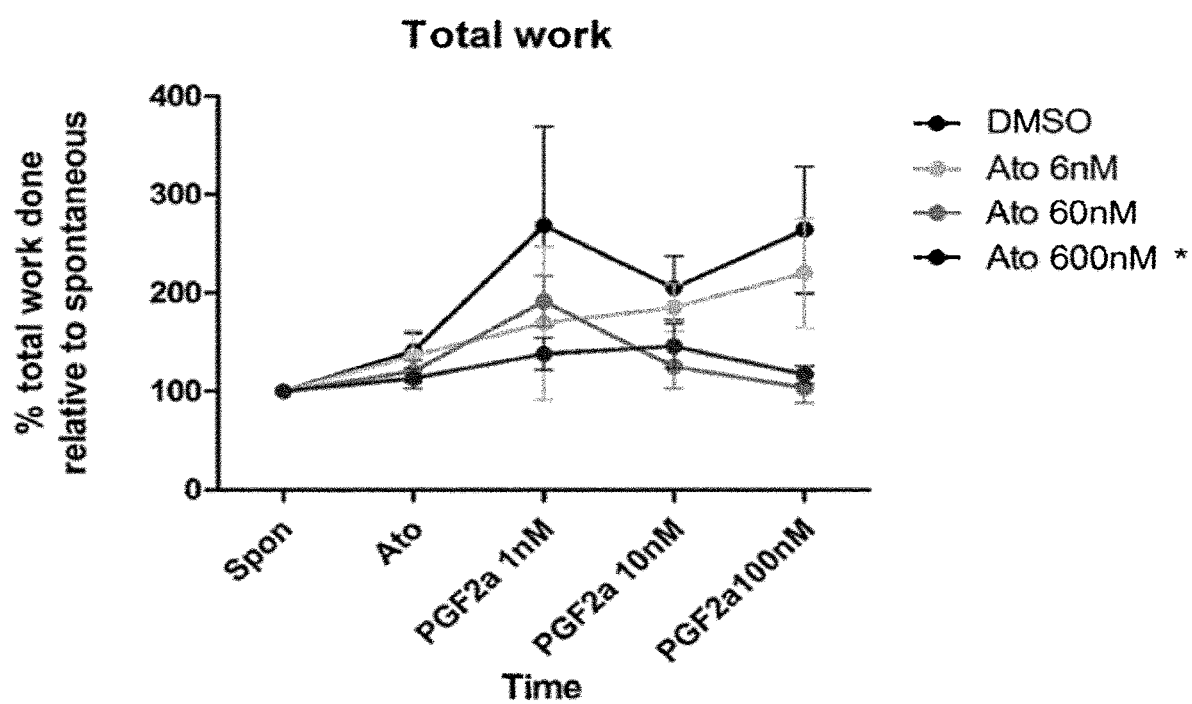
FIG. 74e is a graph demonstrating the effects of varying concentrations of atosiban (6 nM, 60 nM, and 600 nM) on the total work done by all contractions (sum of area under the curve for all contractions) for PGF2α-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Spon." A DMSO control or atosiban was then added to each myometrial sample at the indicated concentrations and the effects of control or atosiban on total work done for all subsequent contractions were measured over the ensuing 10-minute period. This time point is represented on the x-axis as "Ato." The effects of atosiban on total work done by contractions in the presence of PGF2α were subsequently measured by challenging the myometrial tissue samples with increasing concentrations of PGF2α (1 nM, 10 nM, and 100 nM) at sequential 10-minute intervals. These time points are represented on the x-axis as "PGF2α 1 nM," "PGF2α 10 nM," and "PGF2α 100 nM," respectively. Values along the y-axis represent the total work done by contractions as a percentage of the total work done by spontaneous baseline contractions. Asterisk designates a p value of $p<0.05$ versus the DMSO control.
Figure 75A:
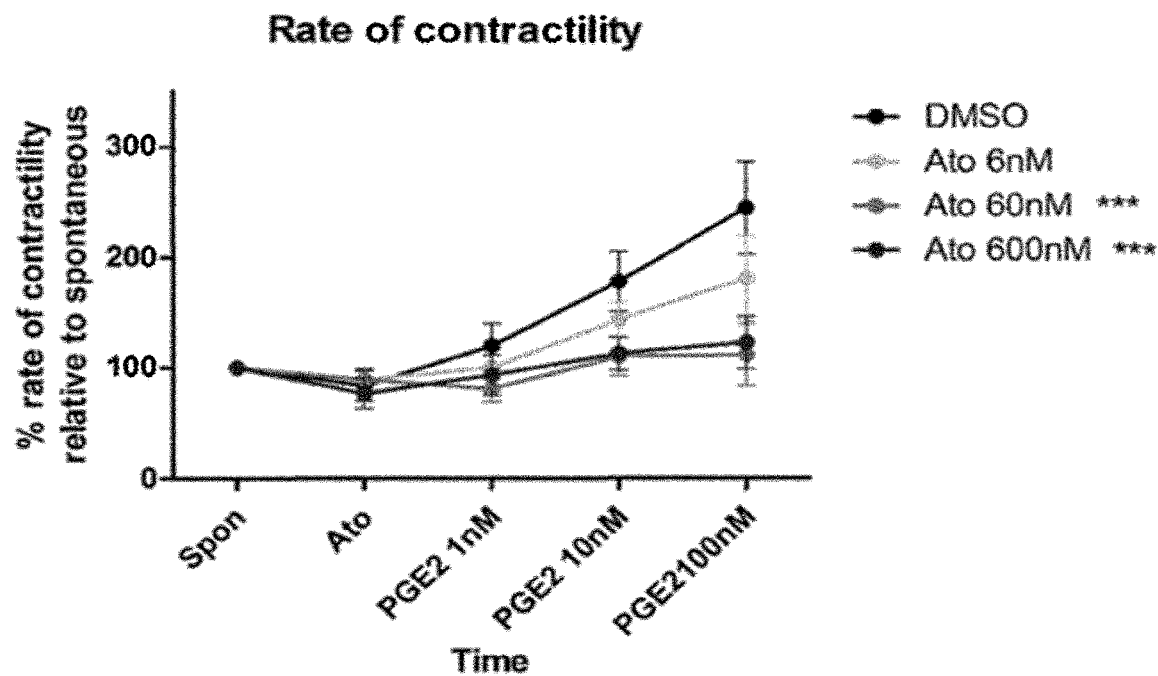
FIG. 75a is a graph demonstrating the effects of varying concentrations of atosiban (6 nM, 60 nM, and 600 nM) on the frequency of PGE2-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control or atosiban ("Ato") was then added to each myometrial sample at the indicated concentrations and the effects of control or atosiban on contractile frequency were measured over the ensuing 10-minute period. This time point is represented on the x-axis as "Ato." The effects of atosiban on contractile frequency in the presence of PGE2 were subsequently measured by challenging the myometrial tissue samples with increasing concentrations of PGE2 (1 nM, 10 nM, and 100 nM) at sequential 10-minute intervals. These time points are represented on the x-axis as "PGE2 1 nM," "PGE2 10 nM," and "PGE2 100 nM," respectively. Values along the y-axis represent the frequency of contractions as a percentage of the frequency of spontaneous baseline contractions. Three asterisks designate a p value of $p<0.001$ versus the DMSO control.
Figure 75B:
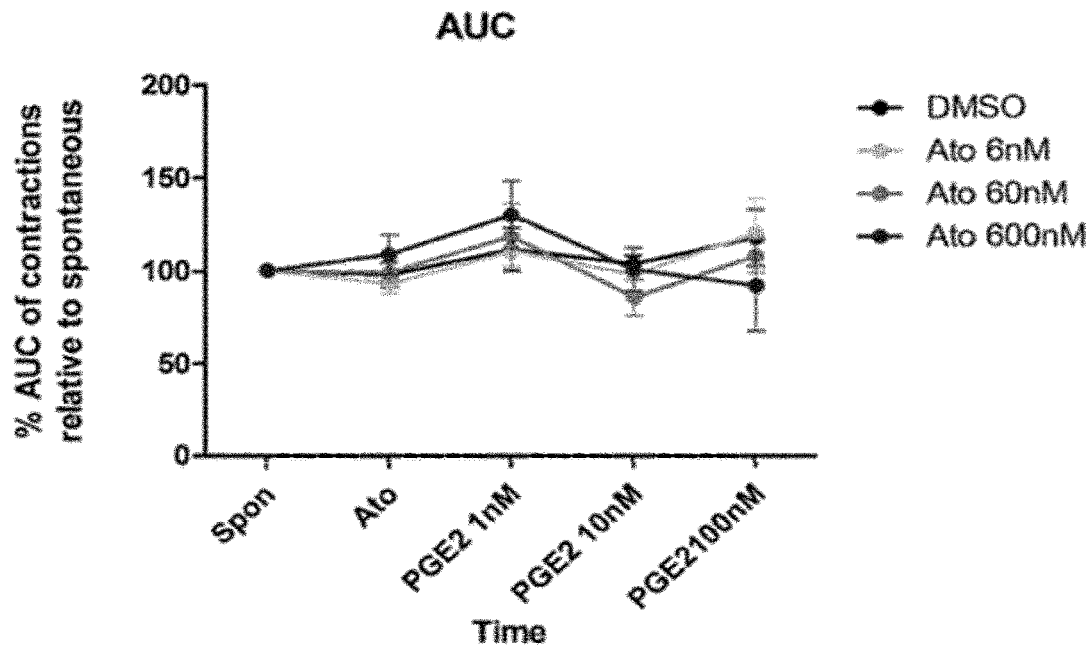
FIG. 75b is a graph demonstrating the effects of varying concentrations of atosiban (6 nM, 60 nM, and 600 nM) on the work done per contraction (area under the curve, or "AUC") of PGE2-induced smooth muscle contractions in N=6 term, pre-laboring myometrial biopsies collected from human female subjects undergoing caesarean section delivery. Experiments were performed using a DMT Myograph 800
Figure 75C:
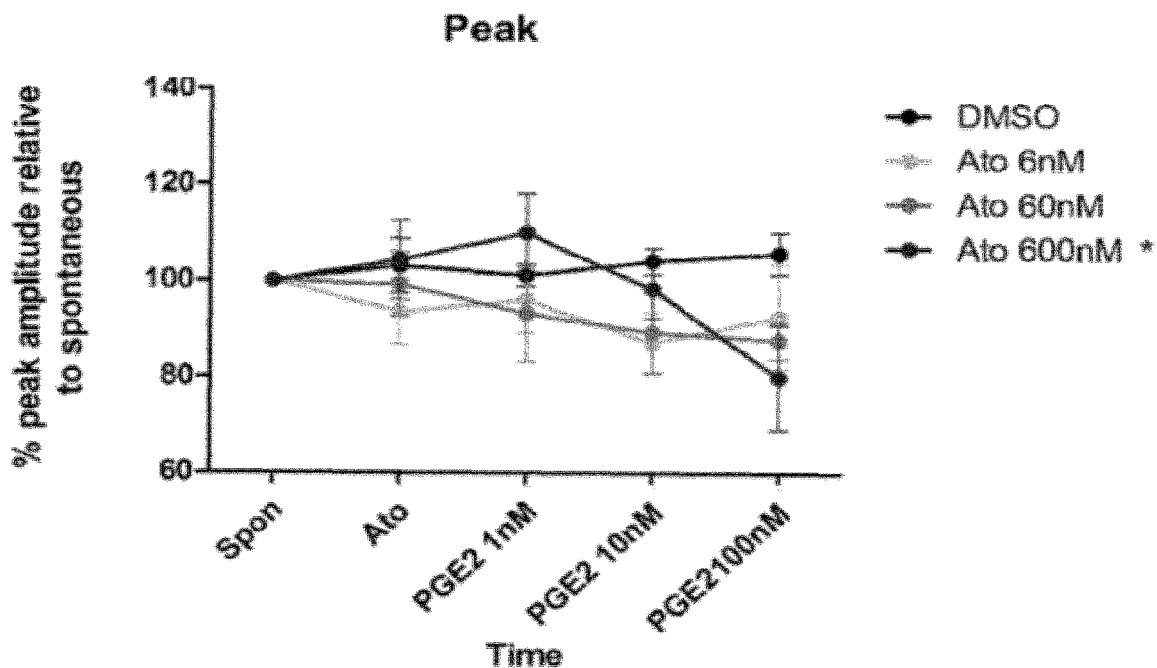
FIG. 75c is a graph demonstrating the effects of varying concentrations of atosiban (6 nM, 60 nM, and 600 nM) on the peak amplitude of PGE2-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Spon." A DMSO control or atosiban was then added to each myometrial sample at the indicated concentrations and the effects of control or atosiban on contraction peak amplitude were measured over the ensuing 10-minute period. This time point is represented on the x-axis as "Ato." The effects of atosiban on contraction peak amplitude in the presence of PGE2 were subsequently measured by challenging the myometrial tissue samples with increasing concentrations of PGE2 (1 nM, 10 nM, and 100 nM) at sequential 10-minute intervals. These time points are represented on the x-axis as "PGE2 1 nM," "PGE2 10 nM," and "PGE2 100 nM," respectively. Values along the y-axis represent the contraction peak amplitude as a percentage of the peak amplitude of spontaneous baseline contractions. Asterisk designates a p value of p<0.05 versus the DMSO control.
Figure 75D:
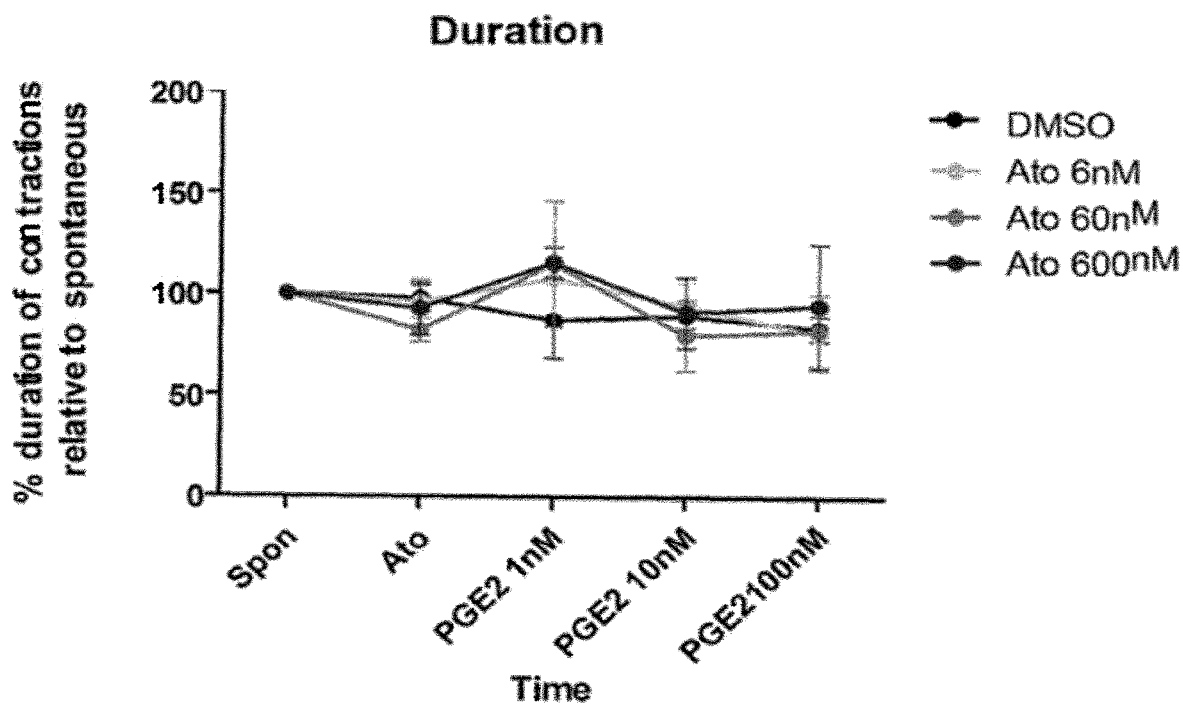
FIG. 75d is a graph demonstrating the effects of varying concentrations of atosiban (6 nM, 60 nM, and 600 nM) on the duration of PGE2-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Spon." A DMSO control or atosiban was then added to each myometrial sample at the indicated concentrations and the effects of control or atosiban on contraction duration were measured over the ensuing 10-minute period. This time point is represented on the x-axis as "Ato." The effects of atosiban on contraction duration in the presence of PGE2 were subsequently measured by challenging the myometrial tissue samples with increasing concentrations of PGE2 (1 nM, 10 nM, and 100 nM) at sequential 10-minute intervals. These time points are represented on the x-axis as "PGE2 1 nM," "PGE2 10 nM," and "PGE2 100 nM," respectively. Values along the y-axis represent the contraction duration as a percentage of the duration of spontaneous baseline contractions.
Figure 75E:
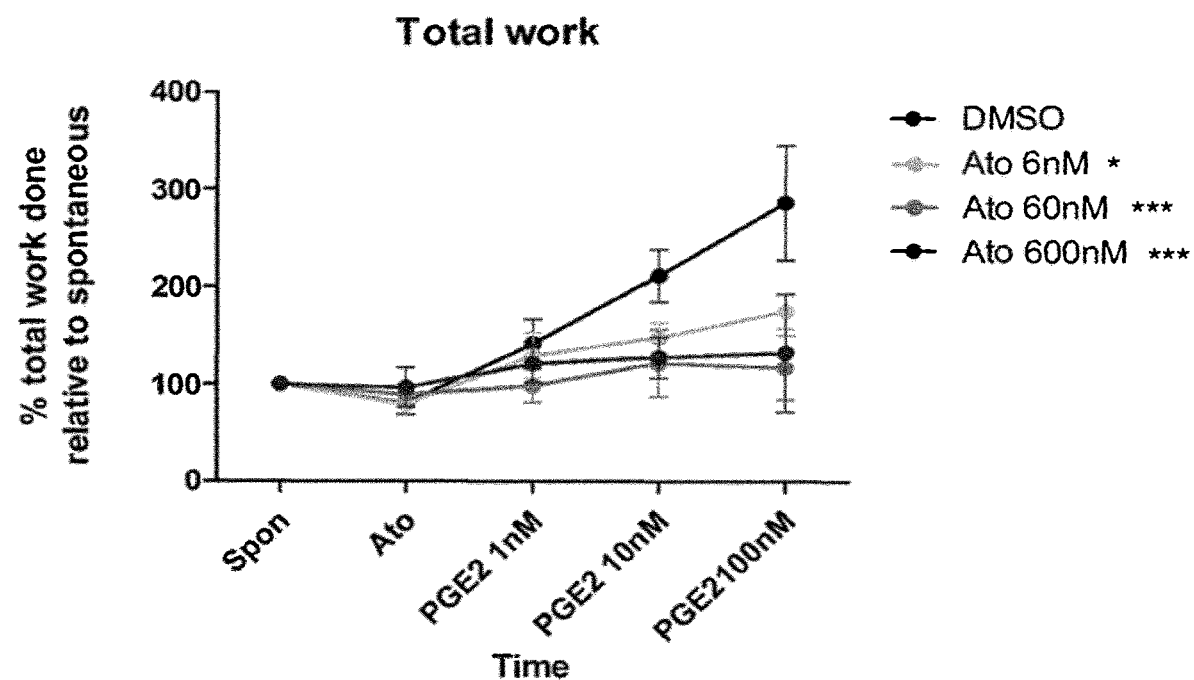
FIG. 75e is a graph demonstrating the effects of varying concentrations of atosiban (6 nM, 60 nM, and 600 nM) on the total work done by all contractions (sum of area under the curve for all contractions) for PGE2-induced smooth muscle contractions in N=6 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Spon." A DMSO control or atosiban was then added to each myometrial sample at the indicated concentrations and the effects of control or atosiban on total work done for all subsequent contractions were measured over the ensuing 10-minute period. This time point is represented on the x-axis as "Ato." The effects of atosiban on total work done by contractions in the presence of PGE2 were subsequently measured by challenging the myometrial tissue samples with increasing concentrations of PGE2 (1 nM, 10 nM, and 100 nM) at sequential 10-minute intervals. These time points are represented on the x-axis as "PGE2 1 nM," "PGE2 10 nM," and "PGE2 100 nM," respectively. Values along the y-axis represent the total work done by contractions as a percentage of the total work done by spontaneous baseline contractions. Asterisk designates a p value of p<0.05 versus the DMSO control. Three asterisks designate a p value of p<0.001 versus the DMSO control.
Figure 76A:
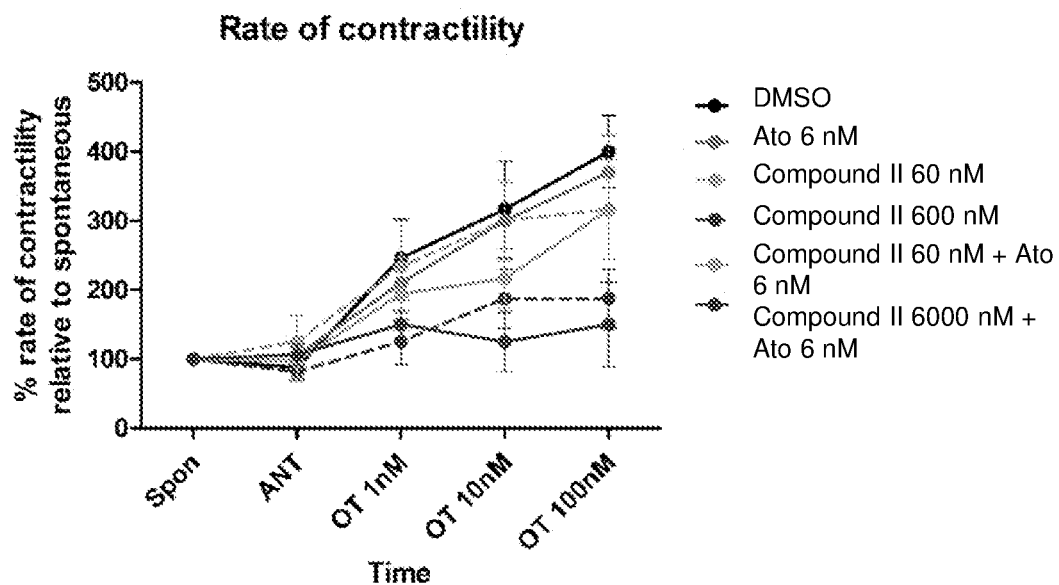
FIG. 76a is a graph demonstrating the effects of varying concentrations of compound II (60 nM and 600 nM), atosiban (6 nM), and combinations of compound II and atosiban on the frequency of OT-induced smooth muscle contractions in N=3 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control, compound II, and/or atosiban was then added to each myometrial sample at the indicated concentrations and the effects of control, compound II, and/or atosiban on contractile frequency were measured over the ensuing 10-minute period. This time point is represented on the x-axis as "ANT." The effects of compound II and/or atosiban on contractile frequency in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the frequency of contractions as a percentage of the frequency of spontaneous baseline contractions.
Figure 76B:
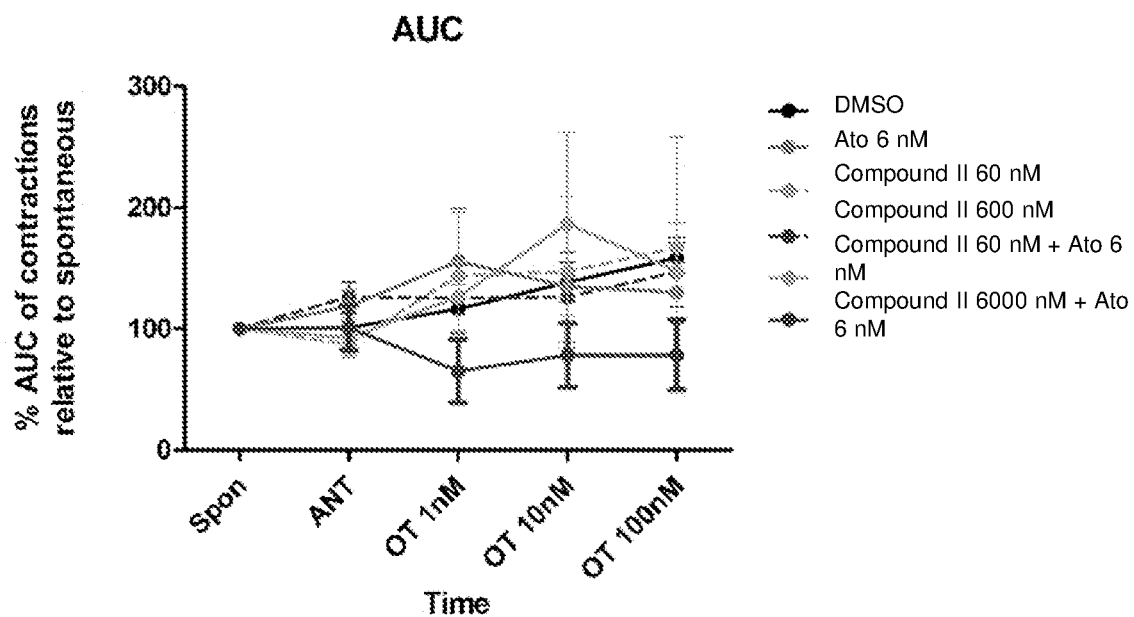
FIG. 76b is a graph demonstrating the effects of varying concentrations of compound II (60 nM and 600 nM), atosiban (6 nM), and combinations of compound II and atosiban on the work done per contraction (area under the curve, or "AUC") of OT-induced smooth muscle contractions in N=3 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spoon." A DMSO control, compound II, and/or atosiban was then added to each myometrial sample at the indicated concentrations and the effects of control, compound II, and/or atosiban on work done per contraction were measured over the ensuing 10-minute period. This time point is represented on the x-axis as "ANT." The effects of compound II and/or atosiban on work done per contraction in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the work done per contraction as a percentage of the work done per contraction for spontaneous baseline contractions.
Figure 76C:
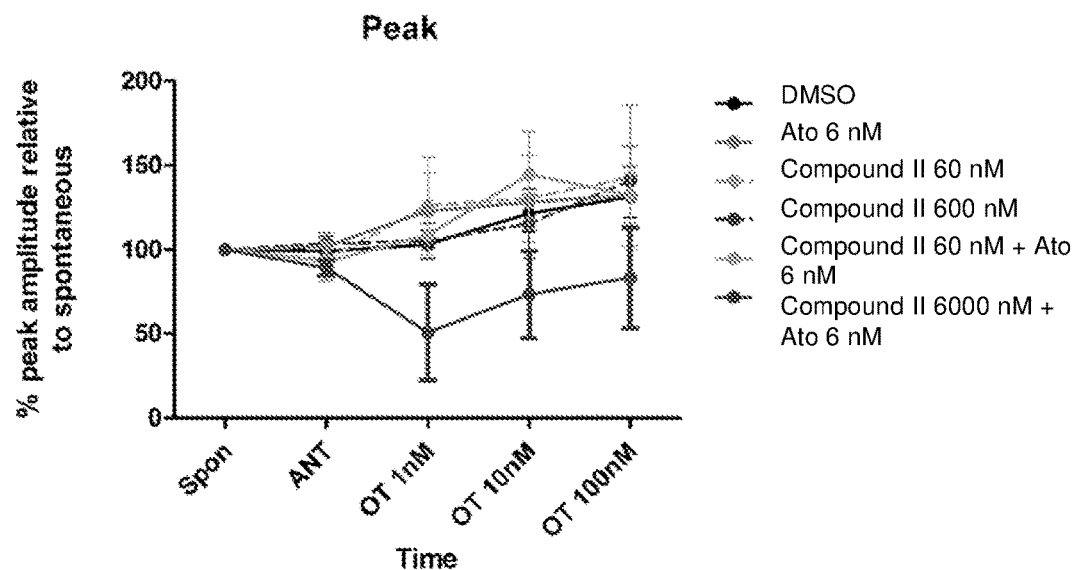
FIG. 76c is a graph demonstrating the effects of varying concentrations of compound II (60 nM and 600 nM), atosiban (6 nM), and combinations of compound II and atosiban on the peak amplitude of OT-induced smooth muscle contractions in N=3 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Spon." A DMSO control, compound II, and/or atosiban was then added to each myometrial sample at the indicated concentrations and the effects of control, compound II, and/or atosiban on contraction peak amplitude were measured over the ensuing 10-minute period. This time point is represented on the x-axis as "ANT." The effects of compound II and/or atosiban on contraction peak amplitude in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction peak amplitude as a percentage of the peak amplitude of spontaneous baseline contractions.
Figure 76D:
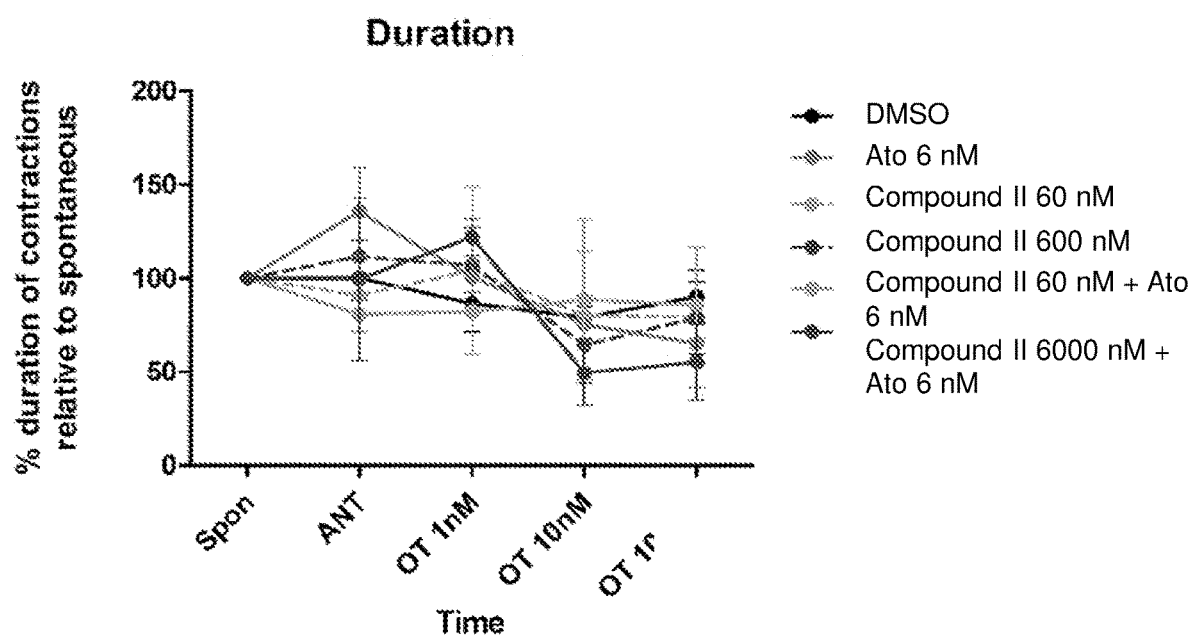
FIG. 76d is a graph demonstrating the effects of varying concentrations of compound II (60 nM and 600 nM), atosiban (6 nM), and combinations of compound II and atosiban on the duration of OT-induced smooth muscle contractions in N=3 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Spon." A DMSO control, compound II, and/or atosiban was then added to each myometrial sample at the indicated concentrations and the effects of control, compound II, and/or atosiban on contraction duration were measured over the ensuing 10-minute period. This time point is represented on the x-axis as "ANT." The effects of compound II and/or atosiban on contraction duration in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction duration as a percentage of the duration of spontaneous baseline contractions.
Figure 76E:
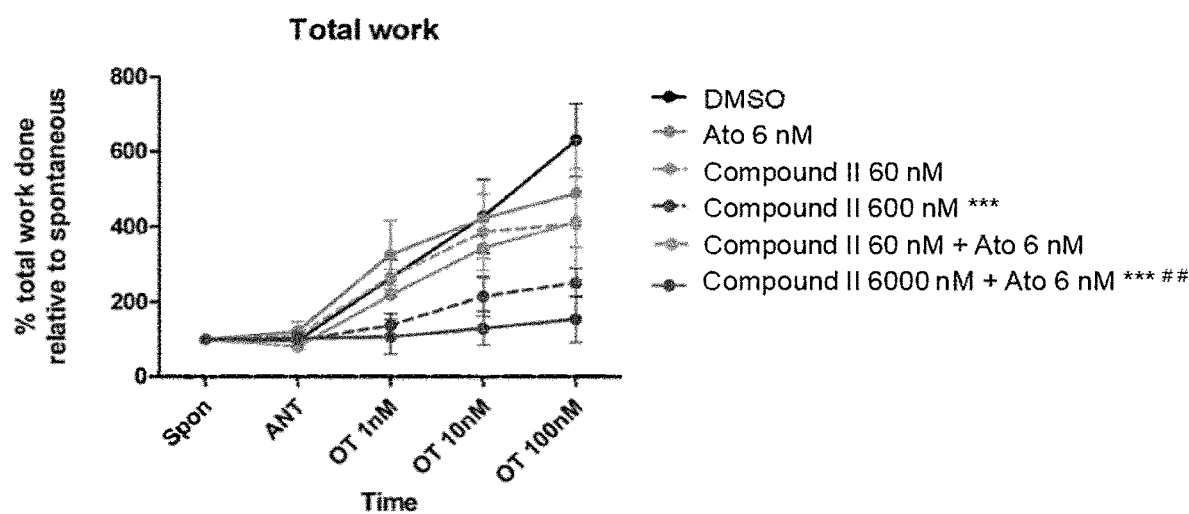
FIG. 76e is a graph demonstrating the effects of varying concentrations of compound II (60 nM and 600 nM), atosiban (6 nM), and combinations of compound II and atosiban on the total work done by all contractions (sum of area under the curve for all contractions) for OT-induced smooth muscle contractions in N=3 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Spon." A DMSO control, compound II, and/or atosiban was then added to each myometrial sample at the indicated concentrations and the effects of control, compound II, and/or atosiban on total work done for all subsequent contractions were measured over the ensuing 10-minute period. This time point is represented on the x-axis as "ANT." The effects of compound II and/or atosiban on total work done by contractions in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the total work done by contractions as a percentage of the total work done by spontaneous baseline contractions. Three asterisks designate a p value of $p<0.001$ versus the DMSO control. Two "#" symbols designate a p value of $p<0.01$ versus treatment with atosiban at a concentration of 6 nM.
Figure 77A:
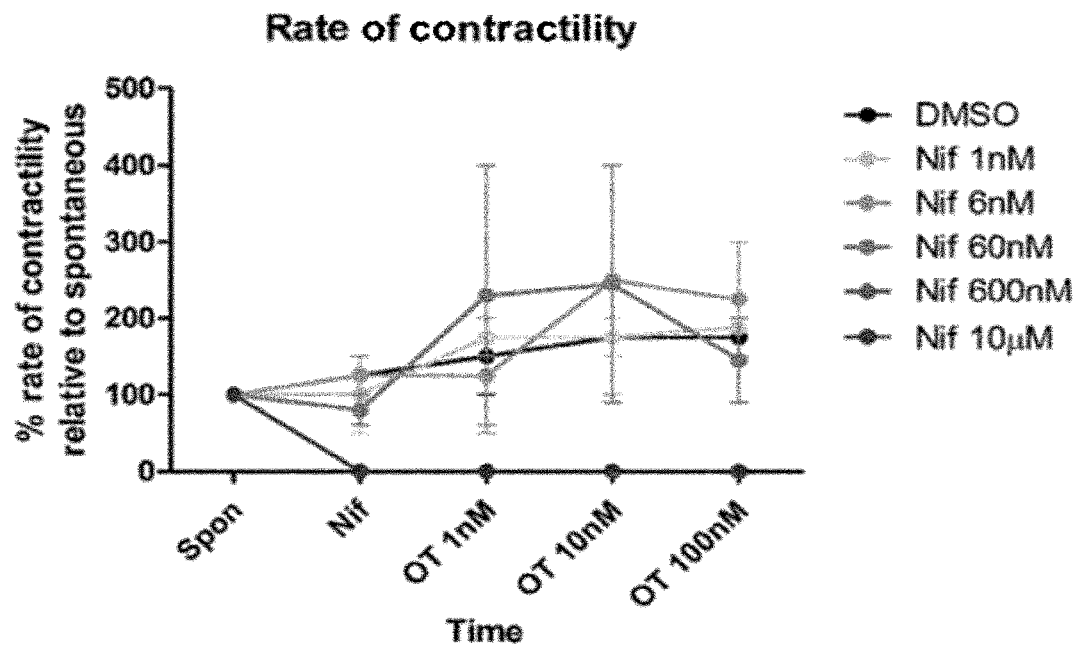
FIG. 77a is a graph demonstrating the effects of varying concentrations of nifedipine (1 nM, 6 nM, 60 nM, 600 nM, and 10 µM) on the frequency of OT-induced smooth muscle contractions in N=2 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control or nifedipine was then added to each myometrial sample at the indicated concentrations and the effects of control or nifedipine on contractile frequency were measured over the ensuing 10-minute period. This time point is represented on the x-axis as "Nif." The effects of nifedipine on contractile frequency in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the frequency of contractions as a percentage of the frequency of spontaneous baseline contractions.
Figure 77B:
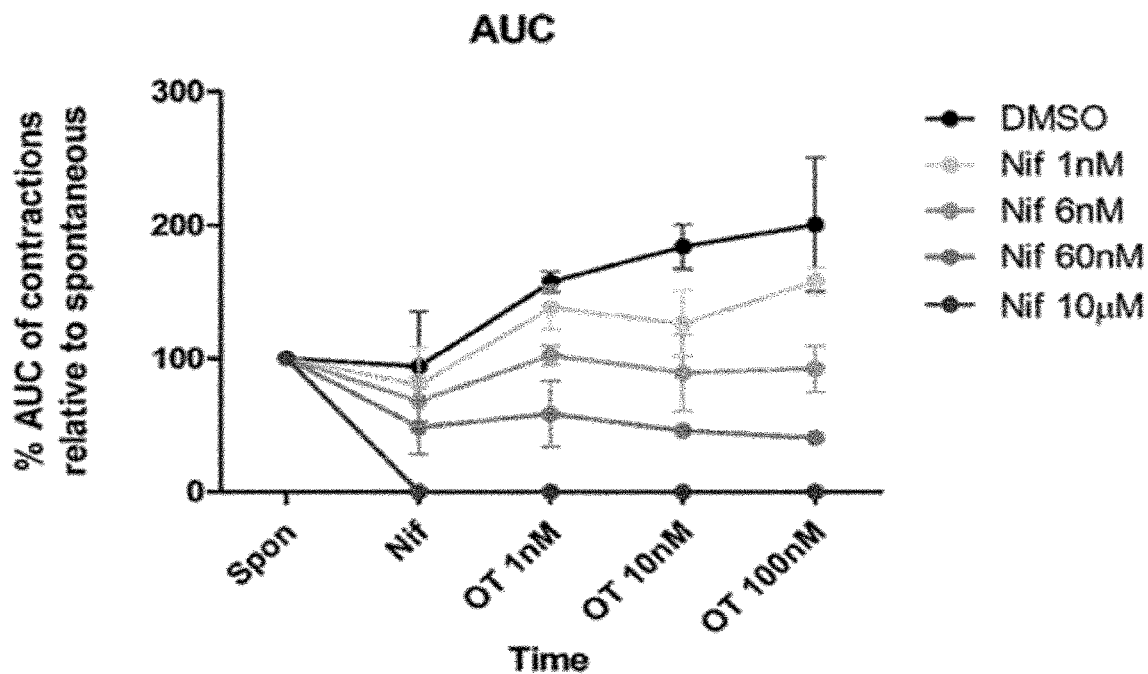
FIG. 77b is a graph demonstrating the effects of varying concentrations of nifedipine (1 nM, 6 nM, 60 nM, 600 nM, and 10 μM) on the work done per contraction (area under the curve, or "AUC") of OT-induced smooth muscle contractions in N=2 term, pre-laboring myometrial biopsies collected from human female subjects undergoing caesarean section delivery. Experiments were performed using a DMT Myograph 800 MS (AD INSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spon." A DMSO control or nifedipine was then added to each myometrial sample at the indicated concentrations and the effects of control or nifedipine on work done per contraction were measured over the ensuing 10-minute period. This time point is represented on the x-axis as "Nif." The effects of nifedipine on work done per contraction in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the work done per contraction as a percentage of the work done per contraction for spontaneous baseline contractions.
Figure 77C:
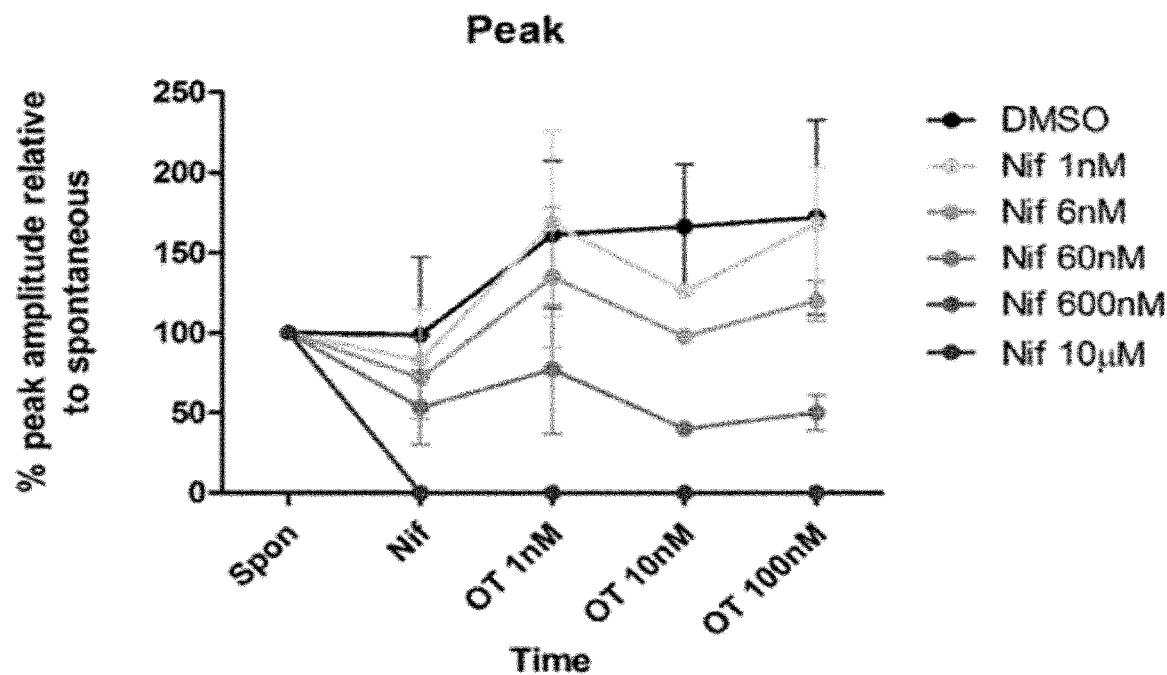
FIG. 77c is a graph demonstrating the effects of varying concentrations of nifedipine (1 nM, 6 nM, 60 nM, 600 nM, and 10 μM) on the peak amplitude of OT-induced smooth muscle contractions in N=2 term, pre-laboring myometrial biopsies collected from human female subjects undergoing caesarean section delivery. Experiments were performed using a DMT Myograph 800 MS (AD INSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Spon." A DMSO control or nifedipine was then added to each myometrial sample at the indicated concentrations and the effects of control or nifedipine on contraction peak amplitude were measured over the ensuing 10-minute period. This time point is represented on the x-axis as "Nif." The effects of nifedipine on contraction peak amplitude in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction peak amplitude as a percentage of the peak amplitude of spontaneous baseline contractions.
Figure 77D:
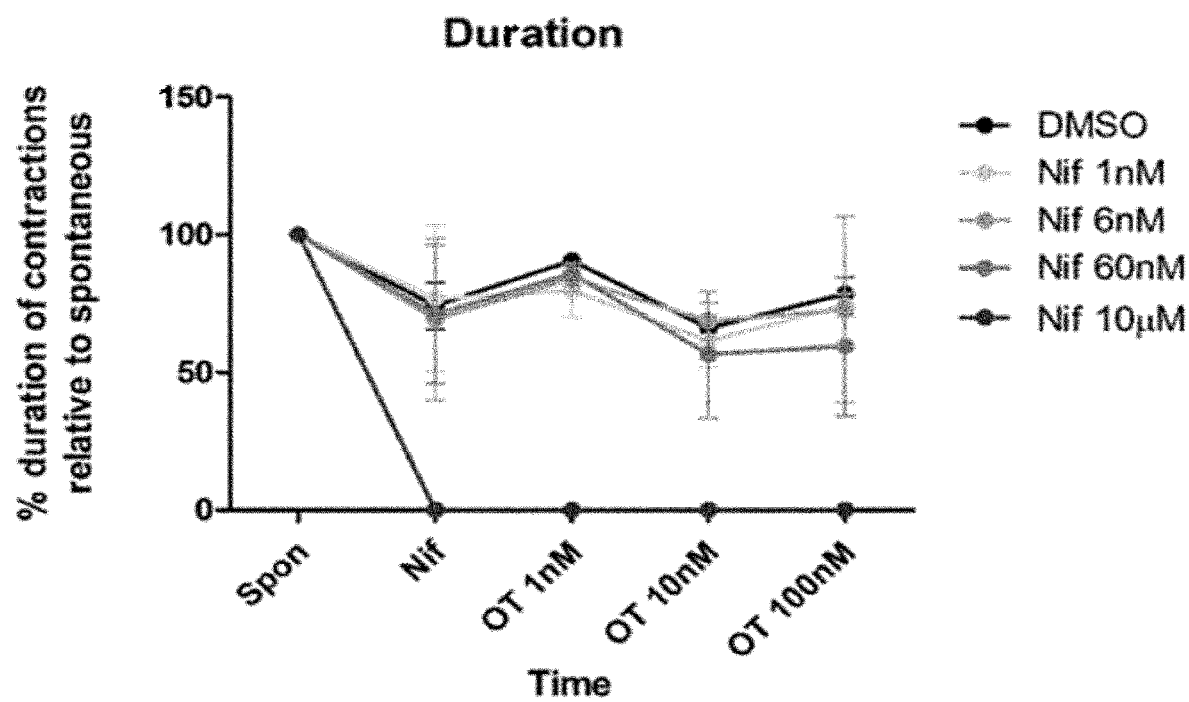
FIG. 77d is a graph demonstrating the effects of varying concentrations of nifedipine (1 nM, 6 nM, 60 nM, 600 nM, and 10 μM) on the duration of OT-induced smooth muscle contractions in N=2 term, pre-laboring myometrial biopsies collected from human female subjects undergoing caesarean section delivery. Experiments were performed using a DMT Myograph 800 MS (AD INSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Spon." A DMSO control or nifedipine was then added to each myometrial sample at the indicated concentrations and the effects of control or nifedipine on contraction duration were measured over the ensuing 10-minute period. This time point is represented on the x-axis as "Nif." The effects of nifedipine on contraction duration in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction duration as a percentage of the duration of spontaneous baseline contractions.
Figure 77E:
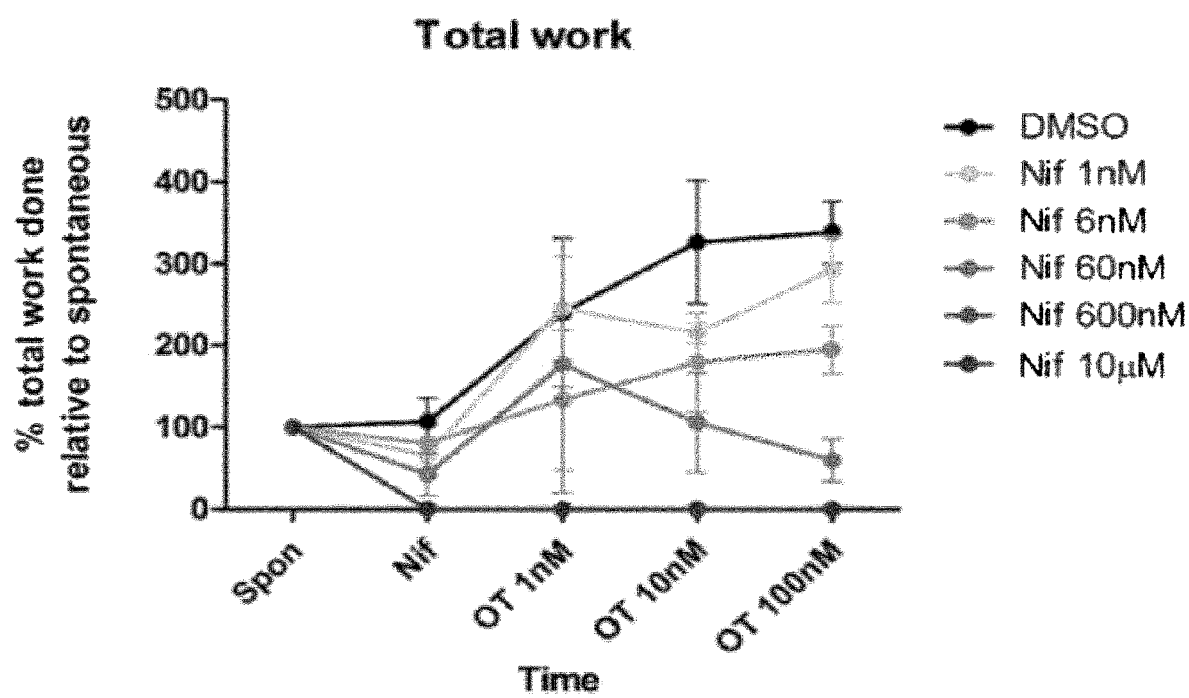
FIG. 77e is a graph demonstrating the effects of varying concentrations of nifedipine (1 nM, 6 nM, 60 nM, 600 nM, and 10 μM) on the total work done by all contractions (sum of area under the curve for all contractions) for OT-induced smooth muscle contractions in N=2 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Spon." A DMSO control or nifedipine was then added to each myometrial sample at the indicated concentrations and the effects of control or nifedipine on total work done for all subsequent contractions were measured over the ensuing 10-minute period. This time point is represented on the x-axis as "Nif." The effects of nifedipine on total work done by contractions in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the total work done by contractions as a percentage of the total work done by spontaneous baseline contractions.
Figure 78A:
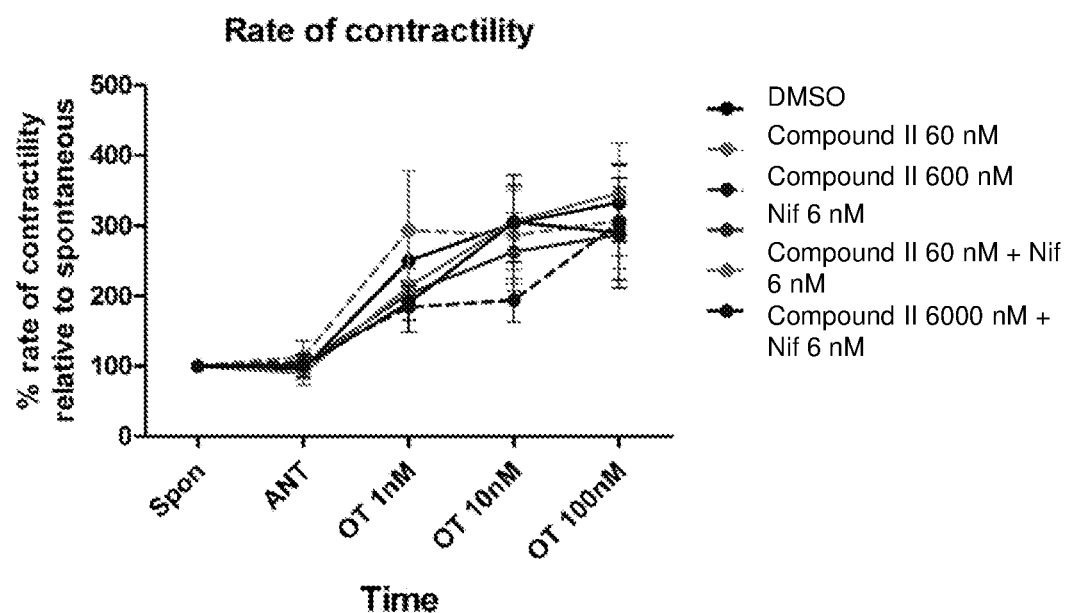
FIG. 78a is a graph demonstrating the effects of varying concentrations of compound II (60 nM and 600 nM), nifedipine (6 nM), and combinations of compound II and nifedipine on the frequency of OT-induced smooth muscle contractions in N=5 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction frequency were recorded. The measurement of spontaneous contraction frequency is represented on the x-axis as "Spon." A DMSO control, compound II, and/or nifedipine was then added to each myometrial sample at the indicated concentrations and the effects of control, compound II, and/or nifedipine on contractile frequency were measured over the ensuing 10-minute period. This time point is represented on the x-axis as "ANT." The effects of compound II and/or nifedipine on contractile frequency in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM,"
Figure 78B:
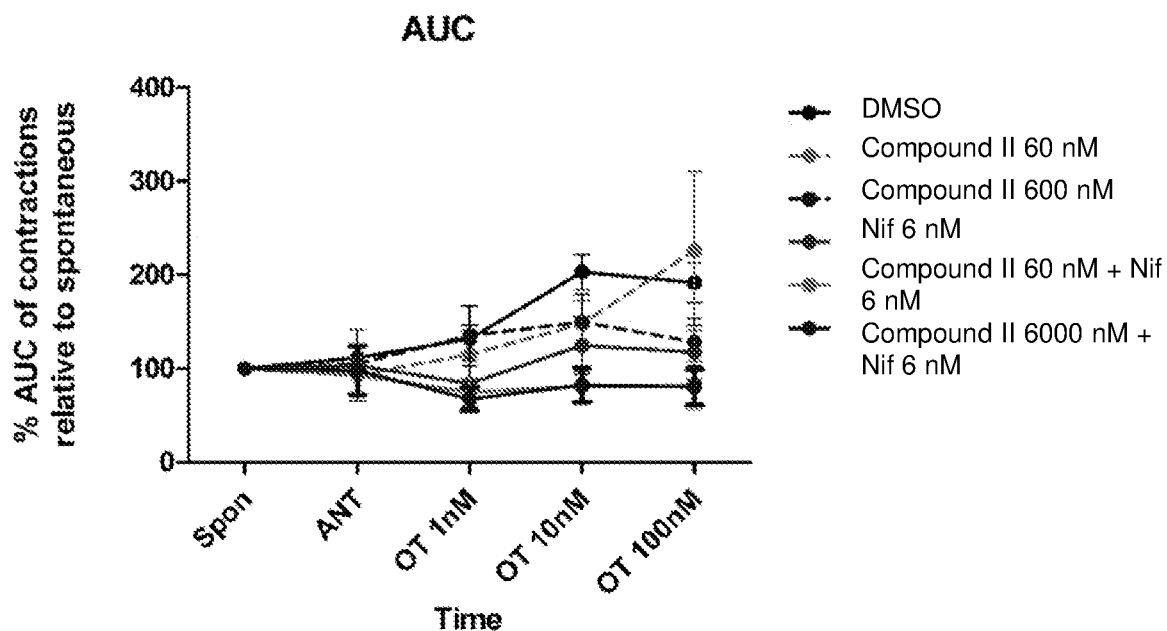
FIG. 78b is a graph demonstrating the effects of varying concentrations of compound II (60 nM and 600 nM), nifedipine (6 nM), and combinations of compound II and nifedipine on the work done per contraction (area under the curve, or "AUC") of OT-induced smooth muscle contractions in N=5 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous work done per contraction were recorded. The measurement of spontaneous work done per contraction is represented on the x-axis as "Spon." A DMSO control, compound II, and/or nifedipine was then added to each myometrial sample at the indicated concentrations and the effects of control, compound II, and/or nifedipine on work done per contraction were measured over the ensuing 10-minute period. This time point is represented on the x-axis as "ANT." The effects of compound II and/or nifedipine on work done per contraction in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the work done per contraction as a percentage of the work done per contraction for spontaneous baseline contractions.
Figure 78C:
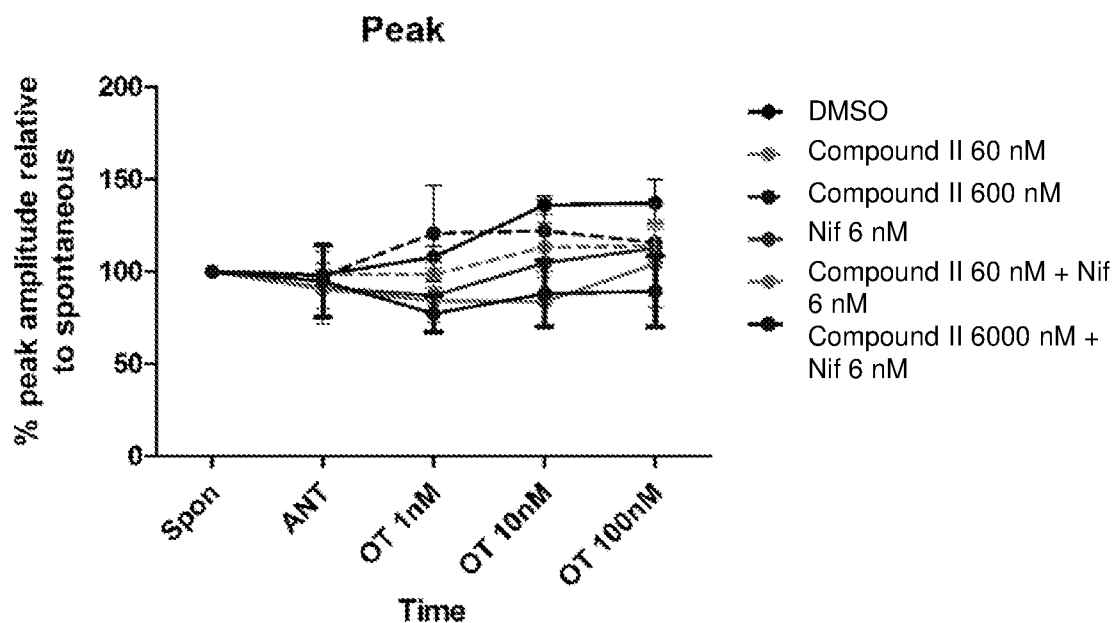
FIG. 78c is a graph demonstrating the effects of varying concentrations of compound II (60 nM and 600 nM), nifedipine (6 nM), and combinations of compound II and nifedipine on the peak amplitude of OT-induced smooth muscle contractions in N=5 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction peak amplitude were recorded. The measurement of spontaneous contraction peak amplitude is represented on the x-axis as "Spon." A DMSO control, compound II, and/or nifedipine was then added to each myometrial sample at the indicated concentrations and the effects of control, compound II, and/or nifedipine on contraction peak amplitude were measured over the ensuing 10-minute period. This time point is represented on the x-axis as "ANT." The effects of compound II and/or nifedipine on contraction peak amplitude in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction peak amplitude as a percentage of the peak amplitude of spontaneous baseline contractions.
Figure 78D:
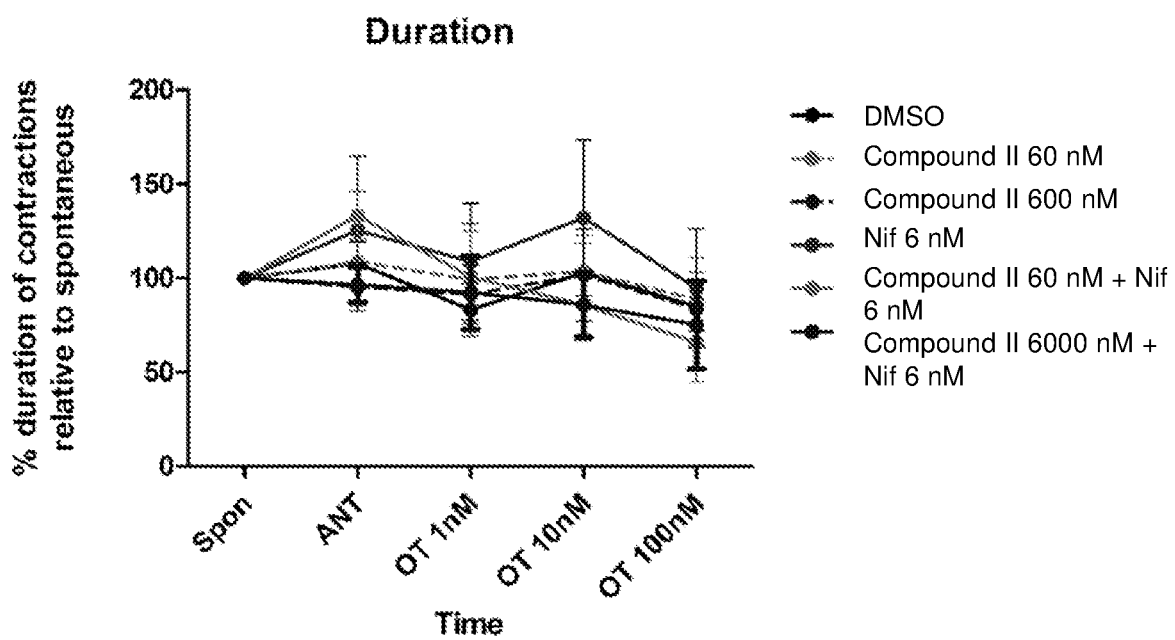
FIG. 78d is a graph demonstrating the effects of compound II (60 nM and 600 nM), nifedipine (6 nM), and combinations of compound II and nifedipine on the duration of OT-induced smooth muscle contractions in N=5 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of spontaneous contraction duration were recorded. The measurement of spontaneous contraction duration is represented on the x-axis as "Span." A DMSO control, compound II, and/or nifedipine was then added to each myometrial sample at the indicated concentrations and the effects of control, compound II, and/or nifedipine on contraction duration were measured over the ensuing 10-minute period. This time point is represented on the x-axis as "ANT." The effects of compound II and/or nifedipine on contraction duration in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the contraction duration as a percentage of the duration of spontaneous baseline contractions.
Figure 78E:
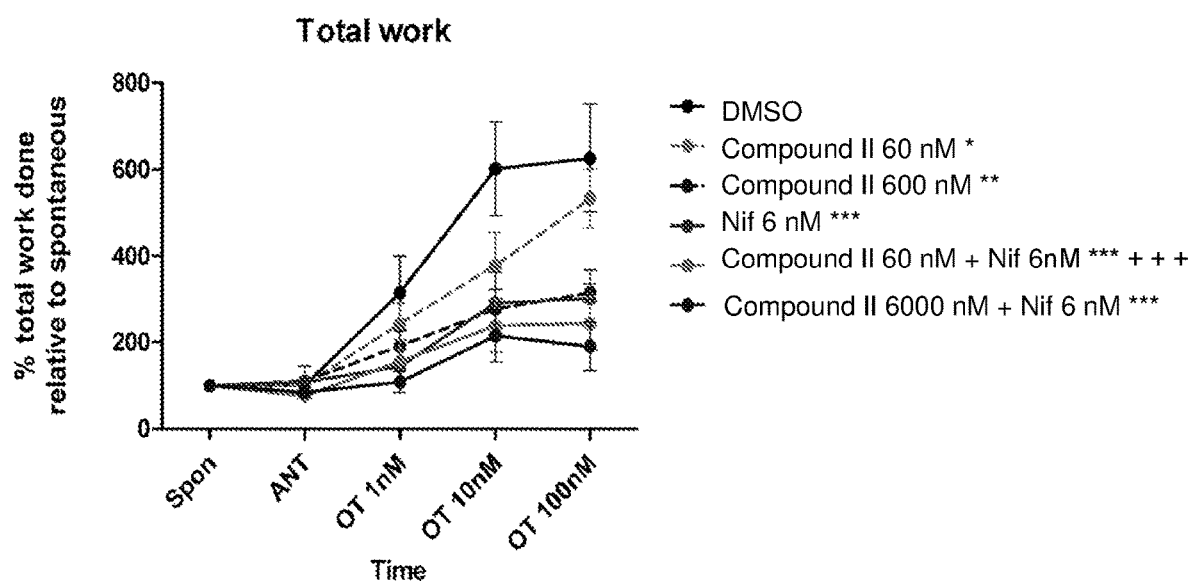
FIG. 78e is a graph demonstrating the effects of compound II (60 nM and 600 nM), nifedipine (6 nM), and combinations of compound II and nifedipine on the total work done by all contractions (sum of area under the curve for all contractions) for OT-induced smooth muscle contractions in N=5 term, pre-laboring myometrial biopsies collected from human female subjects undergoing caesarean section delivery. Experiments were performed using a DMT Myograph 800 MS (ADINSTRUMENTS™) in oxygenated Kreb's solution with ADI Powerlab software. Once regular contractions had been established for at least 20 minutes, baseline measurements of work done for all spontaneous contractions were recorded. The measurement of work done for all spontaneous contractions is represented on the x-axis as "Span." A DMSO control, compound II, and/or nifedipine was then added to each myometrial sample at the indicated concentrations and the effects of control, compound II, and/or nifedipine on total work done for all subsequent contractions were measured over the ensuing 10-minute period. This time point is represented on the x-axis as "ANT." The effects of compound II and/or nifedipine on total work done by contractions in the presence of OT were subsequently measured by challenging the myometrial tissue samples with increasing concentrations of OT (1 nM, 10 nM, and 100 nM) at sequential 10-minute intervals. These time points are represented on the x-axis as "OT 1 nM," "OT 10 nM," and "OT 100 nM," respectively. Values along the y-axis represent the total work done by contractions as a percentage of the total work done by spontaneous baseline contractions. Asterisk designates a p value of p<0.05 versus the DMSO control. Two asterisks designate a p value of p<0.01 versus the DMSO control. Three asterisks designate a p value of p<0.001 versus the DMSO control. Three "+" symbols designate a p value of p<0.001 versus treatment with compound II at a concentration of 60 nM.
Figure 79A:
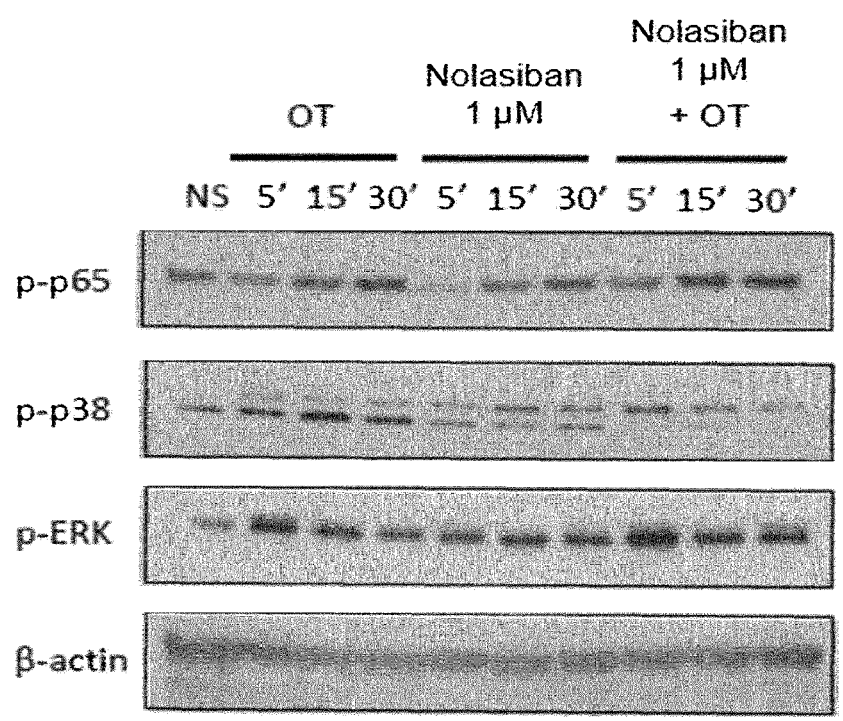
FIG. 79a is a Western blot showing the effects of oxytocin, nolasiban, and a combination thereof on the expression of phosphorylated p65 (p-p65), phosphorylated p38 (p-p38), and phosphorylated extracellular signal-regulated kinase (p-ERK) in N=6 term, pre-laboring myometrial biopsies collected from human female subjects undergoing caesarean section delivery. Samples were either unstimulated ("NS"), stimulated with oxytocin ("OT"), treated with nolasiban at a concentration of 1 µM, or treated with both oxytocin and nolasiban at a concentration of 1 µM for the indicated periods of time. A blot against β-actin was performed as a control.
Figure 79B:
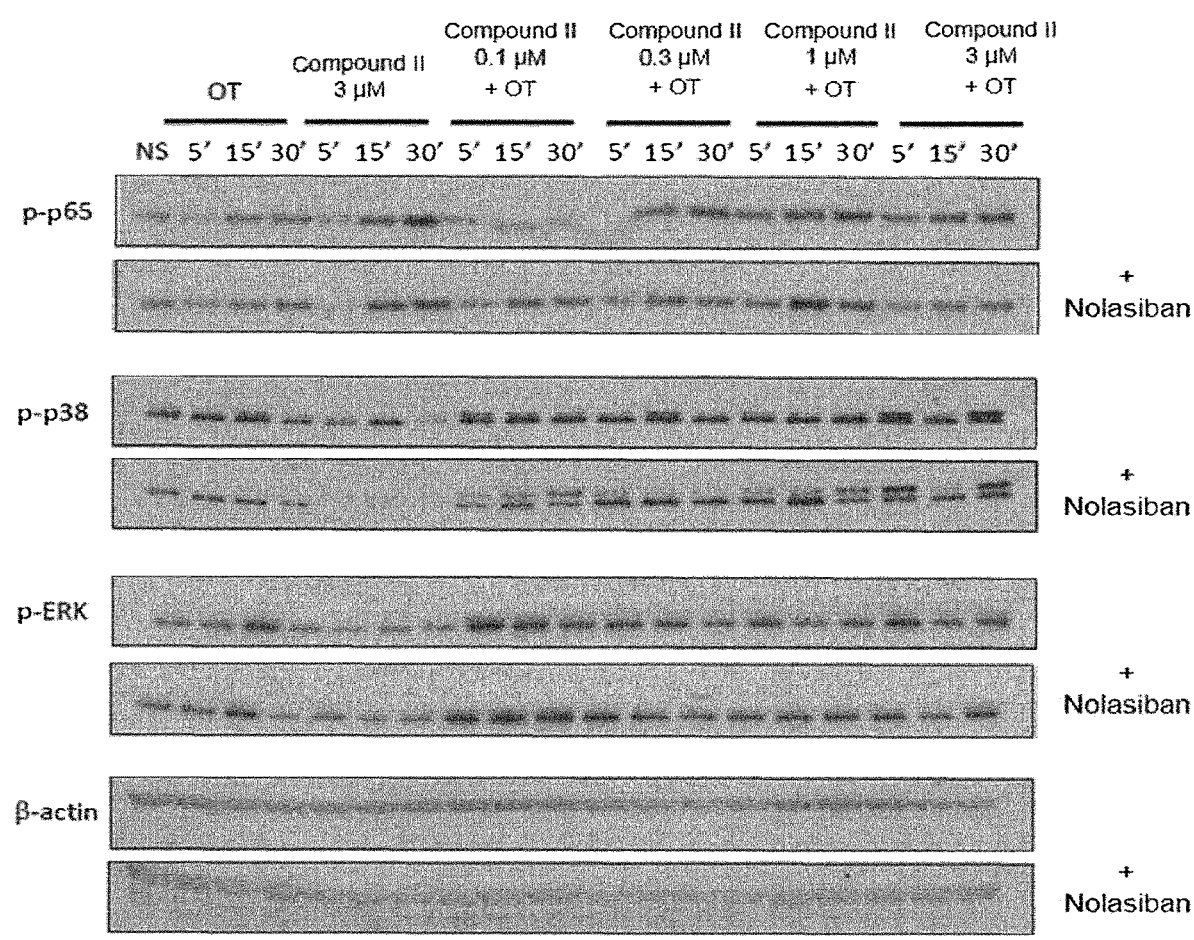
FIG. 79b is a Western blot showing the effects of oxytocin and/or varying concentration of compound II, optionally in combination with nolasiban, on the expression of p-p65, p-p38, and p-ERK in N=6 term, pre-laboring myometrial biopsies collected from human female subjects undergoing caesarean section delivery. Samples were either unstimulated ("NS"), stimulated with oxytocin ("OT"), treated with compound II at a concentration of 3 µM, or treated with both oxytocin and compound II at varying concentrations of compound II, both in the presence and absence of nolasiban at a concentration of 1 µM for the indicated periods of time. A blot against β-actin was performed as a control.
Figure 79C:
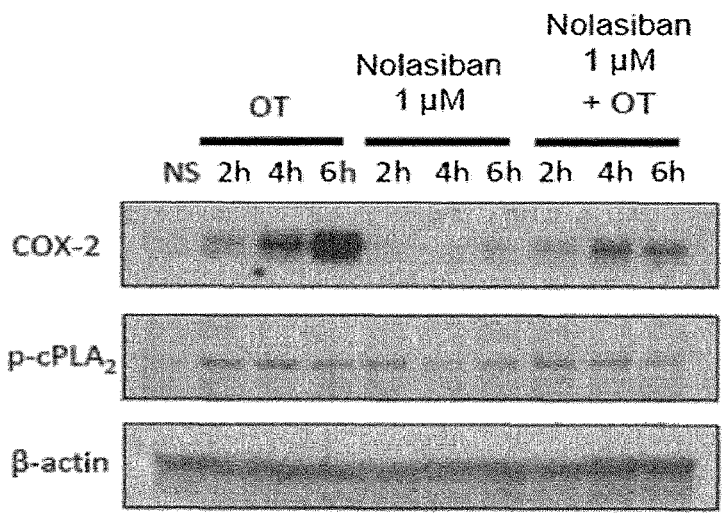
FIG. 79c is a Western blot showing the effects of oxytocin, nolasiban, and a combination thereof on the expression of the proinflammatory genes cyclooxygenase 2 (COX-2) and phosphorylated calcium-dependent phospholipase A2 (p-cPLA2) in N=6 term, pre-laboring myometrial biopsies collected from human female subjects undergoing caesarean section delivery. Samples were either unstimulated ("NS"), stimulated with oxytocin ("OT"), treated with nolasiban at a concentration of 1 µM, or treated with both oxytocin and nolasiban at a concentration of 1 µM for the indicated periods of time. A blot against β-actin was performed as a control.
Figure 79D:
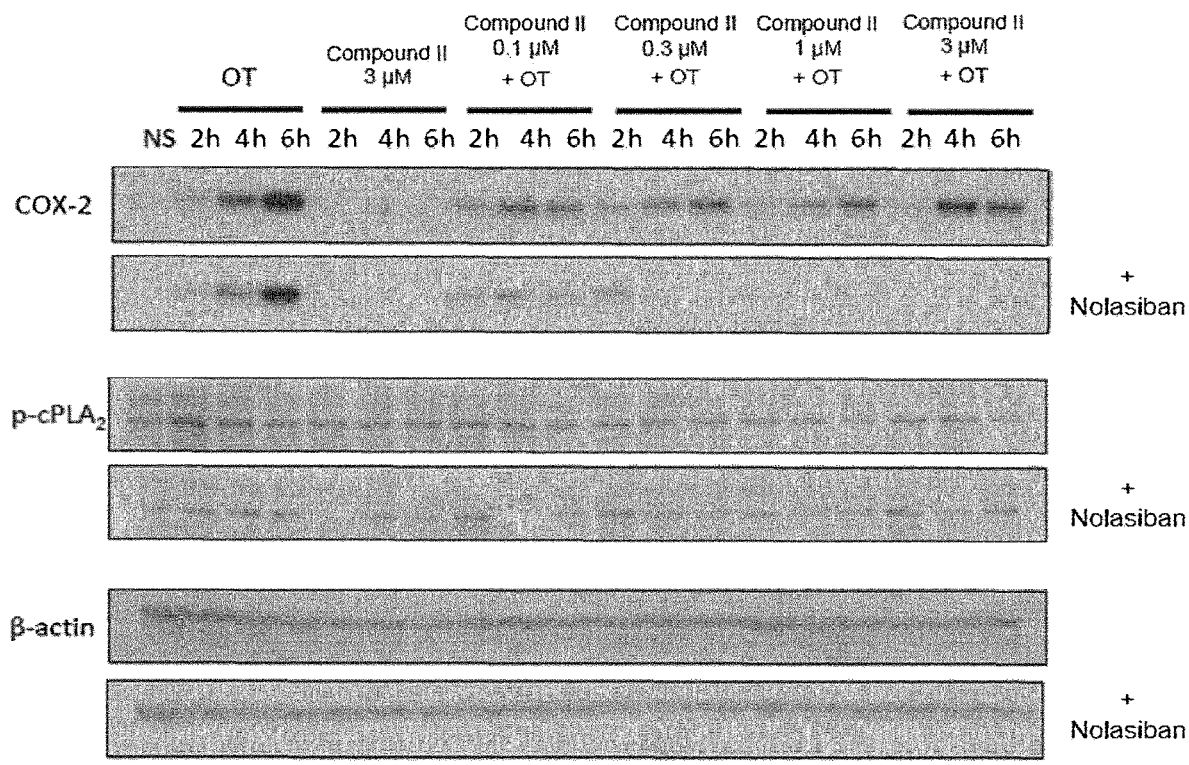
FIG. 79d is a Western blot showing the effects of oxytocin and/or varying concentration of compound II, optionally in combination with nolasiban, on the expression of the proinflammatory genes COX-2 and p-cPLA2 in N=6 term, pre-laboring myometrial biopsies collected from human female subjects undergoing caesarean section delivery. Samples were either unstimulated ("NS"), stimulated with oxytocin ("OT"), treated with compound II at a concentration of 3 µM, or treated with both oxytocin and compound II at varying concentrations of compound II, both in the presence and absence of nolasiban at a concentration of 1 µM for the indicated periods of time. A blot against β-actin was performed as a control.
Figure 79E:
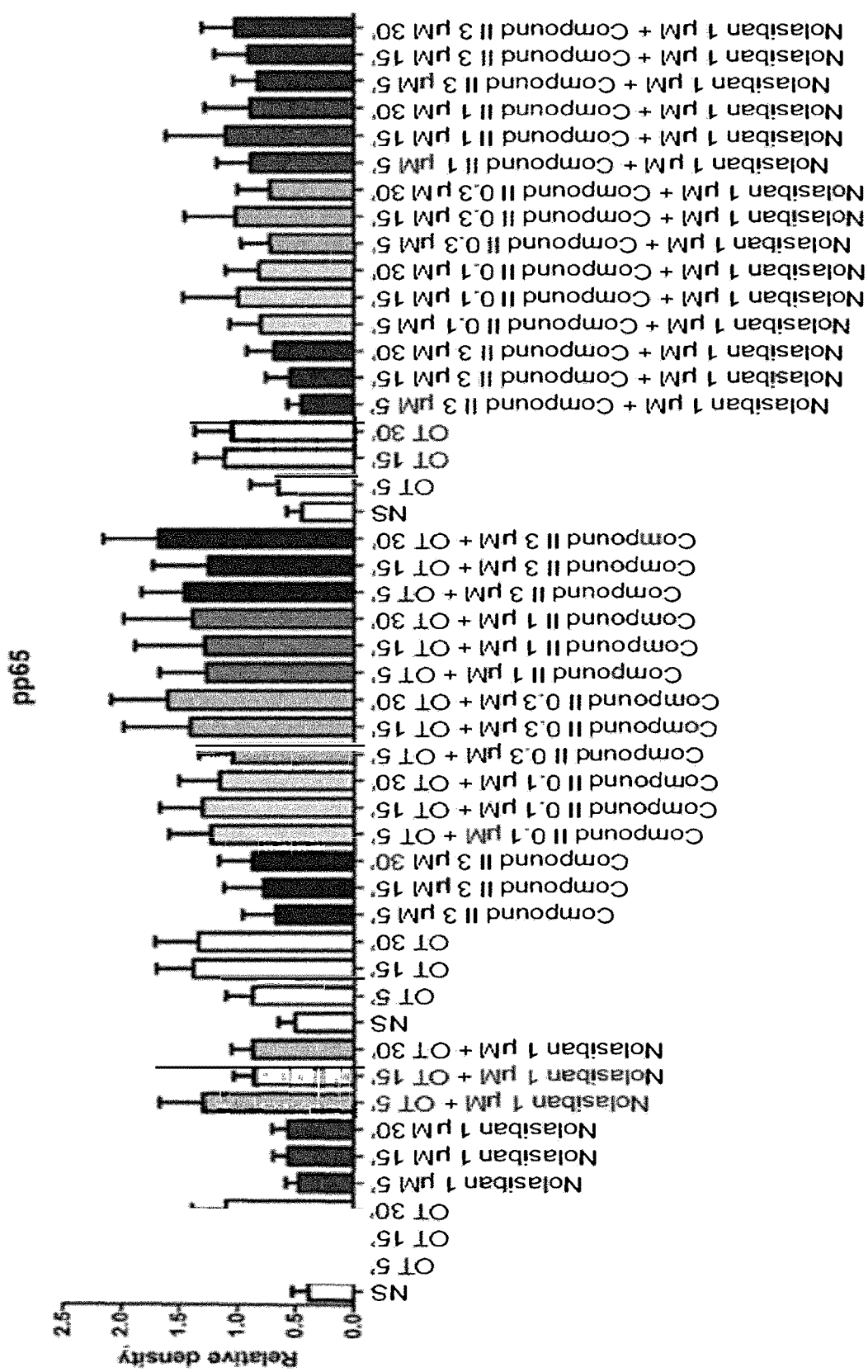
FIG. 79e is a graph quantitating the expression of p-p65 shown in FIGS. 79a and 79b.
Figure 79F:
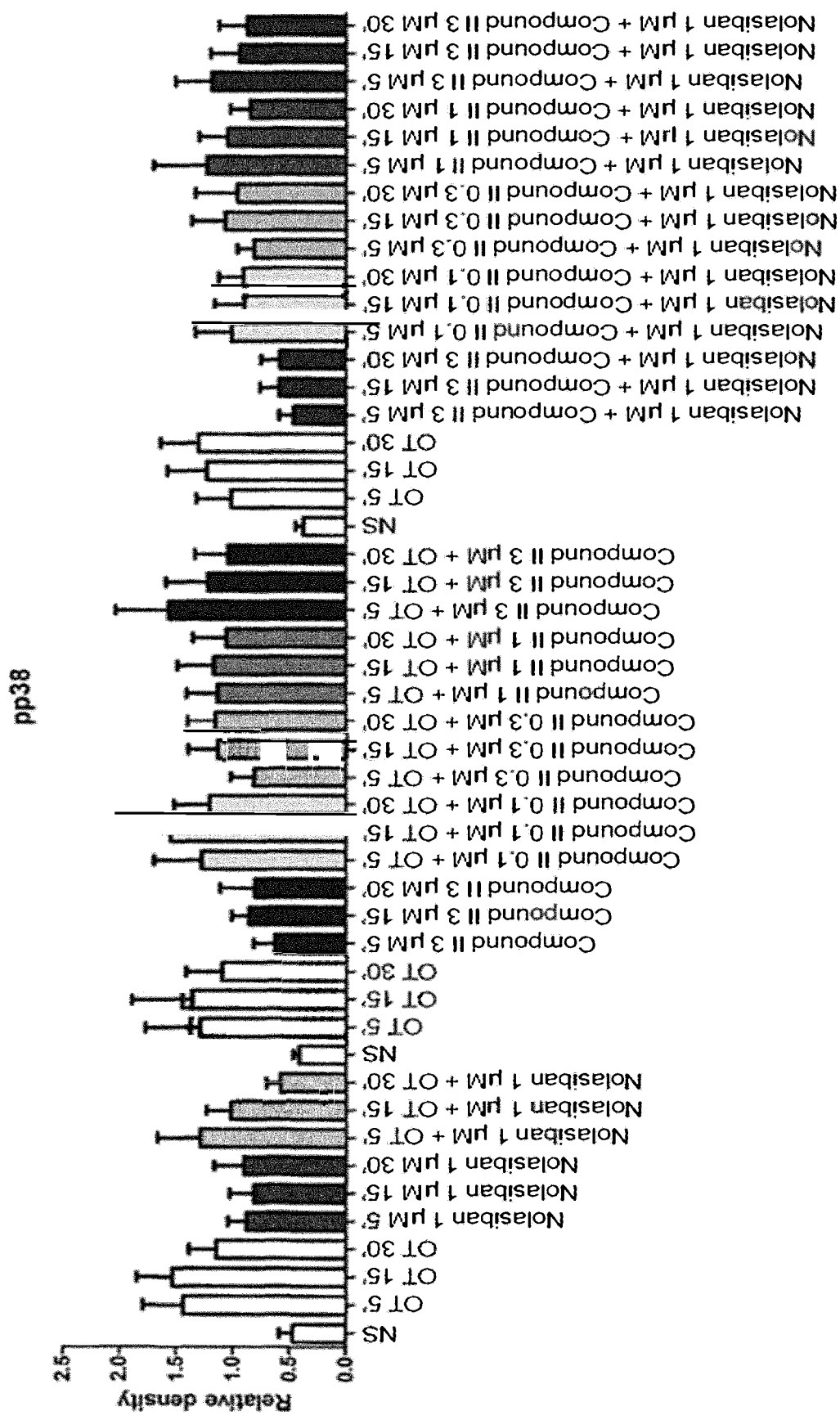
FIG. 79f is a graph quantitating the expression of p-p38 shown in FIGS. 79a and 79b.
Figure 79G:
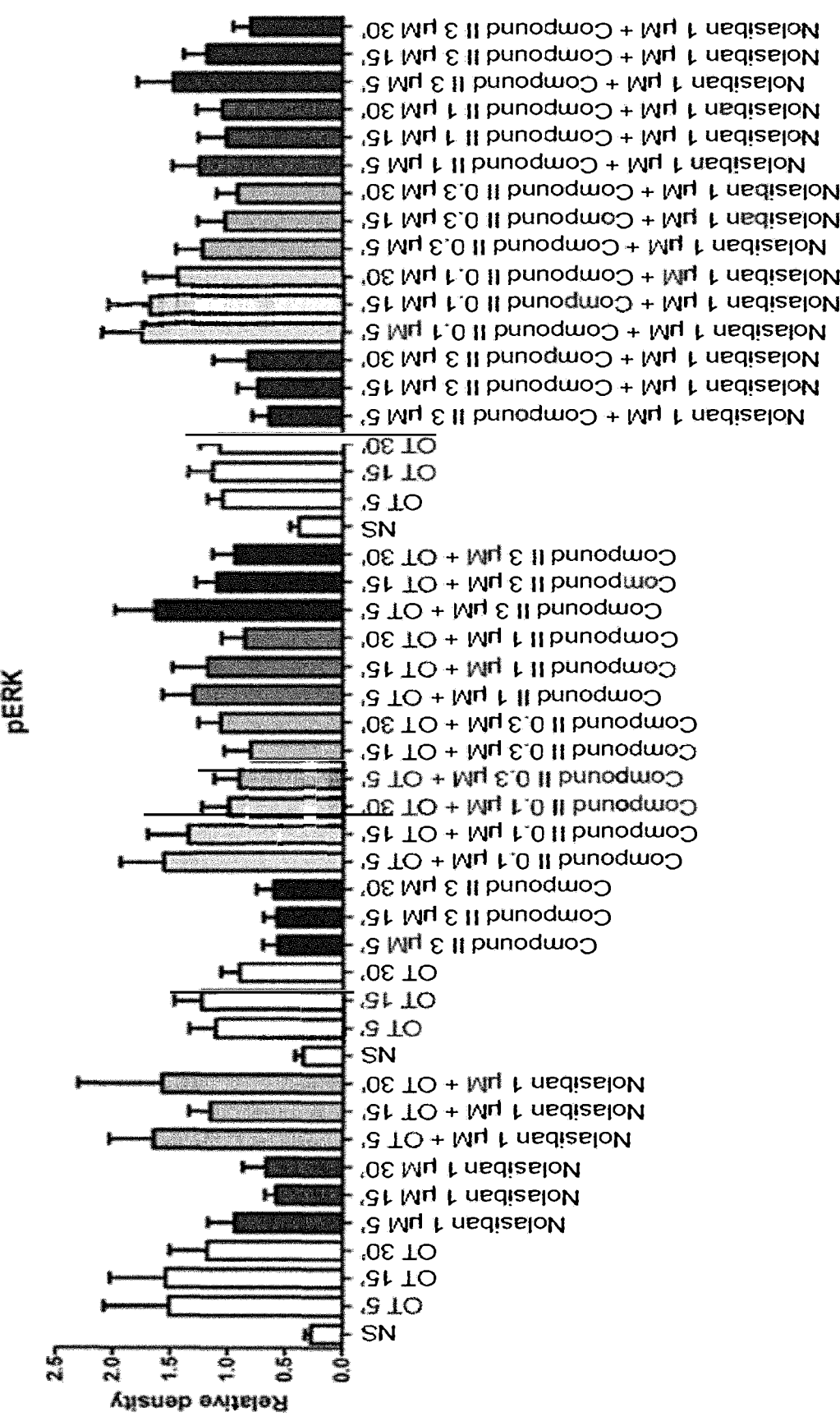
FIG. 79g is a graph quantitating the expression of p-ERK shown in FIGS. 79a and 79b.
Figure 79H:
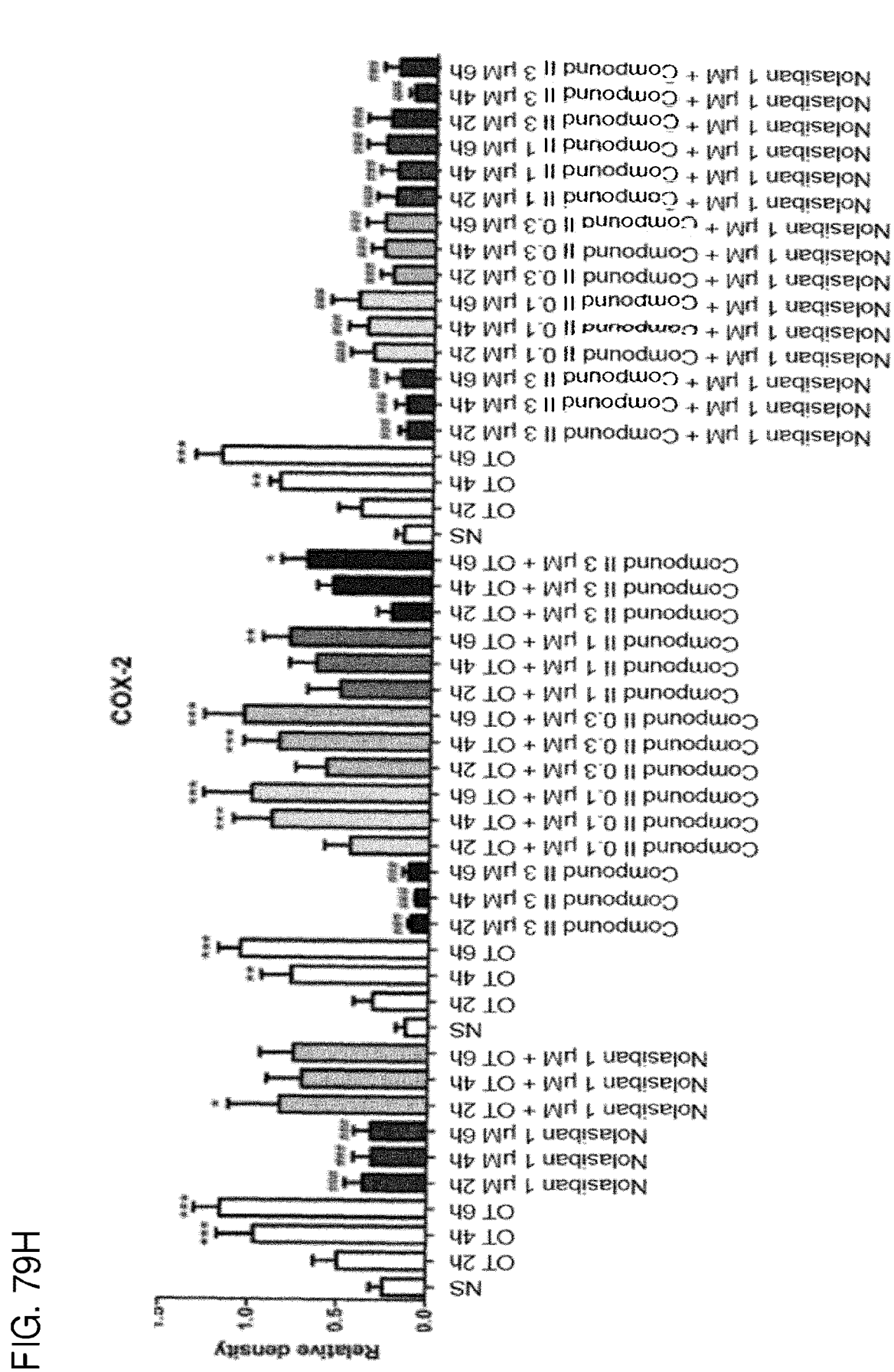
FIG. 79h is a graph quantitating the expression of COX-2 shown in FIGS. 79c and 79d. Asterisk designates a p value of p<0.05 versus the unstimulated ("NS") samples. Two asterisks designate a p value of p<0.01 versus the unstimulated samples. Three asterisks designate a p value of p<0.001 versus the unstimulated samples. Three "#" symbols designate a p value of p<0.001 versus oxytocin (OT)-treated samples.
Figure 79I:
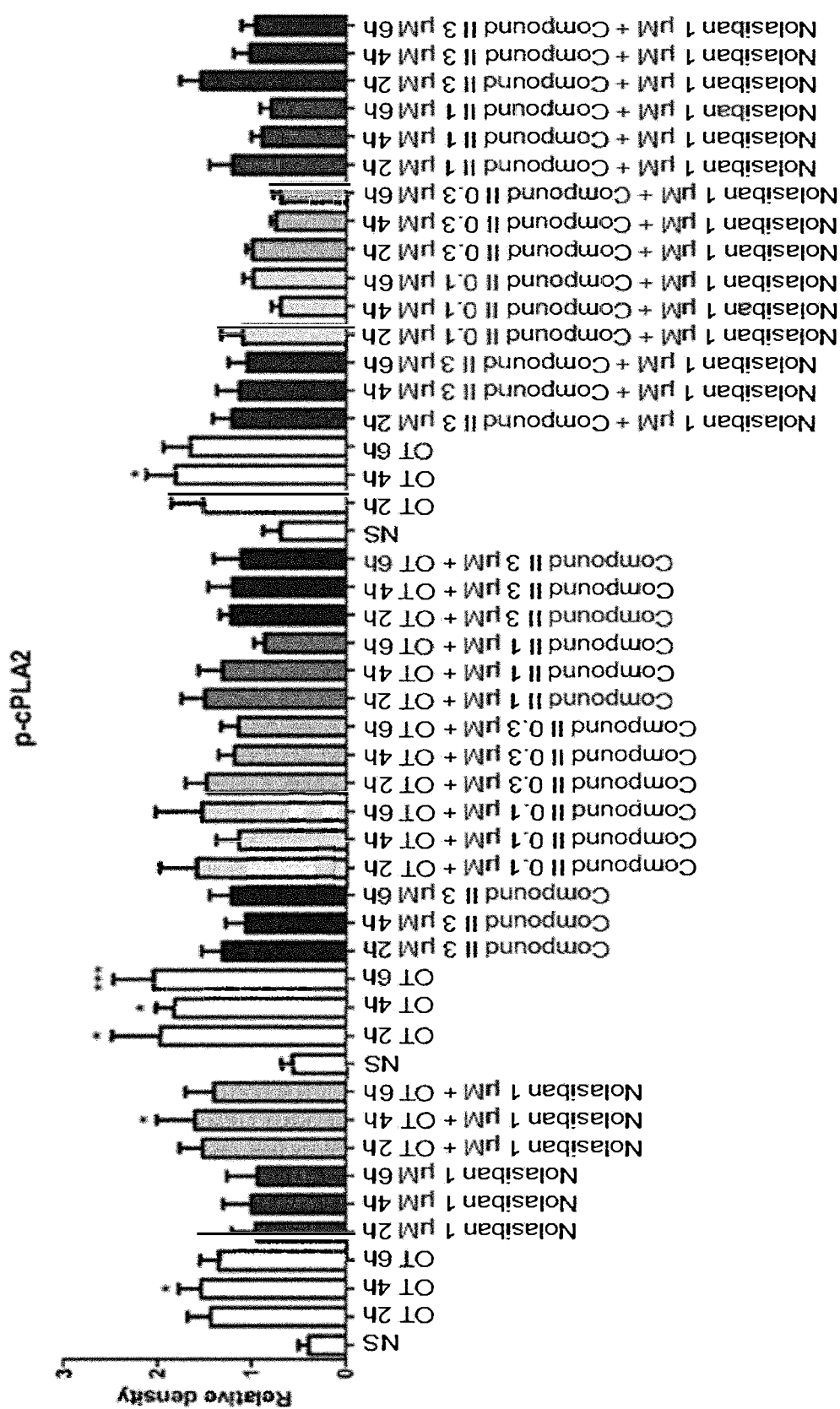
FIG. 79l is a graph quantitating the expression of p-cPLA2 shown in FIGS. 79c and 79d. Asterisk designates a p value of p<0.05 versus the unstimulated ("NS") samples. Three asterisks designate a p value of p<0.001 versus the unstimulated samples.
Figure 80A:
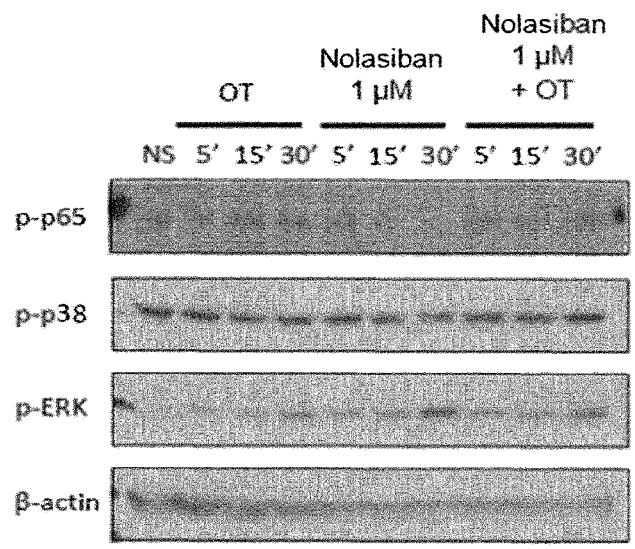
FIG. 80a is a Western blot showing the effects of oxytocin, nolasiban, and a combination thereof on the expression of p-p65, p-p38, and p-ERK in N=3 term, pre-laboring amnion biopsies collected from human female subjects undergoing caesarean section delivery. Samples were either unstimulated ("NS"), stimulated with oxytocin ("OT"), treated with nolasiban at a concentration of 1 µM, or treated with both oxytocin and nolasiban at a concentration of 1 µM for the indicated periods of time. A blot against β-actin was performed as a control.
Figure 80B:
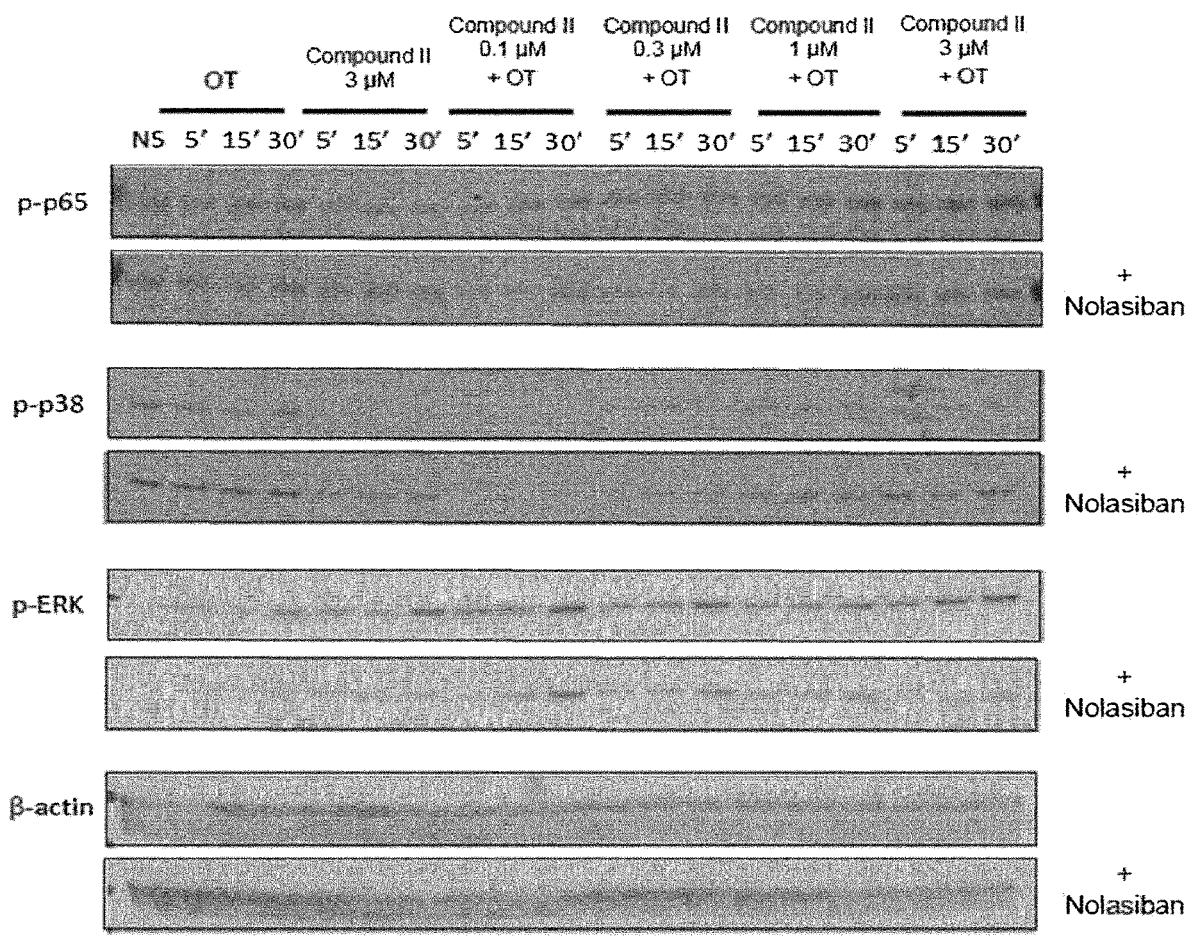
FIG. 80b is a Western blot showing the effects of oxytocin and/or varying concentration of compound II, optionally in combination with nolasiban, on the expression of p-p65, p-p38, and p-ERK in N=3 term, pre-laboring amnion biopsies collected from human female subjects undergoing caesarean section delivery. Samples were either unstimulated ("NS"), stimulated with oxytocin ("OT"), treated with compound II at a concentration of 3 µM, or treated with both oxytocin and compound II at varying concentrations of compound II, both in the presence and absence of nolasiban at a concentration of 1 µM for the indicated periods of time. A blot against β-actin was performed as a control.
Figure 80C:
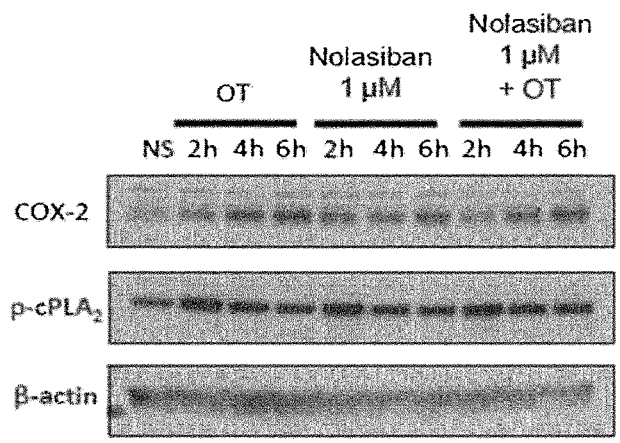
FIG. 80c is a Western blot showing the effects of oxytocin, nolasiban, and a combination thereof on the expression of the proinflammatory genes COX-2 and p-cPLA2 in N=3 term, pre-laboring amnion biopsies collected from human female subjects undergoing caesarean section delivery. Samples were either unstimulated ("NS"), stimulated with oxytocin ("OT"), treated with nolasiban at a concentration of 1 µM, or treated with both oxytocin and nolasiban at a concentration of 1 µM for the indicated periods of time. A blot against β-actin was performed as a control.
Figure 80D:
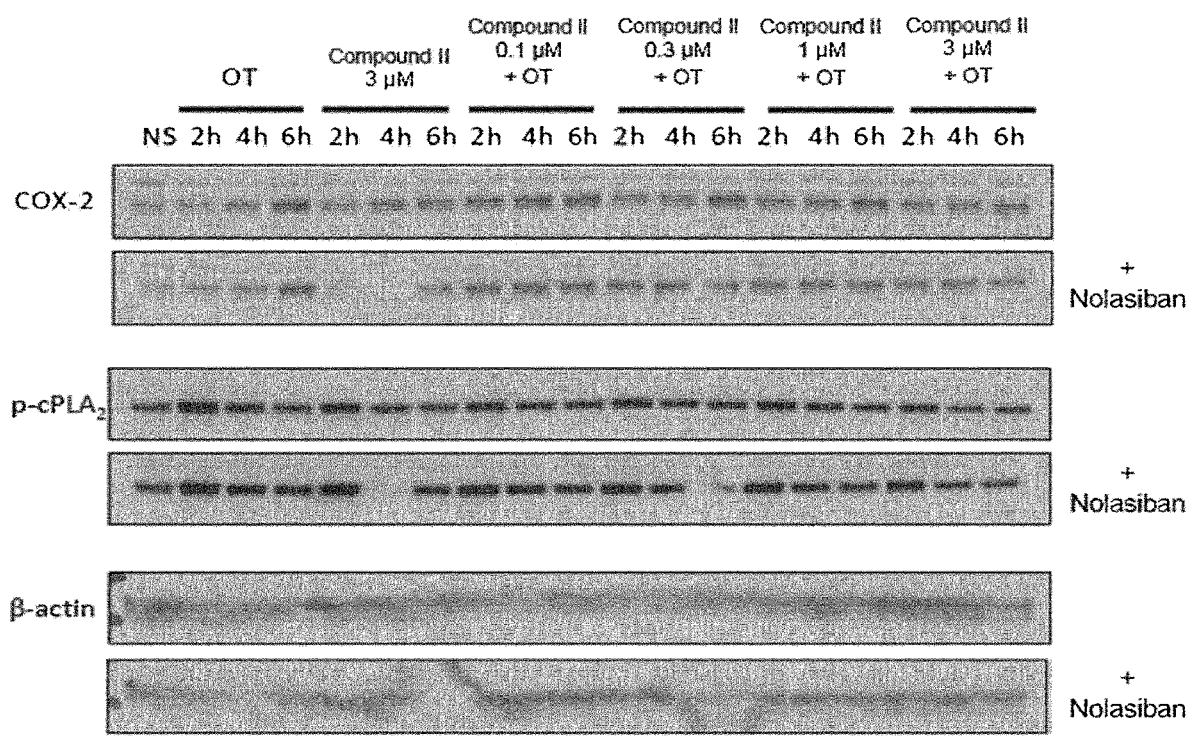
FIG. 80d is a Western blot showing the effects of oxytocin and/or varying concentration of compound II, optionally in combination with nolasiban, on the expression of the proinflammatory genes COX-2 and p-cPLA2 in N=3 term, pre-laboring amnion biopsies collected from human female subjects undergoing caesarean section delivery. Samples were either unstimulated ("NS"), stimulated with oxytocin ("OT"), treated with compound II at a concentration of 3 µM, or treated with both oxytocin and compound II at varying concentrations of compound II, both in the presence and absence of nolasiban at a concentration of 1 µM for the indicated periods of time. A blot against β-actin was performed as a control.

During the investigation, it was observed that treatment with nifedipine alone induced a significant increase in mean time to delivery compared to vehicle (23.53±0.99 hours versus 21.19±1.00 hours; FIG. 65) in RU486-treated mice. Treatment with nifedipine alone additionally promoted an increase in time to delivery and significantly increased fractional viability of offspring in LPS-treated mice compared to vehicle (90.39%±5.34% versus 48.20%±16.45%; FIGS. 68 and 69). Administration of atosiban similarly resulted in an increase in time to delivery in LPS-treated mice (FIG. 70).

Compound III was found to promote an increase in time to delivery compared to vehicle in RU486-treated mice (FIGS. 65 and 67). Particularly, RU486-treated mice administered compound III orally at 30 mg/kg and 100 mg/kg exhibited increases in time to delivery relative to vehicle (p=0.0871 and p=0.0601, respectively). Additionally, administration of compound III to LPS-treated mice resulted in a dose-dependent increase in the fractional viability of offspring (69.41%±15.76% viability observed in response to 100 mg/kg compound III versus 48.20%±16.45% observed in response to vehicle; FIG. 68).

The combination of nifedipine and compound III resulted in a particularly pronounced tocolytic effect (FIGS. 65 and 69). Oral administration of nifedipine (5 mg/kg) and compound III (100 mg/kg) to RU486-treated mice resulted in a clear synergistic effect, as this combination induced a significant increase in time to delivery relative to vehicle (27.91±0.35 hours versus 21.19±1.00 hours), the same dosage of nifedipine alone (27.91±0.35 hours versus 23.53±0.99 hours), and the same dosage of compound III alone (27.91±0.35 hours versus 23.70±0.60 hours). Additionally, oral administration of nifedipine (5 mg/kg) and compound III (10 mg/kg) to LPS-treated mice resulted in a significant increase in time to delivery relative to the cohort treated with 10 mg/kg compound III alone (31.01±1.89 hours versus 23.98±0.66 hours). Oral administration of 10 mg/kg compound III in combination with 5 mg/kg nifedipine also promoted an increase in the viability of pups delivered by LPS-treated mice relative to mice that were administered the same dosage of compound III alone (94.23%±3.68% versus 57.90%±14.89%) and relative to mice that were administered vehicle alone (94.23%±3.68% versus 48.20%±16.45%; FIG. 68).

The combination of atosiban and compound III additionally potentiated the tocolytic effect of each compound used alone. Subcutaneous administration of atosiban (300 mg/kg) and oral administration of compound III (100 mg/kg) to LPS-treated mice induced a significant increase in time to delivery relative to mice that were administered vehicle alone (33.23±2.95 hours versus 26.17±1.98 hours) and relative to mice that were administered the same dosage of atosiban alone (33.23±2.95 hours versus 28.41±2.99 hours; FIG. 71). This combination also exhibited a propensity to increase the fractional viability of offspring compared to mice treated with vehicle alone, the same dosage of atosiban alone, or the same dosage of compound III alone (FIG. 70).

This study further illustrates the tocolytic effect of a salt of FP antagonist compound I in two distinct animal models of preterm parturition and supports the usage of compound I and salts thereof to treat and prevent preterm labor regardless of the underlying biochemical etiology. This investigation additionally supports the usage of FP antagonists, such as compound I and salts thereof (e.g., compound III) in combination with each of a calcium channel antagonist and an oxytocin receptor antagonist for the prevention of preterm birth. The use of compound III in combination with each of nifedipine and atosiban significantly exceeded the therapeutic effects of individual components, and demonstrates that compound I and salts thereof, such as compound III, may synergize with additional tocolytic agents.

Example 7. Tocolytic Effects of Compound II in Combination with Nifedipine, Atosiban, and Nolasiban in Human Tissue Samples To investigate the therapeutic effects of compound II, the active metabolite of compound I and salts thereof (such as compound III), in combination with oxytocin receptor antagonists and calcium channel blockers, myometrial biopsies were obtained from term, pre-laboring human female subjects undergoing caesarean section delivery. Among the aims of this investigation was to characterize the effects of compound II, alone and in combination with additional tocolytic agents, on the frequency, peak amplitude, and duration of myometrial contractions, as well as on the work done per contraction and total work done by all contractions. To this end, experiments were performed using a DMT Myograph 800 MS (ADINSTRUMENTS™) in oxygenated Kreb's solution with ADI Powerlab software, which facilitated the simultaneous measurement of multiple muscle preparations in parallel.

Experiments in myometrial biopsies were initiated by allowing smooth muscle contractions to establish a baseline for at least 20 minutes. Following this time period, baseline measurements of spontaneous contraction frequency, peak amplitude, duration, work done per contraction, and total work done by all contractions were recorded. Myometrial biopsy samples were subsequently treated with a DMSO control, compound II, atosiban, nifedipine, a combination of compound II and atosiban, or a combination of compound II and nifedipine. The effects of these agents on the frequency, amplitude, and duration of, as well as work done by, myometrial contractions were subsequently measured over the ensuing 10-minute period. Myometrial samples were then challenged by the addition increasing concentrations of a contraction-stimulating agent, such as oxytocin, $PGF2\alpha$, or PGE2, over the course of sequential 10-minute intervals, and the contraction frequency, peak amplitude, duration, work done per contraction, and total work done by all contractions were measured accordingly. Oxytocin, PGF2α, and PGE each represent distinct modulators of uterine contractility and preterm parturition. Oxytocin directly induces contraction of the uterine myometrium and enhances the synthesis and release of contractile prostaglandins from the uterine endometrium and decidua. Oxytocin has also been implicated in promoting the production of prostaglandins in human myometrial cells via potentiation of cyclooxygenase 2 (COX-2). The prostaglandins PGF2α and PGE2 have been shown to induce cervical changes and elicit uterine contractility, two key events in the physiology of labor and parturition. Activation of the FP receptor in the human myometrium by PGF2α results in the elevation of intracellular calcium concentration, which, in turn, leads to contraction of the uterine smooth cell muscle. Thus, another aim of this investigation was to evaluate the ability of compound II to attenuate uterine contractile activity as induced by three distinct biochemical modalities.

The results of these experiments demonstrate that compound II alone is capable of suppressing both PGF2α-induced and OT-induced myometrial contractility in a dose-dependent fashion (FIGS. 72 and 73). Moreover, it has presently been discovered that compound II exhibits a surprising synergistic effect on the reduction of myometrial contractility when used in combination with the oxytocin receptor antagonist atosiban (FIG. 76) and the calcium channel blocker nifedipine (FIG. 78). Surprisingly, doses of compound II that exhibited lower potency towards the reduction of myometrial contractility when used in the absence of an additional tocolytic agent (such as 60 nM, FIGS. 72 and 73) exhibited a striking increase in inhibitory activity when combined with atosiban (FIG. 76) and nifedipine (FIG. 78). Similarly, doses of atosiban (6 nM, FIGS. 74 and 75) and nifedipine (6 nM, FIG. 77) that were found to be sub-optimal towards the reduction of myometrial contractility when used in the absence of compound II exhibited an unexpected increase in anti-contractile potency when combined with compound II (FIGS. 76 and 78). These data demonstrate that compound II is capable of synergizing with additional tocolytic agents, such as oxytocin receptor antagonists and calcium channel blockers, to suppress uterine contractile activity that can lead to preterm parturition.

In addition to suppressing myometrial contractility, the tocolytic effects of compound II are also manifest in the ability of this agent to attenuate the expression of downstream proinflammatory genes in human myometrial and amnion biopsies (FIGS. 79 and 80). Western blots were performed in order to characterize the ability of compound II, alone and in combination with additional tocolytic agents, to modulate the expression of various proteins in myometrial and amnion samples isolated from term, pre-laboring human female subjects undergoing caesarean section delivery. The results of these studies demonstrate that compound II is capable of reducing the expression of various proinflammatory proteins, and exhibits a surprising synergy when used in combination with nolasiban towards the reduction of COX-2 expression.

Collectively, the data generated from these experiments demonstrate that compound II is capable of suppressing smooth muscle activity that can lead to preterm parturition as induced by distinct modulators of uterine contractility. Moreover, compound II exhibits an unexpected synergistic effect on the attenuation of uterine contractions when used in combination with oxytocin receptor antagonists and calcium channel blockers. This synergy is manifest both at the level of smooth muscle activity and in the reduction of proinflammatory gene expression in myometrial and amnion biopsies, and demonstrates various benefits of providing compound II in combination with one or more additional tocolytic agents to a subject in need of treatment, such as a subject undergoing or at risk of undergoing preterm labor.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of treating preterm labor in a human patient in need thereof, the method comprising providing to the patient a therapeutically effective amount of a compound represented by formula (II)

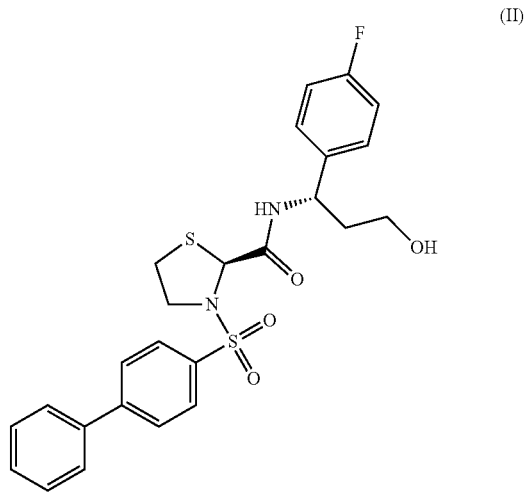 [SMILES: O=C(N[C@@H](CCO)c1ccc(F)cc1)[C@@H]1SCCN1S(=O)(=O)c1ccc(-c2ccccc2)cc1]

and wherein the patient is administered nifedipine or atosiban.

2. A method of delaying labor in a human patient in need thereof, the method comprising providing to the patient a therapeutically effective amount of a compound represented by formula (II)

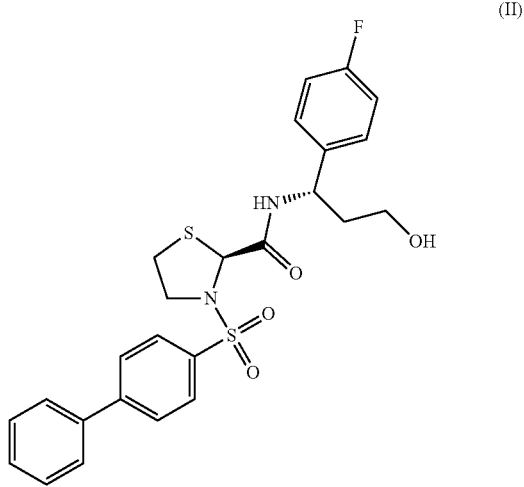 [SMILES: O=C(N[C@@H](CCO)c1ccc(F)cc1)[C@@H]1SCCN1S(=O)(=O)c1ccc(-c2ccccc2)cc1]

and wherein the patient is administered nifedipine or atosiban.

3. The method of claim 1, wherein the patient is administered atosiban.

4. The method of claim 1, wherein the patient is administered nifedipine.

5. The method of claim 1, wherein the patient is further administered a betamimetic, a magnesium salt, a nitric oxide donor, progesterone or a variant thereof, or a corticosteroid.

6. The method of claim 5, wherein the patient is administered a betamimetic selected from the group consisting of terbutaline, ritodrine, hexoprenaline, albuterol, fenoterol, nylidrin, and orciprenaline.

7. The method of claim 5, wherein the patient is administered magnesium sulfate.

8. The method of claim 5, wherein the patient is administered nitroglycerine.

9. The method of claim 5, wherein the patient is administered progesterone or 17-α-hydroxyprogesterone caproate.

10. The method of claim 5, wherein the patient is administered a corticosteroid selected from the group consisting of betamethasone, dexamethasone, or hydrocortisone.

11. The method of claim 1, wherein the patient is characterized by a gestational age of from about 24 weeks to about 34 weeks.

12. The method of claim 2, wherein the patient is administered atosiban.

13. The method of claim 2, wherein the patient is administered nifedipine.

14. The method of claim 2, wherein the patient is further administered a betamimetic, a magnesium salt, a nitric oxide donor, progesterone or a variant thereof, or a corticosteroid.

15. The method of claim 14, wherein the patient is administered a betamimetic selected from the group consisting of terbutaline, ritodrine, hexoprenaline, albuterol, fenoterol, nylidrin, and orciprenaline.

16. The method of claim 14, wherein the patient is administered magnesium sulfate.

17. The method of claim 14, wherein the patient is administered nitroglycerine.

18. The method of claim 14, wherein the patient is administered progesterone or 17-α-hydroxyprogesterone caproate.

19. The method of claim 14, wherein the patient is administered a corticosteroid selected from the group consisting of betamethasone, dexamethasone, or hydrocortisone.

20. The method of claim 2, wherein the patient is characterized by a gestational age of from about 24 weeks to about 34 weeks.

* * * * *